(12) United States Patent
Andruzzi et al.

(10) Patent No.: US 10,844,430 B2
(45) Date of Patent: Nov. 24, 2020

(54) DNA SEQUENCING REACTION ADDITIVE

(71) Applicant: Qiagen Sciences, LLC, Germantown, MD (US)

(72) Inventors: Luisa Andruzzi, Concord, MA (US); Jimmy Adediran, Waltham, MA (US); Timothy Pelletier, Leominster, MA (US); Austin Ricker, Waltham, MA (US); Angela DeLucia, Cambridge, MA (US); Ben McNally, Medford, MA (US); Dona Hevroni, Lexington, MA (US); Mong Sano Marma, Natick, MA (US); John Andrew Sheridan, Marblehead, MA (US)

(73) Assignee: Qiagen Sciences, LLC, Germantown, MD (US)

(*) Notice: Subject to any disclaimer, the term of this patent is extended or adjusted under 35 U.S.C. 154(b) by 127 days.

(21) Appl. No.: 15/878,633

(22) Filed: Jan. 24, 2018

(65) Prior Publication Data

US 2019/0226018 A1 Jul. 25, 2019

(51) Int. Cl.
| | |
|---|---|
| C12P 19/34 | (2006.01) |
| C12Q 1/6869 | (2018.01) |
| C12Q 1/6876 | (2018.01) |
| C12Q 1/6806 | (2018.01) |
| C07D 275/03 | (2006.01) |

(52) U.S. Cl.
CPC ......... *C12Q 1/6869* (2013.01); *C12Q 1/6806* (2013.01); *C12Q 1/6876* (2013.01); *C07D 275/03* (2013.01); *C12Q 2525/113* (2013.01); *C12Q 2525/186* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,756,334 A | 5/1998 | Perler et al. | 435/194 |
| 5,990,300 A | 11/1999 | Hiatt et al. | 536/25.3 |
| 6,833,246 B2 | 12/2004 | Balasubramanian | 435/6 |
| 7,414,116 B2 | 8/2008 | Milton et al. | 536/23.1 |
| 7,785,796 B2 | 8/2010 | Balasubramanian et al. | 536/4.1 |
| 7,883,869 B2 | 2/2011 | Ju et al. | 435/91.1 |
| 8,017,338 B2 | 9/2011 | Zon | 435/6.12 |
| 8,088,575 B2 | 1/2012 | Ju et al. | 435/6 |
| 8,399,188 B2 | 3/2013 | Zhao et al. | 435/6.1 |
| 8,623,598 B2 | 1/2014 | Olejnik et al. | 435/6.1 |
| 8,796,432 B2 | 8/2014 | Ju et al. | 536/4.1 |
| 2002/0015961 A1 | 2/2002 | Kwiatkowski | 554/6 |
| 2007/0117104 A1 | 5/2007 | Buzby | 435/6 |
| 2013/0137091 A1 | 5/2013 | Gordon et al. | 435/91.5 |
| 2015/0140561 A1 | 5/2015 | Bergmann et al. | 435/6.1 |
| 2016/0319374 A1* | 11/2016 | Knapp | C12Q 1/6893 |
| 2017/0183714 A1* | 6/2017 | Shen | C12Q 1/6844 |
| 2017/0211134 A1* | 7/2017 | Marma | C12Q 1/6823 |
| 2017/0233805 A1 | 8/2017 | Dimeo | 435/6.12 |

FOREIGN PATENT DOCUMENTS

WO   WO/2005/024010   3/2005

OTHER PUBLICATIONS

Anisimov, A. V. et al. (2008) "Oxidation of organic sulfur compounds with hydrogen peroxide in the presence of crown ethers," *Moscow University Chemistry Bulletin* 63(1), 48-54.
Arezi, B. et al. (2002) "Efficient and high fidelity incorporation of dye-terminators by a novel archaeal DNA polymerase mutant," *Journal of Molecular Biology* 322(4), 719-729.
Bellamy, A. J. et al. (2007) "The Use of Trifluoroacetyl as an N- and O-Protecting Group during the Synthesis of Energetic Compounds containing Nitramine and/or Nitrate Ester Groups," *Propellants, Explosives, Pyrotechnics* 32(1), 20-31.
Bowers, J. et al. (2009) "Virtual Terminator nucleotides for next generation DNA sequencing," *Nature Methods* 6(8), 593-595.
Burns, J. A. et al. (1991) "Selective reduction of disulfides by tris(2-carboxyethyl)phosphine," *Journal of Organic Chemistry* 56(8), 2648-2650.
Chen, C.-Y. (2014) "DNA Polymerases Drive DNA Sequencing-by-Synthesis Technologies: Both Past and Present," *Frontiers in Microbiology* 5.
Chen, F. et al. (2013) "The History and Advances of Reversible Terminators Used in New Generations of Sequencing Technology," *Genomics, Proteomics & Bioinformatics* 11(1), 34-40.
Clark, D. E. (1999) "Rapid calculation of polar molecular surface area and its application to the prediction of transport phenomena. 2. Prediction of blood-brain barrier penetration," *Journal of Pharmaceutical Sciences* 88(8), 815-821.
Evans, S. J. et al. (2000) "Improving dideoxynucleotide-triphosphate utilisation by the hyper-thermophilic DNA polymerase from the archaeon Pyrococcus furiosus," *Nucleic Acids Research* 28(5), 1059-1066.
Fuller, C. W. et al. (2009) "The challenges of sequencing by synthesis," *Nature Biotechnology* 27(11), 1013-1023.
Gardner, A. F. et al. (2012) "Rapid incorporation kinetics and improved fidelity of a novel class of 3'-OH unblocked reversible terminators," *Nucleic Acids Research* 40(15), 7404-7415.

(Continued)

*Primary Examiner* — Kenneth R Horlick
(74) *Attorney, Agent, or Firm* — Medlen & Carroll, LLP

(57) ABSTRACT

The present invention provides methods, compositions, mixtures and kits utilizing 5-Chloro-2-methyl-4-isothiazolin-3-one in sequencing reactions, and in particular, sequencing reactions where deoxynucleoside triphosphates comprising a 3'-O position capped by a disulfide-based 3'-terminator group are used. In one embodiment, the deoxynucleoside triphosphates comprise a 3'-O position capped by a group comprising methylenedisulfide as a cleavable protecting group and a detectable label reversibly connected to the nucleobase of said deoxynucleoside. In addition, thiol-containing compounds and scavengers of thio-containing compounds are described. Such compounds provide new possibilities for future sequencing technologies, including but not limited to Sequencing by Synthesis.

20 Claims, 100 Drawing Sheets

(56) References Cited

OTHER PUBLICATIONS

Getz, E. B. et al. (1999) "A comparison between the sulfhydryl reductants tris(2-carboxyethyl)phosphine and dithiothreitol for use in protein biochemistry," *Analytical Biochemistry* 273(1), 73-80.

Harpp, D. N. et al. (1968) "Organic sulfur chemistry. I. The disulfide-phosphine reaction. Desulfurization with tris(diethylamino)phosphine," *Journal of the American Chemical Society* 90(15), 4181-4182.

Holmgren, A. et al. (1995) "[21] Thioredoxin and thioredoxin reductase," in *Methods in Enzymology*, pp. 199-208, Academic Press.

Ju, J. et al. (2006) "Four-color DNA sequencing by synthesis using cleavable fluorescent nucleotide reversible terminators," *Proceedings of the National Academy of Sciences of the United States of America* 103(52), 19635-19640.

Jung, A. et al. (2002) "7-Deaza-2'-deoxyguanosine allows PCR and sequencing reactions from CpG islands," *Molecular Pathology* 55(1), 55-57.

Kutyavin, I. V. (2008) "Use of Base-Modified Duplex-Stabilizing Deoxynucleoside 5'-Triphosphates To Enhance the Hybridization Properties of Primers and Probes in Detection Polymerase Chain Reaction," *Biochemistry* 47(51), 13666-13673.

Litosh, V. A. et al. (2011) "Improved nucleotide selectivity and termination of 3'-OH unblocked reversible terminators by molecular tuning of 2-nitrobenzyl alkylated HOMedU triphosphates," *Nucleic Acids Research* 39(6), e39-e39.

Lukesh, J. C. et al. (2012) "A potent, versatile disulfide-reducing agent from aspartic acid," *Journal of the American Chemical Society* 134(9), 4057-4059.

Metzker, M. L. (2010) "Sequencing technologies—the next generation," *Nature Reviews Genetics* 11(1), 31-46.

Metzker, M. L. et al. (1994) "Termination of DNA synthesis by novel 3'-modified-deoxyribonucleoside 5'-triphosphates," *Nucleic Acids Research* 22(20), 4259-4267.

Montazerozohori, M. et al. (2007) "Fast and highly efficient solid state oxidation of thiols," *Molecules* 12(3), 694.

Nardai, G. et al. (2001) "Protein-disulfide Isomerase- and Protein Thiol-dependent Dehydroascorbate Reduction and Ascorbate Accumulation in the Lumen of the Endoplasmic Reticulum," *Journal of Biological Chemistry* 276(12), 8825-8828.

Ruparel, H. et al. (2005) "Design and synthesis of a 3'-O-allyl photocleavable fluorescent nucleotide as a reversible terminator for DNA sequencing by synthesis," *Proceedings of the National Academy of Sciences of the United States of America* 102(17), 5932-5937.

Semenyuk, A. (2006) Novel Methods for Synthesis of High Quality Oligonucleotides, Uppsala University.

Semenyuk, A. et al. (2006) "Synthesis of RNA using 2'-O-DTM protection," *Journal of the American Chemical Society* 128(38), 12356-12357.

Semenyuk, A. et al. (2007) "A base-stable dithiomethyl linker for solid-phase synthesis of oligonucleotides," *Tetrahedron Letters* 48(3), 469-472.

Singh, R. et al. (1995) "Catalysis of reduction of disulfide by selenol," *Analytical Biochemistry* 232(1), 86-91.

Singh, R. et al. (1993) "Thiol-Disulfide Interchange," in *Sulfur-Containing Functional Groups* (Supplement, S., et al., Eds.), pp. 633-658, J. Wiley and Sons, Ltd.

Singh, R. et al. (1994) "Reagents for rapid reduction of native disulfide bonds in proteins," *Bioorganic Chemistry* 22, 109-115.

Southworth, M. W. et al. (1996) "Cloning of thermostable DNA polymerases from hyperthermophilic marine Archaea with emphasis on *Thermococcus* sp. 9 degrees N-7 and mutations affecting 3'-5' exonuclease activity," *Proceedings of the National Academy of Sciences of the United States of America* 93(11), 5281-5285.

Stahl, C. R. et al. (1957) "Determination of Organic Disulfides by Reduction with Sodium Borohydride," *Analytical Chemistry* 29(1), 154-155.

Tabor, S. et al. (1995) "A single residue in DNA polymerases of the *Escherichia coli* DNA polymerase I family is critical for distinguishing between deoxy- and dideoxyribonucleotides," *Proceedings of the National Academy of Sciences of the United States of America* 92(14), 6339-6343.

Wang, Z. et al. (2010) "Desulfurization of Cysteine-Containing Peptides Resulting from Sample Preparation for Protein Characterization by MS," *Rapid Communications in Mass Spectrometry* 24(3), 267-275.

Zeida, A. et al. (2012) "Molecular Basis of the Mechanism of Thiol Oxidation by Hydrogen Peroxide in Aqueous Solution: Challenging the SN2 Paradigm," *Chemical Research in Toxicology* 25(3), 741-746.

PCT International Search Report of International Application No. PCT/US2019/014924 dated Mar. 22, 2019.

\* cited by examiner

FIGURE 32A - C

| 250 nM | AVG rate s⁻¹ |
|---|---|
| dC-Alexa-488 L-Series | 0.021 |
| dC-Alexa-488 B-Series | 0.032 |
| dC-Alexa-488 A-Series | 0.024 |
| dC-Alexa-488 G-Series | 0.015 |

| | Rate s⁻¹ | | |
| | 125nM | 250nM | 500nM |
|---|---|---|---|
| dC-Alexa-488 B-Series | 0.0021 | 0.003 | 0.0051 |
| dC-Alexa-488 A-Series | 0.0015 | 0.0021 | 0.0024 |
| dC-Alexa-488 L-Series | 0.0009 | 0.0015 | 0.0035 |
| dC-Alexa-488 G-Series | 0.0013 | 0.0022 | 0.0033 |

FIGURE 33
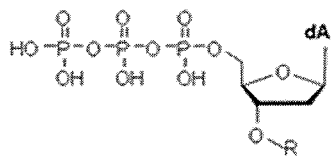
Wherein R =
  -CH2-N3
  -CH2-SS-Et (Et-O-SS-dA)
  -CH2-SS-Me (Me-O-SS-dA)
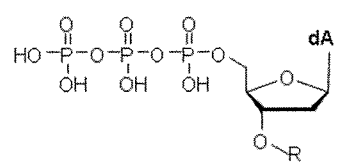
Wherein R =
  -CH2-N3
  -CH2-SS-Et
  -CH2-SS-Me
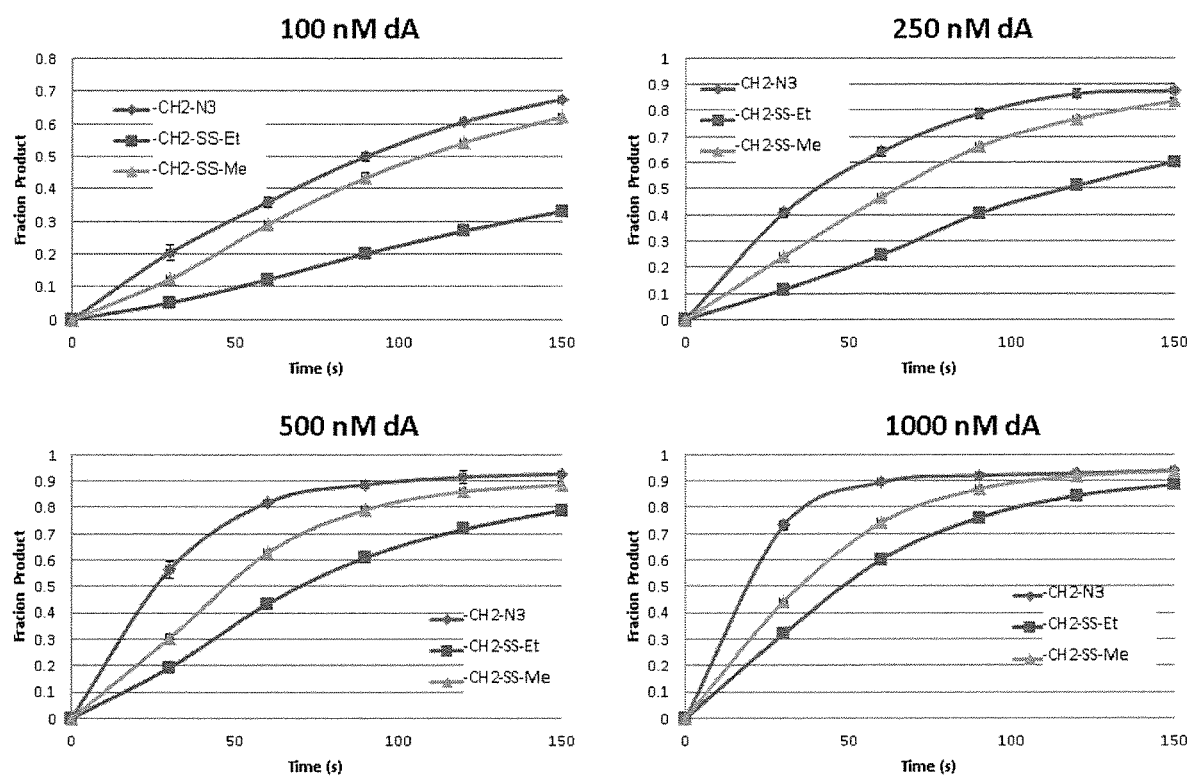

FIGURE 35

|  | L-series (96) | G-series (99) | A-series (98) |
|---|---|---|---|
| labeled C | 400 | 250 | 180 |
| labeled T | 30 | 22.5 | 90 |
| labeled A | 100 | 150 | 120 |
| labeled G | 100 | 80 | 120 |
| unlabeled C | 2000 | 2000 | 2000 |
| unlabeled T | 2000 | 2000 | 2000 |
| unlabeled A | 1000 | 1000 | 1000 |
| unlabeled G | 500 | 500 | 500 |

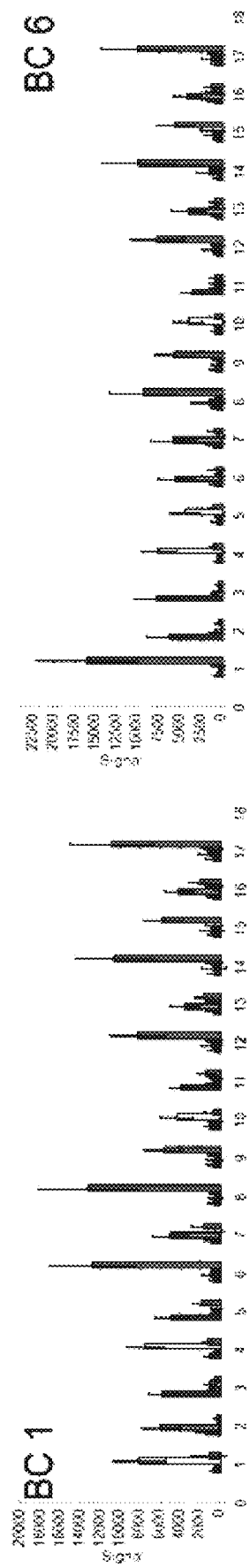
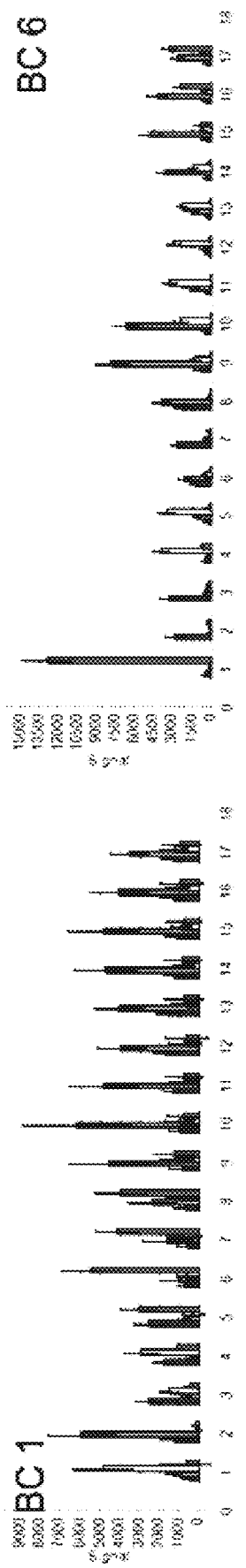
FIGURE 41

FIGURE 49

| | Concentration [nM] | Compound Number |
|---|---|---|
| labeled C | 180 | 72 |
| labeled T | 270 | 74 |
| labeled A | 360 | 76 |
| labeled G | 120 | 78 |
| unlabeled C | 2000 | 126 |
| unlabeled T | 2000 | 138 |
| unlabeled A | 1000 | 73 |
| unlabeled G | 500 | 132 |

FIGURE 68
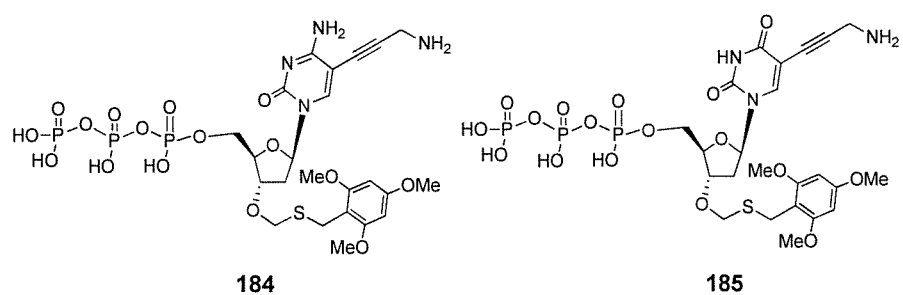
184          185
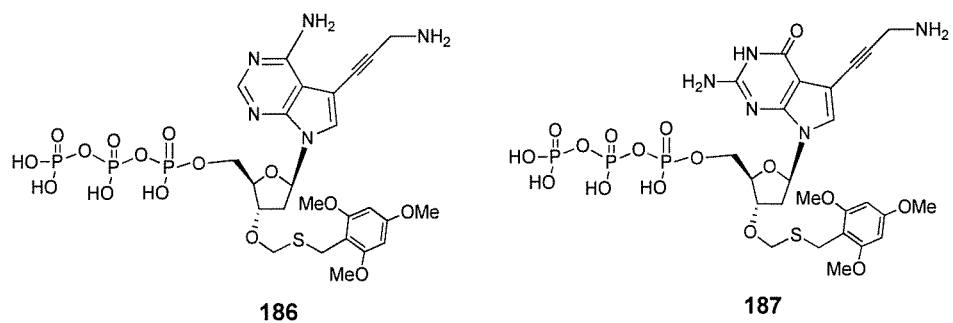
186          187

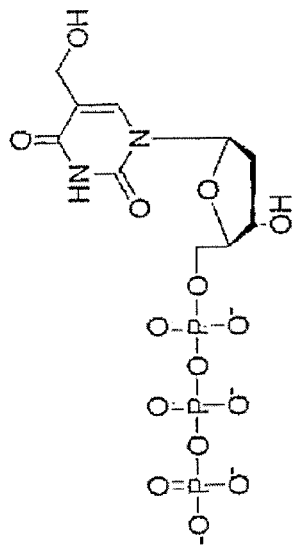
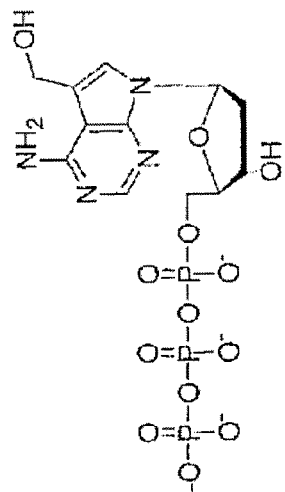
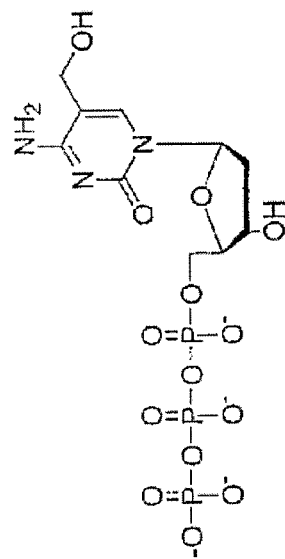
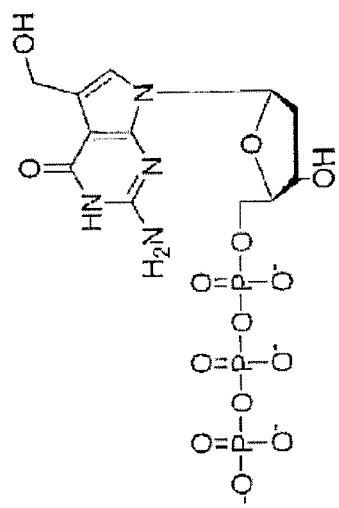
FIGURE 72

FIGURE 79
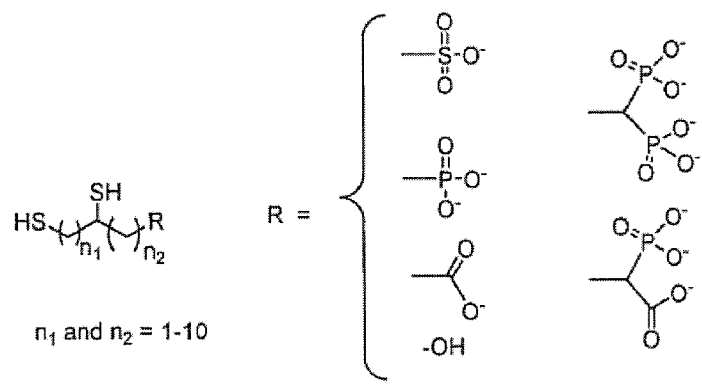
$n_1$ and $n_2$ = 1-10
Specific examples:
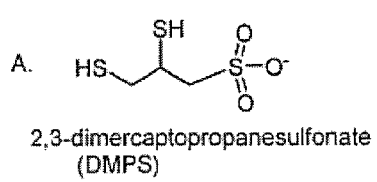
A. 2,3-dimercaptopropanesulfonate (DMPS)
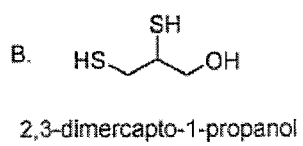
B. 2,3-dimercapto-1-propanol
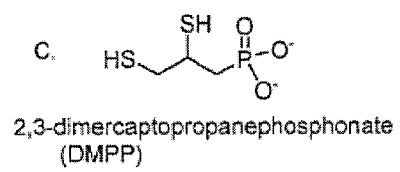
C. 2,3-dimercaptopropanephosphonate (DMPP)

$R_1$ = halogens, $NH_2$, OH, etc.

$n_1$ and $n_2$ = 1-10

FIGURE 83
1. Dithiolsuccinic acid 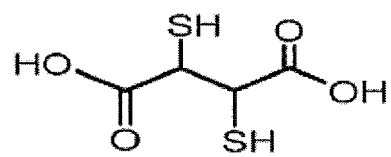
2. Dimercaptopronoic acid 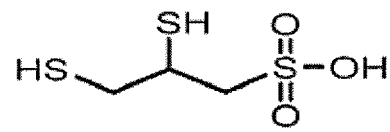
3. L-Cystein 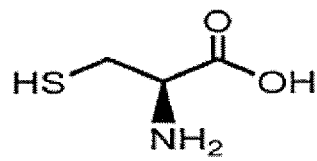
4. DTT 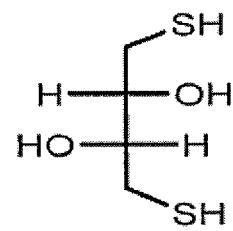
5. Cysteamin 

MANUAL

MANUAL

AUTOMATED

FIGURE 94A - B

1. Active Ingredients:

2.1-2.8% of 5-chloro-2-methyl-4-isothiazolin-3-one (CMIT)
0.6-1.0% of 2-methyl-4-isothiazolin-3-one (MIT)

CMIT   MIT

2. Content of active ingredients:

3%

3. Inert Matrix:

93-95% modified glycol
2-3% alkyl carboxylate

DNA SEQUENCING REACTION ADDITIVE

FIELD OF THE INVENTION

The present invention provides methods, compositions, mixtures and kits utilizing 5-Chloro-2-methyl-4-isothiazolin-3-one in sequencing reactions, and in particular, sequencing reactions where deoxynucleoside triphosphates comprising a 3'-O position capped by a disulfide-based 3'-terminator group are used. Such compounds provide new possibilities for future sequencing technologies, including but not limited to Sequencing by Synthesis (SBS), including automated SBS in a flow cell. The present invention also provides methods, compositions, mixtures and kits utilizing thiol-containing compounds or derivatives (alternatively mercaptol analogues) as cleave agents of the disulfide based linkers and 3'-disulfide capping group of nucleotides.

BACKGROUND OF THE INVENTION

DNA sequencing is one of the most important analytical methods in modern biotechnology. Detailed reviews on current sequencing technologies are provided in M. L. Metzker, Nature Reviews 2010, 11, 31 [1], and C. W. Fuller et al., Nature Biotechnology 2009, 27, 1013 [2].

A well-known sequencing method is the Sequencing-by-synthesis (SBS) method. According to this method, the nucleoside triphosphates are reversibly blocked by a 3'OH-protecting group, in particular esters and ethers. Examples for esters are alkanoic esters like acetyl, phosphates and carbonates. The nucleoside triphosphate usually comprises a label at the base.

A method of enzymatically synthesizing a polynucleotide of a predetermined sequence in a stepwise manner using reversibly 3'OH-blocked nucleoside triphosphates was described by Hiatt and Rose (U.S. Pat. No. 5,990,300) [3]. They disclose besides esters, ethers, carbonitriles, phosphates, phosphoramides, carbonates, carbamates, borates, sugars, phosphoramidates, phenylsulfenates, sulfates and sulfones also nitrates as cleavable 3'OH-protecting group. The deprotection may be carried out by chemical or enzymatic means. There are neither synthesis procedures nor deprotection conditions and enzymatic incorporation data disclosed for the nitrate group. The claimed deblocking solution preferably contains divalent cations like Co2+ and a biological buffer like Tris. 3'OH-blocked nucleoside triphosphates containing a label are not disclosed.

Buzby (US 2007-0117104) [4] discloses nucleoside triphosphates for SBS which are reversibly protected at the 3'-hydroxyl group and carry a label at the base. The label is connected via a cleavable linker such as a disulfide linker or a photocleavable linker. The linker consists of up to about 25 atoms. The 3'OH-protection group can be besides hydroxylamines, aldehydes, allylamines, alkenes, alkynes, alcohols, amines, aryls, esters, ethers, carbonitriles, phosphates, carbonates, carbamates, borates, sugars, phosphoramidates, phenylsulfanates, sulfates, sulfones and heterocycles also nitrates.

Improvements are needed in order to achieve longer read length and better accuracy in nucleic acid sequencing.

SUMMARY OF THE INVENTION

The present invention provides methods, compositions, mixtures and kits utilizing 5-Chloro-2-methyl-4-isothiazolin-3-one in sequencing reactions, and in particular, sequencing reactions where deoxynucleoside triphosphates comprising a 3'-O position capped by a disulfide-based 3'-terminator group are used. Such compounds provide new possibilities for future sequencing technologies, including but not limited to Sequencing by Synthesis (SBS), including automated SBS in a flow cell. The present invention provides methods, compositions, mixtures and kits utilizing deoxynucleoside triphosphates comprising a 3'-O position capped by a group comprising methylenedisulfide as a cleavable protecting group and a detectable label reversibly connected to the nucleobase of said deoxynucleoside. In one embodiment, the present invention contemplates a nucleotide analogue with a reversible protecting group comprising methylenedisulfide and a cleavable oxymethylenedisulfide linker between the label and nucleobase. The present invention also provides methods, compositions, mixtures and kits utilizing thiol derivatives (alternatively mercaptol analogues) as cleave agents of the disulfide based linkers and 3'-disulfide capping group of nucleotides pertinant to DNA sequencing technologies (and other technologies such as protein engineering) where the disulfide reduction or cleavage step is necessary. In one embodiment, the cleave agent is kitted as a solid powder add-on that the customer will add to the cleave pre-mix buffer according to sequencing workflow instructions. Moreover, the present invention provides embodiments where the thiol-containing compounds are scavenged with an oxidative wash step. However, a preferred scavenger is cystamine.

In one embodiment, the present invention contemplates mixing polymerase, a plurality of nucleotide analogues, and 5-Chloro-2-methyl-4-isothiazolin-3-one so as to create a mixture in solution. In one embodiment, said mixture in solution comprises one or more additional compounds. In one embodiment, said mixture in solution is used in an extension reaction, where polymerase incorporates nucleotides and/or nucleotide analogues into a hybridized primer.

In one embodiment, the present invention contemplates a method of incorporating nucleotides, comprising: a) providing i) a plurality of nucleic acid primers and template molecules, and ii) polymerase, a plurality of nucleotide analogues, and 5-Chloro-2-methyl-4-isothiazolin-3-one; b) hybridizing at least a portion of said primers to at least a portion of said template molecules so as to create hybridized primers; and c) exposing said hybridized primers to said polymerase and nucleotide analogues in the presence of said 5-Chloro-2-methyl-4-isothiazolin-3-one, under conditions such at least one nucleotide analogue is incorporated into at least a portion of said hybridized primers so as to create extended primers comprising an incorporated nucleotide analogue. In one embodiment, said 5-Chloro-2-methyl-4-isothiazolin-3-one is in solution with 2-Methyl-4-isothiazolin-3-one. While it is not intended that the method be limited to particular nucleotide analogues, preferred nucleotide analogues comprise a 3'-O position capped by a disulfide-based 3'-terminator group. It is not intended that the method be limited by the nature of the disulfide-based 3'-terminator group, however a preferred group comprises methylenedisulfide as a cleavable protecting group. In one embodiment, said incorporated nucleotide analogue further comprises a label attached through a cleavable disulfide linker to the base. In one embodiment, the method further comprises d) detecting said label of a first labeled nucleotide analogue. In one embodiment, the method further comprises e) cleaving said linker with a cleaving reagent so as to remove said label. In one embodiment, said cleaving reagent also removes said disulfide-based 3'-terminator group. A variety of cleaving reagents are contemplated; however, preferred cleaving reagents are thiol-containing compounds. In one embodiment, the thiol-containing compound is a vicinal dithiol-based compound. In one embodiment, the vicinal dithiol-based compound is di-mercaptopropanesulfonate.

The present invention contemplates in another embodiment a method for detecting labeled nucleotides in a nucleic acid sequence comprising the steps of a) providing i) nucleic acid template and primer capable of hybridizing to said template so as to form a primer/template hybridization complex, ii) polymerase, a plurality of nucleotide analogues, and 5-Chloro-2-methyl-4-isothiazolin-3-one, wherein said nucleotide analogues comprise a nucleobase and a sugar, said sugar comprising a cleavable protecting group on the 3'-O, wherein said cleavable protecting group comprises a disulfide-based 3'-terminator group, and wherein at least a portion of said nucleotide analogues further comprises a first detectable label attached via a cleavable disulfide-containing linker to the nucleobase; and iii) a cleave reagent comprising a thiol-containing compound; b) hybridizing at least a portion of said primers to at least a portion of said template molecules so as to create hybridized primers; and c) exposing said hybridized primers to said polymerase, nucleotide analogues and 5-Chloro-2-methyl-4-isothiazolin-3-one under conditions such that a first nucleotide analogue comprising a first detectable label is incorporated into at least a portion of said hybridized primers in a polymerase catalyzed primer extension reaction so as to create extended primers comprising an incorporated nucleotide analogue in a modified primer/template hybridization complex; d) detecting said first detectable label of said deoxynucleoside triphosphate in said modified primer/template hybridization complex; and e) introducing said cleave reagent under conditions so as to remove said cleavable protecting group and said detectable label from said modified primer/template hybridization complex. In one embodiment, the method further comprises incorporating a second nucleotide analogue comprising a second detectable label during a repeat of step c). In one embodiment, said thiol-containing compound is a vicinal dithiol-based compound. In one embodiment, the vicinal dithiol-based compound is di-mercaptopropanesulfonate. In one embodiment, the nucleobase of said second nucleotide analogue is different from the nucleobase of said first nucleotide analogue. In one embodiment, the nucleotide analogues comprises a mixture of at least 4 differently labeled nucleotide analogues representing analogs of A, G, C and T or U. In one embodiment, said detecting allows for the determination of the nucleobase of said incorporated first nucleotide analogue. In one embodiment, said disulfide-based 3'-terminator group comprises methylenedisulfide as a cleavable protecting group. In one embodiment, said conditions of step c) further comprises 2-Methyl-4-isothiazolin-3-one. In one embodiment, the method further comprises f) introducing a scavenger that interacts with the cleave reagent. In one embodiment, said scavenger is cystamine.

As noted, the present invention also contemplates compositions and mixtures. In one embodiment, the present invention contemplates a composition comprising primers hybridized to template in a solution, said solution comprising 5-Chloro-2-methyl-4-isothiazolin-3-one. In one embodiment, said hybridized primers and template are immobilized. In one embodiment, hybridized primers and template are in a flow cell. In one embodiment, said solution further comprises 2-Methyl-4-isothiazolin-3-one.

In one embodiment, the present invention contemplates kits comprising primers, nucleotide analogues, polymerase and 5-Chloro-2-methyl-4-isothiazolin-3-one. In one embodiment, each reagent is in a separate tube. In one embodiment, the kit comprises instructions to mix said polymerase, nucleotide analogues and 5-Chloro-2-methyl-4-isothiazolin-3-one into a solution. In one embodiment, said solution further comprises 2-Methyl-4-isothiazolin-3-one.

In yet another embodiment, the present invention contemplates a method of incorporating nucleotides, comprising: a) providing i) a plurality of nucleic acid primers and template molecules, and ii) an extend reagent comprising polymerase, a plurality of nucleotide analogues, and 5-Chloro-2-methyl-4-isothiazolin-3-one (e.g. in solution); b) hybridizing at least a portion of said primers to at least a portion of said template molecules so as to create hybridized primers; and c) exposing said hybridized primers to said extend reagent under conditions such that a first nucleotide analogue is incorporated into at least a portion of said hybridized primers so as to create extended primers comprising an incorporated nucleotide analogue. In one embodiment, said incorporated nucleotide analogue comprises a 3'-O position capped by a disulfide-based 3'-terminator group. In one embodiment, said disulfide-based 3'-terminator group comprises methylenedisulfide as a cleavable protecting group. In one embodiment, said incorporated nucleotide analogue further comprises a label attached through a cleavable disulfide linker to the base. In one embodiment, said extend reagent further comprises 2-Methyl-4-isothiazolin-3-one. In one embodiment, the method further comprises d) detecting said label of a first labeled nucleotide analogue. In one embodiment, the method further comprises e) cleaving said linker with a cleaving reagent so as to remove said label. In one embodiment, said cleaving reagent also removes said disulfide-based 3'-terminator group. In one embodiment, said cleaving reagent is a thiol-containing compound. In one embodiment, the thiol-containing compound is a vicinal dithiol-based compound. In one embodiment, the vicinal dithiol-based compound is di-mercaptopropanesulfonate.

In yet another embodiment, the present invention contemplates a method for detecting labeled nucleotides in a nucleic acid sequence comprising the steps of a) providing i) nucleic acid template and primer capable of hybridizing to said template so as to form a primer/template hybridization complex, ii) an extend reagent comprising polymerase, a plurality of nucleotide analogues, and 5-Chloro-2-methyl-4-isothiazolin-3-one, wherein said nucleotide analogues comprise a nucleobase and a sugar, said sugar comprising a cleavable protecting group on the 3'-O, wherein said cleavable protecting group comprises a disulfide-based 3'-terminator group, and wherein at least a portion of said nucleotide analogues further comprises a first detectable label attached via a cleavable disulfide-containing linker to the nucleobase; and iii) a cleave reagent comprising a thiol-containing compound; b) hybridizing at least a portion of said primers to at least a portion of said template molecules so as to create hybridized primers; and c) exposing said hybridized primers to said extend reagent under conditions such that a first nucleotide analogue comprising a first detectable label is incorporated into at least a portion of said hybridized primers in a polymerase catalyzed primer extension reaction so as to create extended primers comprising an incorporated nucleotide analogue in a modified primer/template hybridization complex; d) detecting said first detectable label of said deoxynucleoside triphosphate in said modified primer/template hybridization complex; and e) introducing said cleave reagent under conditions so as to remove said cleavable protecting group and said detectable label from said modified primer/template hybridization complex. In one embodiment, the method further comprises incorporating a second nucleotide analogue comprising a second detectable label during a repeat of step c). In one embodiment, the thiol-containing compound is a vicinal dithiol-based compound. In one embodiment, the vicinal dithiol-based compound is di-mercaptopropanesulfonate. In one embodiment, the nucleobase of said second nucleotide analogue is different from the nucleobase of said first nucleotide analogue. In one embodiment, said extend reagent comprises a mixture of at least 4 differently labeled nucleotide analogues representing analogs of A, G, C and T or U. In one embodiment, said detecting allows for the determination of the nucleobase of said incorporated first nucleotide analogue. In one embodiment, said disulfide-based 3'-terminator group comprises methylenedisulfide as a cleavable protecting group. In one embodiment, said extend reagent further comprises 2-Methyl-4-isothiazolin-3-one. In one embodiment, the method further comprises f) introducing a scavenger that interacts with the cleave reagent. In one embodiment, said scavenger is cystamine.

In terms of mixtures, the present invention in one embodiment contemplates deoxynucleoside triphosphates comprising a cleavable oxymethylenedisulfide linker between the label and nucleobase and a 3'-O position capped by a group comprising methylenedisulfide as a cleavable protecting group in mixtures with one or more additional sequencing reagents, including but not limited to buffers, polymerases, primers, template and the like. In terms of kits, the present invention contemplates in one embodiment a sequencing kit where sequencing reagents are provided together in separate containers (or in mixtures), including deoxynucleoside triphosphates comprising a 3'-O position capped by a group comprising methylenedisulfide as a cleavable protecting group, along with (optionally) instructions for using such reagents in sequencing. It is not intended that the present invention be limited by the number or nature of sequencing reagents in the kit. In one embodiment, the kit comprises one or more additional sequencing reagents, including but not limited to buffers, polymerases, primers and the like.

It is not intended that the present invention be limited to any particular polymerase. The present invention contemplates engineered (e.g. mutated) polymerases with enhanced incorporation of nucleotide derivatives. For example, Tabor, S. and Richardson, C. C. ((1995) Proc. Natl. Acad. Sci (USA) 92:6339 [6]) describe the replacement of phenylalanine 667 with tyrosine in T. aquaticus DNA polymerase and the effects this has on discrimination of dideoxynucleotides by the DNA polymerase. In one embodiment, the present invention contemplates polymerases that lack 3'-5' exonuclease activity (designated exo-). For example, an exo- variant of 9° N polymerase is described by Perler et al., 1998 U.S. Pat. No. 5,756,334 [7] and by Southworth et al., 1996 Proc. Natl Acad. Sci USA 93:5281 [8]. Another polymerase example is an A486Y variant of Pfu DNA polymerase (Evans et al., 2000. Nucl. Acids. Res. 28:1059 [9]). Another example is an A485T variant of Tsp JDF-3 DNA polymerase (Arezi et al., 2002. J. Mol. Biol. 322:719 [10]). WO 2005/024010 A1 relates to the modification of the motif A region and to the 9° N DNA polymerase, hereby incorporated by reference [11].

In terms of methods, the present invention contemplates both methods to synthesize deoxynucleoside triphosphates comprising a cleavable oxymethylenedisulfide linker between the label and nucleobase and a 3'-O position capped by a group comprising methylenedisulfide as a cleavable protecting group, as well as methods to utilize deoxynucleoside triphosphates comprising a 3'-O position capped by a group comprising methylenedisulfide as a cleavable protecting group.

In one embodiment, the present invention contemplates, a method for detecting labeled nucleotides in a DNA sequence comprising the steps of a) providing a nucleic acid template and primer capable of hybridizing to said template so as to form a primer/template hybridization complex (and in some embodiments, providing it where it has in fact hybridized together), and a cleave reagent comprising a thiol-containing compound; b) adding DNA polymerase and a first deoxynucleoside triphosphate to said primer and template so as to create a reaction mixture, said first deoxynucleoside triphosphate comprising a nucleobase and a sugar, said sugar comprising a cleavable protecting group on the 3'-O, wherein said cleavable protecting group comprises methylenedisulfide, wherein said deoxynucleoside triphosphate further comprises a first detectable label attached via a cleavable oxymethylenedisulfide-containing linker to the nucleobase; c) subjecting said reaction mixture to conditions which enable a DNA polymerase catalyzed primer extension reaction so as to create a modified primer/template hybridization complex, wherein said first deoxynucleoside triphosphate is incorporated (into the primer so as to extend the primer); d) detecting said first detectable label of said deoxynucleoside triphosphate in said modified primer/template hybridization complex (e.g. imaging); and e) introducing said cleave reagent under conditions so as to remove said cleavable protecting group (e.g. by cleaving it) and (optionally) said detectable label from said modified primer/template hybridization complex (e.g. by cleaving the linker). In one embodiment, the method further comprises adding a second deoxynucleoside triphosphate during a repeat of step b), wherein said second deoxynucleoside triphosphate comprises a second detectable label. In one embodiment, the thiol-containing compound is a vicinal dithiol-based compound. In one embodiment, the vicinal dithiol-based compound is di-mercaptopropanesulfonate. In one embodiment, said thiol-containing compound comprises first and second thiol groups. In one embodiment, said first and second thiol groups are separated by at least one hydrocarbon atom. In one embodiment, said first and second thiol groups are separated by a hydrocarbon spacer. In one embodiment, the hydrocarbon spacer comprises at least one functional group. In one embodiment, said at least one functional group is selected from the group consisting of a halogen, an amine, a phosphate, a phosphonate, a phosphoric acid, a carboxylic acid, a sulfoxide and a hydroxyl. In one embodiment, the nucleobase of said second deoxynucleoside triphosphate is different from the nucleobase of said first deoxynucleoside triphosphate. In one embodiment, more than 1 labeled nucleotide is used, e.g. a mixture of at least 4 differently labeled, 3'-O methylenedisulfide capped deoxynucleoside triphosphate compounds representing analogs of A, G, C and T or U are used in step b). In a preferred embodiment, said detecting allows for the determination of the nucleobase of said incorporated first deoxynucleoside triphosphate.

The present invention contemplates another embodiment of a method for detecting labeled nucleotides in a DNA sequence comprising the steps of a) providing a nucleic acid template and primer capable of hybridizing to said template so as to form a primer template hybridization complex (and in some embodiments, providing it where it is in fact hybridized together), a cleave reagent comprising a thiol-containing compound and a cleave scavenger reagent; b) adding DNA polymerase and a first deoxynucleoside triphosphate to said primer and template so as to create a reaction mixture, said first deoxynucleoside triphosphate comprising a nucleobase and a sugar, said sugar comprising a cleavable protecting group on the 3'-O, wherein said cleavable protecting group comprises methylenedisulfide, wherein said deoxynucleoside triphosphate further comprises a first detectable label attached via a cleavable oxymethylenedisulfide-containing linker to the nucleobase; c) subjecting said reaction mixture to conditions which enable a DNA polymerase catalyzed primer extension reaction so as to create a modified primer/template hybridization complex, wherein said first deoxynucleoside triphosphate is incorporated (e.g. into the primer so as to extend the primer); d) detecting said first detectable label of said deoxynucleoside triphosphate in said modified primer/template hybridization complex (e.g. by imaging); e) introducing said cleave reagent under conditions so as to remove said cleavable protecting group (by cleaving) and (optionally) said detectable label from said modified primer/template hybridization complex (by cleaving the linker); and f) introducing said cleave scavenger reagent (e.g. to scavenge any residual cleave reagent). In one embodiment, said thiol-containing compound comprises first and second thiol groups. In one embodiment, said first and second thiol groups are separated by at least one hydrocarbon atom. In one embodiment, said first and second thiol groups are separated by a hydrocarbon spacer. In one embodiment, the hydrocarbon spacer comprises at least one functional group. In one embodiment, said at least one functional group is selected from the group consisting of a halogen, an amine, a phosphate, a phosphonate, a phosphoric acid, a carboxylic acid, a sulfoxide and a hydoxyl. In one embodiment, said cleave reagent comprises di-mercaptopropanesulfonate. In one embodiment, said di-mercaptopropanesulfonate is in a buffer. In one embodiment, said buffer is CHES. In one embodiment, the pH of said cleave reagent is between 9.0 and 10.0. In a preferred embodiment, said pH of said cleave reagent is 9.5. In one embodiment, said cleave scavenger is an oxidative scavenger. In one embodiment, said oxidative scavenger is hydrogen peroxide. In one embodiment, said oxidative scavenger is ter-butyl peroxide. In one embodiment, said hydrogen peroxide is in a buffer. In one embodiment, said buffer is TRIS. In one embodiment, said TRIS buffer is at a pH of between 8.5 and 9.0. In a preferred embodiment, said TRIS buffer is at a pH of 8.8. In a preferred embodiment, said reaction mixture of step b) is in a flow cell. In one embodiment, said flow cell is positioned on a moving support. In one embodiment, said moving support is a rotary stage. In one embodiment, at least a portion of said flow cell is transparent. In one embodiment, said flow cell is incorporated within an instrument. In one embodiment, the steps of the method are repeated. In one embodiment, the method further comprises adding a second deoxynucleoside triphosphate during a repeat of step b), wherein said second deoxynucleoside triphosphate comprises a second detectable label attached via a second cleavable oxymethylenedisulfide linker, wherein said second detectible detectable label is different from said first detectible detectable label. In one embodiment, the thiol-containing compound is a vicinal dithiol-based compound. In one embodiment, the nucleobase of said second deoxynucleoside triphosphate is different from the nucleobase of said first deoxynucleoside triphosphate. In one embodiment, a mixture of at least 4 differently labeled, 3'-O methylenedisulfide capped deoxynucleoside triphosphate compounds representing analogs of A, G, C and T or U are used in step b). In a preferred embodiment, said detecting allows for the determination of the nucleobase of said incorporated first deoxynucleoside triphosphate.

The present invention, in yet another embodiment, contemplates a method for detecting labeled nucleotides in a DNA sequence comprising the steps of a) providing nucleic acid template and primer capable of hybridizing to said template so as to form a primer/template hybridization complex (and in some embodiments, providing it where it is in fact hybridized), and a flow cell, said flow cell in fluidic communication (e.g. via tubing) with a first reservoir comprising a cleave reagent comprising a thiol-containing compound and a second reservoir comprising an oxidative wash; b) adding DNA polymerase and a first deoxynucleoside triphosphate to said primer and template so as to create a reaction mixture in said flow cell, said first deoxynucleoside triphosphate comprising a nucleobase and a sugar, said sugar comprising a cleavable protecting group on the 3'-O, wherein said cleavable protecting group comprises methylenedisulfide, wherein said deoxynucleoside triphosphate further comprises a first detectable label attached via a cleavable oxymethylenedisulfide-containing linker to the nucleobase; c) subjecting said reaction mixture to conditions which enable a DNA polymerase catalyzed primer extension reaction so as to create a modified primer/template hybridization complex, wherein said first deoxynucleoside triphosphate is incorporated (e.g. into the primer so as to extend the primer); d) detecting said first detectable label of said deoxynucleoside triphosphate in said modified primer/template hybridization complex (e.g. by imaging); e) introducing said cleave reagent from said first reservoir into said flow cell under conditions so as to remove said cleavable protecting group (by cleaving) and (optionally) said detectable label from said modified primer/template hybridization complex (by cleaving the linker); and f) introducing said oxidative wash from said second reservoir into said flow cell (so as to remove or inactivate any residual cleave reagent). In one embodiment, said thiol-containing compound comprises first and second thiol groups. In one embodiment, said first and second thiol groups are separated by at least one hydrocarbon atom. In one embodiment, said first and second thiol groups are separated by a hydrocarbon spacer. In one embodiment, the hydrocarbon spacer comprises at least one functional group. In one embodiment, said at least one functional group is selected from the group consisting of a halogen, an amine, a phosphate, a phosphonate, a phosphoric acid, a carboxylic acid, a sulfoxide and a hydoxyl. In one embodiment, said cleave reagent comprises di-mercaptopropanesulfonate (e.g. in solution). In one embodiment, said di-mercaptopropanesulfonate is in a buffer. In one embodiment, said buffer is CHES. In one embodiment, the pH of said cleave reagent is between 9.0 and 10.0. In one embodiment, said pH of said cleave reagent is 9.5. In one embodiment, said oxidative wash comprises hydrogen peroxide. In one embodiment, said oxidative wash comprises ter-butyl peroxide. In one embodiment, said hydrogen peroxide is in a buffer. In one embodiment, said buffer is TRIS.

The present invention also contemplates kits. In one embodiment, the present invention contemplates a kit comprising one or more DNA sequencing reagents, instructions and a cleave reagent comprising a thiol-containing compound. In one embodiment, said thiol-containing compound comprises first and second thiol groups. In one embodiment, said first and second thiol groups are separated by at least one hydrocarbon atom. In one embodiment, said first and second thiol groups are separated by a hydrocarbon spacer. In one embodiment, the hydrocarbon spacer comprises at least one functional group. In one embodiment, said at least one functional group is selected from the group consisting of a halogen, an amine, a phosphate, a phosphonate, a phosphoric acid, a carboxylic acid, a sulfoxide and a hydoxyl. In one embodiment, the thiol-containing compound is selected from the group consisting 2,3-dimercaptopropanesulfonate, 2,3-dimercapto-1-propanol and 2,3-dimercaptopropanephosphonate (or salts thereof). In a preferred embodiment, said thiol-containing compound is di-mercaptopropanesulfonate. In one embodiment, wherein said di-mercaptopropanesulfonate is in a buffer. The thiol-containing compound can be in various forms. In one embodiment, said di-mercaptopropanesulfonate is in solid form (e.g. as a powder in a tube, vial or other container) in said kit. In one embodiment, the kit further comprises a buffer (e.g. in a tube, vial or other container). In one embodiment, said buffer is CHES. In one embodiment, the kit further comprises a cleave scavenger. In a preferred embodiment, said cleave scavenger is an oxidative scavenger. In one embodiment, said oxidative scavenger is hydrogen peroxide. In one embodiment, said oxidative scavenger is ter-butyl peroxide. In one embodiment, said one or more DNA sequencing reagents are selected from the group comprising polymerase, primer, template and nucleotides.

The present invention also contemplates compositions, including mixtures. In one embodiment, the present invention contemplates a composition comprising primers hybridized to template in solution, said solution comprising a thiol-containing compound. In one embodiment, said thiol-containing compound comprises first and second thiol groups. In one embodiment, said first and second thiol groups are separated by at least one hydrocarbon atom. In one embodiment, said first and second thiol groups are separated by a hydrocarbon spacer. In one embodiment, the hydrocarbon spacer comprises at least one functional group. In one embodiment, said at least one functional group is selected from the group consisting of a halogen, an amine, a phosphate, a phosphonate, a phosphoric acid, a carboxylic acid, a sulfoxide and a hydoxyl. In one embodiment, the thiol-containing compound is selected from the group consisting 2,3-dimercaptopropanesulfonate, 2,3-dimercapto-1-propanol and 2,3-dimercaptopropanephosphonate. In one embodiment, said hybridized primers and template are immobilized. In one embodiment, said hybridized primers and template are in a flow cell.

The present invention also contemplates flow cells containing solutions and mixtures. In one embodiment, the present invention contemplates a flow cell, comprising primers hybridized to template in solution, said solution comprising a thiol-containing compound and an oxidative scavenger. In one embodiment, said thiol-containing compound comprises first and second thiol groups. In one embodiment, said first and second thiol groups are separated by at least one hydrocarbon atom. In one embodiment, said first and second thiol groups are separated by a hydrocarbon spacer. In one embodiment, the hydrocarbon spacer comprises at least one functional group. In one embodiment, said at least one functional group is selected from the group consisting of a halogen, an amine, a phosphate, a phosphonate, a phosphoric acid, a carboxylic acid, a sulfoxide and a hydoxyl. In one embodiment, the thiol-containing compound is selected from the group consisting 2,3-dimercaptopropanesulfonate, 2,3-dimercapto-1-propanol and 2,3-dimercaptopropanephosphonate. In one embodiment, said hybridized primers and template are immobilized. In one embodiment, said oxidative scavenger is hydrogen peroxide. In one embodiment, said oxidative scavenger is ter-butyl peroxide.

In one embodiment, the invention relates to (a) nucleoside triphosphates with 3'-O capped by a group comprising methylenedisulfide (e.g. of the general formula —CH$_2$—SS—R) as cleavable protecting group; and (b) their labeled analogs, where labels are attached to the nucleobases via cleavable oxymethylenedisulfide linker (—OCH$_2$—SS—) (although the linker may contain additional groups). Such nucleotides can be used in nucleic acid sequencing by synthesis (SBS) technologies. In one embodiment, the invention relates to the synthesis of nucleotides 3'-O capped by a group comprising methylenedisulfide (e.g. —CH$_2$—SS—R) as cleavable protecting group, the deprotection conditions or enzymatic incorporation.

In one embodiment, the invention relates to a deoxynucleoside triphosphate comprising a cleavable oxymethylenedisulfide linker between the label and nucleobase and a 3'-O capped by a group comprising methylenedisulfide as a cleavable protecting group. In one embodiment, the nucleobase of said nucleoside is non-natural. In one embodiment, the non-natural nucleobase of said nucleoside is selected from the group comprising 7-deaza guanine, 7-deaza adenine, 2-amino,7-deaza adenine, and 2-amino adenine. In one embodiment, said group comprising methylenedisulfide is —CH$_2$—SS—R, wherein R is selected from the group comprising alkyl and substituted alkyl groups. In one embodiment, said detectable label is attached to said nucleobase via cleavable oxymethylenedisulfide linker (e.g. of the formula —OCH$_2$—SS—). In one embodiment, said detectable label is a fluorescent label. In one embodiment, R in the formula (—CH$_2$—S—S—R) could be alkyl or allyl.

In one embodiment, the invention relates to a deoxynucleoside triphosphate according to the following structure:

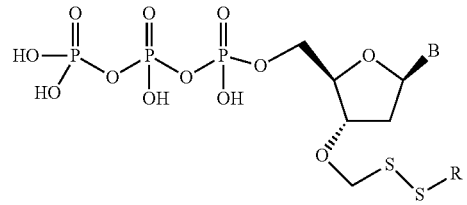

wherein B is a nucleobase and R is selected from the group comprising alkyl and substituted alkyl groups. In one embodiment, said nucleobase is a natural nucleobase (cytosine, guanine, adenine, thymine and uracil). In one embodiment, said nucleobase is a non-natural nucleobase selected from the group comprising 7-deaza guanine, 7-deaza adenine, 2-amino,7-deaza adenine, and 2-amino adenine. In the case of analogs, the detectable label may also include a linker section between the nucleobase and said detectable label.

In one embodiment, the invention relates to a labeled deoxynucleoside triphosphate according to the following structure:

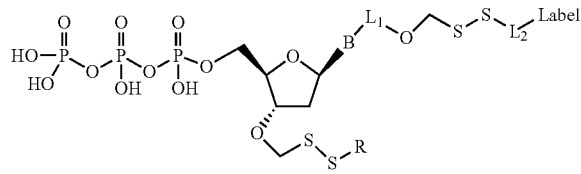

wherein B is a nucleobase, R is selected from the group comprising alkyl and substituted alkyl groups, and $L_1$ and $L_2$ are connecting groups. In one embodiment, said nucleobase is a natural nucleobase analog. In one embodiment, said nucleobase is a non-natural nucleobase analog selected from the group comprising 7-deaza guanine, 7-deaza adenine, 2-amino,7-deaza adenine, and 2-amino adenine. In the case of analogs, the detectable label may also include a linker section between the nucleobase and said detectable label. In one embodiment, $L_1$ and $L_2$ are independently selected from the group comprising —CO—, —CONH—, —NHCONH—, —O—, —S—, —ON, and —N=N—, alkyl, aryl, branched alkyl, branched aryl or combinations thereof. It is preferred that $L_2$ not be "—S—." In one embodiment, the present invention contemplates $L_1$ to be either an amine on the base or a hydroxyl on the base. In one embodiment, said label is selected from the group consisting of fluorophore dyes, energy transfer dyes, mass-tags, biotin, and haptenes. In one embodiment, said label is a detectable label.

In one embodiment, the invention relates to a labeled deoxynucleoside triphosphate according to the following structure:

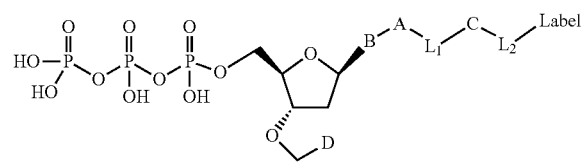

wherein D is selected from the group consisting of disulfide allyl, and disulfide substituted allyl groups; B is a nucleobase; A is an attachment group; C is a cleavable site core; $L_1$ and $L_2$ are connecting groups; and Label is a label (e.g. a detectable moiety).

In one embodiment, the invention relates to a labeled deoxynucleoside triphosphate according to the following structure:

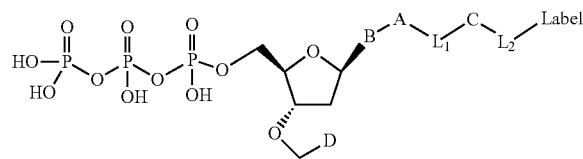

wherein D is selected from the group consisting of an azide, disulfide alkyl, disulfide substituted alkyl groups; B is a nucleobase; A is an attachment group; C is a cleavable site core; $L_1$ and $L_2$ are connecting groups; and Label is a label. In one embodiment, said nucleobase is a non-natural nucleobase analog selected from the group consisting of 7-deaza guanine, 7-deaza adenine, 2-amino,7-deaza adenine, and 2-amino adenine. In one embodiment, said attachment group A is chemical group selected from the group consisting of propargyl, hydroxymethyl, exocyclic amine, propargyl amine, and propargyl hydroxyl. In one embodiment, said cleavable site core is selected from the group consisting of:

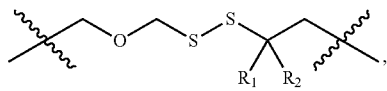

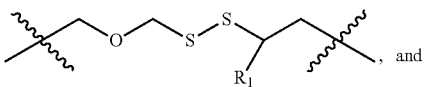, and

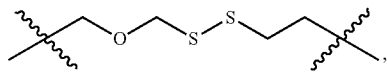, wherein $R_1$ and $R_2$ are independently selected alkyl groups. In one embodiment, $L_1$ is selected from the group consisting of —CONH(CH$_2$)$_x$—, —CO—O(CH$_2$)$_x$—, —CONH—(OCH$_2$CH$_2$O)$_x$—, —CO—O(CH$_2$CH$_2$O)—, and —CO(CH$_2$)$_x$—, wherein x is 0-10, but more preferably from 1-6. In one embodiment, $L_2$ is selected from the group consisting of —NH—, —(CH$_2$)$_x$—NH—, —C(Me)$_2$(CH$_2$)$_x$NH—, —CH(Me)CH$_2$)$_x$NH—, —C(Me)$_2$(CH$_2$)$_x$CO—, —CH(Me)CH$_2$)$_x$CO—, —(CH$_2$)$_x$OCONH(CH$_2$)$_y$O(CH$_2$)NH—, —(CH$_2$)$_x$CONH(CH$_2$CH$_2$O)$_y$(CH$_2$)$_2$NH—, and —CONH(CH$_2$)$_x$—, —CO(CH$_2$)$_x$—, wherein x, y, and z are each independently selected from is 0-10, but more preferably from 1-6. In one embodiment, said label is selected from the group consisting of fluorophore dyes, energy transfer dyes, mass-tags, biotin, and haptenes. In one embodiment, the compound has the structure:

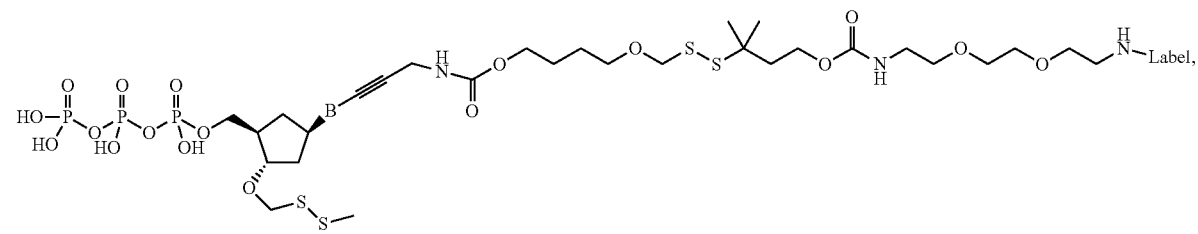

wherein said label is a dye. In one embodiment, the compound ha the structure:
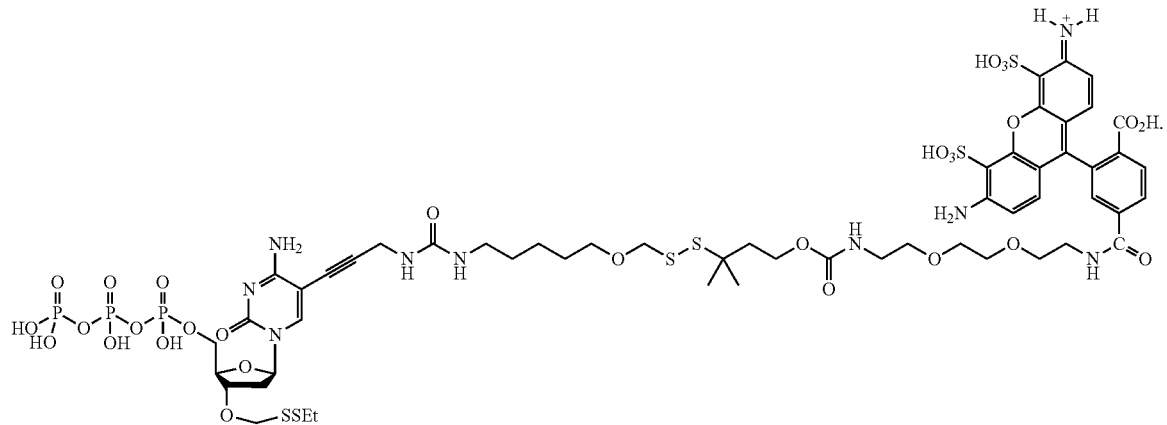
In one embodiment, the compound has the structure:
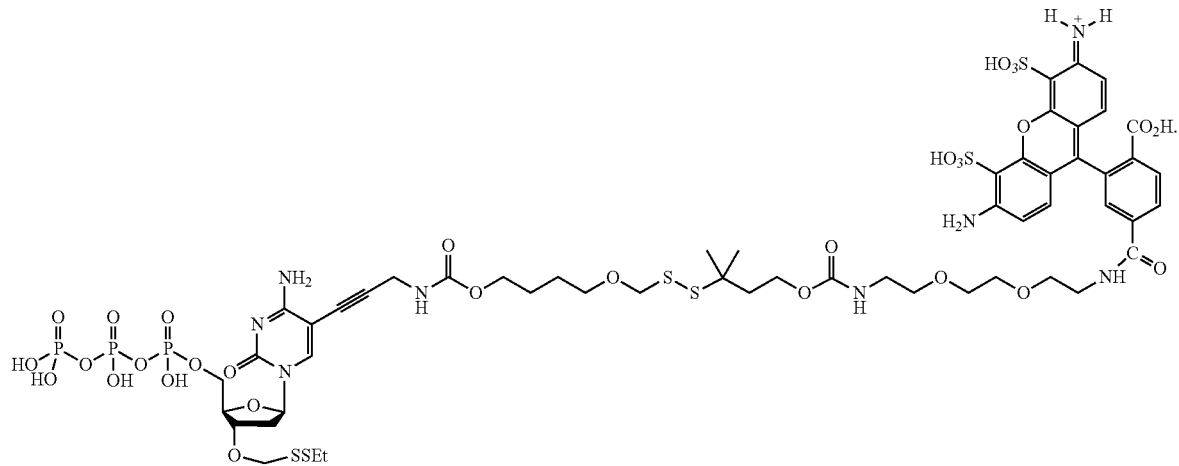
In one embodiment, the compound has the structure:
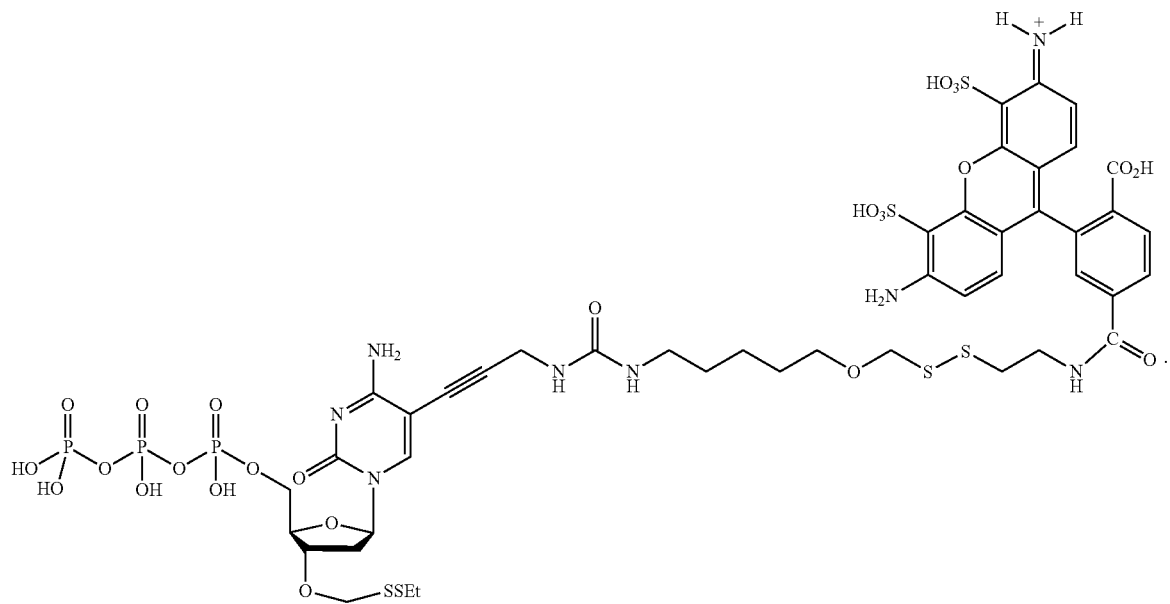

In one embodiment, the compound has the structure:
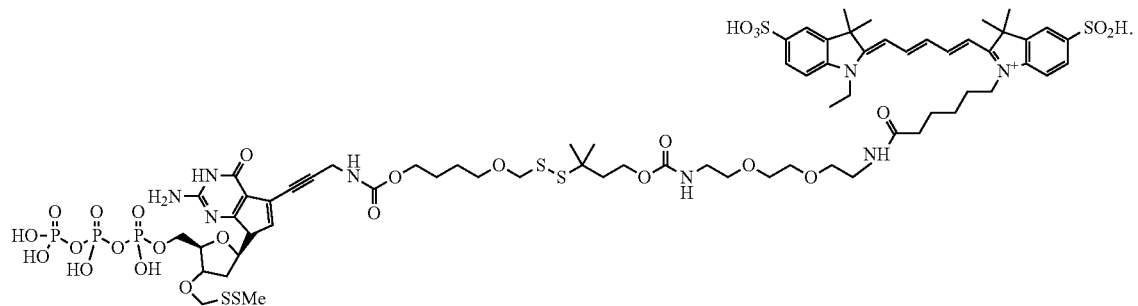
In one embodiment, the compound has the structure:
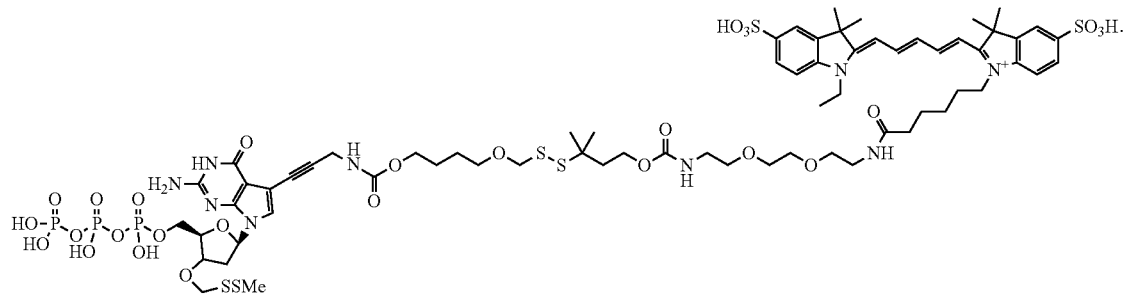
In one embodiment, the compound has the structure:
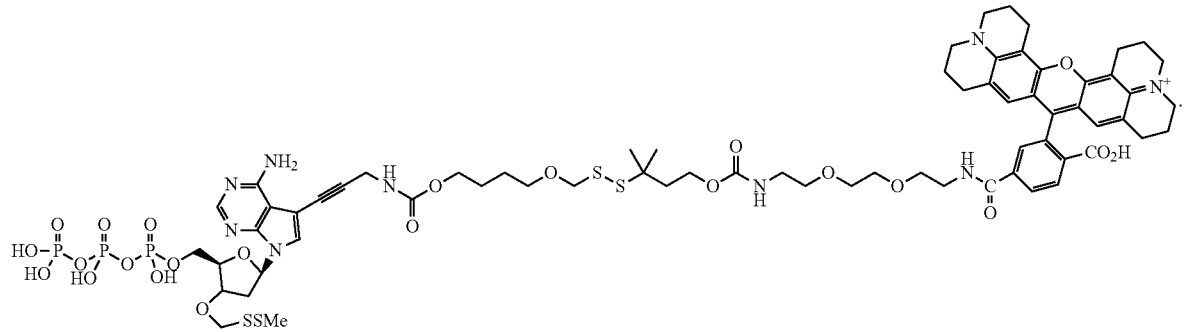
In one embodiment, the compound has the structure:
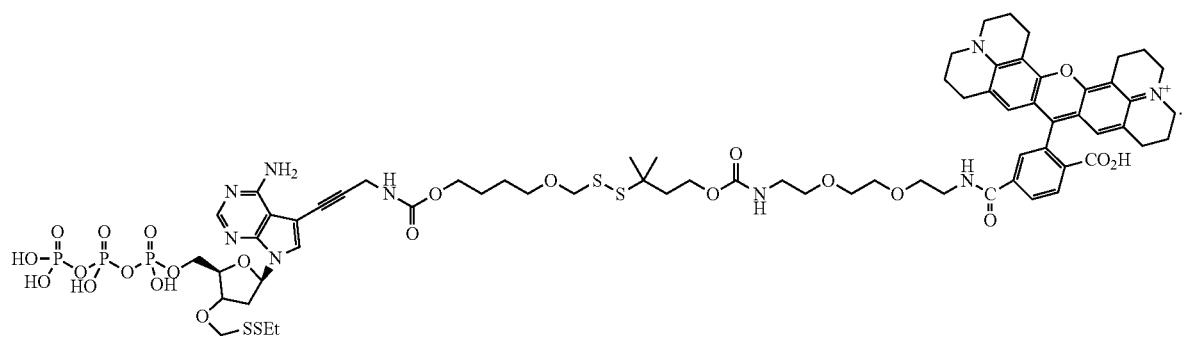

In one embodiment, the compound has the structure:
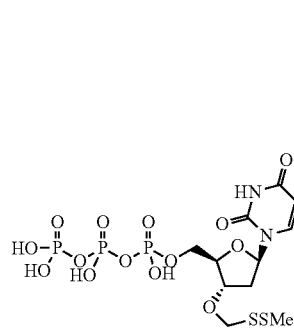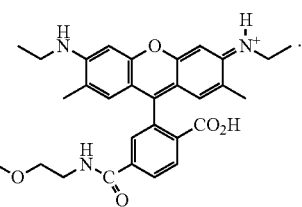
In one embodiment, the compound has the structure:
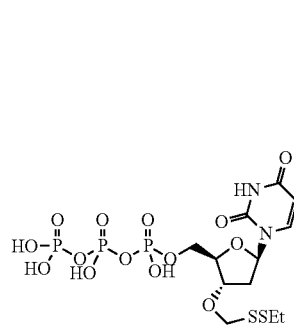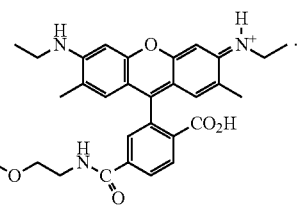
In one embodiment, the compound has the structure:
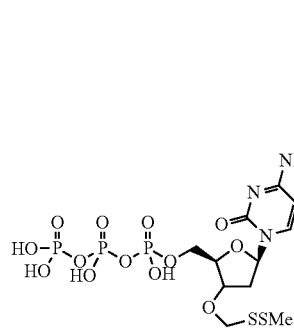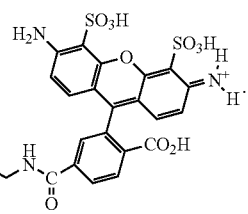
In one embodiment, the compound has the structure:
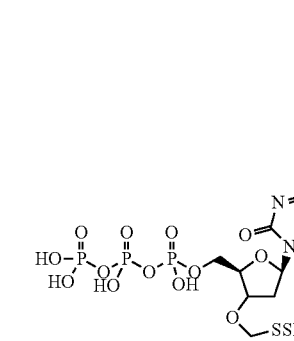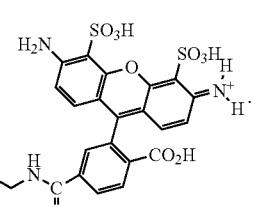

In one embodiment, the compound has the structure:
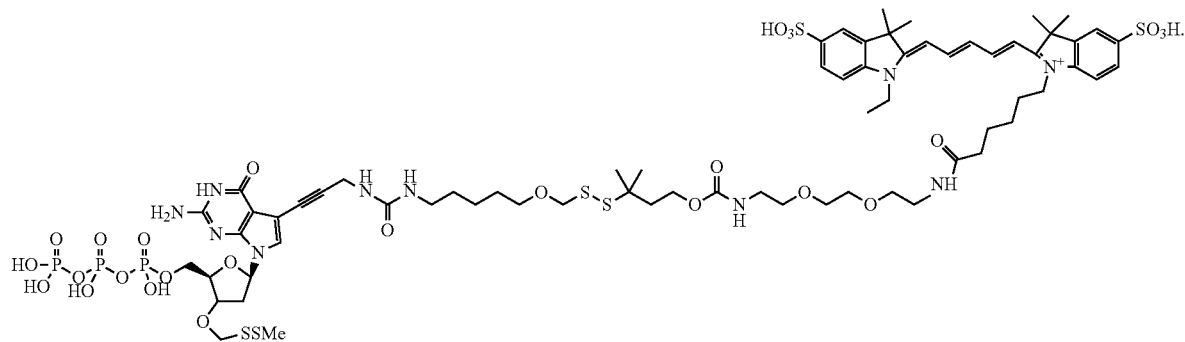
In one embodiment, the compound has the structure:
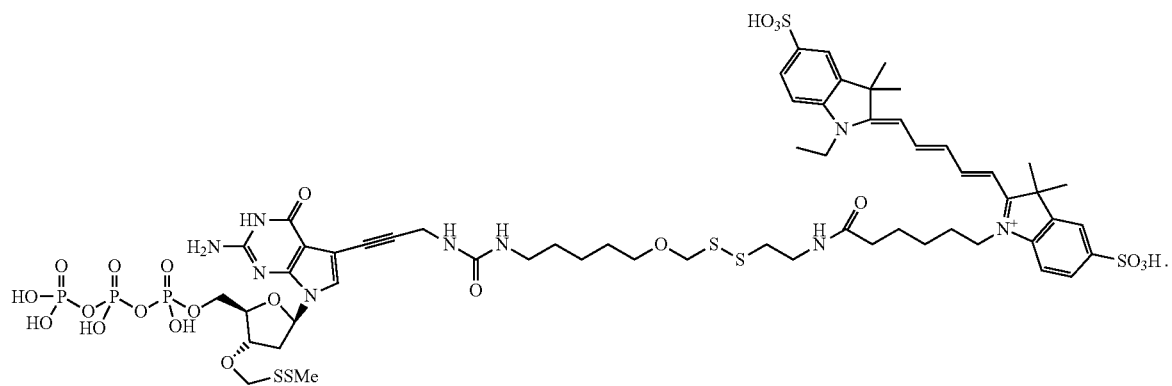
In one embodiment, the compound has the structure:
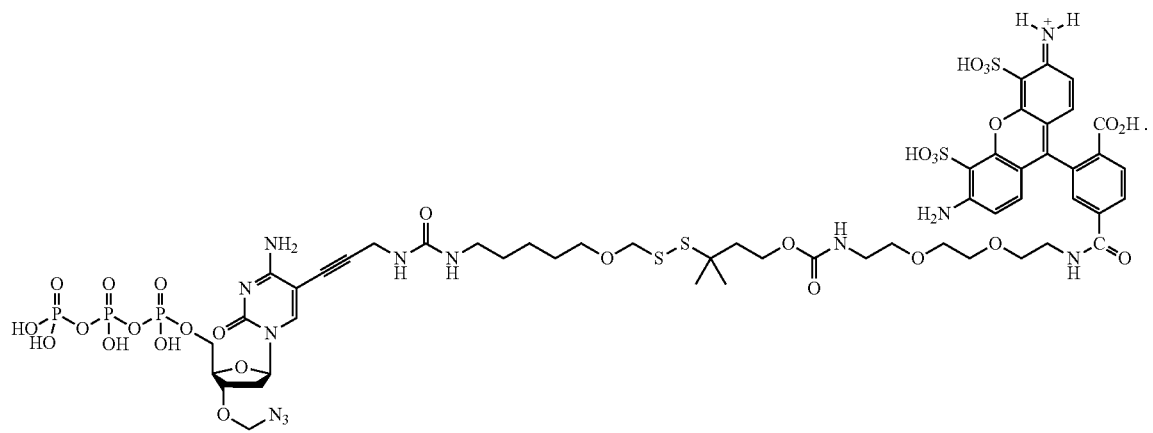

In one embodiment, the compound has the structure:

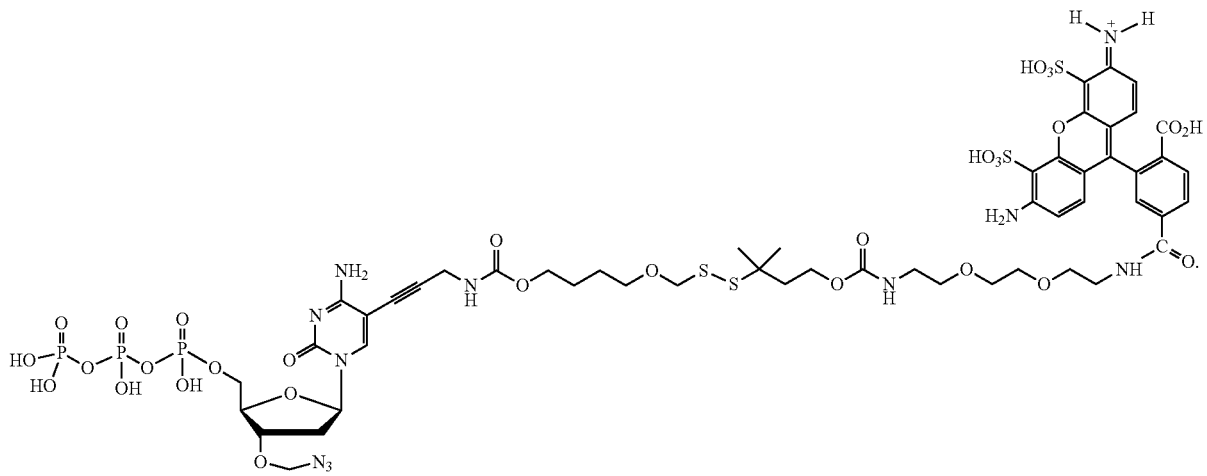

In one embodiment, the compound has the structure:

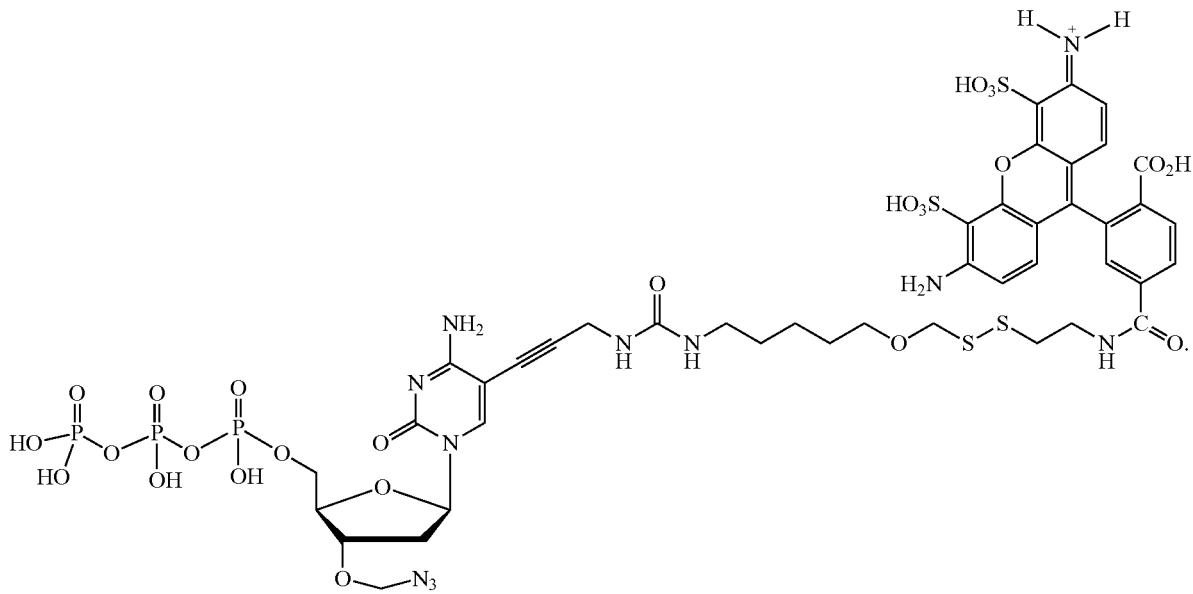

In one embodiment, the invention relates to a deoxynucleoside triphosphate according to the following structure:

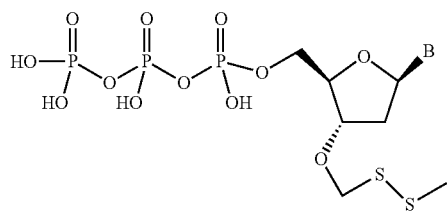

wherein B is a nucleobase.

In one embodiment, the invention relates to a kit comprising one or more sequencing reagents (e.g. a DNA polymerase) and at least one deoxynucleoside triphosphate comprising a cleavable oxymethylenedisulfide linker between the label and nucleobase, a 3'-O capped by a group comprising methylenedisulfide as a cleavable protecting group. In one embodiment, said nucleobase is a natural nucleobase analog. In one embodiment, the nucleobase of said nucleoside is non-natural. In one embodiment, the non-natural nucleobase of said nucleoside is selected from the group comprising 7-deaza guanine, 7-deaza adenine, 2-amino,7-deaza adenine, and 2-amino adenine.

The present invention also contemplates mixtures, i.e. at least one deoxynucleoside triphosphate comprising a cleavable oxymethylenedisulfide linker between the label and nucleobase, a 3'-O capped by a group comprising methylenedisulfide as a cleavable protecting group in a mixture with one or more additional reagents (whether dry or in solution). In one embodiment, the invention relates to a reaction mixture comprising a nucleic acid template with a primer hybridized to said template, a DNA polymerase, and at least one deoxynucleoside triphosphate comprising a nucleobase, a label and a sugar, a cleavable oxymethylenedisulfide linker between the label and nucleobase, said sugar comprising a 3'-O capped by a group comprising methylenedisulfide as a cleavable protecting group, wherein said nucleoside further comprises a detectable label covalently bound to the nucleobase of said nucleoside.

In one embodiment, the invention relates to a method of performing a DNA synthesis reaction comprising the steps of a) providing a reaction mixture comprising a nucleic acid template with a primer hybridized to said template, a DNA polymerase, at least one deoxynucleoside triphosphate comprising a cleavable oxymethylenedisulfide linker between the label and nucleobase, with a 3'-O capped by a group comprising methylenedisulfide as a cleavable protecting group, and b) subjecting said reaction mixture to conditions which enable a DNA polymerase catalyzed primer extension reaction. This permits incorporation of at least one deoxynucleoside triphosphate (comprising a cleavable oxymethylenedisulfide linker between the label and nucleobase, with a 3'-O capped by a group comprising methylenedisulfide as a cleavable protecting group) into the bound primer. In one embodiment, said DNA polymerase catalyzed primer extension reaction is part of a sequencing reaction (e.g. SBS). In one embodiment, said detectable label is removed from said nucleobase by exposure to a reducing agent. It is not intended that the invention is limited to one type of reducing agent. Any suitable reducing agent capable of reducing disulfide bonds can be used to practice the present invention. In one embodiment the reducing agent is phosphine [12], for example, triphenylphosphine, tributylphosphine, trihydroxymethyl phosphine, trihydroxypropyl phosphine, tris carboethoxy-phosphine (TCEP) [13, 14]. In one embodiment, said reducing agent is TCEP. In one embodiment, said detectable label and 3'-OCH2-SS—R group are removed from said nucleobase by exposure to compounds carrying a thiol group [15] so as to perform cleavage of dithio-based linkers and terminating (protecting) groups, such thiol-containing compounds including (but not limited to) cysteine, cysteamine, dithio-succinic acid, dithiothreitol, 2,3-Dimercapto-1-propanesulfonic acid sodium salt, dithiobutylamine [16], meso-2,5-dimercapto-N,N,N',N'-tetramethyladipamide, 2-mercapto-ethane sulfonate, and N,N'-dimethyl, N,N'-bis(mercaptoacetyl)-hydrazine [17]. Reactions can be further catalyzed by inclusion of selenols [18]. In addition borohydrides, such as sodium borohydrides can also be used for this purpose [19] (as well as ascorbic acid [20]. In addition, enzymatic methods for cleavage of disulfide bonds are also known such as disulfide and thio-reductase and can be used with compounds of the present invention [21].

In one embodiment, the invention relates to a method for analyzing a DNA sequence comprising the steps of a) providing a reaction mixture comprising nucleic acid template with a primer hybridized to said template forming a primer/template hybridization complex, b) adding DNA polymerase, and a first deoxynucleoside triphosphate comprising a nucleobase, a cleavable oxymethylenedisulfide linker between the label and nucleobase, with a 3'-O capped by a group comprising methylenedisulfide as cleavable protecting group, c) subjecting said reaction mixture to conditions which enable a DNA polymerase catalyzed primer extension reaction so as to create a modified primer/template hybridization complex, and d) detecting said first detectable label of said deoxynucleoside triphosphate in said modified primer/template hybridization complex. In one embodiment, the detecting allows one to determine which type of analogue (A, T, G, C or U) has been incorporated. In one embodiment, the method further comprises the steps of e) removing said cleavable protecting group and optionally said detectable label from said modified primer/template hybridization complex, and f) repeating steps b) to e) at least once (and typically repeating these steps many times, e.g. 10-200 times). In one embodiment, the cleavable oxymethylenedisulfide-containing linker is hydrophobic and has a log P value of greater than 0. In one embodiment, the cleavable oxymethylenedisulfide-containing linker is hydrophobic and has a log P value of greater than 0.1. In one embodiment, the cleavable oxymethylenedisulfide-containing linker is hydrophobic and has a log P value of greater than 1.0. In one embodiment, the method further comprises adding a second deoxynucleoside triphosphate is added during repeat of step b), wherein said second deoxynucleoside triphosphate comprises a second detectable label, wherein said second detectible label is different from said first detectible label. In one embodiment, the nucleobase of said second deoxynucleoside triphosphate is different from the nucleobase of said first deoxynucleoside triphosphate In one embodiment, a mixture of at least 4 differently labeled, 3'-O methylenedisulfide capped deoxynucleoside triphosphate compounds representing analogs of A, G, C and T or U are used in step b). In one embodiment, said mixture of at least 4 differently labeled, 3'-O methylenedisulfide capped deoxynucleoside triphosphate compounds with the structures:

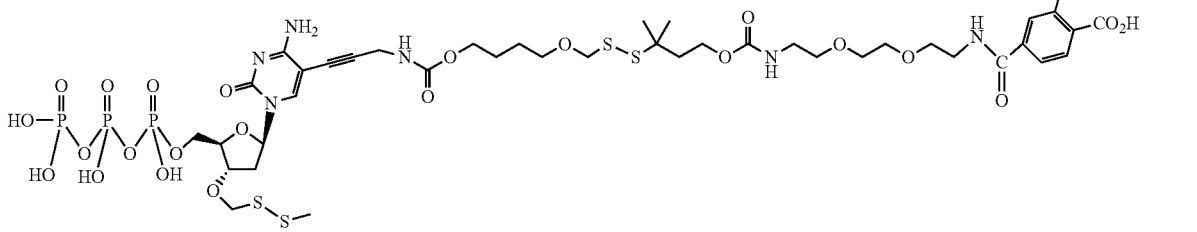

-continued
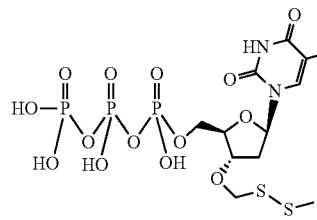
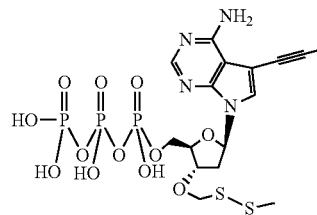
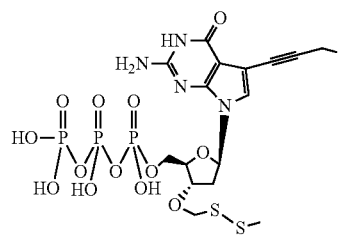
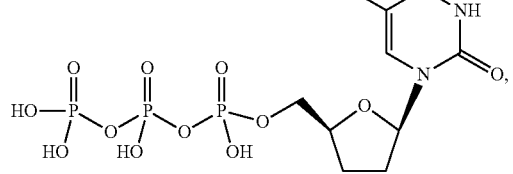
are used in step b). In one embodiment, said mixture further comprises unlabeled 3'-O methylenedisulfide capped deoxynucleoside triphosphate compounds such as those structures:
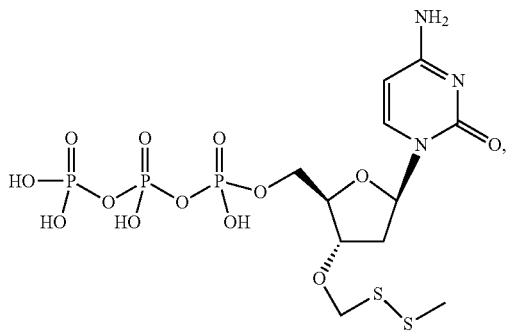
-continued
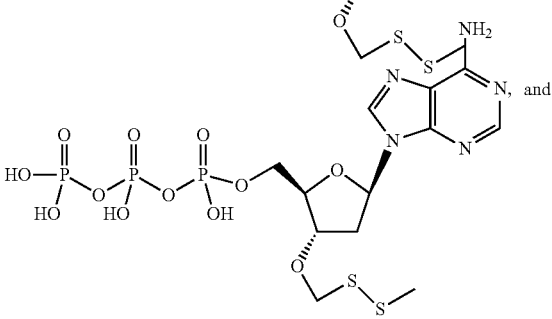

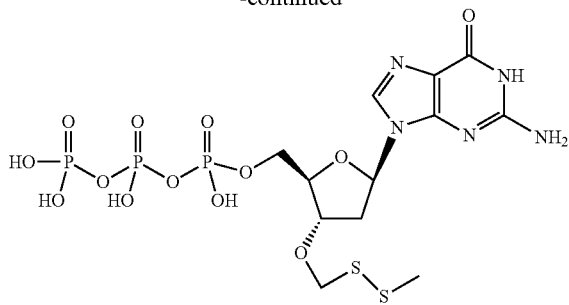

also used in step b). In one embodiment, step e) is performed by exposing said modified primer/template hybridization complex to a reducing agent. In one embodiment, said reducing agent is TCEP. In one embodiment, said detectable label is removed from said nucleobase by exposure to compounds carrying a thiol group so as to perform cleavage of dithio-based linkers and terminating (protecting) groups, such thiol-containing compounds including (but not limited to) cysteine, cysteamine, dithio-succinic acid, dithiothreitol, 2,3-Dimercapto-1-propanesulfonic acid sodium salt, dithiobutylamine, meso-2,5-dimercapto-N,N,N',N'-tetramethyl-adipamide, 2-mercapto-ethane sulfonate, and N,N'-dimethyl, N,N'-bis(mercaptoacetyl)-hydrazine.

It is not intended that the present invention be limited to a particular sequencing platform. However, a preferred instrument is QIAGEN's GeneReader DNA sequencing system (GR). In one embodiment, a DNA sequence is determined by a method of sequencing by synthesis (SBS). In one embodiment, each cycle of sequencing consists of eight steps: extension 1, extension 2, wash 1, addition imaging solution, imaging, wash 2, cleave, and wash 3. Data collected during imaging cycles is processed by analysis software yielding error rates, throughput values, and applied phasing correction values. In another embodiment, an oxidative wash (Wash 11) is used after the cleave step (see FIG. 93A-C).

It is contemplated that the same or similar method could improve the performance of other SBS platforms in general (i.e. any sequencing-by-synthesis methods that operate under similar conditions), as well as specific SBS platforms, such as HiSeq and miSeq platforms from Illumina; Roche 454; the Ion Torrent PGM and Proton platforms; and the PacificBio platform.

It is not intended that the present invention be limited to only one type of sequencing. In one embodiment, said deoxynucleoside triphosphate (comprising a nucleobase, a label and a sugar, a cleavable oxymethylenedisulfide linker between the label and nucleobase, said sugar comprising a 3'-O capped by a group comprising methylenedisulfide as cleavable protecting group) may be used in pyrosequencing.

In one embodiment, the invention relates to a deoxynucleoside triphosphate comprising a nucleobase and a sugar, said nucleobase comprising a detectable label attached via a cleavable oxymethylenedisulfide linker, said sugar comprising a 3'-O capped by a group comprising a methylenedisulfide group as a cleavable protecting group. In one embodiment, said nucleoside is in a mixture with a polymerase (or some other sequencing reagent). In one embodiment, the nucleobase of said nucleoside is non-natural. In one embodiment, the non-natural nucleobase of said nucleoside is selected from the group comprising 7-deaza guanine, 7-deaza adenine, 2-amino,7-deaza adenine, and 2-amino adenine. In one embodiment, said group comprising a methylenedisulfide group is of the formula —$CH_2$—SS—R, wherein R is selected from the group comprising alkyl and substituted alkyl groups. In one embodiment, said mixture further comprises a primer. In one embodiment, said primer is hybridized to nucleic acid template. In one embodiment, said detectable label is a fluorescent label. In one embodiment, said nucleic acid template is immobilized (e.g. in a well, channel or other structure, or alternatively on a bead).

In one embodiment, the invention relates to a method of preparing a 3'-O-(methylthiomethyl)-5'-O-(tert-butyldimethylsilyl)-2'-deoxynucleoside, comprising: a) providing a 5'-O-(tert-butyldimethylsilyl)-2'-deoxynucleoside, wherein said 5'-O-(tert-butyldimethylsilyl)-2'-deoxynucleoside comprises a nucleobase and a sugar, and ii) a methylthiomethyl donor; and b) treating said 5'-O-(tert-butyldimethylsilyl)-2'-deoxynucleoside under conditions so as to create a 3'-O-(methylthiomethyl)-5'-O-(tert-butyldimethylsilyl)-2'-deoxynucleoside. In one embodiment, said methylthiomethyl donor is DMSO. In one embodiment, said conditions comprise acidic conditions. In one embodiment, said 5'-O-(tert-butyldimethylsilyl)-2'-deoxynucleoside comprises a protecting group on the nucleobase of said nucleoside. In one embodiment, said 3'-O-(methylthiomethyl)-5'-O-(tert-butyldimethylsilyl)-2'-deoxynucleoside is purified with column chromatography.

In one embodiment, the invention relates to a method of preparing a 3'-O—(R-substituted-dithiomethyl)-5'-O-(tert-butyldimethylsilyl)-2'-deoxynucleoside, comprising: a) providing i) a 3'-O-(methylthiomethyl)-5'-O-(tert-butyldimethylsilyl)-2'-deoxynucleoside, and ii) R—SH, wherein R comprises alkyl or substituted alkyl; and b) treating said 3'-O-(methylthiomethyl)-5'-O-(tert-butyldimethylsilyl)-2'-deoxynucleoside under conditions so as to create a 3'-O—(R-substituted-dithiomethyl)-5'-O-(tert-butyldimethylsilyl)-2'-deoxynucleoside. In one embodiment, said R—SH is ethanethiol. In one embodiment, said conditions comprise basic conditions.

In one embodiment, the invention relates to a method of preparing a 3'-O—(R-substituted-dithiomethyl)-2'-deoxynucleoside, comprising: a) providing a 3'-O—(R-substituted-dithiomethyl)-5'-O-(tert-butyldimethylsilyl)-2'-deoxynucleoside; and b) treating said 3'-O—(R-substituted-dithiomethyl)-5'-O-(tert-butyldimethylsilyl)-2'-deoxynucleoside under conditions so as to create a 3'-O—(R-substituted-dithiomethyl)-2'-deoxynucleoside. In one embodiment, said conditions comprise exposing said 3'-O—(R-substituted-dithiomethyl)-2'-deoxynucleoside to $NH_4F$.

In one embodiment, the invention relates to a method of preparing a triphosphate of 3'-O—(R-substituted-dithiomethyl)-2'-deoxynucleoside, comprising: a) providing a 3'-O—(R-substituted-dithiomethyl)-2'-deoxynucleoside; and b) treating said 3'-O—(R-substituted-dithiomethyl)-2'-deoxynucleoside under conditions so as to create a triphosphate of 3'-O—(R-substituted-dithiomethyl)-2'-deoxynucleoside. In one embodiment, said conditions comprises exposing said 3'-O—(R-substituted-dithiomethyl)-2'-deoxynucleoside to $(MeO)_3PO$ with $POCl_3$ and $Bu_3N$. In one embodiment, said method further comprises step c) removal of said nucleobase protecting group. In one embodiment, said protecting group comprises a N-trifluoroacetyl-aminopropargyl protecting group. In one embodiment, said N-trifluoroacetyl-aminopropargyl protecting group is removed by solvolysis to produce a 5'-O-(triphosphate)-3'-O—(R-substituted-dithiomethyl)-5-(aminopropargyl)-2'-deoxynucleoside.

In one embodiment, the invention relates to a compound wherein the structure is:

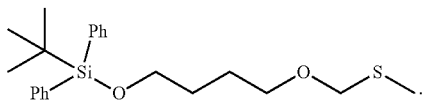 [SMILES: CSCOCCCCO[Si](c1ccccc1)(c1ccccc1)C(C)(C)C]

In one embodiment, the invention relates to a compound wherein the structure is:

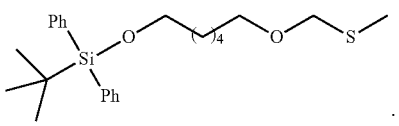

In one embodiment, the invention relates to a compound wherein the structure is:

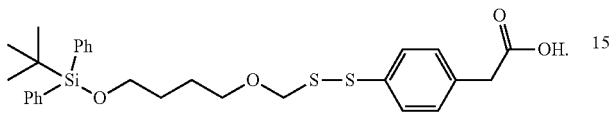

In one embodiment, the invention relates to a compound wherein the structure is:

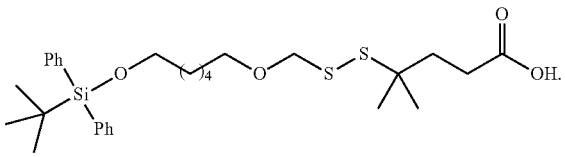

In one embodiment, the invention relates to a compound wherein the structure is:

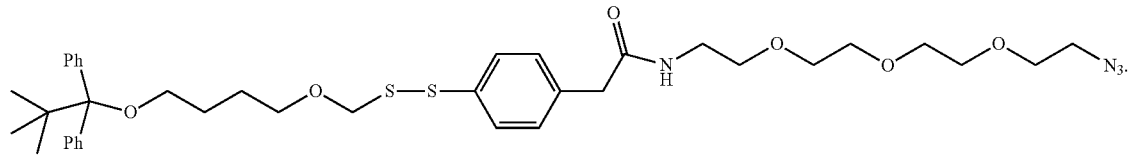 [SMILES: CC(C)(C)C(OCCCCOCSSc1ccc(CC(=O)NCCOCCOCCOCCN=[N+]=[N-])cc1)(c1ccccc1)c1ccccc1]

In one embodiment, the invention relates to a compound wherein the structure is:

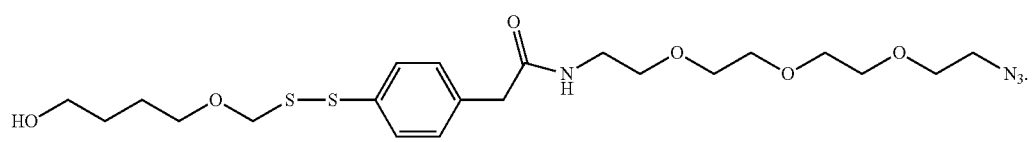 [SMILES: [N-]=[N+]=NCCOCCOCCOCCNC(=O)Cc1ccc(SSCOCCCCO)cc1]

In one embodiment, the invention relates to a compound wherein the structure is:

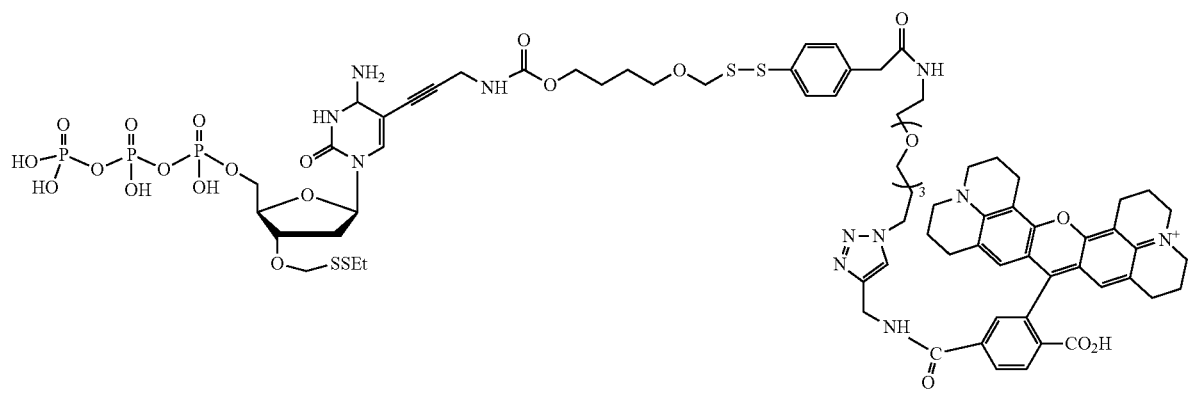

In one embodiment, the invention relates to a compound wherein the structure is:

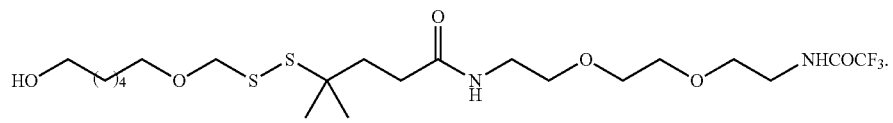
In one embodiment, the invention relates to a compound wherein the structure is:
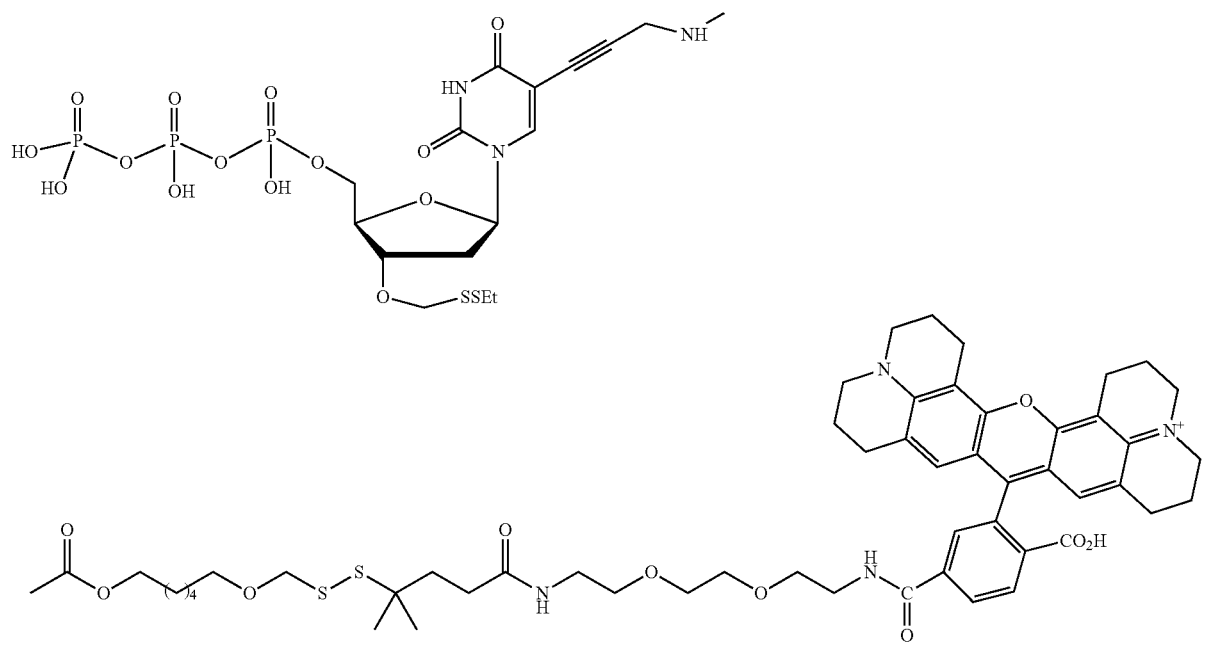
In one embodiment, the invention relates to a compound wherein the structure is:
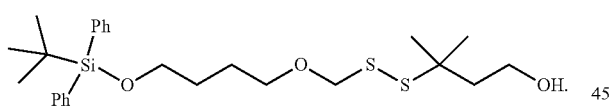
in one embodiment, the invention relates to a compound wherein the structure is:
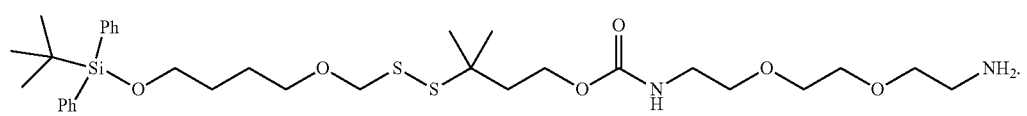 [SMILES: CC(C)(CCOC(=O)NCCOCCOCCN)SSCOCCCCO[Si](c1ccccc1)(c1ccccc1)C(C)(C)C]
In one embodiment, the invention relates to a compound wherein the structure is:
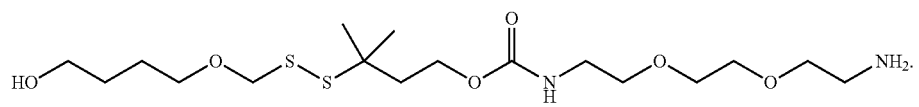 [SMILES: CC(C)(CCOC(=O)NCCOCCOCCN)SSCOCCCCO]

In one embodiment, the invention relates to a compound wherein the structure is:

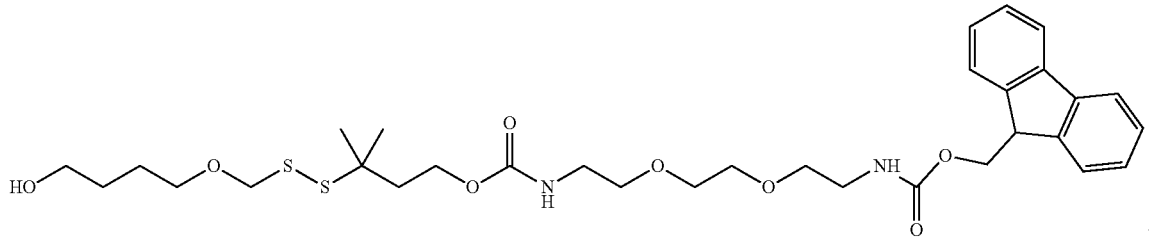 [SMILES: CC(C)(CCOC(=O)NCCOCCOCCNC(=O)OCC1c2ccccc2-c2ccccc21)SSCOCCCCO]

In one embodiment, the invention relates to a compound wherein the structure is:

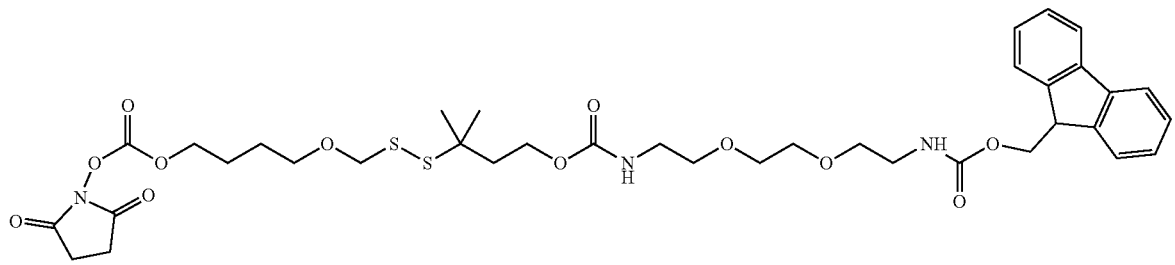 [SMILES: CC(C)(CCOC(=O)NCCOCCOCCNC(=O)OCC1c2ccccc2-c2ccccc21)SSCOCCCCOC(=O)ON1C(=O)CCC1=O]

In one embodiment, the invention relates to a compound wherein the structure is:

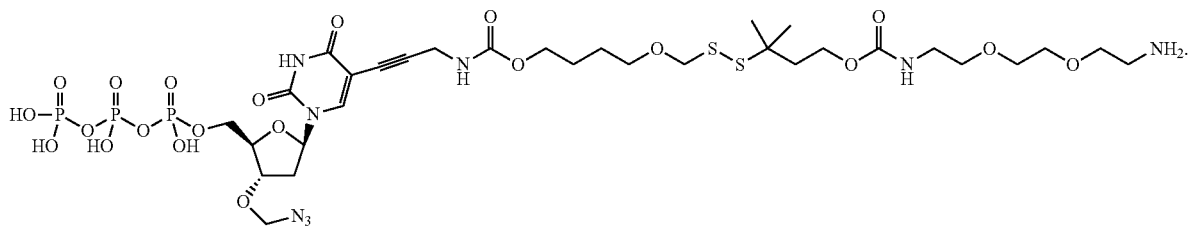 [SMILES: CC(C)(CCOC(=O)NCCOCCOCCN)SSCOCCCCOC(=O)NCC#Cc1cn([C@H]2C[C@H](OCN=[N+]=[N-])[C@@H](COP(=O)(O)OP(=O)(O)OP(=O)(O)O)O2)c(=O)[nH]c1=O]

In one embodiment, the invention relates to a labeled deoxynucleoside triphosphate according to the following structure:

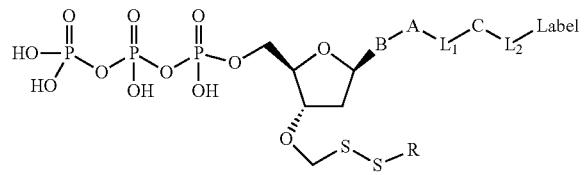

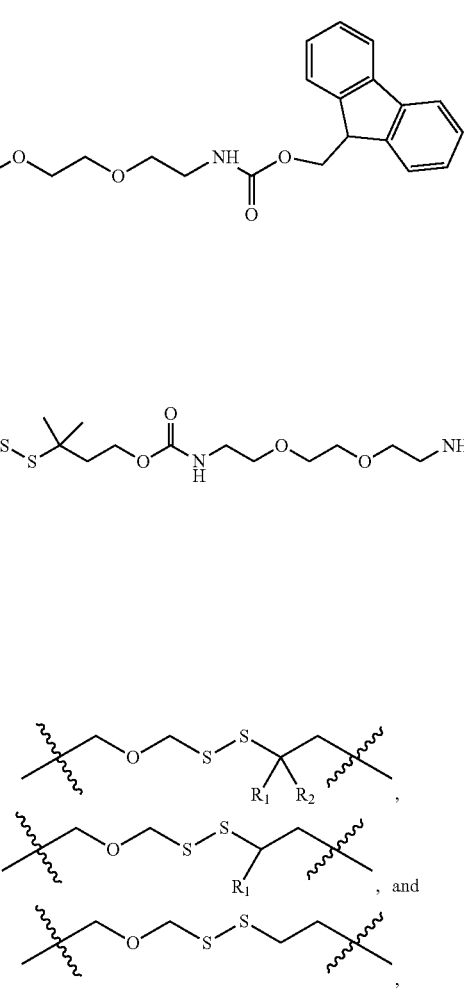

wherein R is selected from the group consisting of alkyl, substituted alkyl groups, allyl, substituted allyl: B is a nucleobase; A is an attachment group; C is a cleavable site core; $L_1$ and $L_2$ are connecting groups; and Label is a label. In one embodiment, said nucleobase is a non-natural nucleobase analog selected from the group consisting of 7-deaza guanine, 7-deaza adenine, 2-amino,7-deaza adenine, and 2-amino adenine. In one embodiment, said attachment group A is chemical group selected from the group consisting of propargyl, hydroxymethyl, exocyclic amine, propargyl amine, and propargyl hydroxyl. In one embodiment, said cleavable site core selected from the group consisting of:

wherein $R_1$ and $R_2$ are independently selected alkyl groups. In one embodiment, wherein $L_1$ is selected from the group consisting of —CONH(CH$_2$)$_x$—, —COO(CH$_2$)$_x$—, —CO(CH$_2$)$_x$—, wherein x is 0-10, but more preferably from 1-6. In one embodiment, wherein $L_2$ is selected from the group consisting of —NH—, —(CH$_2$)$_x$OCONH(CH$_2$)$_y$, O(CH$_2$)$_2$NH—, —(CH$_2$)$_x$OCONH(CH$_2$)$_y$O(CH$_2$)$_y$, O(CH$_2$)$_2$NH—, —CONH(CH$_2$)$_x$—, —CO(CH$_2$)$_x$—, wherein x, y, and z are each independently selected from is 0-10, but more preferably from 1-6. In one embodiment, said label is selected from the group consisting of fluorophore dyes, energy transfer dyes, mass-tags, biotin, and haptenes. In one embodiment, the compound has the structure:

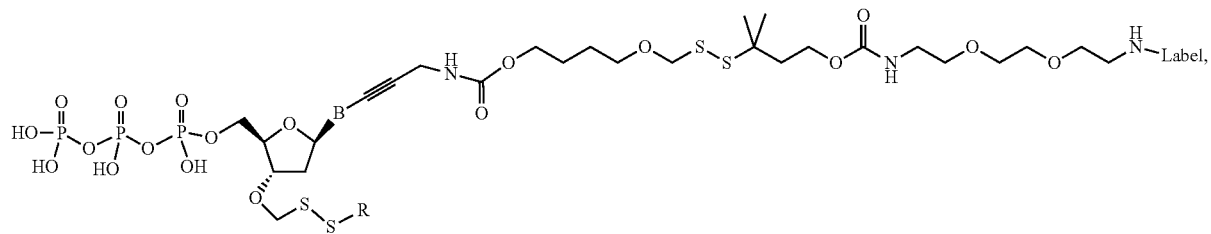
wherein said label is a dye and wherein R is selected from the group consisting of alkyl, substituted alkyl groups, allyl, substituted allyl. In one embodiment, the compound has the structure:
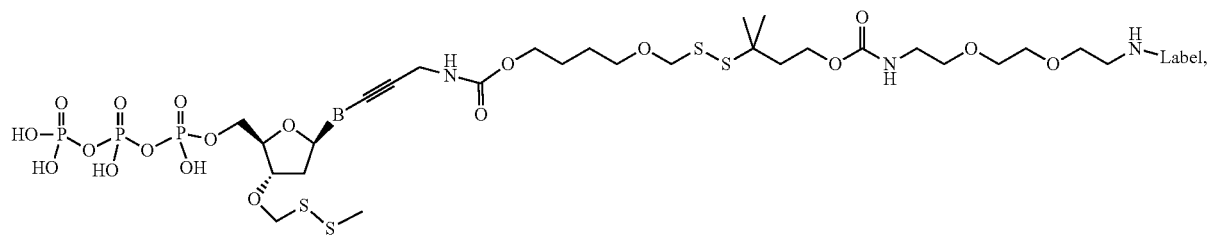
wherein said label is a dye.
In one embodiment, the compound has the structure:
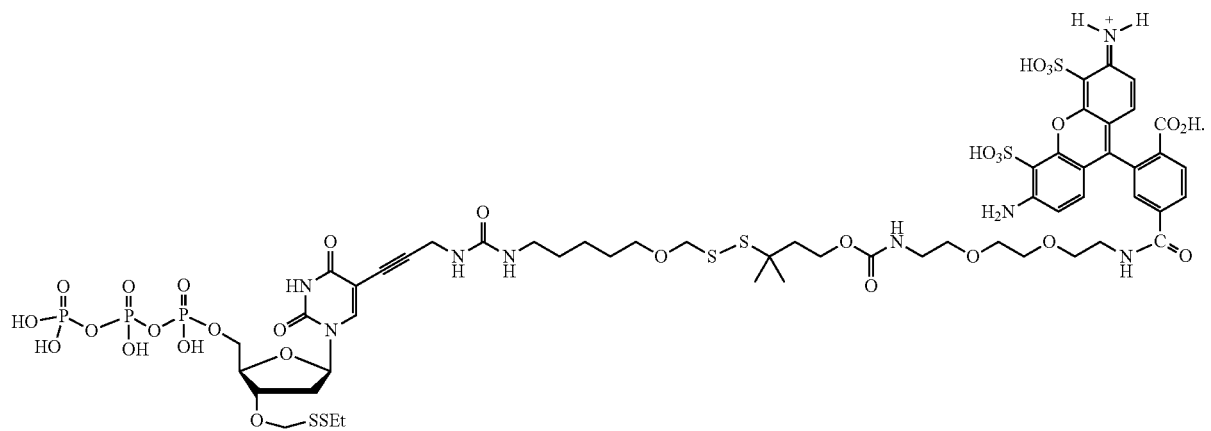

In one embodiment, the compound has the structure:

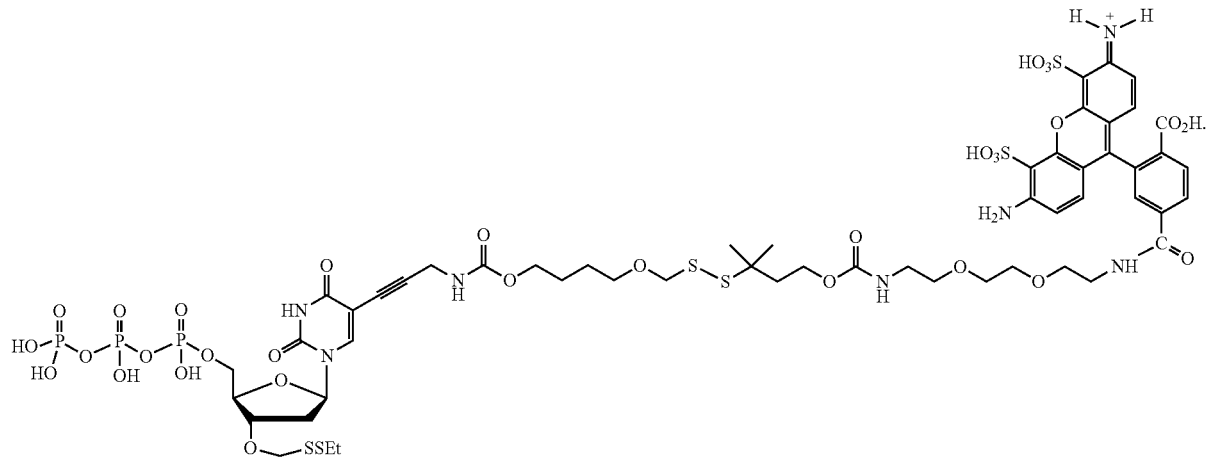

In one embodiment, the compound has the structure:

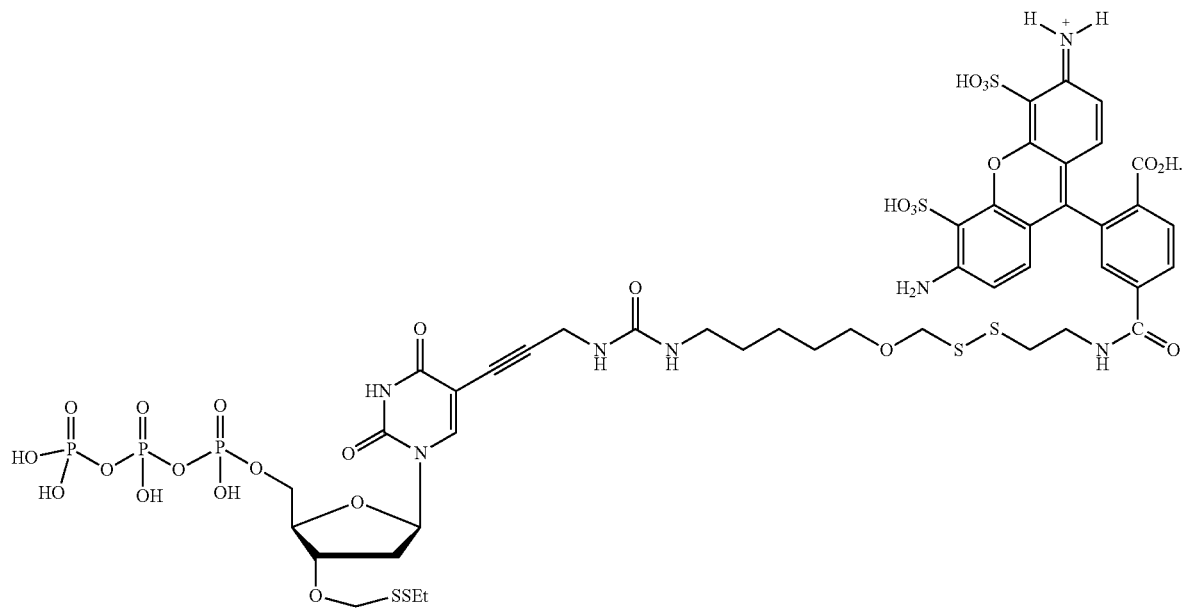

In one embodiment, the invention relates to a labeled deoxynucleoside triphosphate according to the following structure:

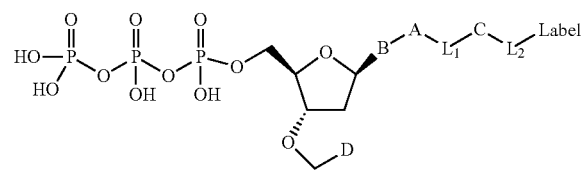

wherein D is selected from the group consisting of an azide (—N$_3$), disulfide alkyl (—SS—R) and disulfide substituted alkyl groups, B is a nucleobase, A is an attachment group, C is a cleavable site core, L$_1$ and L$_2$ are connecting groups, and Label is a label. In one embodiment, said nucleobase is a natural nucleobase. In one embodiment, said nucleobase is a non-natural nucleobase analog selected from the group consisting of 7-deaza guanine, 7-deaza adenine, 2-amino,7-deaza adenine, and 2-amino adenine. In one embodiment, said attachment group (A) is chemical group selected from the group consisting of propargyl, hydroxymethyl, exocyclic amine, propargyl amine, and propargyl hydroxyl. In one embodiment, said cleavable (C) site core selected from the group consisting of:

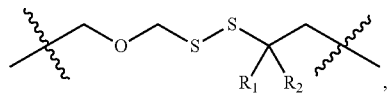

39

-continued

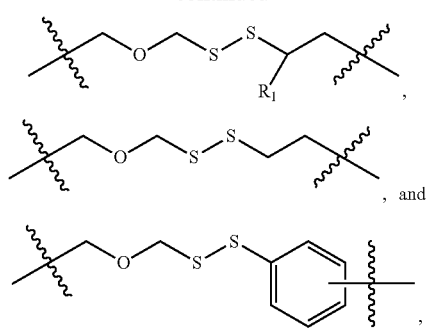

wherein R₁ and R₃ are independently selected alkyl groups. In one embodiment, said cleavable site core selected from the group consisting of:

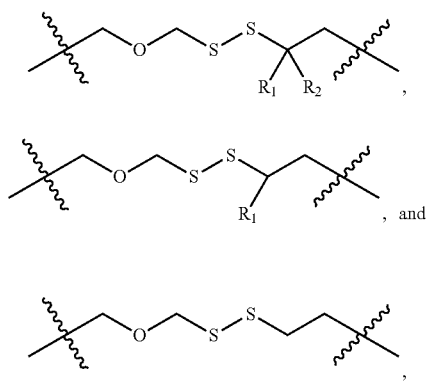

wherein R₁ and R₂ are independently selected alkyl groups. In one embodiment, L₁ is selected from the group consisting of —CONH(CH₂)$_x$—, —CO—O(CH₂)$_x$—, —CONH—(OCH₂CH₂O)$_x$—, —CO—O(CH₂CH₂O)$_x$—, and —CO(CH₂)$_x$—, wherein x is 0-100. In some embodiments, x is 0-10, but more preferably from 1-6. In one embodiment, L₂ is selected from the group consisting of

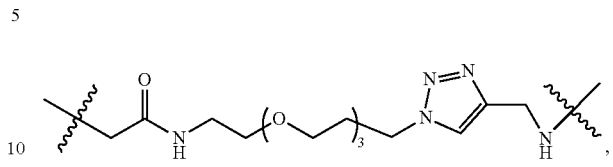

—NH—, —(CH₂)$_x$—NH—, —C(Me)₂(CH₂)$_x$NH—, —CH(Me)(CH₂)$_x$NH—, —C(Me)₂(CH₂)$_x$CO—, —CH(Me)(CH₂)$_x$CO—, —(CH₂)$_x$OCONH(CH₂)$_y$O(CH₂)₂NH—, —(CH), CONH(CH₂CH₂O)$_y$(CH)₂NH—, and —CONH(CH₂)$_x$—, —CO(CH₂)$_x$—, wherein x, y, and z are each independently selected from is 0-10, but more preferably from 1-6. In one embodiment, L₂ is selected from the group consisting of —NH—, —(CH₂)$_x$—NH—, —C(Me)₂(CH₂)$_x$NH—, —CH(Me)(CH₂)$_x$NH—, —C(Me)₂(CH₂)$_x$CO—, —CH(Me)(CH₂)$_x$CO—, —(CH₂)$_x$OCONH(CH₂)$_y$O(CH₂)₂NH—, and —CONH(CH₂)$_x$—, —CO(CH₂)$_x$—, wherein x, y, and z are each independently selected from is 0-100. In one embodiment, x, y, and z are each independently selected from is 0-10, but more preferably from 1-6. In one embodiment, said label is selected from the group consisting of fluorophore dyes, energy transfer dyes, mass-tags, biotin, and haptenes. In one embodiment, the compound has the following structure (while a particular nucleobase and label are shown below, other analogous nucleotide counterparts are contemplated, i.e. any of the various labels in the specification and figures could be substituted, and the nucleobase could be different):

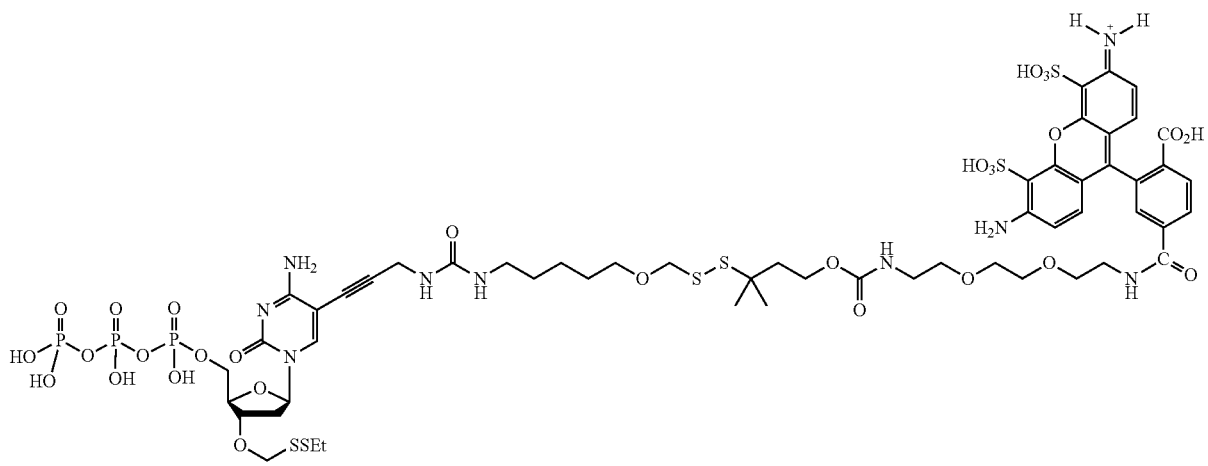

In one embodiment, the compound has the following structure (while a particular nucleobase and label are shown below, other analogous nucleotide counterparts are contemplated, i.e. any of the various labels in the specification and figures could be substituted, and the nucleobase could be different):

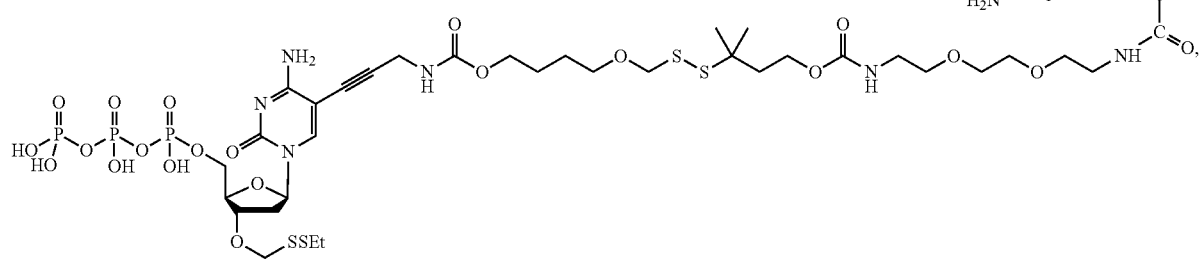

In one embodiment, the compound has the following structure (while a particular nucleobase and label are shown below, other analogous nucleotide counterparts are contemplated, i.e. any of the various labels in the specification and figures could be substituted, and the nucleobase could be different):

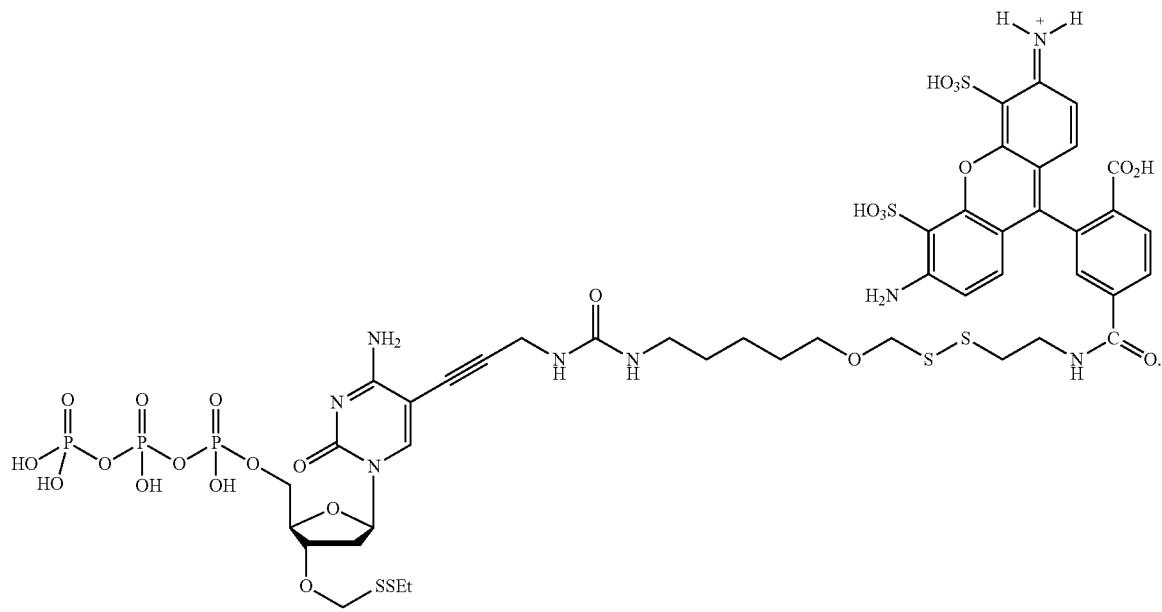

In one embodiment, the compound has the following structure (while a particular nucleobase and label are shown below, other analogous nucleotide counterparts are contemplated, i.e. any of the various labels in the specification and figures could be substituted, and the nucleobase could be different):

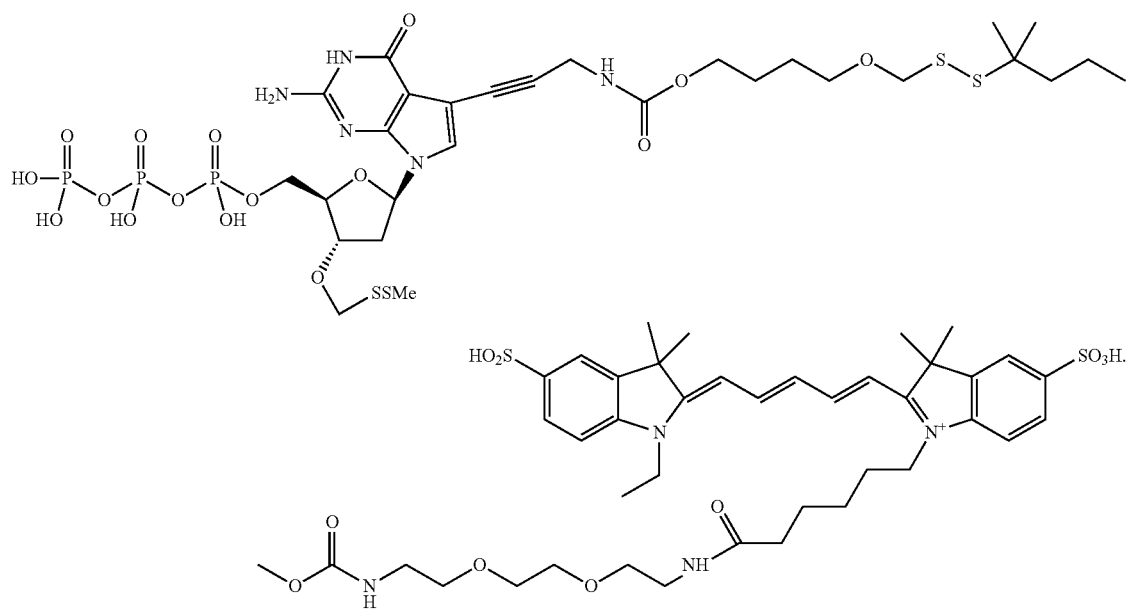

In one embodiment, the compound has the following structure (while a particular nucleobase and label are shown below, other analogous nucleotide counterparts are contemplated, i.e. any of the various labels in the specification and figures could be substituted, and the nucleobase could be different):

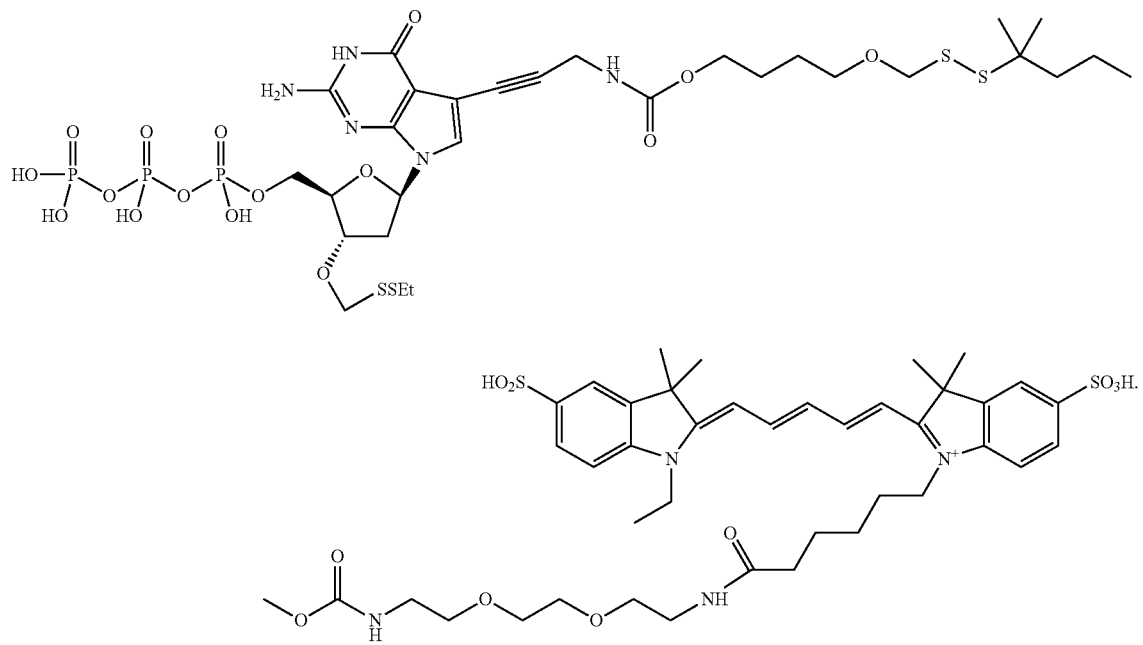

In one embodiment, the compound has the following structure (while a particular nucleobase and label are shown below, other analogous nucleotide counterparts are contemplated, i.e. any of the various labels in the specification and figures could be substituted, and the nucleobase could be different):

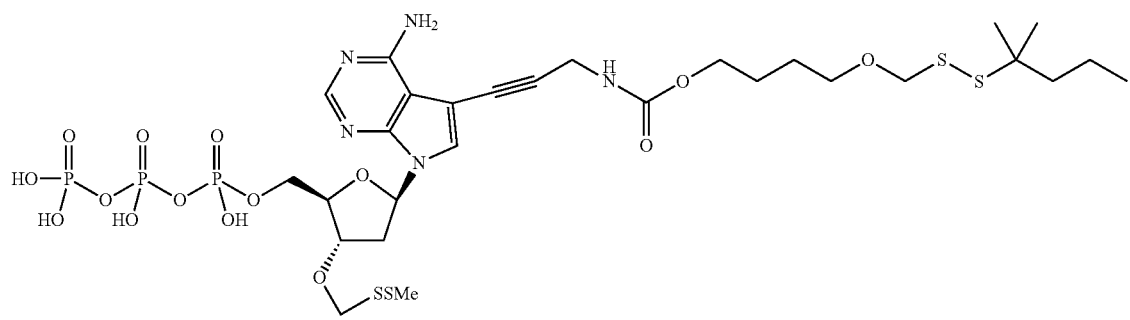

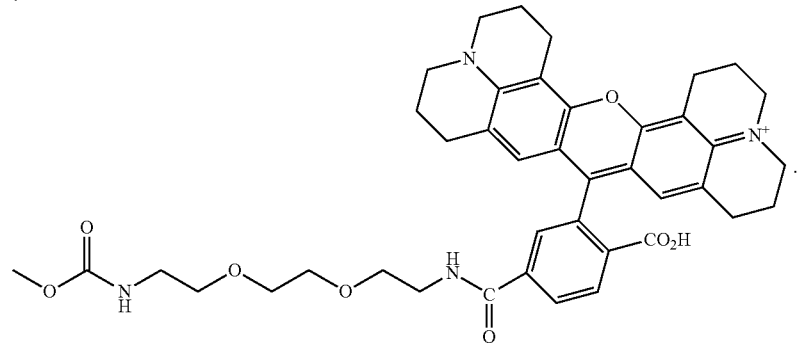

In one embodiment, the compound has the following structure (while a particular nucleobase and label are shown below, other analogous nucleotide counterparts are contemplated, i.e. any of the various labels in the specification and figures could be substituted, and the nucleobase could be different):

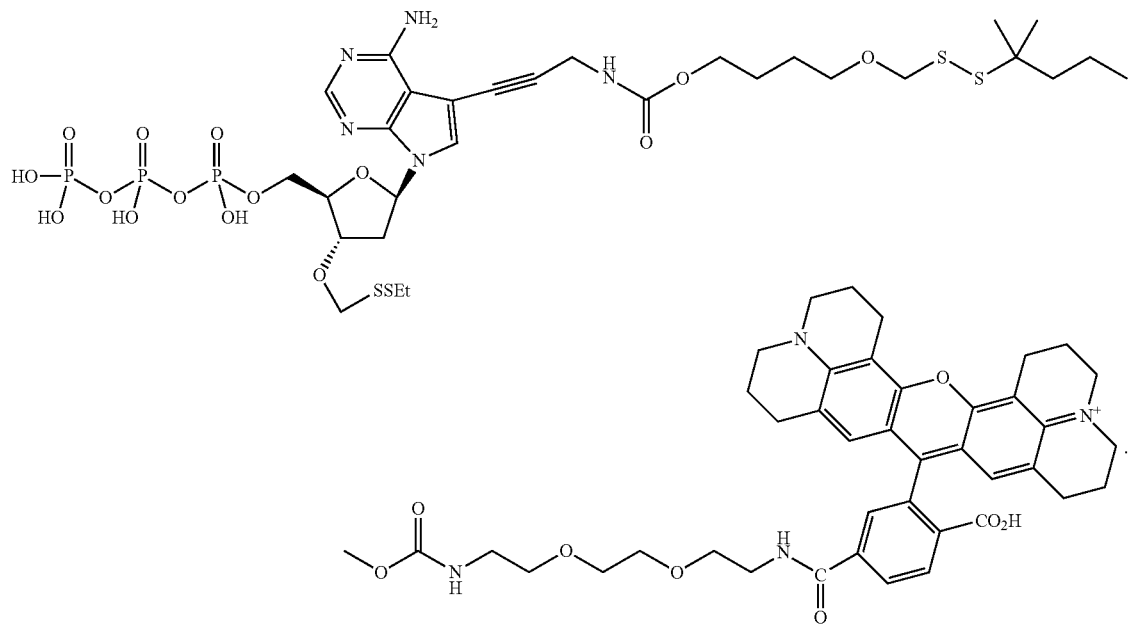

In one embodiment, the compound has the following structure (while a particular nucleobase and label are shown below, other analogous nucleotide counterparts are contemplated, i.e. any of the various labels in the specification and figures could be substituted, and the nucleobase could be different):

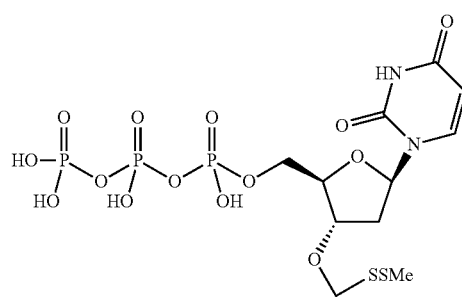
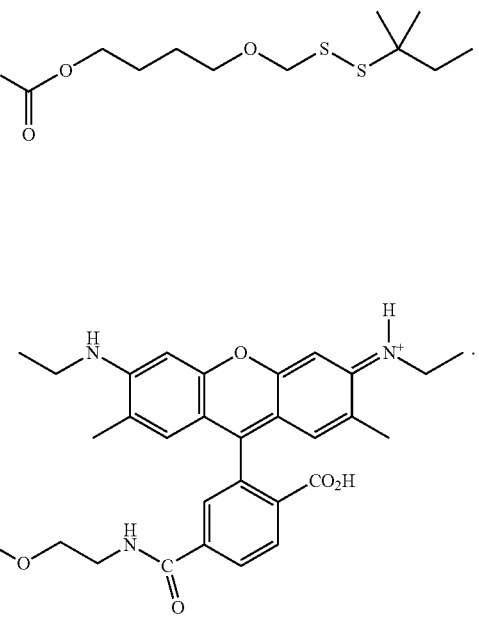

In one embodiment, the compound has the following structure (while a particular nucleobase and label are shown below, other analogous nucleotide counterparts are contemplated, i.e. any of the various labels in the specification and figures could be substituted, and the nucleobase could be different):

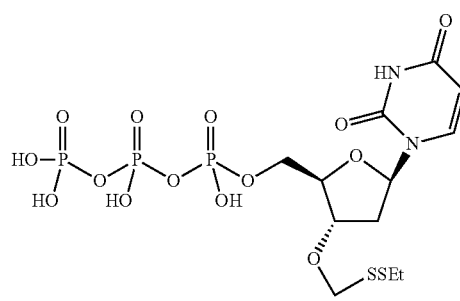
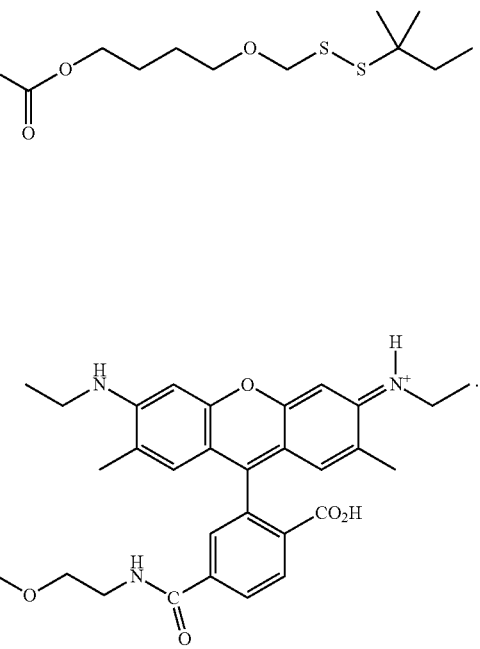

In one embodiment, the compound has the following structure (while a particular nucleobase and label are shown below, other analogous nucleotide counterparts are contemplated, i.e. any of the various labels in the specification and figures could be substituted, and the nucleobase could be different):

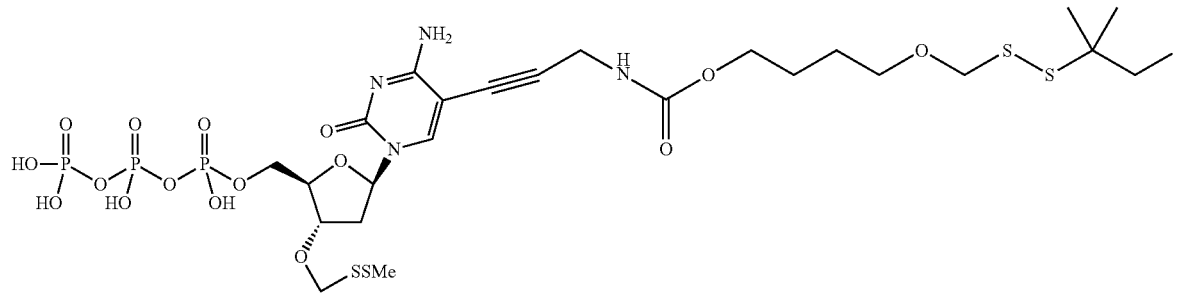

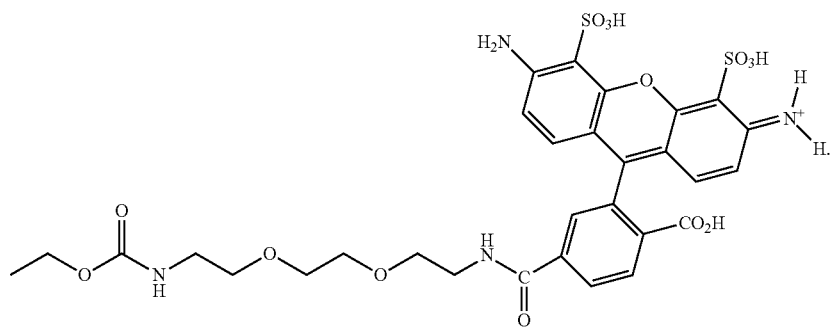

In one embodiment, the compound has the following structure (while a particular nucleobase and label are shown below, other analogous nucleotide counterparts are contemplated, i.e. any of the various labels in the specification and figures could be substituted, and the nucleobase could be different):

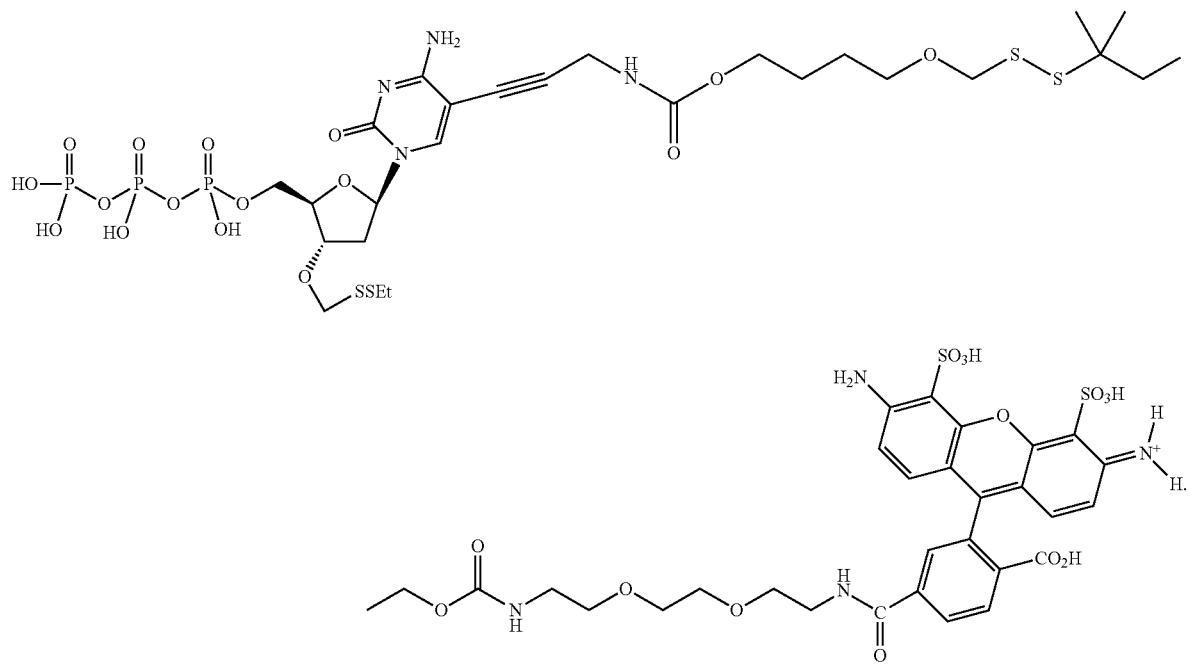

In one embodiment, the compound has the following structure (while a particular nucleobase and label are shown below, other analogous nucleotide counterparts are contemplated, i.e. any of the various labels in the specification and figures could be substituted, and the nucleobase could be different):

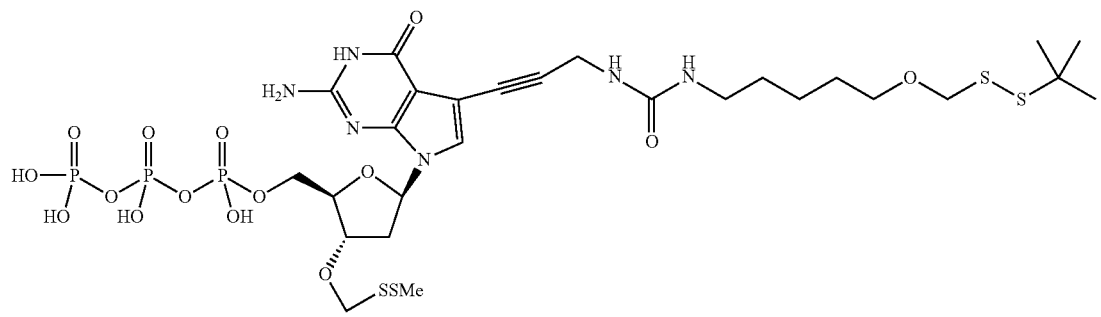

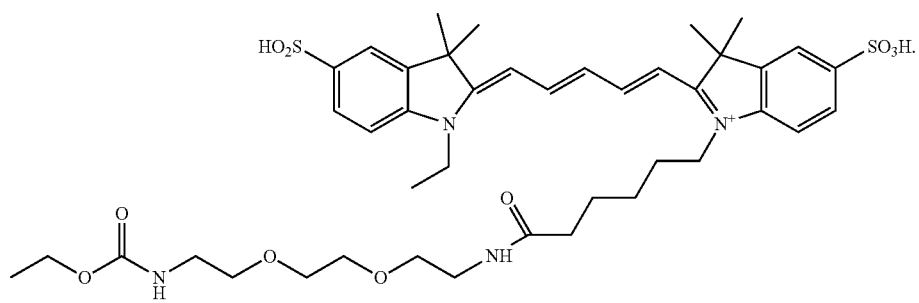

In one embodiment, the compound has the following structure (while a particular nucleobase and label are shown below, other analogous nucleotide counterparts are contemplated, i.e. any of the various labels in the specification and figures could be substituted, and the nucleobase could be different):

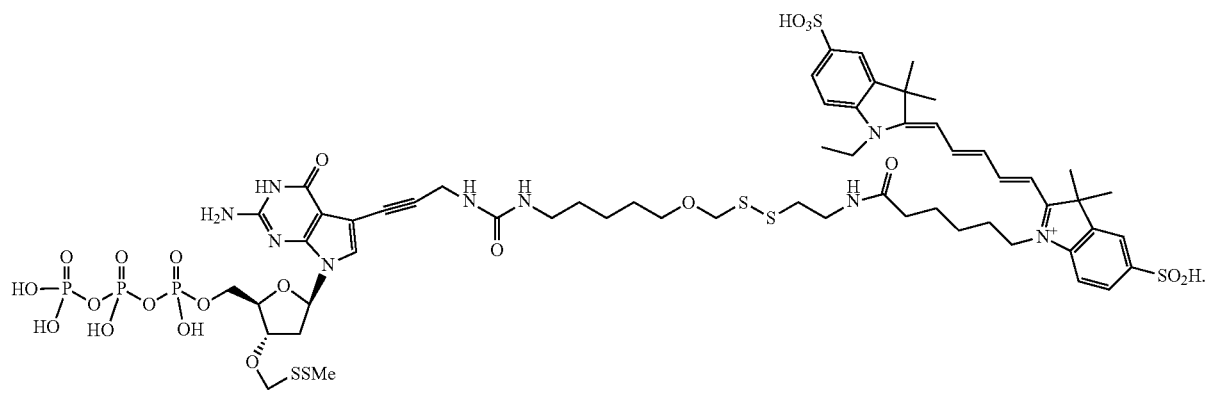

In one embodiment, the compound has the following structure (while a particular nucleobase and label are shown below, other analogous nucleotide counterparts are contemplated, i.e. any of the various labels in the specification and figures could be substituted, and the nucleobase could be different):

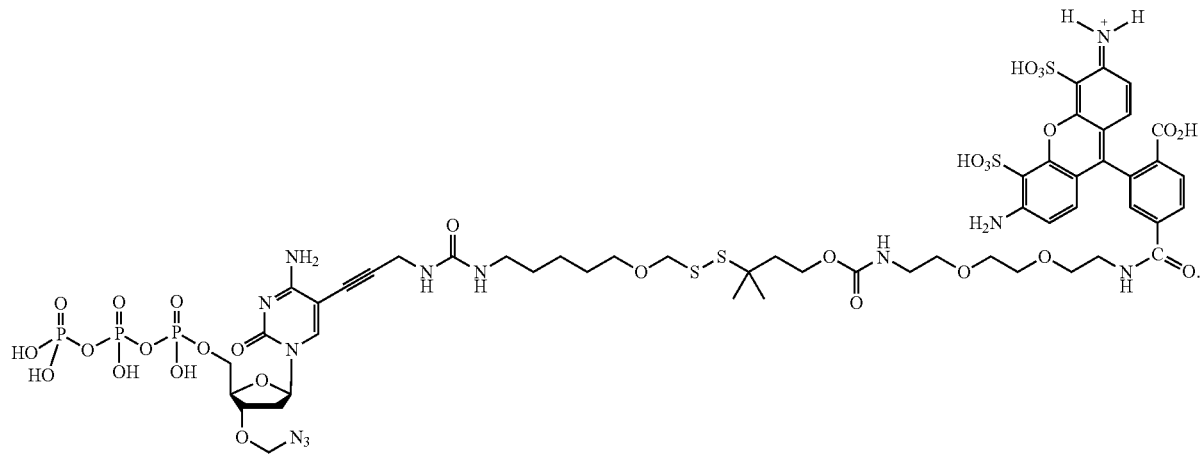

In one embodiment, the compound has the following structure (while a particular nucleobase and label are shown below, other analogous nucleotide counterparts are contemplated, i.e. any of the various labels in the specification and figures could be substituted, and the nucleobase could be different):

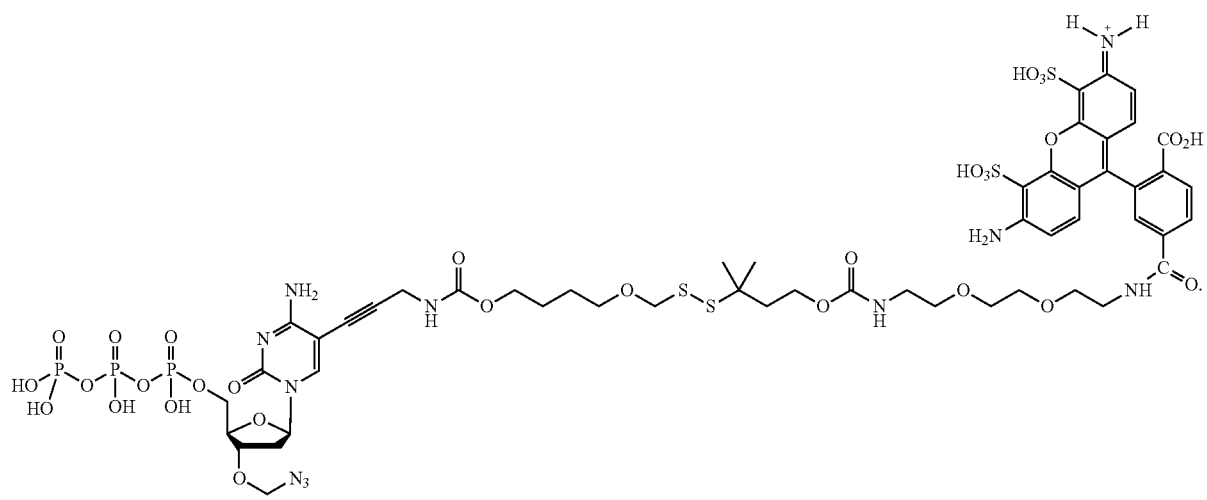

In one embodiment, the compound has the following structure (while a particular nucleobase and label are shown below, other analogous nucleotide counterparts are contemplated, i.e. any of the various labels in the specification and figures could be substituted, and the nucleobase could be different):

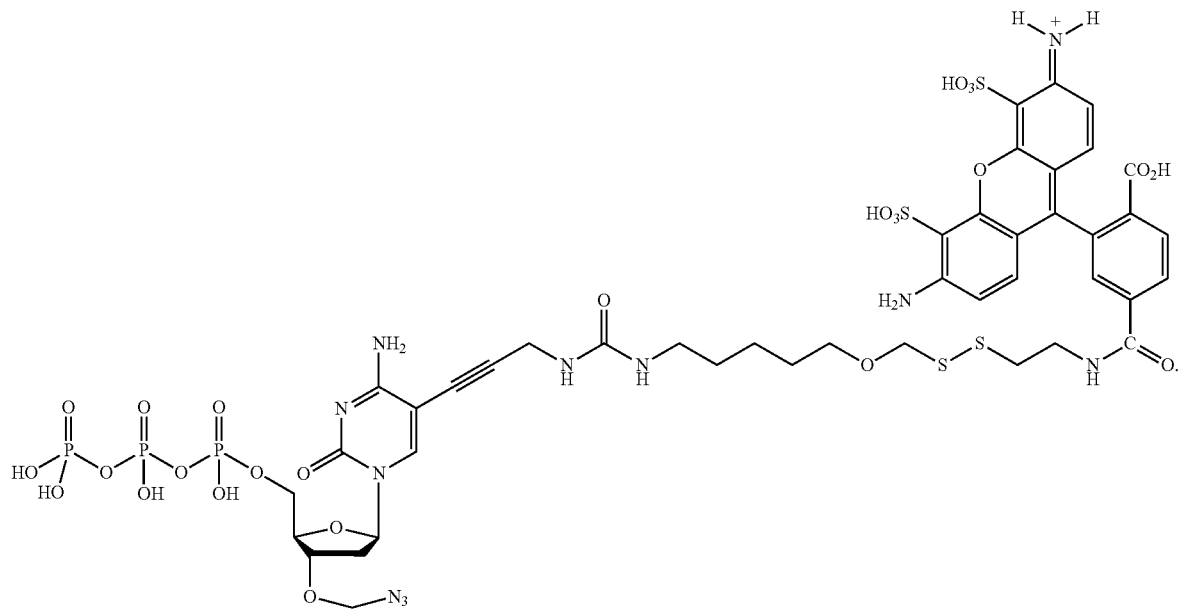

In one embodiment, the present invention contemplates unlabeled compounds. In one embodiment, the compound has the structure:

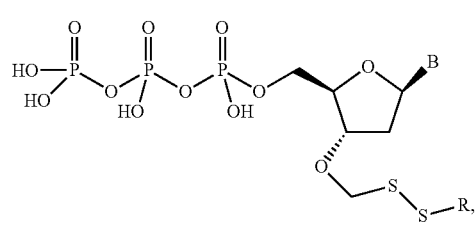

wherein R is selected from the group consisting of alkyl, substituted alkyl groups, allyl, substituted allyl; and B is a nucleobase. In one embodiment, the compound has the structure (again B is a nucleobase):

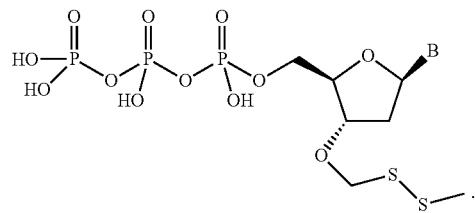

In one embodiment, the compound has the structure:

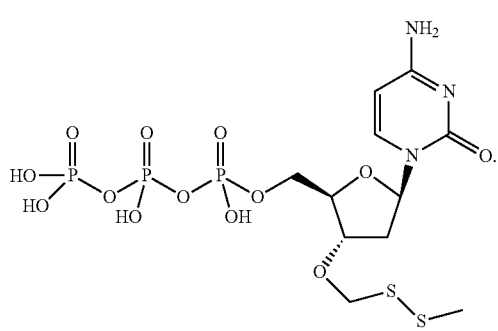 [SMILES: CSSCO[C@H]1C[C@H](n2ccc(N)nc2=O)O[C@@H]1COP(=O)(O)OP(=O)(O)OP(=O)(O)O]

In one embodiment, the compound has the structure:

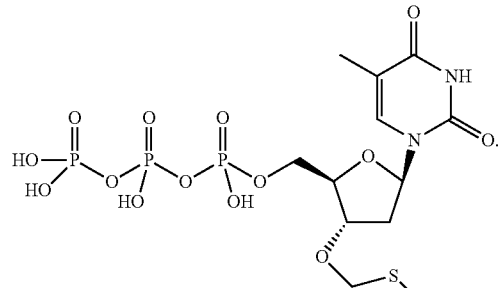

In one embodiment, the compound has the structure:

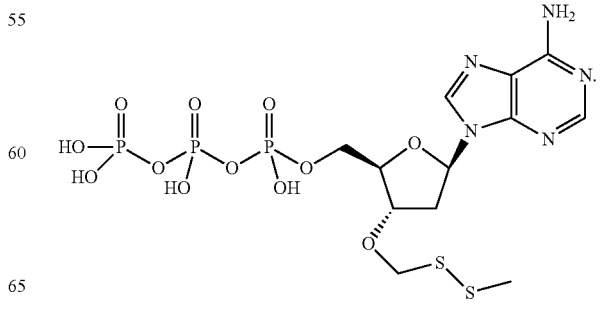

In one embodiment, the compound has the structure:

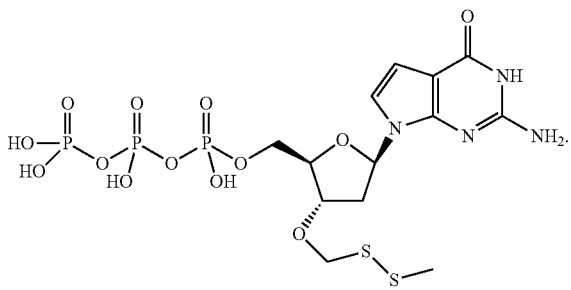 [SMILES: CSSCO[C@H]1C[C@H](n2ccc3c(=O)[nH]c(N)nc32)O[C@@H]1COP(=O)(O)OP(=O)(O)OP(=O)(O)O]

In one embodiment, said nucleobase is a non-natural nucleobase analog selected from the group consisting of 7-deaza guanine, 7-deaza adenine, 2-amino,7-deaza adenine, and 2-amino adenine.

In one embodiment, the invention relates to a method of synthesizing 3'-OCH$_2$—SSMe nucleotide analogs using 3'-(2,4,6-trimethoxyphenyl)methanethiol nucleoside as intermediate, and DMTSF and dimethyldisulfide as sulfur source shown in FIG. 43.

In one embodiment, the invention relates to a labeled deoxynucleoside triphosphate according to the following structure:

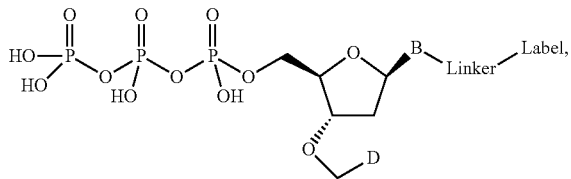

wherein D is selected from the group consisting of an azide, disulfide alkyl, disulfide substituted alkyl groups, disulfide allyl, and disulfide substituted allyl groups; B is a nucleobase; Linker comprises a cleavable oxymethylenedisulfide-containing site core. In one embodiment, said cleavable site core is selected from the group consisting of:

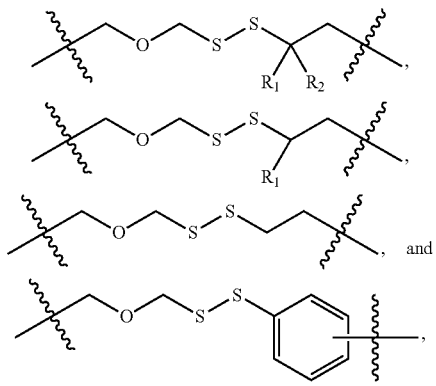

wherein R$_1$ and R$_2$ are independently selected alkyl groups; and Label is a label. In one embodiment, said Linker is hydrophobic. In one embodiment, said Linker has a log P value of greater than 0. In one embodiment, said Linker has a log P value of greater than 0.1. In one embodiment, said Linker has a log P value of greater than 0.5. In one embodiment, said Linker has a log P value of greater than 1.0.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; "imino" means =NH (see below for definitions of groups containing the term imino, e.g., alkylamino); "cyano" means —CN; "azido" means —N$_3$; "mercapto" means —SH; "thio" means =S; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "silyl" means —SiH$_3$ (see below for definitions of group(s) containing the term silyl, e.g., alkylsilyl).

As used herein, "methylene" means a chemical species in which a carbon atom is bonded to two hydrogen atoms. The —CH$_2$— group is considered to be the standard methylene group. Methylene groups in a chain or ring contribute to its size and lipophilicity. In this context dideoxy also refers the methylene groups. In particular a 2,3-dideoxy compound is the same as 2,3-methylene (2,3-methylene-glycoside=2,3-dideoxy-glycoside).

For the groups below, the following parenthetical subscripts further define the groups as follows: "(C$_n$)" defines the exact number (n) of carbon atoms in the group; "(C≤n)" defines the maximum number (n) of carbon atoms that can be in the group; (C$_{n-n'}$) defines both the minimum (n) and maximum number (n') of carbon atoms in the group. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). Similarly, "alkyl$_{(C≤10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$(n-Pr), —CH(CH$_3$)$_2$ (iso-Pr or i-Pr), —CH(CH$_2$)$_2$(cyclopropyl), —CH$_2$CH$_2$CH$_2$CH$_3$ (n-Bu), —CH(CH$_3$)CH$_2$CH$_3$ (sec-butyl or sec-Bu), —CH$_2$CH(CH$_3$)$_2$(iso-butyl or i-Bu), —C(CH$_3$)$_3$(tert-butyl or t-Bu), —CH$_2$C(CH$_3$)$_3$(neo-pentyl), cyclobutyl, cyclopentyl, cyclohexyl, cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_3$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The terms "cleavable oxymethylenedisulfide linker" and "cleavable oxymethylenedisulfide-containing linker" are meant to indicate that the linker comprises an oxymethylenedisulfide group, and are not to be considered limited to only an oxymethylenedisulfide group, but rather linkers that may contain more than just that group, for example as seen in the compounds in FIG. 25. Similarly, the terms "oxymethylenedisulfide site core" and "oxymethylenedisulfide-containing site core" are meant to indicate that the site core comprises an oxymethylenedisulfide group, and are not to be considered limited to only an oxymethylenedisulfide group, but rather site cores that may contain more than just that group.

The term "nucleic acid" generally refers to both DNA or RNA, whether it is a product of amplification, synthetically created, products of reverse transcription of RNA or naturally occurring. Typically, nucleic acids are single- or double-stranded molecules and are composed of naturally occurring nucleotides. Double-stranded nucleic acid molecules can have 3'- or 5'-overhangs and as such are not required or assumed to be completely double-stranded over their entire length. Furthermore, the nucleic acid can be composed of non-naturally occurring nucleotides and/or modifications to naturally occurring nucleotides. Examples are listed herein, but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; phosphorothioate, methylphosphonates, phosphoroamidates and phosphotriester linkages between nucleotides to prevent degradation; methylation; and modified bases or nucleosides such as deoxy-inosine, 5-bromo-dU, 2'-deoxy-uridine, 2-aminopurine, 2',3'-dideoxy-cytidine, 5-methyl-dC, locked nucleic acids (LNA's), iso-dC and -dG bases, 2' —O-methyl RNA bases and fluorine modified nucleosides.

In some of the methods contemplated herein, primers are at least partially complementary to at least a portion of template to be sequenced. The term "complementary" generally refers to the ability to form favorable thermodynamic stability and specific pairing between the bases of two nucleotides (e.g. A with T) at an appropriate temperature and ionic buffer conditions. This pairing is dependent on the hydrogen bonding properties of each nucleotide. The most fundamental examples of this are the hydrogen bond pairs between thymine/adenine and cytosine/guanine bases. In the present invention, primers for amplification of target nucleic acids can be both fully complementary over their entire length with a target nucleic acid molecule or "semi-complementary" wherein the primer contains an additional, non-complementary sequence minimally capable or incapable of hybridization to the target nucleic acid.

The term "hybridize" generally refers to the base-pairing between different nucleic acid molecules consistent with their nucleotide sequences. The terms "hybridize" and "anneal" can be used interchangeably.

The term "oligonucleotide" generally refers to a nucleic acid sequence typically designed to be single-stranded DNA and less than 75 nucleotides in length.

The term "primer" generally refers to an oligonucleotide that is able to anneal, or hybridize, to a nucleic acid sequence and allow for extension under sufficient conditions (buffer, dNTP's, polymerase, mono- and divalent salts, temperature, etc. . . . ) of the nucleic acid to which the primer is complementary.

The terms "template nucleic acid", "template molecule", "target nucleic acid", and "target molecule" can be used interchangeably and refer to a nucleic acid molecule that is the subject of an amplification reaction that may optionally be interrogated by a sequencing reaction in order to derive its sequence information. The template nucleic acid may be a nucleic acid which has been generated by a clonal amplification method and which may be immobilized on a solid surface, i.e. immobilized on beads or an array.

The term "nucleoside" refers to a compound consisting of a base linked to the C-1' carbon of a sugar, for example, ribose or deoxyribose. The base portion of the nucleoside is usually a heterocyclic base, e.g., a purine or pyrimidine.

The term "nucleotide" refers to a phosphate ester of a nucleoside, as a monomer unit or within a polynucleotide. "Nucleoside 5'-triphosphate" refers to a nucleotide with a triphosphate ester group attached to the sugar 5'-carbon position, and is sometimes denoted as "NTP", "dNTP" (2'-deoxynucleoside triphosphate or deoxynucleoside triphosphate) and "ddNTP" (2',3'-dideoxynucleoside triphosphate or dideoxynucleoside triphosphate). "Nucleoside 5'-tetraphosphate" refers to an alternative activated nucleotide with a tetraphosphate ester group attached to the sugar 5'-carbon position. PA-nucleotide refers to a propargyl analogue.

The term "protecting group," as that term is used in the specification and/or claims, is used in the conventional chemical sense as a group, which reversibly renders unreactive a functional group under certain conditions of a desired reaction and is understood not to be H. After the desired reaction, protecting groups may be removed to deprotect the protected functional group. In a preferred embodiment, all protecting groups should be removable (and hence, labile) under conditions which do not degrade a substantial proportion of the molecules being synthesized. A protecting group may also be referred to as a "capping group" or a "blocking group" or a "cleavable protecting group." It should be noted that, for convenience, the functionality protected by the protecting group may also be shown or referred to as part of the protecting group. In the context of the nucleotide derivatives described herein, a protecting group is used on the 3' position. It is not intended that the present invention be limited by the nature or chemistry of this protecting group on the reversibly terminating nucleotides used in sequencing. A variety of protecting groups is contemplated for this purpose, including but not limited to: 3'-O-azidomethyl nucleotides, 3'-O-aminoxy nucleotides, 3'-O-allyl nucleotides; and disulfide nucleotides, 3'-O-azidoalkyl, 3'-O-dithiomethyl alkyl, 3'-O-dithiomethyl aryl, 3'-O-acetyl, 3'-O-carbazate, 3'-O-alkyl ether, 3'-O-alkyl ester, 3'-O-aldoxime (—O—N—CH—R), 3'-O-ketoxime (—O—N—C(R, R')).

One embodiment of the present invention contemplates attaching markers directly on the 3'-OH function of the nucleotide via functionalization of the protective groups.

The term "label" or "detectable label" in its broadest sense refers to any moiety or property that is detectable, or allows the detection of that which is associated with it. For example, a nucleotide, oligo- or polynucleotide that comprises a label is detectable. Ideally, a labeled oligo- or polynucleotide permits the detection of a hybridization complex, particularly after a labeled nucleotide has been incorporated by enzymatic means into said hybridization complex of a primer and a template nucleic acid. A label may be attached covalently or non-covalently to a nucleotide, oligo- or polynucleotide. In various aspects, a label can, alternatively or in combination: (i) provide a detectable signal; (ii) interact with a second label to modify the detectable signal provided by the second label, e.g., FRET; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior. Labels vary widely in their structures and their mechanisms of action. Examples of labels include, but are not limited to, fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes of the fluorescein family, dyes of the rhodamine family, dyes of the cyanine family, or a coumarine, an oxazine, a boradiazaindacene or any derivative thereof. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), Texas Red is commercially available from, e.g., Life Technologies (Molecular Probes, Inc.) (Grand Island, N.Y.). Dyes of the cyanine family include, e.g., CY2, CY3, CY5, CY5.5 and CY7, and are commercially available from, e.g., GE Healthcare Life Sciences (Piscataway, N.J., USA).

The term "differently labeled," as used herein, refers to the detectible label being a different label, rather than the label being found in a different position upon the labeled nucleoside nucleobase.

The term "analogs of A, G, C and T or U" refers to modified deoxynucleoside triphosphate compounds, wherein the nucleobase of said deoxynucleoside closely resembles the corresponding nucleoside Deoxyadenosine, Deoxyguanosine, Deoxycytidine, and Thymidine or Deoxyuridine. In the case of detectable labeled deoxynucleoside triphosphate compounds an analog of A or Deoxyadenosine would be represented as

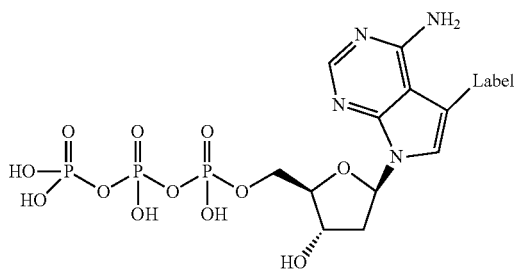

though it is preferred that there be a linker between the nucleobase and the label. In the case of detectable labeled deoxynucleoside triphosphate compounds an analog of G or Deoxyguanosine would be represented as

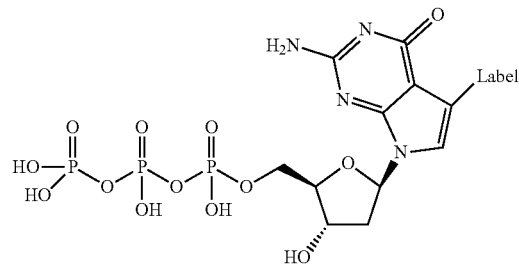

though it is preferred that there be a linker between the nucleobase and the label. In the case of detectable labeled deoxynucleoside triphosphate compounds an analog of C or Deoxycytidine would be represented as

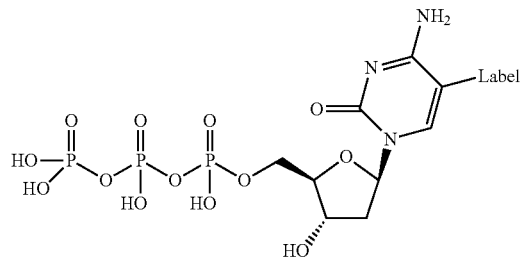

although it is preferred that there be a linker between the nucleobase and the label. In the case of detectable labeled deoxynucleoside triphosphate compounds an analog of T or U or Thymidine or Deoxyuridine would be represented as

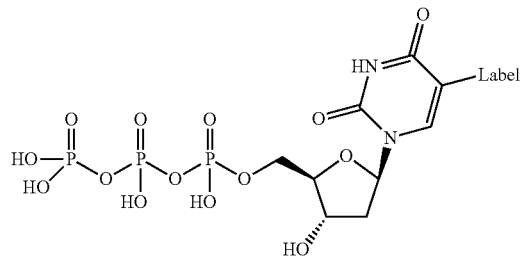

although it is preferred that there be a linker between the nucleobase and the label. Additional nucleobase may include: non-natural nucleobase selected from the group consisting of 7-deaza guanine, 7-deaza adenine, 2-amino,7-deaza adenine, and 2-amino adenine. In the case of analogs, the detectable label may also include a linker section between the nucleobase and said detectable label.

The term "TCEP" or "tris(2-carboxyethyl)phosphine)" refers to a reducing agent frequently used in biochemistry and molecular biology applications. It is often prepared and used as a hydrochloride salt (TCEP-HCl) with a molecular weight of 286.65 gram/mol. It is soluble in water and available as a stabilized solution at neutral pH and immobilized onto an agarose support to facilitate removal of the reducing agent. It is not intended that the invention is limited to one type of reducing agent. Any suitable reducing agent capable of reducing disulfide bonds can be used to practice the present invention. In one embodiment the reducing agent is phosphine [12], for example, triphenylphosphine, tributylphosphine, trihydroxymethyl phosphine, trihydroxypropyl phosphine, tris carboethoxy-phosphine (TCEP) [13, 14]. It is not intended that the present invention be limited to the use of TCEP. In one embodiment, said detectable label and 3'-OCH2-SS—R group are removed from said nucleobase by exposure to compounds carrying a thiol group so as to perform cleavage of dithio-based linkers and terminating (protecting) groups, such thiol-containing compounds including (but not limited to) cysteine, cysteamine, dithiosuccinic acid, dithiothreitol, 2,3-Dimercapto-1-propanesulfonic acid sodium salt, dithiobutylamine, meso-2,5-dimercapto-N,N,N',N'-tetramethyladipamide, 2-mercaptoethane sulfonate, and N,N'-dimethyl, N,N'-bis(mercaptoacetyl)-hydrazine [17]. Reactions can be further catalyzed by inclusion of selenols [18]. In addition borohydrides, such as sodium borohydrides can also be used for this purpose [19] (as well as ascorbic acid [20]. In addition, enzymatic methods for cleavage of disulfide bonds are also well known such as disulfide and thioreductase and can be used with compounds of the present invention [21].

N-Cyclohexyl-2-aminoethanesulfonic acid, also known as CHES, is a buffering agent.

High pH is defined as a pH in the range of 9.0-10.0, e.g. pH 9.5. Low pH is defined as 8.5 and lower.

ATP on FFPE sample type is indicated as ATPf("f" for FFPE)

ATP on liquid biopsy sample type is indicated as ATPp ("p" for plasma)

"Acrometrix" refers to the commercially available DNA sample type used.

Reactions can take place in a variety of places, e.g. wells, channels, slides, flow cells, etc. Flow cells can have channels, as described in U.S. Pat. No. 8,940,481, hereby incorporated by reference. Flow cells can be on moving supports within instruments as described in U.S. Pat. No. 8,900,810, hereby incorporated by reference.

In a preferred embodiment, the present invention contemplates the use of a sequencing additive, namely CMIT, in an extend reagent (e.g. a buffered solution of nucleotide analogues and polymerase) for the primer extension step. CMIT is commercially available. For example, the reagent "Proclin300" (which is a mixture of 5-Chloro-2-methyl-4-isothiazolin-3-one (CMIT); 2-Methyl-4-isothiazolin-3-one (MIT); glycol: 93-95%; modified alkyl carboxylate: 2-3%) is commercially available from Sigma-Aldrich. Structures for these components are shown in FIG. 95. A small amount of Proclin300 can be added to the buffered solution, e.g. 15 ul of Proclin300 can be added to 15 ml of extend reagent, and be effective. While not intending in any manner to limit the present invention to any particular mechanism of action, it is believed that the CMIT in "Proclin300" inhibits (and may even prevent) terminator cleavage during the extension reaction, and in particular, during sequencing reactions where deoxynucleoside triphosphates comprising a 3'-O position capped by a disulfide-based 3'-terminator group are used. In a preferred embodiment, Proclin300 is added fresh to the extend reagent. While it may be used when it is under 48 hours old (and more preferably less than 24 hours old), it is most preferred that the extend reagent with Proclin300 is made just before (e.g. within minutes to 2 hours before) the sequencing run. It is also preferred that the oxidative scavenger $H_2O_2$ not be used when CMIT is used as an additive. When CMIT is used, the preferred scavenger is cystamine.

Regardless of the mechanism, the use of CM IT (e.g. in Proclin300) in the extension step is observed to control (and even reduce) "lead." Lead as a function per cycle is one of the key metric of sustaining sequencing performance. When lead is observed to be a linear function increasing from 0.0 to 0.5, it is deemed to be "within spec."

Regardless of the mechanism, the use of CMIT (e.g. in Proclin300) in the extension step is observed to increase read length. This could not be predicted.

Regardless of the mechanism, the use of CMIT in the extension step is observed to decrease DNA template damage. DNA template damage has been observed to be more prominent at the outlet region of the flow cell due to fluidic patterns and manifests itself as a read quality degradation gradient from the inlet to the outlet region of the flow cell. With CMIT in the extend reagent, a dramatic improvement in inlet-to-outlet is observed.

In some embodiments, the method of sequencing includes a pre-Extend wash step prior to the extension step. Without being bound to any mechanism or theory, it is believed that the pre-Extend wash step is a mitigation measure to ensure that any potential cystamine/cysteamine by-products (e.g. in the post-cleave step from a previous cycle) do not carry over into the Extension step. In a preferred embodiment, the pre-Extend wash does not contain methylenediphosphonic acid (PcPi). It is preferred that methylenediphosphonic acid is used in an earlier wash step to prevent nucleotide build up on the surface (e.g. in the Wash 9/10 step).

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 33 shows incorporation kinetics for the dA 3'-reversibly terminating nucleotides: —$CH_2$—$N_3$, —$CH_2$—SS-Et, —$CH_2$—SS-Me.

FIG. 35 shows optimized concentrations of nucleotides used in Extend A reactions on GR sequencer [nM].

FIG. 41 shows identification of multiplex barcodes from sequencing runs containing 3'-O—$CH_2$—SS-Et nucleotides in ExtB and in both ExtB and A.

FIG. 49 shows example concentrations of nucleotides used in sequencing on GR instrument (labeled, compounds 72, 74, 76, 78) and non-labeled (compounds 120, 126, 132, 138), all carrying the —$CH_3$—SS-Me on their 3' as reversibly terminating group.

FIG. 68 shows the key intermediates for the synthesis of 3'-($OCH_2$SSMe)-dNTP-PAs.

FIG. 72 shows structures of hydroxymethyl derivatives nucleobases derivatives after cleavage has been performed.

FIG. 79 presents exemplary dithiol compounds at a vicinal position or separated by at least one hydrocarbon and alternatively attached to a hydrocarbon spacer with an anionic functional group (R).

FIG. 83 presents representative structures of various thiol based cleave reagents using in the cleavage study presented in Table 1.

FIG. 87A: An exemplary Box 1A comprising containers of extension premix and a cleave base buffer.

FIG. 87B: An exemplary Box 1B comprising containers of base wash premix and wash buffer.

FIG. 87C: An exemplary Box 2 comprising containers of extension add-on reagents, a DNA polymerase and an imaging reagent.

FIG. 89A; high pH DMPS TRIS cleave reagent.

FIG. 89B: DMPS CHES baseline b128.

FIG. 89C: TCEP baseline SBS sequencing method.

FIG. 93A shows one embodiment of a workflow for primer hybridization. FIG. 93B shows on embodiment of a workflow for flow cell preparation. FIG. 93C shows one embodiment of an automated workflow for sequencing by synthesis (SBS), wherein an oxidative wash (Wash 11) is used after the cleave step.

DESCRIPTION OF THE INVENTION

Figure 25:
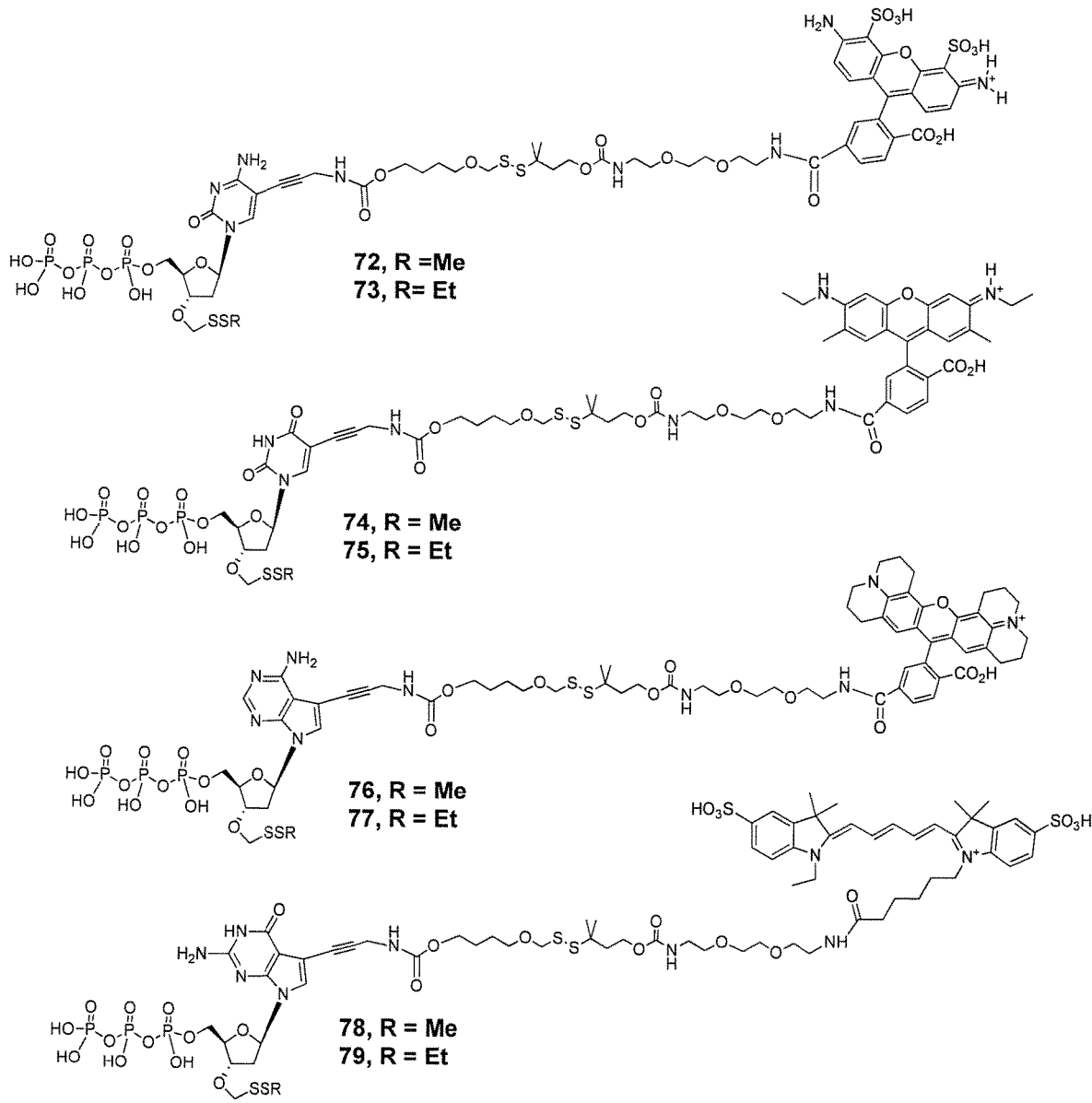
FIG. 25 shows the structure of 4-nucleotide analogues labeled by different fluorophore reporting groups, where R=Me- or Et-.
Figure 51:
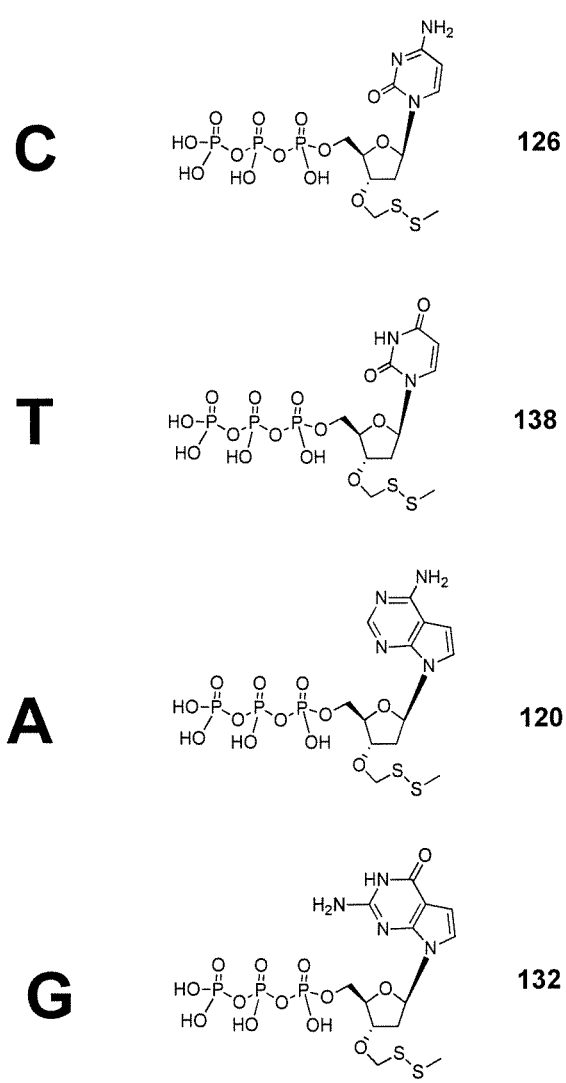
FIG. 51 shows a series of non-linker examples of nucleoside triphosphates with 3'-O capped by a group comprising methylenedisulfide methyl.
Figure 52:
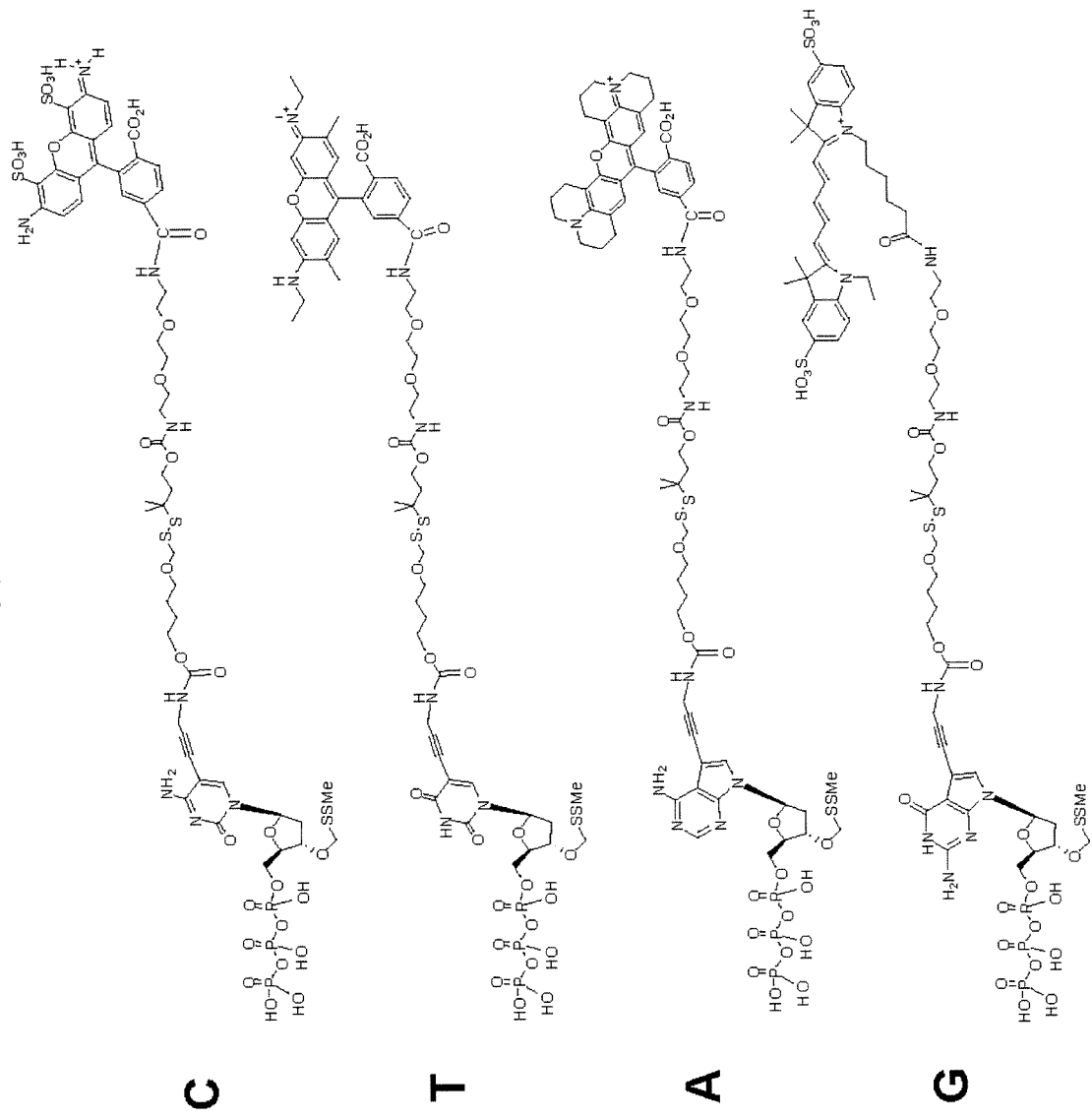
FIG. 52 shows the structure of 4-nucleotide analogues labeled by different fluorophore reporting groups with 3'-O capped by a group comprising methylenedisulfide methyl.

The present invention provides methods, compositions, mixtures and kits utilizing 5-Chloro-2-methyl-4-isothiazolin-3-one in sequencing reactions, and in particular, sequencing reactions where deoxynucleoside triphosphates comprising a 3'-O position capped by a disulfide-based 3'-terminator group are used. In one embodiment, the present invention provides methods, compositions, mixtures and kits utilizing 5-Chloro-2-methyl-4-isothiazolin-3-one together with deoxynucleoside triphosphates comprising a 3'-O position capped by group comprising methylenedisulfide as a cleavable protecting group and a detectable label reversibly connected to the nucleobase of said deoxynucleoside. Such compounds provide new possibilities for future sequencing technologies, including but not limited to Sequencing by Synthesis (SBS) and particularly automated SBS in a flow cell. The present invention contemplates, as compositions of matter, the various structures shown in the body of the specification and the figures. These compositions can be used in reactions, including but not limited to primer extension reactions. These compositions can be in mixtures. For example, one or more of the labeled nucleotides (e.g. such as those shown in FIG. 25) can be in a mixture (and used in a mixture) with one ore more unlabeled nucleotides (e.g. such as those shown in FIG. 51). They can be in kits with other reagents (e.g. buffers, polymerases, primers, etc.)

In one embodiment, the labeled nucleotides of the present invention require several steps of synthesis and involve linking variety of dyes to different bases. It is desirable to be able to perform linker and dye attachment in a modular fashion rather than step by step process. The modular approach involves pre-building of the linker moiety with protecting group on one end and activated group on the other. Such pre-built linker can then be used to couple to apropargylamine nucleotide; one can then, deprotect the masked amine group and then couple the activated dye. This has the advantage of fewer steps and higher yield as compare to step-by-step synthesis.

In one embodiment, the labeled nucleotides of the present invention are used in DNA sequencing. DNA sequencing is a fundamental tool in biology. It is a widely used method in basic research, biomedical, diagnostic, and forensic applications, and in many other areas of basic and applied research. New generation DNA sequencing technologies are changing the way research in biology is routinely conducted. It is poised to play a critical role in the coming years in the field of precision medicines, companion diagnostics, etc.

Sequencing by synthesis (SBS) is a revolutionary next-generation sequencing (NGS) technology, where millions of DNA molecules, single or cluster thereof can be sequenced simultaneously. The basis of this technology is the use of modified nucleotides known as cleavable nucleotide terminators that allow just a single base extension and detection of the DNA molecules on solid surface allowing massive parallelism in DNA sequencing (for comprehensive reviews: Cheng-Yao, Chen, Frontiers in Microbiology, 2014, 5, 1 [22]; Fei Chen, et al, Genomics Proteomics Bioinformatics, 2013, 11, 34-40 [5]; C. W. Fuller et al, Nature Biotechnology, 2009, 27, 1013 [2]; M. L. Metzker, Nature Reviews, 2010, 11, 31 [1])—all of which are hereby incorporated by reference.

Modified nucleotides, with 3'-OH positions blocked by a cleavable protecting group, which after incorporation into DNA primers and subsequent detection, can be removed by chemical reaction, are the key to the success of the SBS chemistry (Ju et al, U.S. Pat. No. 7,883,869, 2011 [23]; Ju et al, U.S. Pat. No. 8,088,575, 2012 [24]; Ju et al, U.S. Pat. No. 8,796,432, 2014 [25]; Balasubramanian, U.S. Pat. No. 6,833,246, 2004 [26]; Balasubramanian et al, U.S. Pat. No. 7,785,796B2, 2010 [27]; Milton et al, U.S. Pat. No. 7,414,116 B2, 2008 [28]; Metzker, M. L., et al, Nucleic Acids Res, 1994, 22:4259-4267 [29]; Ju et al, Proc. Nat. Acad, Sci. USA, 103 (52), 19635, 2006 [30]; Ruparel et. al, Proc. Nat. Acad, Sci. USA, 102 (17). 5932, 2005 [31]; Bergmann et al, US 201510140561 A1 [32]; Kwiatkowski, US 2002/0015961 A1 [33])—all of which are hereby incorporated by reference.

There have also been attempts to develop nucleotide analogs, known as virtual terminators, where the 3'-OH is unprotected but the bases are modified in such a manner that the modifying group prevents further extension after a single base incorporation to the DNA templates, forcing chain termination event to occur (Andrew F. Gardner et al., NucleicAcidsRes 40(15), 7404-7415 2012 [34], Litosh et al, Nuc. Acids, Res., 2011, vol 39, No. 6, e39 [35], Bowers et al, Nat. Methods, 2009, 6, 593 [36])—all of which are hereby incorporated by reference.

Also disclosed were ribo-nucleotide analogs, where the 2'-OH is protected by removable group, which prevents the adjacent 3'-OH group from participating in chain extension reactions, thereby stopping after a single base extension (Zhao et al, U.S. Pat. No. 8,399,188 B2, 2013 [37]), incorporated by reference.

On the other hand, Zon proposed the use of dinucleotide terminators containing one of the nucleotides with the 3'-OH blocked by removable group (Gerald Zon, U.S. Pat. No. 8,017,338 B2, 2011 [38]), incorporated by reference.

Previously a cleavable disulfide linker (—SS—) has been used to attach fluorescent dye in the labeled nucleotides for use in the GeneReader sequencing. It is believed that the —SH scars left behind on the growing DNA strain after cleaving step, causes a number of side reactions which limit achieving a longer read-length.

It is known that —SH residues can undergo free radical reactions in the presence of TCEP used in cleaving step, creating undesired functional group, and it potentially can damage DNA molecules (Desulfurization of Cysteine-Containing Peptides Resulting from Sample Preparation for Protein Characterization by MS, Zhouxi Wang et all, Rapid Commun Mass Spectrom, 2010, 24(3), 267-275 [39]).

The —SH scars can also interact with the incoming nucleotides inside the flow-cell cleaving the 3' OH protecting group prematurely causing further chain elongation and thereby it can cause signal de-phasing.

The end result of the detrimental side reactions of —SH is the reduction of the read-length and increased error rates in the sequencing run.

DETAILED DESCRIPTION OF THE INVENTION

The present invention provides methods, compositions, mixtures and kits utilizing 5-Chloro-2-methyl-4-isothiazolin-3-one in sequencing reactions, and in particular, sequencing reactions where deoxynucleoside triphosphates comprising a 3'-O position capped by a disulfide-based 3'-terminator group are used. The present invention provides methods, compositions, mixtures and kits utilizing 5-Chloro-2-methyl-4-isothiazolin-3-one together with deoxynucleoside triphosphates comprising a 3'-O position capped by group comprising methylenedisulfide as a cleavable protecting group and a detectable label reversibly connected to the nucleobase of said deoxynucleoside. The present invention also provides methods, compositions, mixtures and kits utilizing thiol derivatives (alternatively mercaptol analogues) as cleave agents of the disulfide based linkers and 3'-disulfide capping group of nucleotides pertinant to DNA sequencing technologies (and other technologies such as protein engineering) where the disulfide reduction or cleavage step is necessary. In one embodiment, the cleave agent is kitted as a solid powder add-on that the customer will add to the cleave pre-mix buffer according to sequencing workflow instructions. Moreover, the present invention provides embodiments where the thiol-containing compounds are scavenged with an oxidative wash step. Such compounds provide possibilities for use in future sequencing technologies, including but not limited to Sequencing by Synthesis (SBS), including automated SBS in a flow cell.

Figure 1:
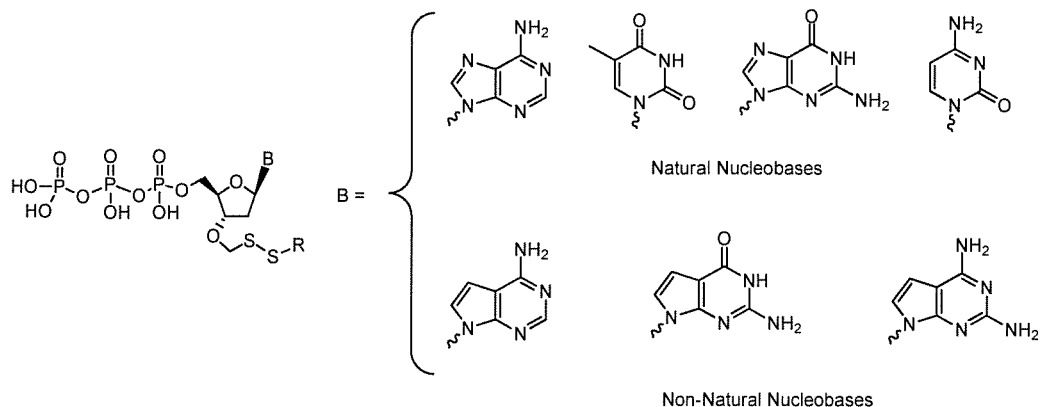
FIG. 1 shows examples of nucleoside triphosphates with 3'-O capped by a group comprising methylenedisulfide, where the R represents alkyl group such as methyl, ethyl, isopropyl, t-butyl, n-butyl, or their analogs with substituent group containing hetero-atoms such as O, N, S etc.

The present invention, in one embodiment involves the synthesis and use of a labeled nucleoside triphosphates comprising a cleavable oxymethylenedisulfide linker between the label and nucleobase, with a 3'-O group comprising methylenedisulfide as a protecting group, having the formula —CH$_2$—SS—R, in DNA sequencing (e.g. sequencing by synthesis), where the R represents alkyl group such as methyl, ethyl, isopropyl, t-butyl, n-butyl, or their analogs with substituent group containing hetero-atoms such as O, N, S etc (see FIG. 1). In one embodiment, the R group may contain a functional group that could modulate the stability and cleavability of the 3'-O capping group, while being acceptable to DNA polymerase enzymes.

In another aspect, the invention relates to a labeled nucleoside triphosphates comprising a cleavable oxymethylenedisulfide linker between the label and nucleobase, with 3'-O positions capped by a group comprising methylenedisulfide wherein the nucleobases can be natural, or non-natural bases which can form DNA duplex by hydrogen bond interactions with natural nucleobases of the DNA templates, and that can be 7-deaza analog of dG and dA, and 2-amino-dA. 7-deaza analogs of dA and dG can reduce the formation of DNA tertiary structures due to the lack of 7-N atom. It is envisioned that in one embodiments, such nucleosides could potentially improve DNA sequencing read-length by enhancing DNA templates and polymerase interaction. It may also be possible that the 2-amino-dA can increase DNA duplex stability due to its ability to form more stable 3 hydrogen bonds with its complimentary base (rather than 2 bond in natural state), therefore, it can reduce the risk of losing DNA primers during sequencing run (A Jung et all, Mol. Pathol., 2002, 55 (1), 55-57 [40]; 2-amino-dATP: Igor V. Kutyavin, Biochemistry, 2008, 47(51), 13666-73 [41]).

In another embodiment, said nucleotides may have detectable reporter molecules, such as fluorescent dyes linked to nucleobases via cleavable linker —OCH$_2$SS—. Labeled nucleotides, where the —OCH$_2$—SS— group is directly attached to the nucleobases and the use thereof as cleavable linker are not known in prior-art. Contrary to the traditional, widely used disulfide linkers (—SS—), this class of cleavable linker (—OCH$_2$—SS—) leaves no sulfur trace on the DNA molecule, cleanly converting it to —OH group by rapid hydrolysis of the resulting intermediate, —OCH$_2$—SH, after reductive cleavage. Because of this, such linkers may be better alternatives to the traditional disulfide linkers. In traditional disulfide based linkers (—SS—), the resulting thiol group (—SH) can undergo side reactions when cleaved by reducing reagents such as TCEP as presented in the following FIG. 4 (Ref: Desulfurization of Cysteine-Containing Peptides Resulting from Sample Preparation for Protein Characterization by MS, Zhouxi Wang et all, Rapid Commun Mass Spectrom, 2010, 24(3), 267-275 [39]).

In another embodiment, the reporter groups may be attached to the pyrimidine bases (dT, dC) at 5-C position and to purine bases (dA, dG) at 7-N of natural bases, or 7-C of de-aza analogs.

Figure 5:
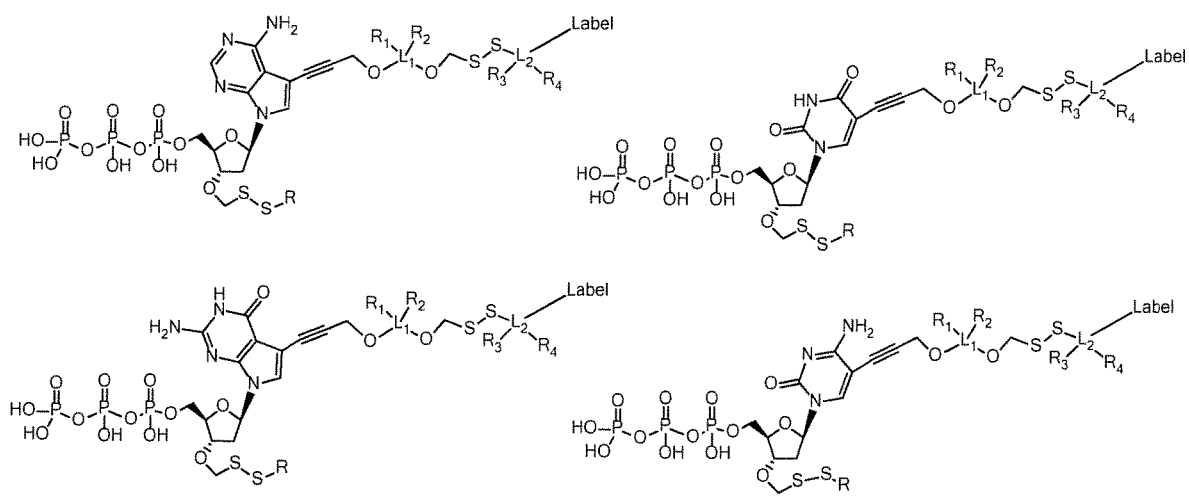
FIG. 5 shows an example of the labeled nucleotides where the spacer of the cleavable linker includes the propargyl ether linker. The analogs are (clockwise from the top left) for Deoxyadenosine, Thymidine or Deoxyuridine, Deoxycytidine and Deoxyguanosine.

In another embodiment, the structure of the labeled nucleotides may be as shown in FIG. 5, where the spacer of the cleavable linker includes the propargyl ether linker. The nucleobases with progargyl ether can be synthesized following prior arts of chemical synthesis. The $L_1$ and $L_2$ represent chemical spacers, and substituents $R_1$, $R_2$, $R_3$ and $R_4$ are group of atoms that modulate stability and cleavability to the cleavable linker. They can be hydrogen atom, geminal dimethyl, or any alkyl, phenyl, or substituted alkyl group, such as methyl, ethyl, n-butyl, phenyl, etc. They may also contain a hydrocarbon chain with O—, =O, NH, —N—N, acid, amide, poly ethyleneglycol chain (PEG) etc. The label on the nucleotides may be fluorescent dyes, energy transfer dyes, radioactive label, chemi-luminiscence probe, heptane and other form of label that allows detection by chemical or physical methods.

Figure 6:
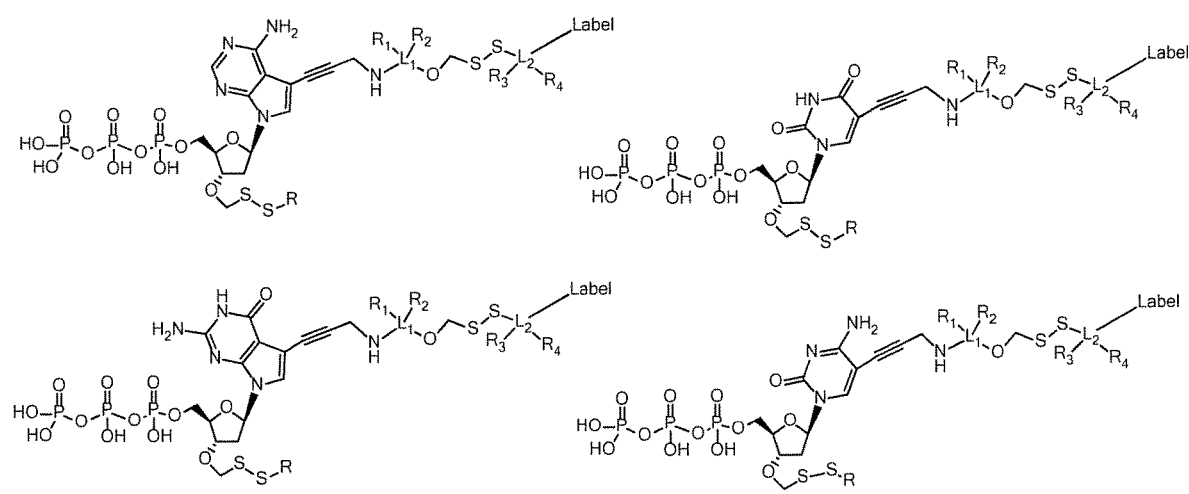
FIG. 6 shows an example of the labeled nucleotides where the spacer of the cleavable linker includes the propargylamine linker. The analogs are (clockwise from the top left) for Deoxyadenosine, Thymidine or Deoxyuridine, Deoxycytidine and Deoxyguanosine.
Figure 42:
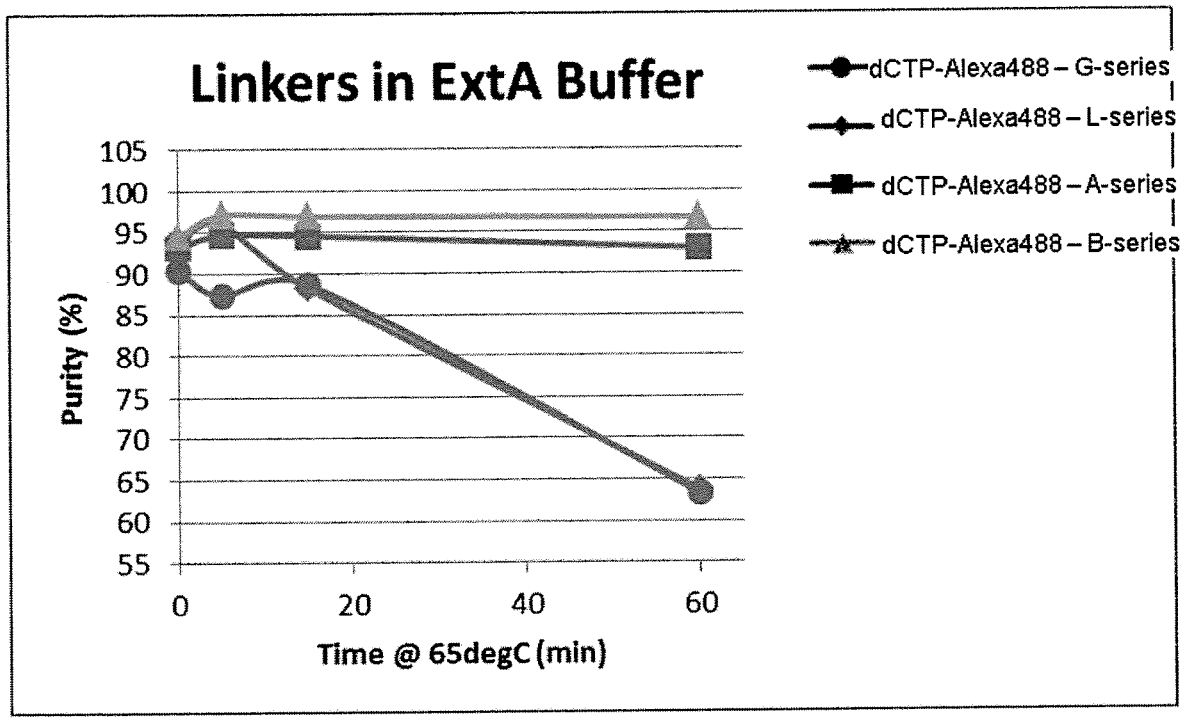
FIG. 42 shows a comparison of stability at elevated temperature in Extend A buffer of labeled, reversibly terminating dC with various cleavable linkers: B=B-series (97, 116, 117, and 118), G=G-series (99, 103, 104, and 105), A=A-series (98, 100, 101, and 102), and SS=L-series (96, 50, 106, and 115).

In another embodiment, the structure of the labeled nucleotides may be as shown FIG. 6. The spacers of the cleavable linker include the propargylamine linker. Again, the $L_1$ and $L_2$ represent spacers, and substituents $R_1$, $R_2$, $R_3$ and $R_4$ are group of atoms that provide stability and modulate cleavability of the linker as described earlier. They may be hydrogen atoms, alkylgroups such as methyl, ethyl and other substituted groups or their salts. Geminal dialkyl group on the α-carbon of the cleavable disulfide linker (e.g. germinal dimethyl analogue according to the following structure:

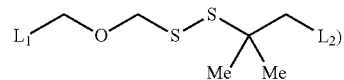

provides better stability to the linker allowing modular synthesis of labeled nucleotides. It presumably prevents disproportional reactions prevalent among disulfide based organic compounds. It also adds greater hydrophobicity to the linker which helps the synthesis and purification of labeled nucleotide analogues [42-44]. The gem dimethyl functionality present in the linker is believed to not only serve to stabilize the disulfide bond electronically, but also prevents disulfide exchange from occurring both inter- and intra-molecularly, likely via sterric effects. It has been demonstrated that in the presence of cystamine, the disulfide functionality on the terminator participates in disulfide exchange, while linkers equipped with gem dimethyl groups do not. The linker study in FIG. 42 compares linkers with and without the gem dimethyl group. As can be seen from this study, linkers G and L without the gem dimethyl group quickly exchange with cystamine leading to degradation of the product. As expected, this phenomenon is not observed with our chosen linker A, nor with analogous linker B. In addition, since the labelled nucleotides contain two disulfides, one on the terminator and one on the linker portion of the molecule, it is believed that this stabilizing effect prevents scrambling between the dye and the terminator from occurring. This stability is important to performance of our nucleotides in sequencing.

Figure 7:
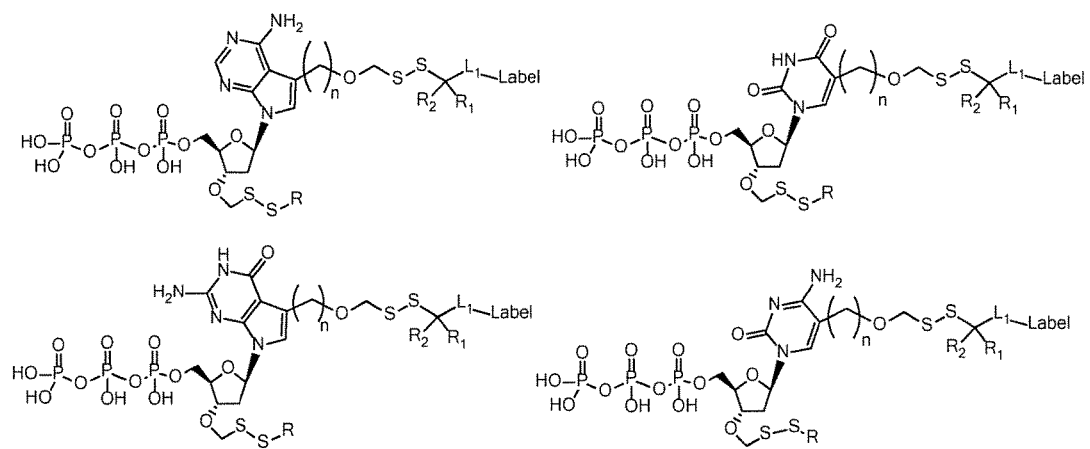
FIG. 7 shows an example of the labeled nucleotides where the spacer of the cleavable linker includes the methylene $(-(CH_2)_n-$ directly attached to the nucleobases at 5-position for pyrimidine, and at 7-de-aza-carbon for purines. This linker may be methylene (n=1) or polymethylene (n>1) where after cleavage, the linker generates $-(CH_2)_n OH$ group at the point of attachment on the nucleobases, and where the $L_1$ and $L_2$ represent spacers, and substituents $R_1$, $R_2$, $R_3$ and $R_4$ are group of atoms that provide stability to the cleavable linker as described earlier. The analogs are (clockwise from the top left) for Deoxyadenosine, Thymidine or Deoxyuridine, Deoxycytidine and Deoxyguanosine.

In another embodiment, the structure of the labeled nucleotides may be as in FIG. 7. The spacer of the cleavable linker include the methylene (—$(CH_2)_n$— directly attached to the nucleobases at 5-position for pyrimidine, and at 7-de-aza-carbon for purines. This linker may be methylene (n=1) or polymethylene (n>1) where after cleavage, the linker generates —$(CH_2)_n$OH group at the point of attachment on the nucleobases, and where the $L_1$ and $L_2$ represent spacers, and substituents $R_1$, $R_2$, $R_3$ and $R_4$ are group of atoms that provide stability to the cleavable linker as described earlier.

Figure 8:
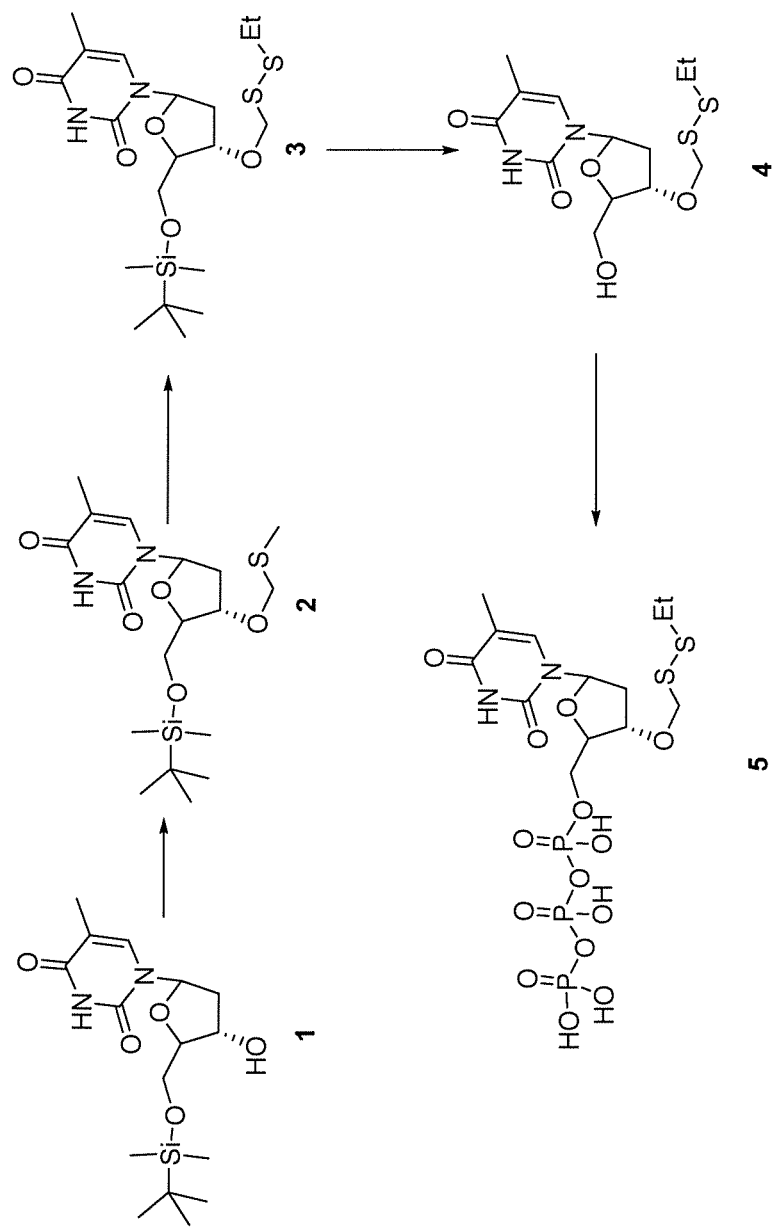
FIG. 8 shows a synthesis of the unlabeled dT analog (compound 5).

In another embodiment, the invention relates to synthetic methods for the nucleotides claimed. The capping group and linker may be synthesized modifying prior arts described For example, the unlabeled dT analog (compound 5) can be synthesized as shown in FIG. 8.

In one embodiment the invention involves: (a) nucleoside triphosphates with 3'-O capped by a group comprising methylenedisulfide (e.g. of the formula —$CH_2$—SS—R) as a cleavable protecting group (see FIG. 1); and (b) their labeled analogs (see FIG. 2), where labels are attached to the nucleobases via a cleavable oxymethylenedisulfide linker (—$OCH_2$—SS—). Such nucleotides can be used in nucleic acid sequencing by synthesis (SBS) technologies. General methods for the synthesis of the nucleotides claimed are also described.

In one embodiment, as shown in FIG. 1, the general structures of unlabeled nucleotides have the 3'-O group protected by a group comprising methylenedisulfide with a common structure —$CH_2$—SS—R, where the R can be regular alkyl or substituted alkyl groups such as -Me, -Et, -nBu, -tBu, —$CH_2CH_2NH_2$, —$CH_2CH_2NMe$ etc., and B, can be natural or non-natural nucleobases. Some specific examples of non-natural nucleobases are 7-deaza dG and dA, 2-amino-dA etc.

Figure 2:
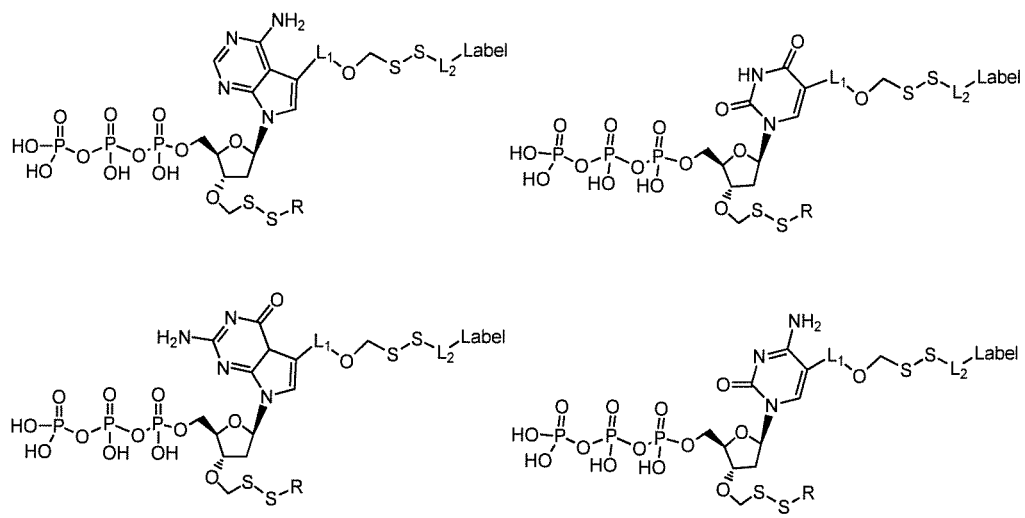
FIG. 2 shows labeled analogs of nucleoside triphosphates with 3'-O methylenedisulfide-containing protecting group, where labels are attached to the nucleobase via cleavable oxymethylenedisulfide linker (—OCH$_2$—SS—). The analogs are (clockwise from the top left) for Deoxyadenosine, Thymidine or Deoxyuridine, Deoxycytidine and Deoxyguanosine.

In FIG. 2, the general structures of labeled analogs are shown with 3'-O protected by a group comprising methylenedisulfide as in FIG. 1, in addition to that a detectable reporter (label) such as fluorophore is attached to the nucleobases via a cleavable linker having a general structure -$L_1$-$OCH_2$—SS-$L_2$-. $L_1$ represents molecular spacer that separates nucleobase from the cleavable linker, while $L_2$ between cleavable linker and the label, respectively. Both $L_1$ and $L_2$ can have appropriate functional groups for connecting to the respective chemical entities such as —CO—, —CONH—, —NHCONH—, —O—, —S—, —C=N, —N=N—, etc. The label may be fluorophore dyes, energy transfer dyes, mass-tags, biotin, haptenes, etc. The label may be different on different nucleotides for detection of multiple bases simultaneously, or the same for step-wise detection of spatially separated oligonucleotides or their amplified clones on solid surface.

In one embodiment, the invention relates to a new class of nucleotide that has 3'-O capped with —$CH_2$—SS—R group and a label attached to the nucleobase through a cleavable linker having a general structure —O—$CH_2$—SS—. Such capping group and linker can be cleanly cleaved simultaneously by single treatment with TCEP or related chemicals leaving no sulfur traces on the DNA molecules.

This class of nucleotides may be stable enough to endure the relatively high temperature (~65° C.) necessary for nucleotide incorporation onto the DNA templates catalyzed by thermo active polymerases, yet labile enough to be cleaved under DNA compatible conditions such as reduction with TCEP etc. In some embodiments, cleavage may be accomplished by exposure to dithiothreitol.

Figure 3:
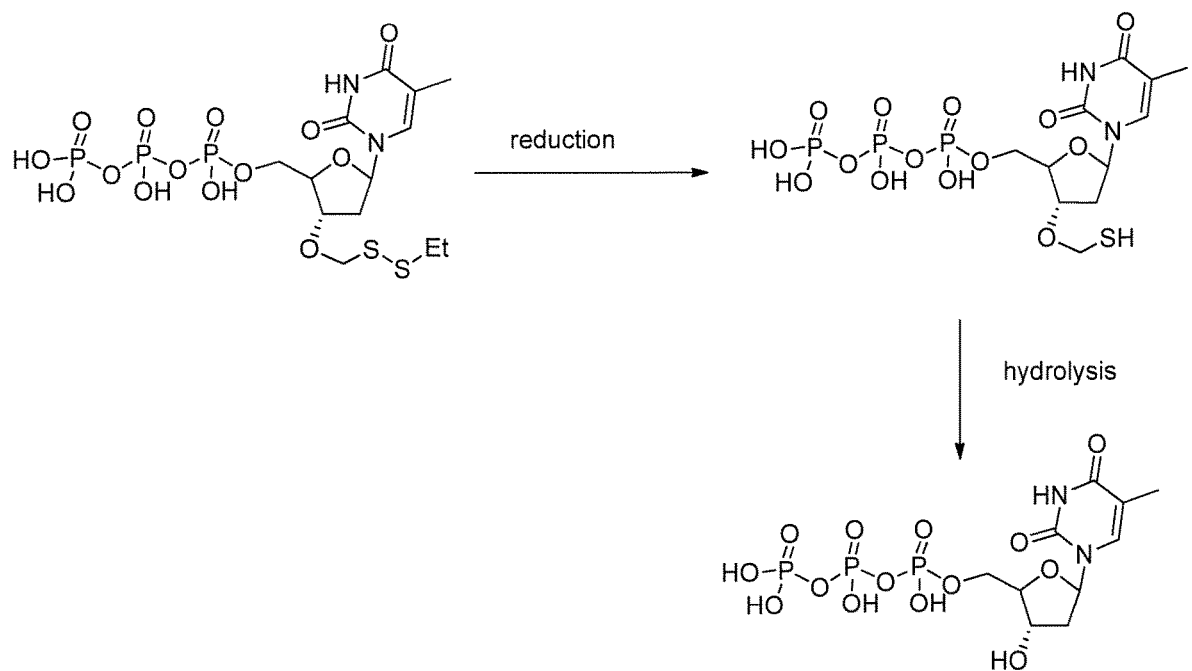
FIG. 3 shows a step-wise mechanism of deprotection of the 3'-o protection group with a reducing agent, such as TCEP.

The nucleotide when exposed to reducing agents such as TCEP de-cap the 3'-o protection group via step-wise mechanism shown in FIG. 3, thus restoring the natural state of the 3'-OH group. TCEP and its analogs are known to be benign to bio-molecules which is a pre-requisite for application in SBS.

Figure 28:
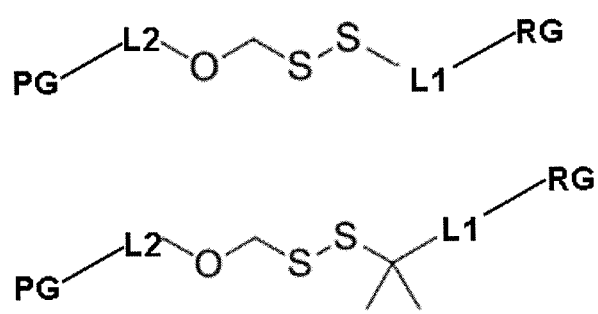
FIG. 28 shows Generic universal building blocks structures comprising new cleavable linkers of present invention. PG=Protective Group, L1, L2—linkers (aliphatic, aromatic, mixed polarity straight chain or branched). RG=Reactive Group. In one embodiment of present invention such building blocks carry an Fmoc protective group on one end of the linker and reactive NHS carbonate or carbamate on the other end. This preferred combination is particularly useful in modified nucleotides synthesis comprising new cleavable linkers. A protective group should be removable under conditions compatible with nucleic acid/nucleotides chemistry and the reactive group should be selective. After reaction of the active NHS group on the linker with amine terminating nucleotide, an Fmoc group can be easily removed using base such as piperidine or ammonia, therefore exposing amine group at the terminal end of the linker for the attachment of cleavable marker. A library of compounds comprising variety of markers can be constructed this way very quickly.

In one embodiment, the invention relates to a generic universal building blocks structures comprising new cleavable linkers, shown in FIG. 28. PG=Protective Group, L1, L2—linkers (aliphatic, aromatic, mixed polarity straight chain or branched). RG=Reactive Group. In one embodiment of present invention such building blocks carry an Fmoc protective group on one end of the linker and reactive NHS carbonate or carbamate on the other end. This preferred combination is particularly useful in modified nucleotides synthesis comprising new cleavable linkers. A protective group should be removable under conditions compatible with nucleic acid/nucleotides chemistry and the reactive group should be selective. After reaction of the active NHS group on the linker with amine terminating nucleotide, an Fmoc group can be easily removed using base such as piperidine or ammonia, therefore exposing amine group at the terminal end of the linker for the attachment of cleavable marker. A library of compounds comprising variety of markers can be constructed this way very quickly.

Figure 29:
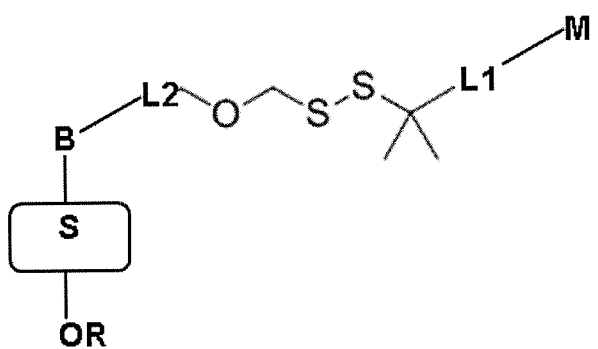
FIG. 29 shows generic structure of nucleotides carrying cleavable marker attached via novel linker of present invention. S . . . sugar (i.e., ribose, deoxyribose), B=nucleobase, R=H or reversibly terminating group (protective group). Preferred reversibly terminating groups include but are not limited to: Azidomethyl (—CH_2N_3), Dithio-alkyl (—CH2—SS—R), aminoxy (—ONH_2).
Figure 30:
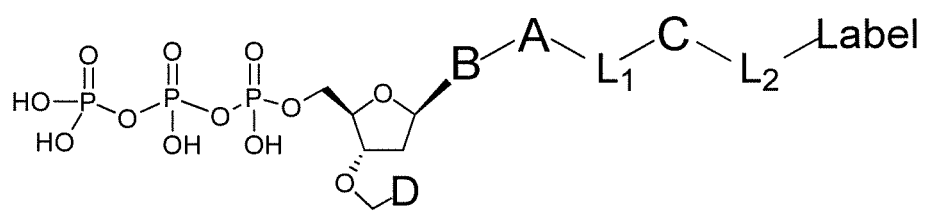
FIG. 30 shows another generic structure for nucleotides carrying cleavable marker attached via the cleavable linker of present invention, wherein D is selected from the group comprising an azide, disulfide alkyl and disulfide substituted alkyl groups, B is a nucleobase, A is an attachment group, C is a cleavable site core, $L_1$ and $L_2$ are connecting groups, and Label is a label (in the compounds with a label).
Figure 31:
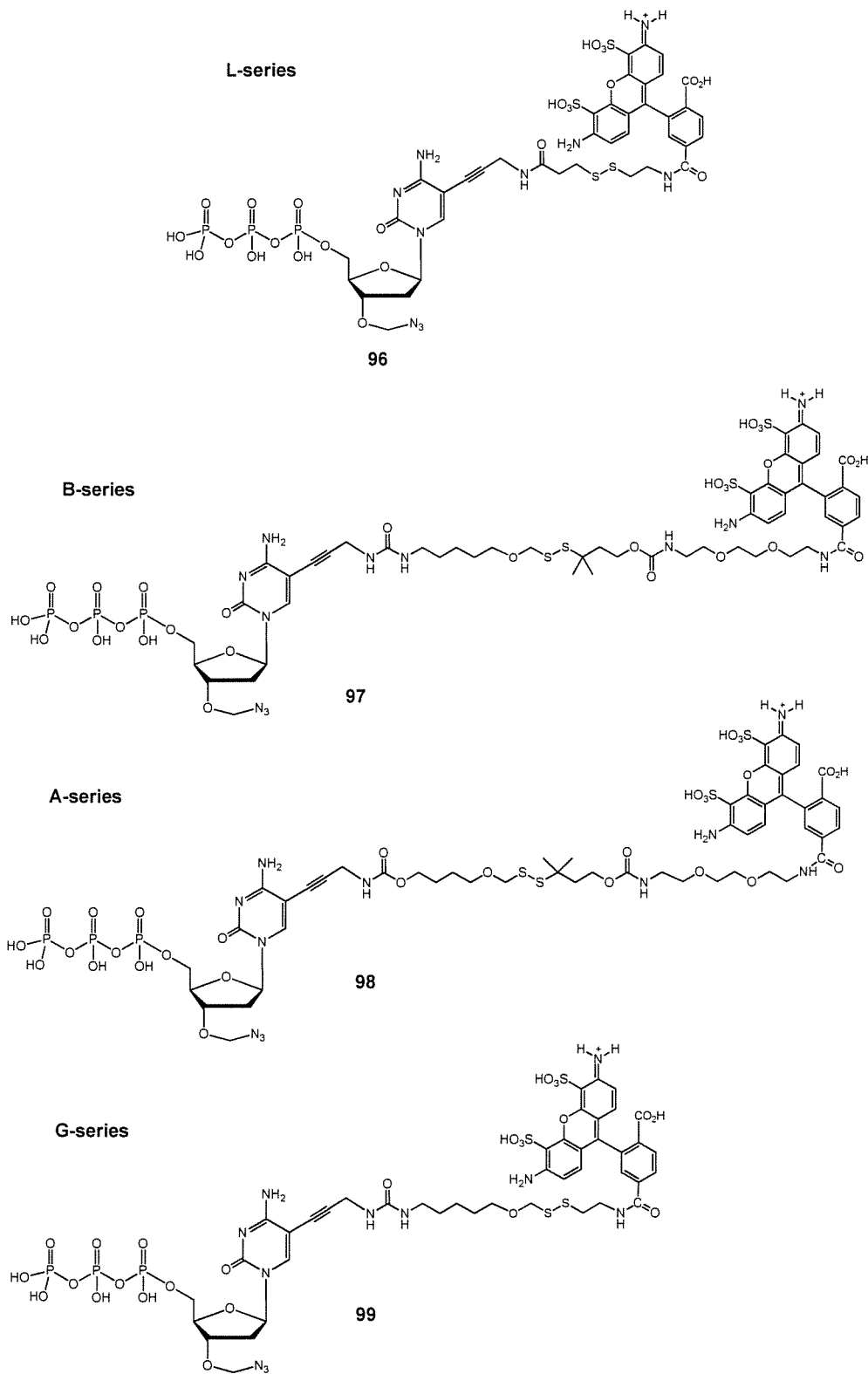
FIG. 31 shows the chemical structures of compounds (L-series (96), B-series (97), (A-series, (98), and (G-series (99) family) tested in FIG. 32A-C.
Figures 32A, 32B, 32C:
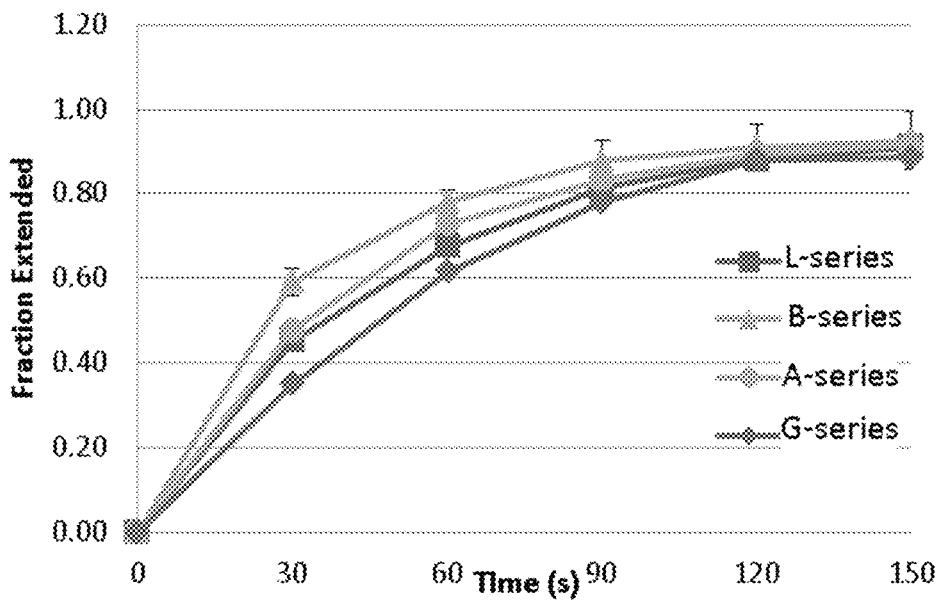
FIG. 32A shows a time course of incorporation of 3'-O-azidomethyl Alexa488 labeled nucleotide analogs with various disulfide based cleavable linkers: L-Series (96), B-series (97), A-series (98), and G-series (99) family.
FIG. 32B shows reaction rates of incorporation for 3'-O-azidomethyl Alexa488 labeled nucleotide analogs with various disulfide based cleavable linkers: L-series (96), B-series (97), A-series (98), and G-series (99) family.
FIG. 32C shows reaction rates of incorporation for 3'-O-azidomethyl Alexa488 labeled nucleotide analogs with various disulfide based cleavable linkers: L-series (96), B-series (97), A-series (98), and G-series (99) family vs concentration of nucleotides.
Figure 34:
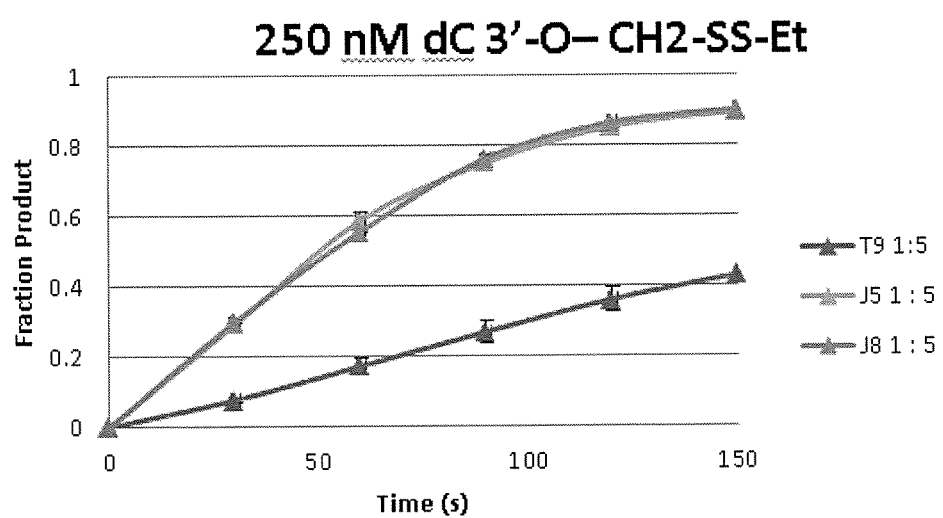
FIG. 34 shows incorporation kinetics of dC 3'-reversibly terminating nucleotide with 3'-O—$CH_2$—SS-Et terminating group with 3 different DNA polymerases: T9, J5 and J8.
Figure 36:
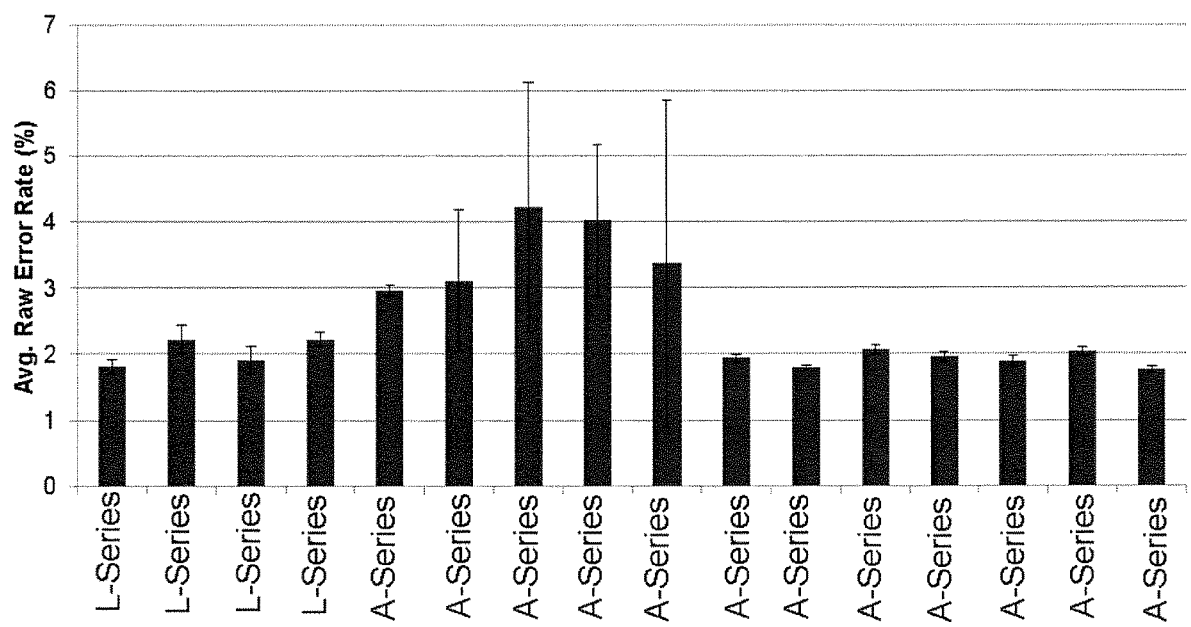
FIG. 36 shows sequencing performance of A-series (98) nucleotides as measured by raw error rate.
Figure 37:
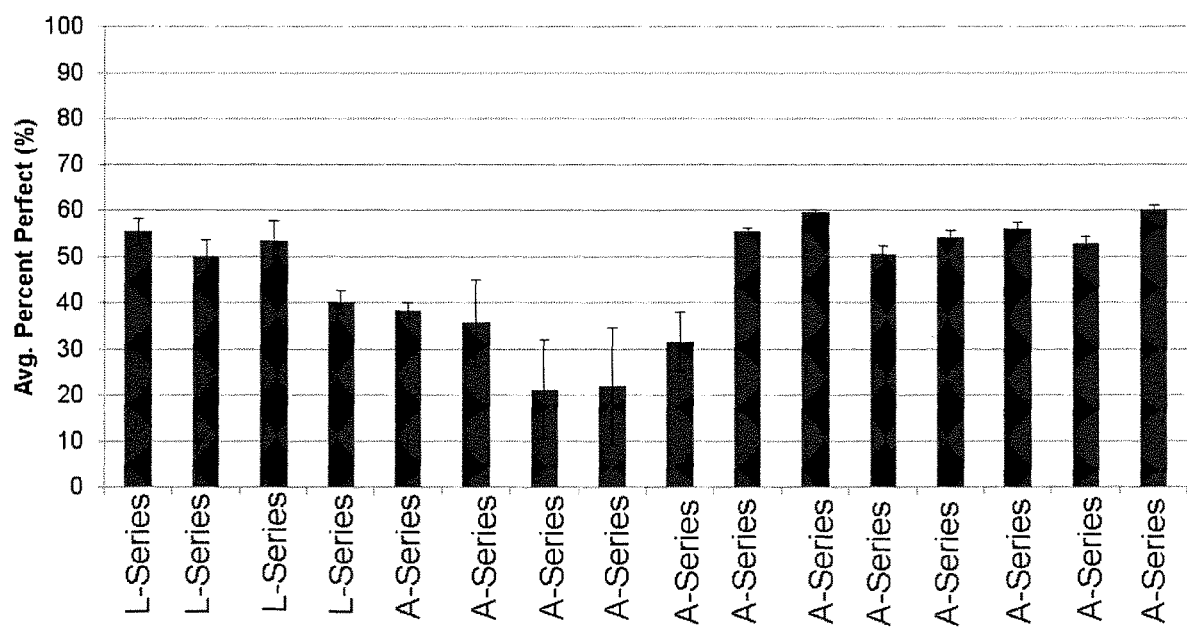
FIG. 37 shows sequencing performance of A-series (98) nucleotides as measured by percentage of perfect (error free) reads.
Figure 38:
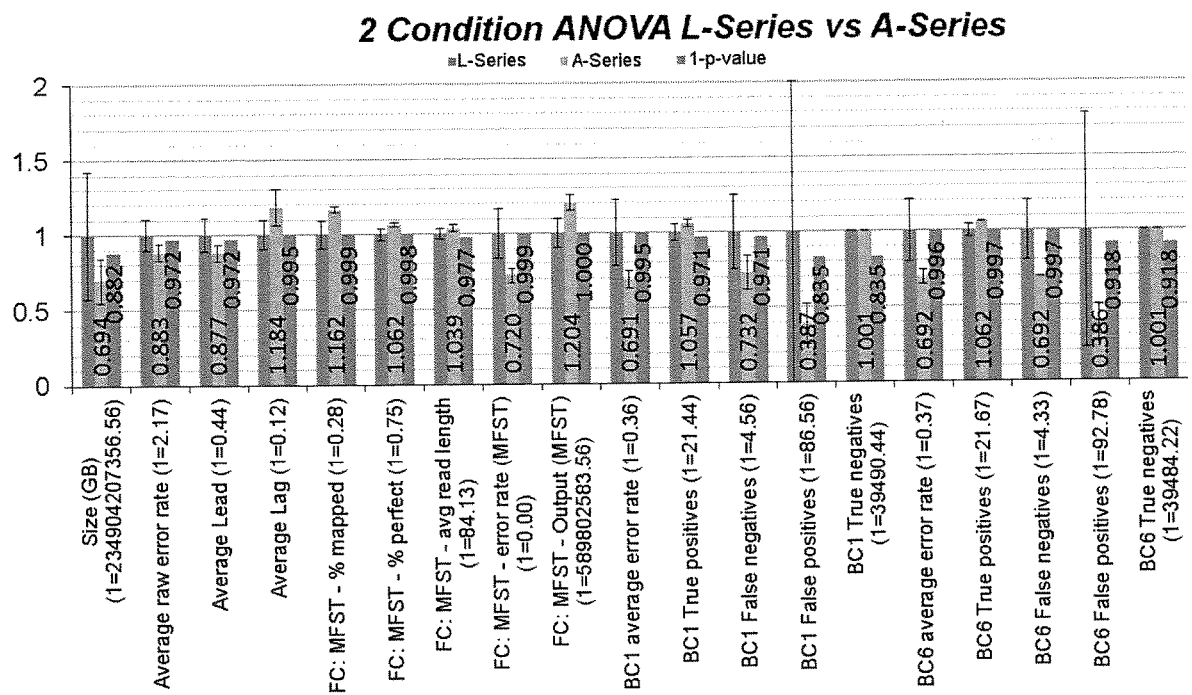
FIG. 38 shows sequencing performance of A-series (98) nucleotides as measured by variety of sequencing metrics.
Figure 39:
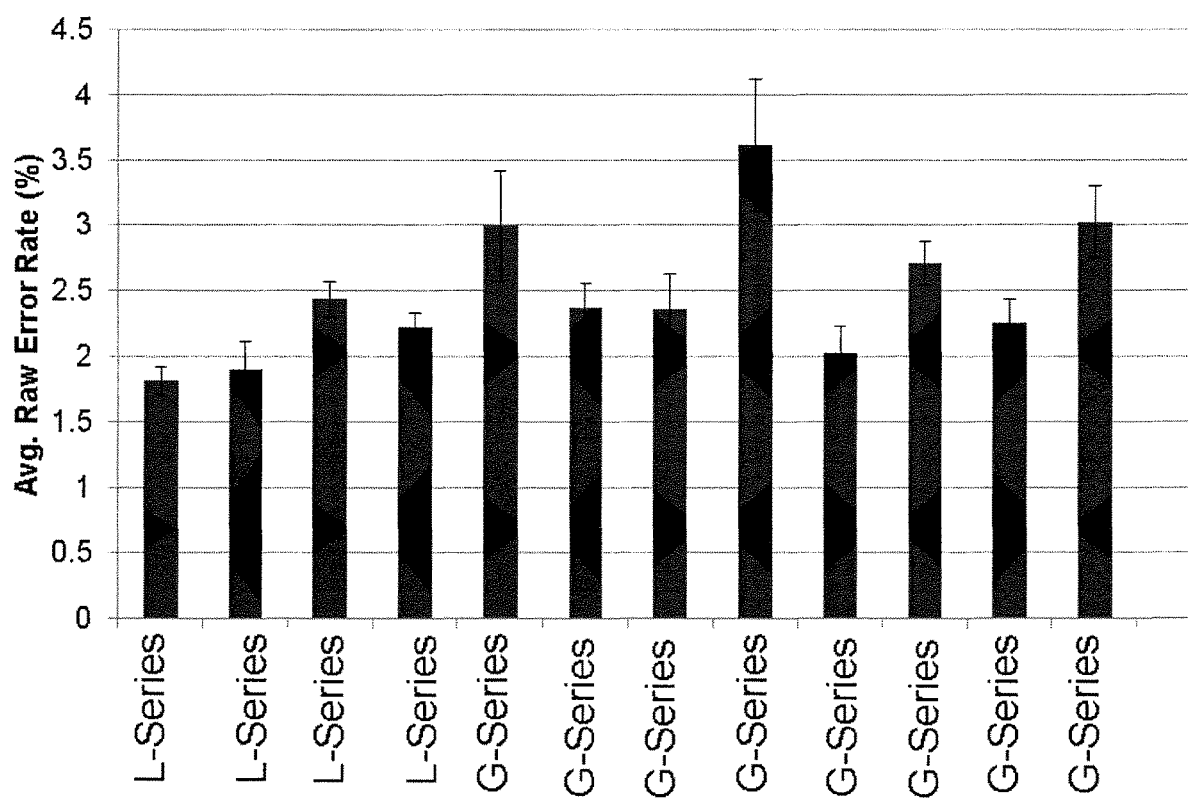
FIG. 39 shows sequencing performance of G-series (99) nucleotides as measured by raw error rate.
Figure 40:
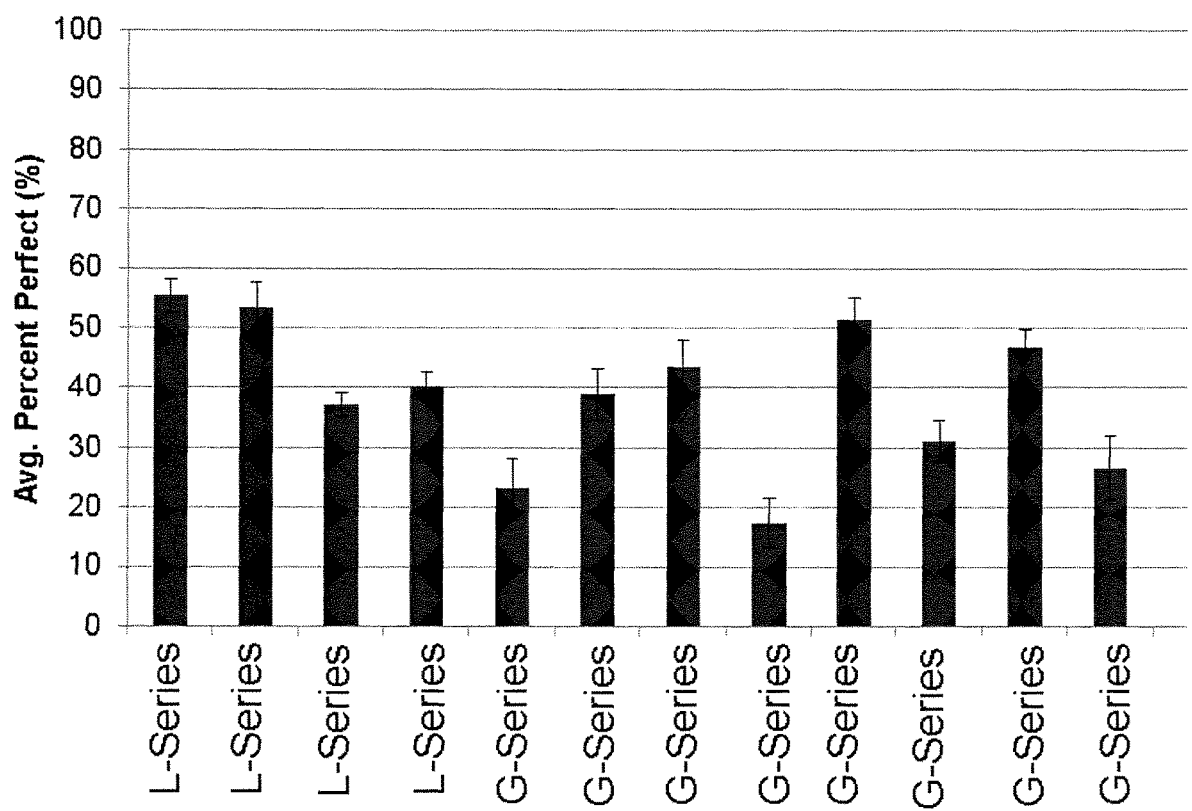
FIG. 40 shows sequencing performance of G-series (99) nucleotides as measured by percentage of perfect (error free) reads.

In one embodiment, the invention relates to a generic structure of nucleotides carrying cleavable marker attached via novel linker, shown in FIG. 29. S=sugar (i.e., ribose, deoxyribose), B=nucleobase, R=H or reversibly terminating group (protective group). Preferred reversibly terminating groups include but are not limited to: Azidomethyl (—$CH_2N_3$), Dithio-alkyl (—$CH_2$—SS—R), aminoxy (—$ONH_2$).

In one embodiment, the present invention contemplates a thiol reagent comprising at least two or more thiol groups either at a vicinal position (e.g., n1=1) or separated by at least one hydrocarbon bond (e.g., n1=>1), which further attached to anionic functional group (R) with hydrocarbon spacer (e.g., n2=>1). See, FIG. 79.

In one embodiment, the present invention contemplates compounds with a thiol group (—SH) that is adjacent to a functional group (R1) including, but not limited to, a halogen, an amine, a phosphate, a phosphonate, a phosphoric acid, a carboxylic acid, a sulfoxide and/or a hydoxyl etc., which could modulate the pKa of the functional group. See, FIG. 80.

DNA sequencing plays a role as a useful analytical tools in modern biotechnology. For example, new generation DNA sequencing (NGS) is revolutionizing in the studies of genetics, diagnostics and basic biomedical research. Detailed reviews on current NGS technologies are provided in M. L. Metzker, Nature Reviews 2010, 11, 31, and C. W. Fuller et al., Nature Biotechnology 2009, 27, 1013.

One well-known sequencing method is the sequencing-by-synthesis (SBS) where many DNA templates comprising nucleoside triphosphates are sequenced simultaneously during enzymatic synthesis of complementary strains of DNA molecules. According to this method, the nucleoside triphosphates are reversibly blocked by a 3'-OH-protecting group including, but not limited to, acetyl, phosphates, carbonates, azidomethyl, nitro etc. In one embodiment, the nucleoside triphosphate comprises a label at the base via a cleavable linker.

Although it is not necessary to understand the mechanisms of an invention, it is believed that sequencing-by-synthesis (SBS) largely depends on an ability to achieve a longer read length and a better accuracy. It is also believed that the use of a 3'-OH capping group and a cleavable linker can be removed under DNA compatible conditions. For example, the present invention contemplates reversible nucleotide terminators where a 3'-OH group is capped with alkyl methylenedisulfide (e.g., R—SS—$CH_2$—) and a cleavable linker having the same functional moiety (e.g., —OCH2-SS—). For simultaneous cleavage of both, a DNA compatible cleave reagent is preferred. Unfortunately, many reducing agents are detrimental to DNA molecules and often are too harsh to the solid surface of the flow cell, and difficult to wash away from the flow-cell.

There are a number of reducing agents are known to cleave disulfide bonds. Examples include, but are not limited to, TCEP, DTT, glutathione, borohydride etc. These reducing agents are widely used in protein engineering and anti-body chemistry. But such compounds can also have certain limitations not only due to slower reaction rate, but also difficulty in complete removal in a wash step from the flow cell when applied to NGS. Further, the reducing power of thiol-based compounds depends on the pH of the medium. It is known that at higher pH, the thiol group (RSH) undergoes ionization to form thiolate (RS—), which can speed up the reaction rate, by many times. But at higher pH, DNA molecules and the surface can undergo hydrolytic damage, thereby limiting its application. Therefore, in one embodiment, thiol compounds that can reduce disulfide at reduced pH, so that it is compatible to both DNA and the flowcell surface, are preferred for application in SBS chemistry.

Figure 80:
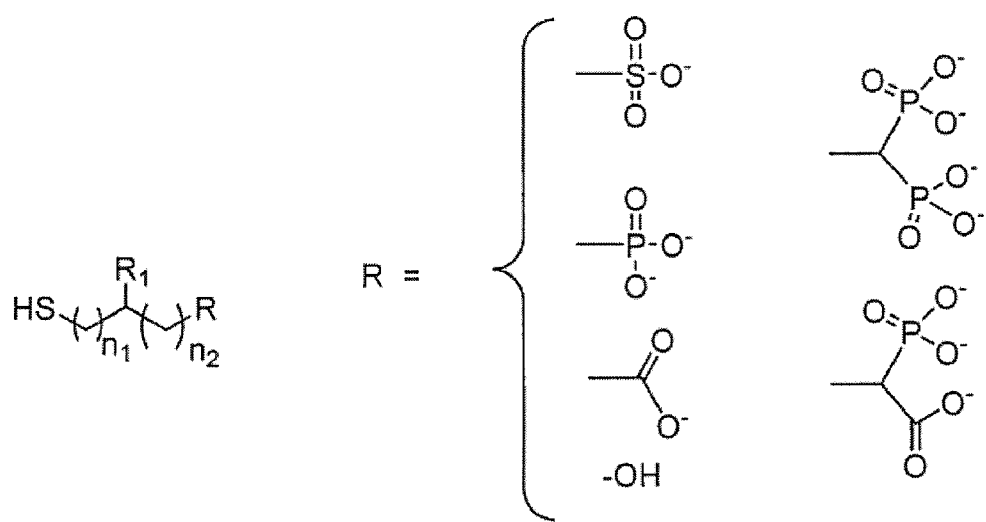
FIG. 80 presents exemplary a thiol compound comprising a functional group at an adjacent hydrocarbon.
Figure 81:
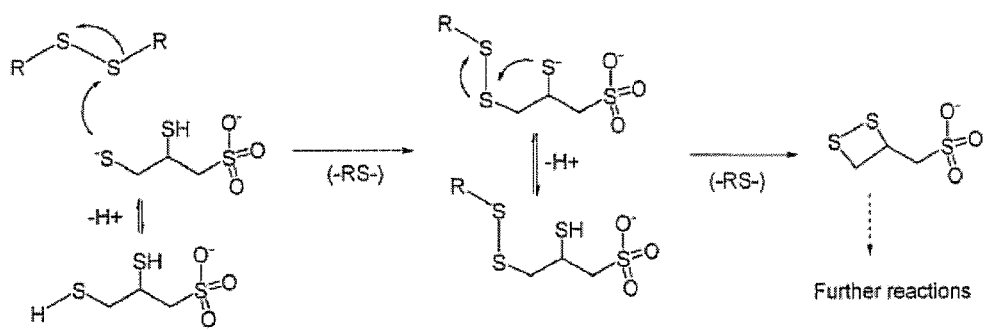
FIG. 81 presents an exemplary mechanism of disulfide bond reduction by 2,3-dimercaptopropanedulfonate (DMPS).

Although it is not necessary to understand the mechanism of an invention, it is believed that the thiol compounds shown in FIGS. 79 and 80 can undergo ionization to form thiolate at a relatively low pH due to the presence of adjacent functional group (i.e., for example, adjacent —SH and electron-withdrawing R1) via neighboring group participation. Consequently, they could reduce the disulfide bonds at relatively lower pH and can have increased reaction rate than those of standard thiols. Furthermore, the neighboring group participation of thiol at an α-position via anchimeric assistance can speed up the second step of the reduction process due to formation of intra-molecular disulfide bond. See, FIG. 81, as shown in FIG. 3. This reaction is not believed to undergo a nucleophilic attack by another thiol molecule to form sulfide molecule as currently believed in the art. "Thioldisulfide interchange, The Chemistry of Sulphur Containing Functional Group" Chapter 13, p 633-658, by Rajeeva Singh and George M. Whitesides). Due to negatively charged pending group (R=sulfonate, phosphonate, carboxylate etc) it is believed that molecules are expected to be non-sticky to the surface, thereby making them easily washable from the flow-cell. The data herein presents a cleavage study of a 3' disulfide capped with an attached disulfide linker with thiol-based compounds that showed a complete cleavage of both the capping group and the linker in less than ten (10) minutes at 65° C. in TRIS buffer (pH 8.5). Interestingly, the complete cleavage was not observed in the presence of dithiosuccinate. See, FIG. 82 and Table 1.

TABLE 1

Dithiol Compound Cleavage Of Nucleosides

| Cleaving Agent | Reaction Conditions | Time & Temperature | Compound A [%] | Compound B [%] | Compound C [%] |
|---|---|---|---|---|---|
| Dithiosuccinic acid | Compound A- 0.2 mM, Cleave agent- 20 mM, buffer- 200 mM TE, pH 8.5 | 10 min @ 65 degree C. | 0 | 50 | 50 |
| Dimercaptopropanesulfonate | | | 0 | 0 | 100 |
| L-Cysteine | | | 0 | 0 | 100 |
| DTT | | | 0 | 0 | 100 |
| Cysteamine | | | 0 | 0 | 100 |

Figure 82:
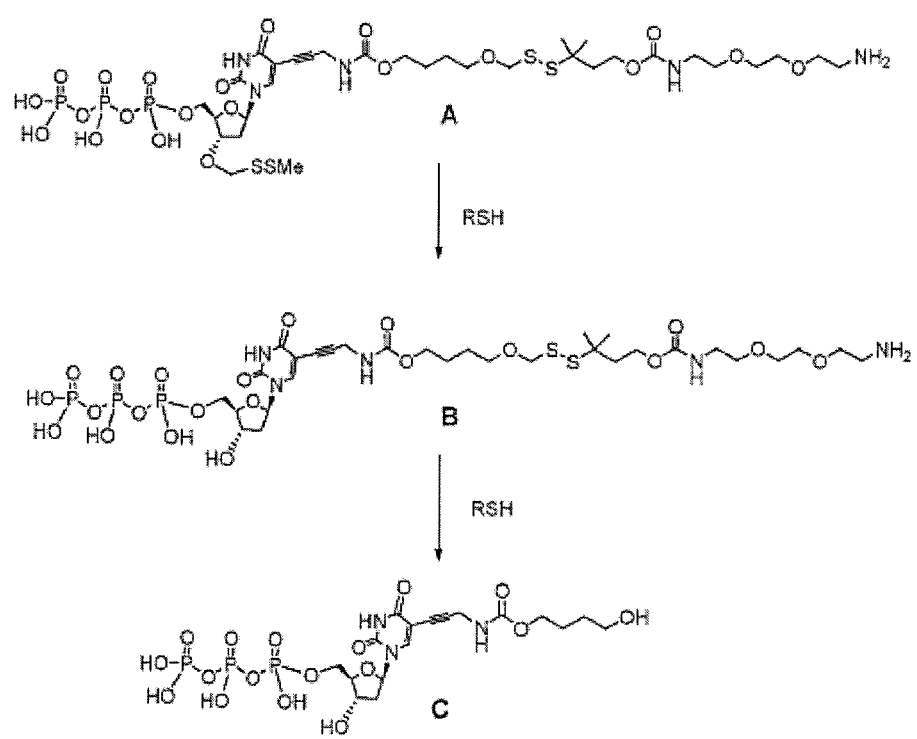
FIG. 82 presents one embodiment of the present invention showing cleavage of 3'-(MeSSCH2) capped nucleotide with attached disulfide linker by thiol based cleave reagents (the LC-MS data for Compounds A, B and C is shown in FIG. 84).
Figure 84:
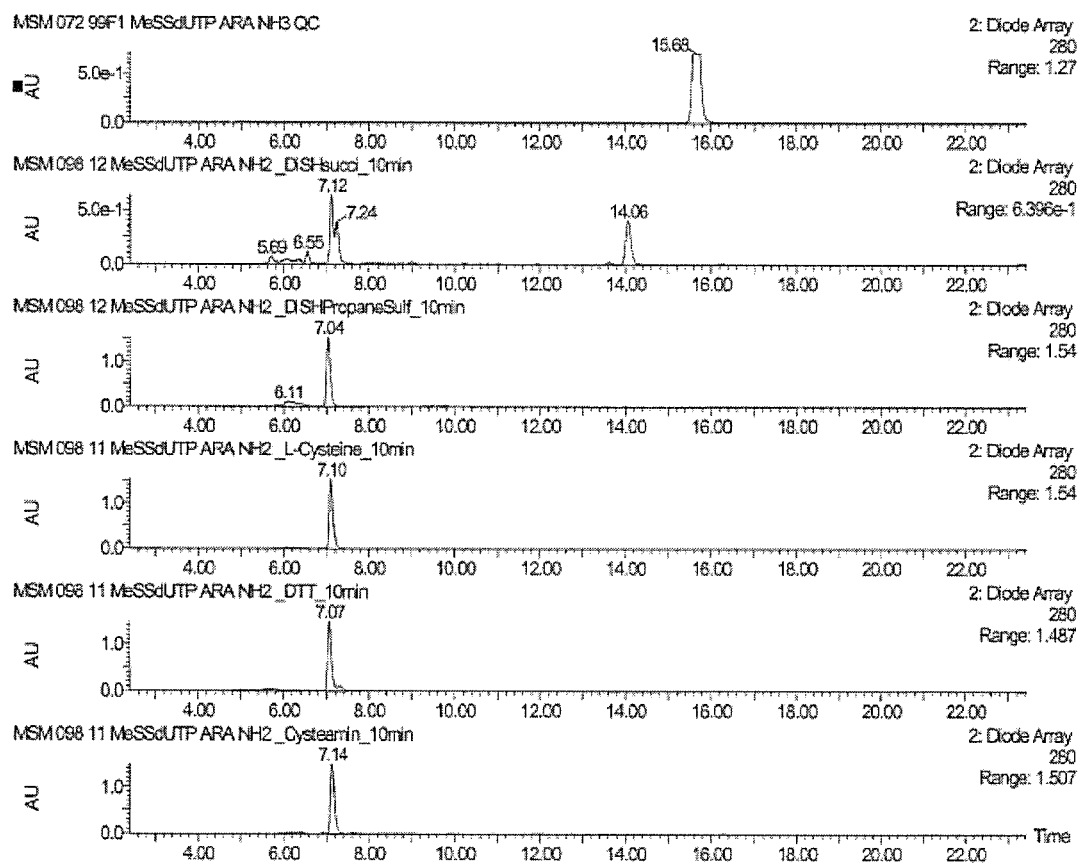
FIG. 84 presents exemplary LC-MS data of the cleavage studies of compound A; 15.8 min compound A, 14.0 min compound B, and 7.10 min compound C.

The structures of these cleave reagents are shown. See, FIG. 83. The cleavage products were then characterized by liquid chromatography/mass spectrometry ((LC/MS). See, FIG. 84. Compounds A, B and C are shown in FIG. 82.

In one embodiment, the present invention contemplates a method comprising a cleaving step comprising a cleave agent capable of cleaving a methyl-disulfide 3'-OH protected nucleotide in a high pH nucleophilic condition. In one embodiment, the cleave agent is a di-mercaptan compound. In one embodiment, the cleaving step occurs in a sequencing by synthesis (SBS) step. In one embodiment, the cleaving step is followed by a wash step comprising oxidative scavenging to effectively remove residual cleave agent.

Although it is not necessary to understand the mechanism of an invention, it is believed that such oxidative scavenging unlocks the efficiency of di-mercaptan based cleaving and enables sequencing with good performance, in particular with respect to reduction of lead and significantly improved raw error rate and longer read length. It is further believed that such effects may be due to, for example: (1) more efficient cleave reaction under high pH conditions (e.g. 9.0 to 10.0, and preferably 9.5) due to formation of more reactive nucleophilic cleaving species; and/or (2) effective scavenging of cleave reagent that is retained in the flow cell likely via surface adsorption mechanisms (e. g., chelation to iron-containing surfaces such as silicate, titania, magnetic bead ferrite). For example, such cleave residual can build up in a flow cell leading to carry over into the subsequent extension step thus causing premature de-protection of the 3'-OH moiety and impairing single base incorporation with very significant detriment to sequencing performance. In one embodiment, a di-mercaptan species as disclosed herein may be di-mercaptan propane sulfonate (DMPS), also referred to as dimercaptopropanesulfonate. In other embodiments, a di-mercaptan cleave agent may include, but is not limited to, sodium 2-mercaptoethanesulfonate (MESNA) and/or glutathione. In one embodiment, DMPS has the following structure:

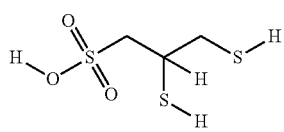

In one embodiment, the present invention contemplates a method comprising the steps of cleaving and washing the are compatible with SBS sequencing with compounds including, but not limited to, DMPS, MESNA and/or glutathione. In one embodiment, the cleaving step comprises DMPS in CHES buffer at pH 9.5. In one embodiment, the washing step comprises H2O2 in TRIS buffer at pH 8.5. In one embodiment, the washing step may further comprise an oxidative scavenging agent including, but not limited to, H2O2, tert-butyl peroxide and/or NaBO3.

In one embodiment, 30% and 3% are concentration of H2O2 stocks going into the add-on. In a preferred embodiment, the final concentration of H2O2 in the wash mix is H2O2 0.3%.

In one embodiment, the present invention contemplates a kit comprising at least one container and a set of instructions for performing SBS sequencing. In one embodiment, the kit further comprises at least one first container comprising an extension premix buffer. In one embodiment, the kit further comprises at least one second container comprising a cleave base buffer. In one embodiment, the kit further comprises at least one third container comprising a wash buffer premix. In one embodiment, the kit further comprises at least one container comprising a wash buffer. In one embodiment, the kit further comprises at least one container comprising an extension add-on reagent. In one embodiment, the extension add-on reagent is A2 (PMA). In one embodiment, the extension add-on reagent is B2 (PMB). In one embodiment, the kit further comprises at least one container comprising a DNA polymerase enzyme. In one embodiment, the kit further comprises at least one container comprising an imaging buffer. In one embodiment, the kit further comprises at least one container comprising a wash add-on reagent. In one embodiment, the wash add-on reagent is hydrogen peroxide ($H_2O_2$). In one embodiment, the hydrogen peroxide is in a stock solution at a concentration of between one percent and five percent, and more preferably three percent (3%) that is later diluted to a lower concentration for the wash. In one embodiment, the kit further comprises at least one container comprising a cleave-solid add-on reagent. In one embodiment, the cleave-solid add-on reagent is di-mercaptan propane sulfonate (DMPS).

In one embodiment, the kit comprises a cleave reagent formulation comprising DMPS (75 mM), CHES (300 mM), NaCl (300 mM) at pH 9.5.

In one embodiment, the kit comprises a Cleave 1 Add-on and/or a Cleave 2 Add-on.

In one embodiment, the kit comprises a frozen liquid (e.g., (−20° C.) cleave reagent add-on comprising concentrated DMPS in H2O or H2O/NaCl.

In one embodiment, the kit comprises a solid cleave reagent add-on comprising DMPS+NaCl In one embodiment, the kit comprises a liquid (+2-8° C.) cleave reagent add-on comprising DMPS as a neat reagent.

In one embodiment, the kit comprises a wash reagent formulation comprising TRIS at pH 8.8, H2O2 (0.3%) and EDTA (1%).

In one embodiment, the kit comprises a liquid (2-8° C.) wash reagent add-ons comprising H2O2 (3.0%). In one embodiment, the kit provides instructions to dilute this to a lower concentration (e.g. 0.3%).

In one embodiment, the kit comprising improved stability liquid (2-8° C.) wash reagent add-ons including, but not limited to, TBHP, APS and/or NaBO3.

In one embodiment, the present invention contemplates cleave reagents that have been developed to function under SBS sequencing conditions. In one embodiment, such a cleave reagent is di-mercaptan propane sulfonate.

As described herein, the cleave reagents are designed to meet the following SBS criteria: i) average read length of approximately 85 bp; ii) average raw error rate of approximately five percent (5%); iii) bead retention that is greater than ninety percent (>90%); and/or iv) a dwell time of approximately one and one-half times (1.5×). These criteria were evaluated for performance improvement and optimization indicators including, but not limited to: i) buffer formulation; ii) DMPS titration; and/or cleave and iron scavenging condition optimization. The data discussed below demonstrate that at least one cleave reagent, di-mercapto propane sulfonate (DMPS), meets and/or exceeds these criteria. Although it is not necessary to understand the mechanism of an invention, it is believed that SBS sequencing with a DMPS-based cleave reagent is enabled by nucleophilic conditions at a cleave step comprising CHES buffer at pH 9.5 followed by a post-cleave washing step comprising an oxidative scavenging condition, using for example, hydrogen peroxide ($H_2O_2$)

Candidate cleave reagents including but not limited to, di-mercapto reagents, mono-mercapto reagents and/or helico reagents were screened by high performance liquid chromatography. The screening configuration was performed on a GeneReader and aside from a candidate cleave reagent included reagents such as oxidative scavengers, capping agents and/or chelators. This screening assay observed optimization of the extending and washing steps using an SBS sequencing method including reagents such as, DMPS/MESNA, inorganic compounds and/or enzymatic compounds. Additionally, off-GeneReader assays including, but not limited to clearance, activity and/or FC integrity were also performed. The observations to optimize the cleaving step included, but are not limited to, pH, concentration, buffer type/counterion, dwell-time and/or temperature.

A DMPS baseline was constructed using commercially available DNA standards (Acrometrix) using an AIT for 107 cycles. Preliminary observations found that the inclusion of an oxidative scavenger in the washing step controlled lead significantly and that the pH level played a role in mediating the overall cleave efficiency. Subsequent verification studies identified that a preferred DMPS baseline configuration comprises a DMPS cleave reagent in CHES 300 mM pH 9.5 followed by a dilute H2O2, wherein the GeneReader is operated at 65° C. for cleave; 1× dwell (TAT requirement compliant) and a 3× fluidic wash. See, Table 2.

TABLE 2

| Cleave Configuration (GDPn) | Cockpit Code | % Bead Ret | % Perfect | %@Q25*** | AVG RI. | Raw Error | Filtered Error | Lead | Lag |
|---|---|---|---|---|---|---|---|---|---|
| DMPS CHES 300 mM pH 9.5 (GDP4) | b128 | 97% | 52% | 82% | 84 | 4.37% | 1.00% | 0.58** | 0.07 |
| SDev | | 0.80% | 5.60% | 2.60% | 2.28 | 0.80% | 0.20% | 0.02 | 0.01 |
| DMPS CHES 50 mM pH 9.5 (GDP3) | b124 | 95% | 44% | 82% | 80 | 7.10% | 1.30% | n.m.* | 0.12 |
| SDev | | 2.67% | 2.89% | 1.34% | 3.02 | 0.07% | 0.05% | | 0.02 |
| DMPS CHES 50 mM pH 9 (GDP3) | b121 | 95% | 45% | 80% | 74 | 9.10% | 1.92% | n.m.* | 0.12 |
| SDev | | 1.78% | 2.45% | 1.78% | 1.99 | 0.03% | 0.03% | | 0.02 |
| DMPS TRIS pH 8.5 (GDP3) | b77 | 97% | 40% | 75% | 65 | 17.03% | 3.0% | n.m.* | 0.12 |
| SDev | | 1.90% | 2.01% | 1.89% | 1.89 | 0.02% | 0.03% | | 0.02 |
| New SBS TCEP Baseline (GDPS) | b34 | 97% | 67% | 85% | 89 | 3.25% | 0.60% | 0.49 | 0.12 |
| SDev | | 1.50% | 2.31% | 1.56% | 1.56 | 0.03% | 0.03% | 0.03 | 0.02 |

These data showed that DMPS CHES 300 mM at pH 9.5 provided a measurable lead and that the raw error rate and average read length met the above described criteria.

Figure 88:
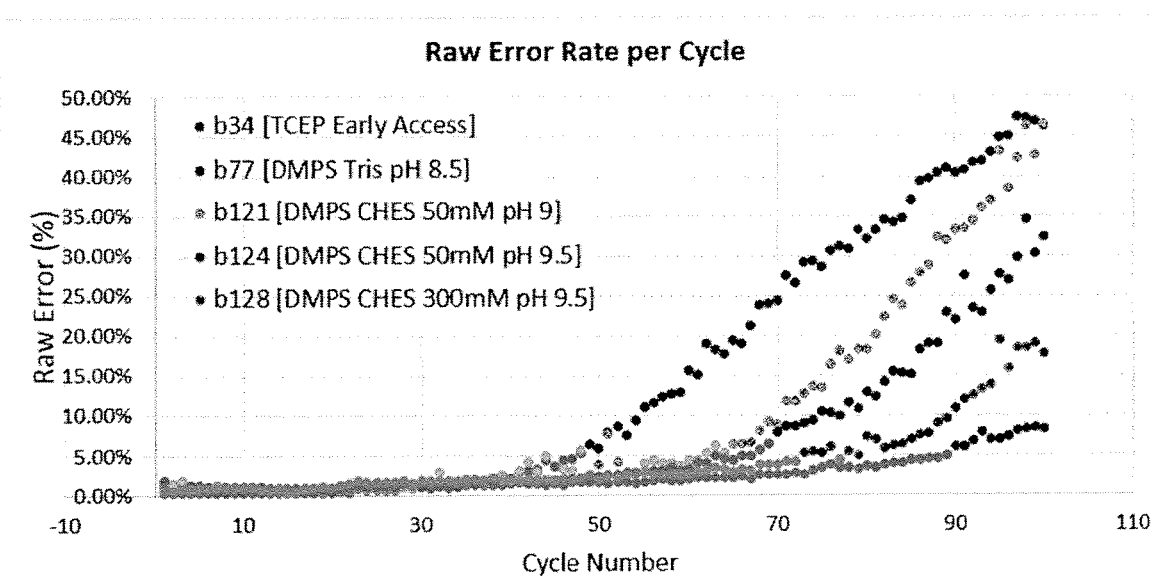
FIG. 88 presents exemplary data showing a dose response of DMPS CHES high pH cleave reagent on the raw error rate of an SBS sequencing method.

The data presented herein demonstrates that the raw error rate improves as a function of configuration evolution. See, FIG. 88. For example, having DMPS in the cleave step without the H2O2 in the wash step does not allow sequencing past 25 cycles (data not shown). Consequently, the data suggests that SBS sequencing with both DMPS and H2O2 enables better performance because of the higher pH as seen when comparing; i) poor sequencing performance (pH 8.5; red curve); ii) high quality performance (pH 9.5; blue curve); and iii) TCEP benchmark (green curve). FIG. 88.

Figure 89A:
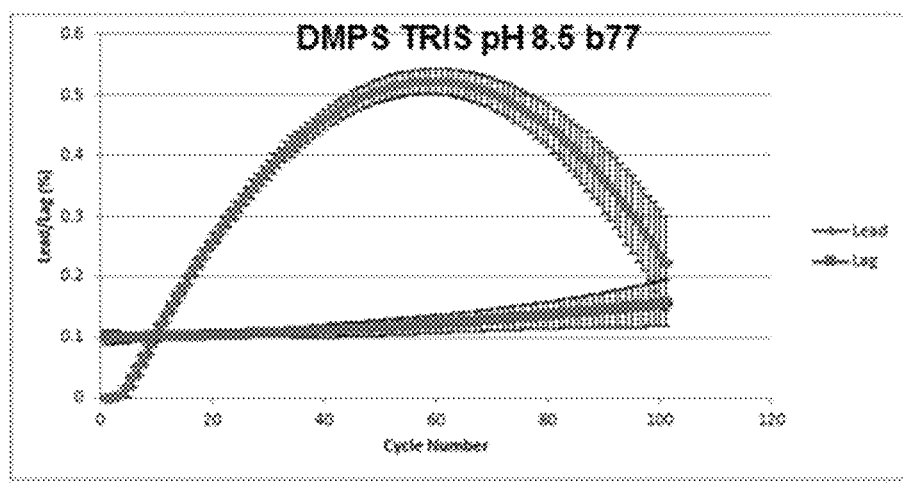
FIG. 89A-C presents exemplary SBS sequencing data showing a lead/lag comparison using a DMPS TRIS high pH cleave reagent and a DMPS CHES reagent.
Figure 89B:
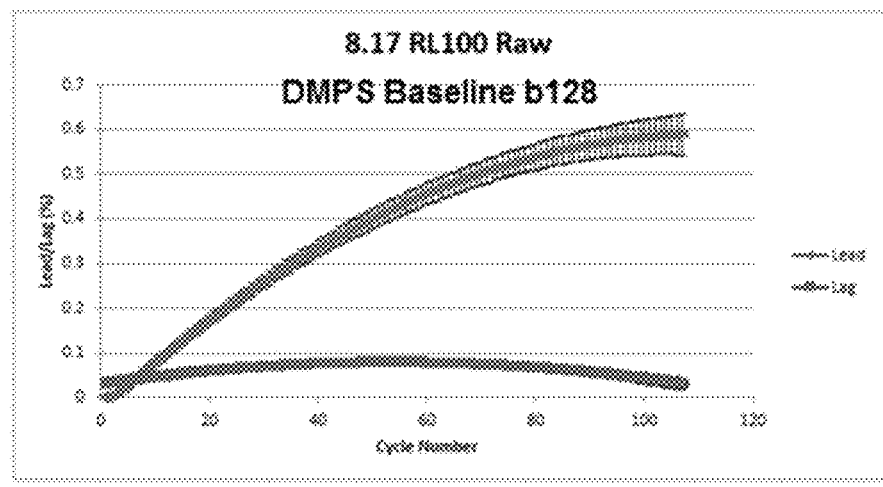
Figure 89C:
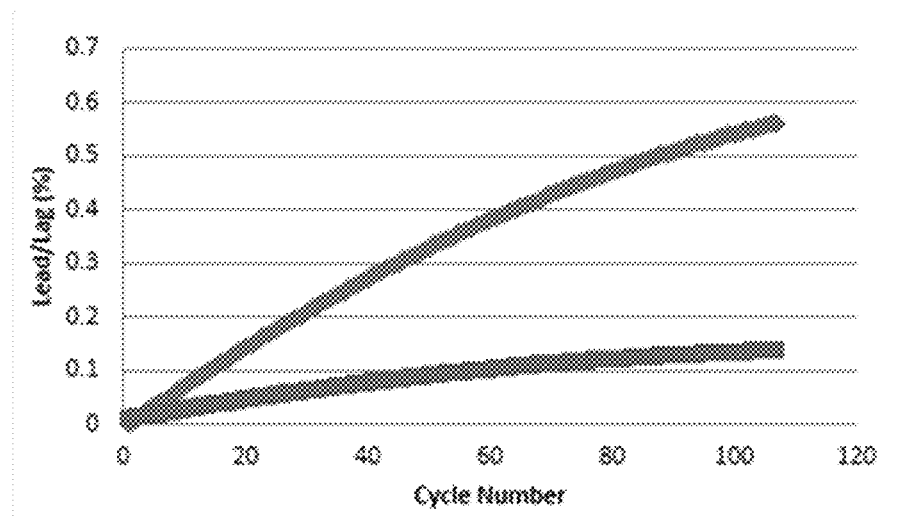
Figure 90:
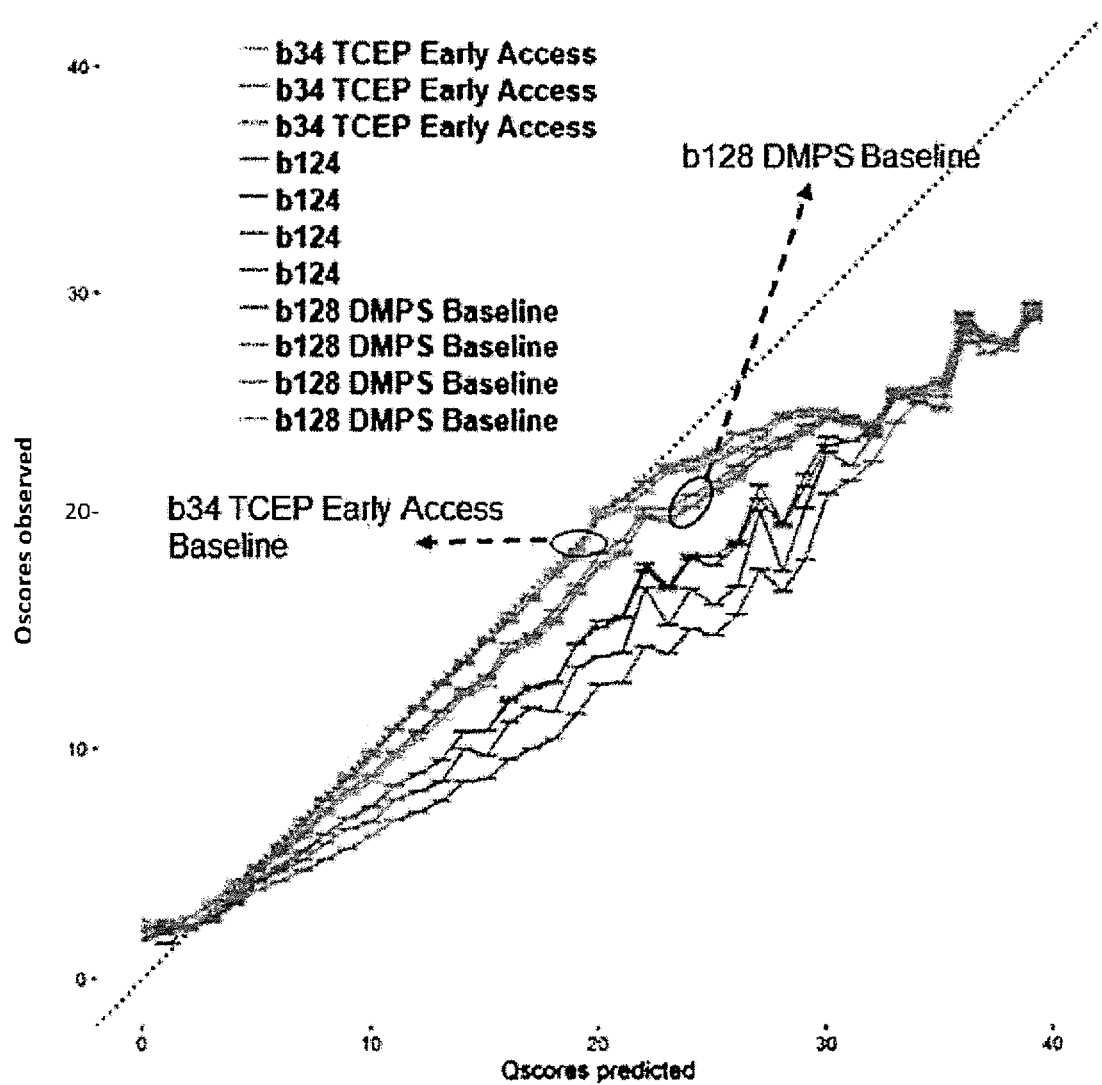
FIG. 90 presents exemplary data showing a Q Score comparison between DMPS baseline b128 and TCEP baseline cleave reagents.
Figure 91A:
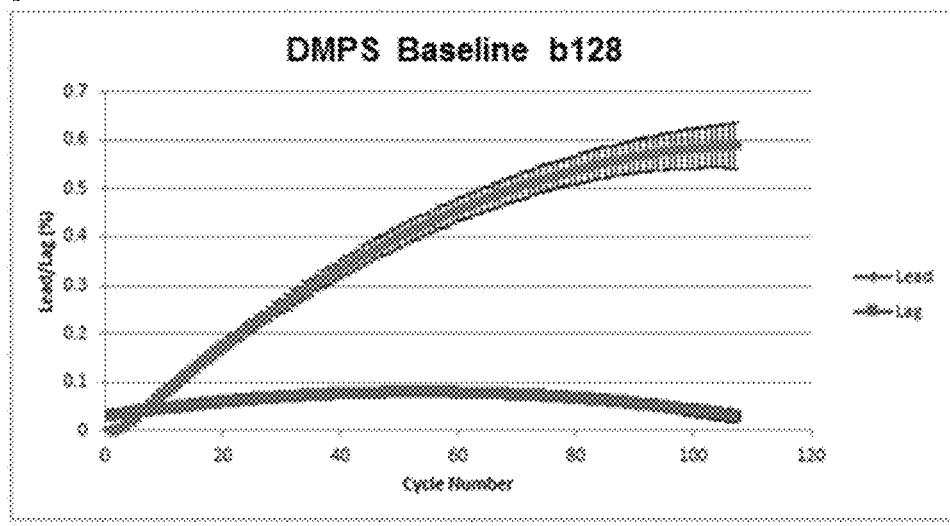
FIGS. 91A-C present exemplary data comparing two DMPS concentrations (75 versus 50 mM) to a TECP standard to demonstrate improvements in lead/lag.
Figure 91B:
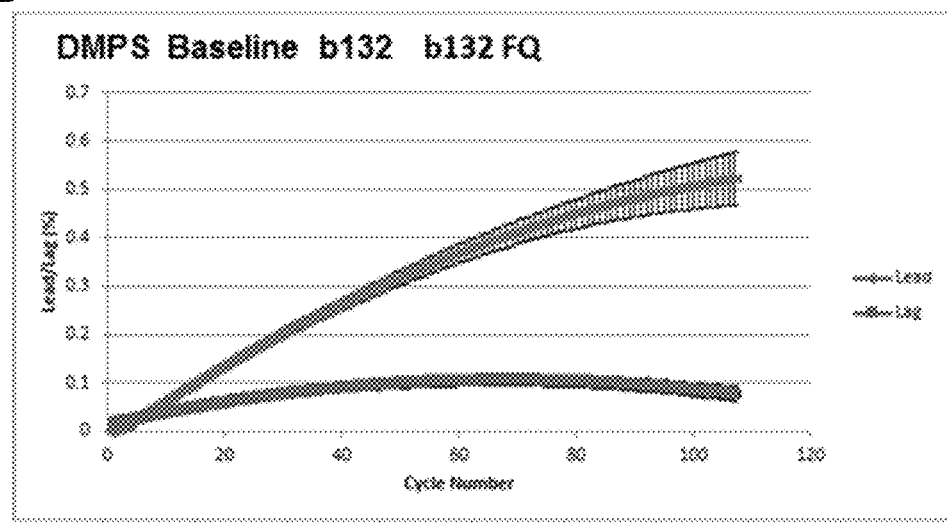
Figure 91C:
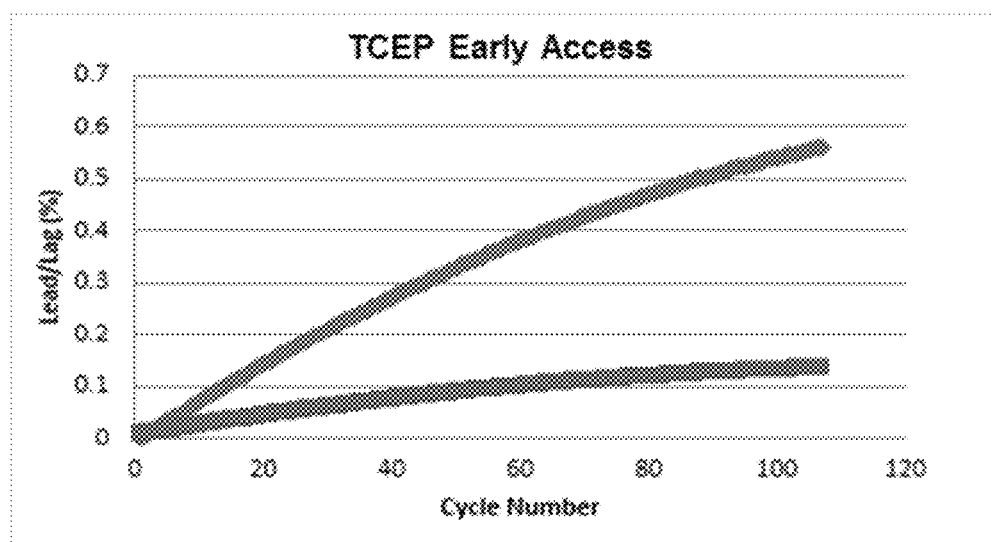
Figure 92:
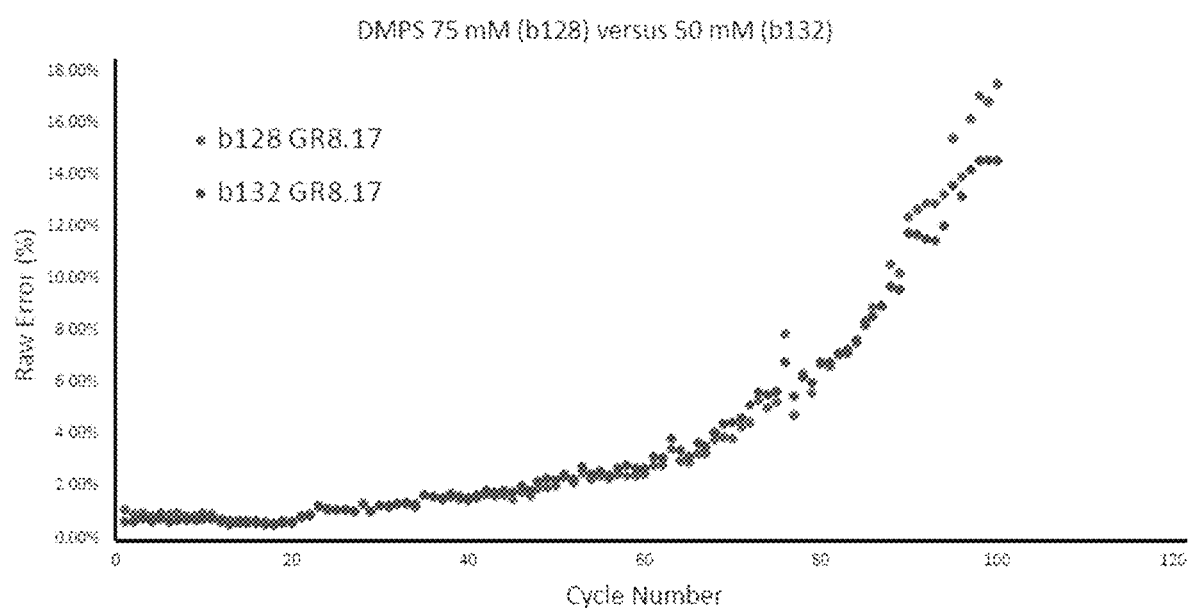
FIG. 92 presents exemplary data comparing two DMPS concentrations (75 versus 50 mM) to a TECP standard to demonstrate improvements in average error rate.
Figure 93A:
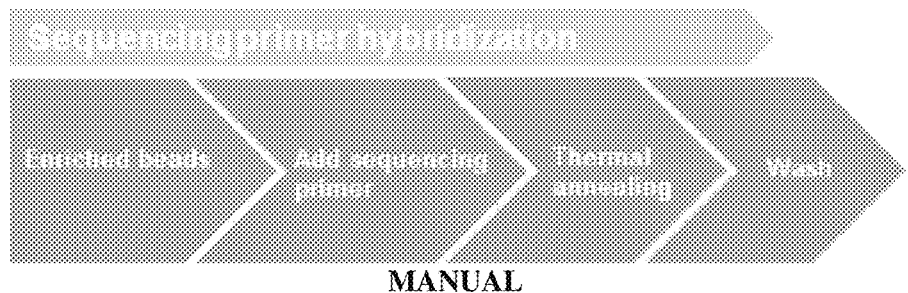
FIG. 93A-C shows one embodiment of a sequencing workflow.
Figure 93B:
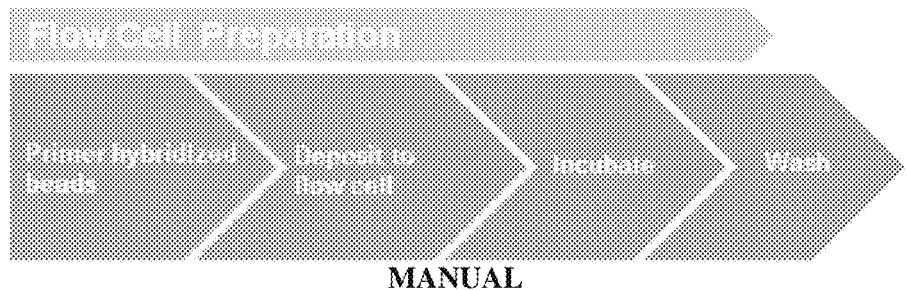
Figure 93C:
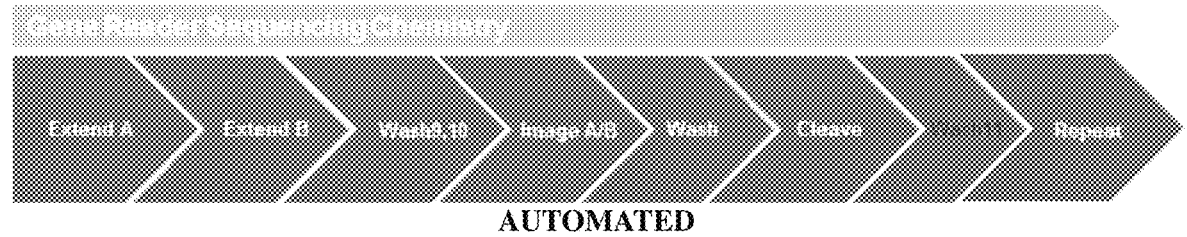
Figure 94A:
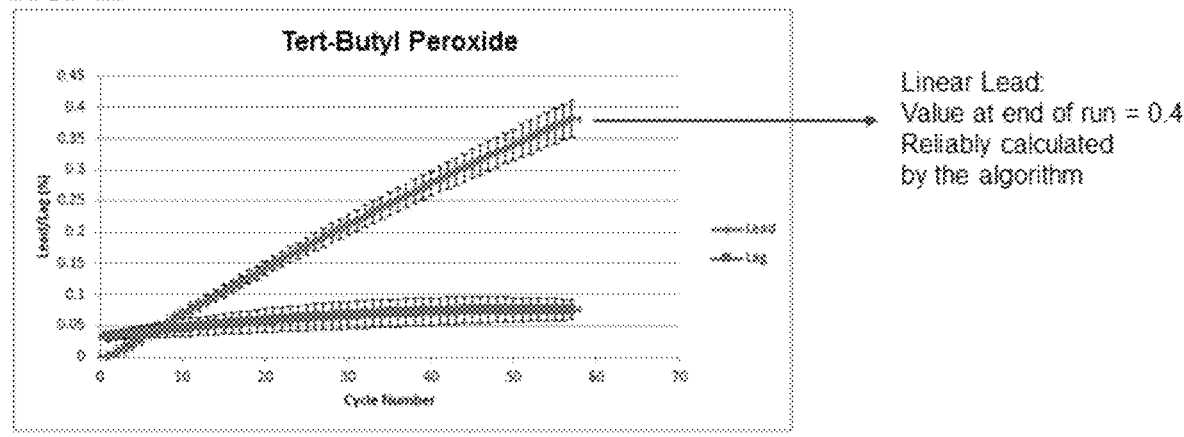
FIG. 94A shows lead/lag results when tert-butyl peroxide is used in the oxidative wash (Wash 11), as compared to lead/lag results when hydrogen peroxide is (FIG. 94B) or is not (FIG. 94C) in the oxidative wash. Lead as a function of cycle needs to be a linear function in order for the algorithm to be able to measure an accurate number.
Figure 94B:
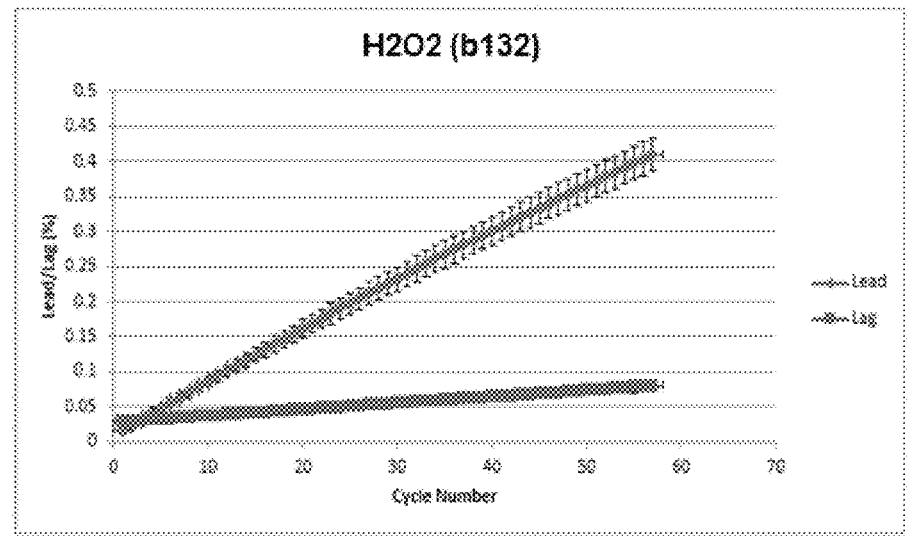
FIG. 94C shows non-linear lead results when the wash does not contain hydrogen peroxide. However, when the chemistry was optimized properly by including hydrogen peroxide (FIG. 94B) or tert-butyl peroxide (FIG. 94A) in the oxidative wash, a linear function was achieved and a reliable value for lead was provided by the algorithm.
Figure 94C:
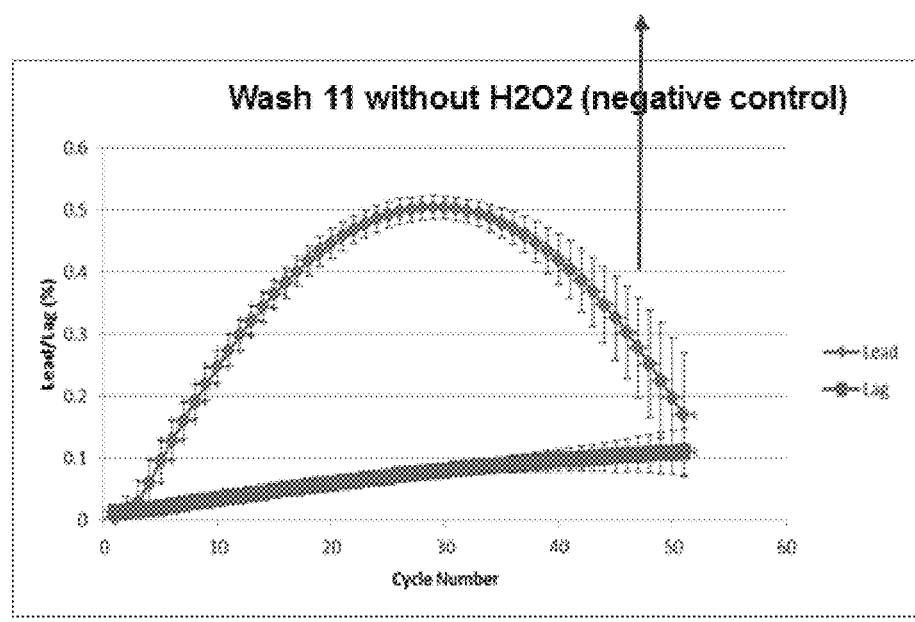
Figure 95:
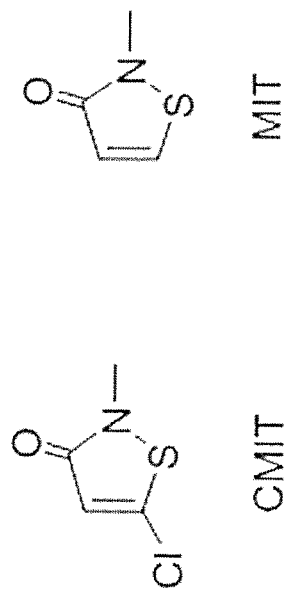
FIG. 95 shows the structures for CMIT and MIT found in the commercially available reagent "Proclin300" (which is a mixture of 5-Chloro-2-methyl-4-isothiazolin-3-one (CMIT); 2-Methyl-4-isothiazolin-3-one (MIT); glycol: 93-95%; modified alkyl carboxylate: 2-3%).

The data presented herein demonstrate that the lead/lag comparison is improved (when compared to a 8.5 pH DMPS TRIS cleave reagent) when using either a DMPS baseline b128 or a TCEP baseline SBS sequencing method. See, FIG. 89A cf FIG. 89B and FIG. 89C. It can be seen that lead is near-linear in the high pH configuration and comparable to TCEP Early Access Baseline. Further, a Q Score analysis show that AVG values for DMPS baseline b128 are about 4 Q scores lower than TCEP Early Access Baseline. See, FIG. 90.

A secondary analysis benchmarking analysis found that the average FP for 0.5% AF calls is 2 as compared to null for TCEP Early Access. See, Table 3.

TABLE 3

Secondary Analysis Benchmarking

| Configuration | Q85 | Coverage >200x | TP | FN | FP @0.5% calls |
|---|---|---|---|---|---|
| b34 (TCEP Early Access) | | | | | |
| 001146_MAN08_RA01.BC3.fastq | 26 | 100% | 68 | 5 (0) | 0 |
| 001146_MAN08_BA01.BC4.fastq | 26 | 100% | 68 | 5 (0) | 0 |
| 001154_MAN08_RA01.BC3.fastq | 26 | 100% | 68 | 5 (0) | 0 |
| 001154_MAN08_RA01.BC4.fastq | 26 | 100% | 68 | 5 (0) | 0 |
| | | | | | AVG FP = 0 |
| b124 | | | | | |
| 000215_man09_RA01.BC3 | 23 | 100% | 67 | 6 (1) | 4 |
| 000215_man09_RA01.BC4 | 23 | 100% | 67 | 6 (1) | 5 |
| 000879_Man08_clones_RA01.BC3 | 26 | 89% | 65 | 8 (3) | 35 |
| 000879_Man08_clones_RA01.BC4 | 22 | 100% | 67 | 6 (1) | 8 |
| 000965_man09_RA01.BC3 | 25 | 100% | 66 | 7 (2) | 38 |
| 000965_man09_RA01.BC4 | 22 | 100% | 67 | 6 (1) | 8 |
| | | | | | AVG FP = 16 |
| b128 (DMPS Baseline) | | | | | |
| 000243_Man11_RA01.BC3.fastq | 24 | 100% | 67 | 6 (1) | 0 |
| 000243_Man11_RA01.BC4.fastq | 24 | 100% | 67 | 6 (1) | 0 |
| 000988_MAN09_RA01.BC3.fastq | 22 | 100% | 66 | 7 (2) | 1 |
| 000988_MAN09_RA01.BC4.fastq | 22 | 100% | 66 | 7 (2) | 4 |
| 001038_Man11_RA01.BC3.fastq | 24 | 100% | 67 | 6 (1) | 0 |
| 001038_Man11_RA01.BC4.fastq | 24 | 100% | 67 | 6 (1) | 3 |
| 001039_MAN09_RA01.BC3.fastq | 24 | 100% | 67 | 6 (1) | 1 |
| 001039_MAN09_RA01.BC4.fastq | 24 | 100% | 67 | 6 (1) | 4 |
| | | | | | AVG FP = 2 |

DMPS baseline reproducibility was tested during eight (8) SBS runs using DMPS in CHES 300 mM pH 9.5 followed by a dilute H2O2-containing wash operated at 65° C. cleave, a 1× dwell that was TAT requirement compliant, and a 3× fluidic wash. See, Table 4.

TABLE 4

DMPS Baseline Reproducibility

| Run Date/b228 | GR | % Bead Ret | % Mapped | % @ Q25 | AVG RI. | Raw Error | Filtered Error | Output | Lead | Lag |
|---|---|---|---|---|---|---|---|---|---|---|
| Dec. 16, 2016 | 8.1 | 97% | 28% | 79% | 85 | 4.17% | 1.10% | 1.31 | 0.53 | 0.04 |
| Dec. 16, 2016 | 8.17 | 95% | 27% | 85% | 86 | 3.83% | 0.85% | 1.26 | 0.58 | 0.05 |
| Dec. 16, 2016 | 8.31 | 97% | 30% | 84% | 84 | 3.88% | 0.85% | 1.41 | 0.61 | 0.02 |
| Dec. 16, 2016 | 8.26 | 97% | 29% | 84% | 84 | 4.07% | 0.85% | 1.37 | 0.57 | 0.03 |
| Dec. 19, 2016 | 8.1 | 97% | 26% | 81% | 85 | 4.56% | 1.10% | 1.29 | 0.54 | 0.05 |
| Dec. 19, 2016 | 8.17 | 97% | 29% | 84% | 86 | 3.95% | 0.89% | 1.38 | 0.58 | 0.04 |
| Dec. 19, 2016 | 8.31 | 95% | 29% | 84% | 85 | 4.39% | 1.02% | 1.38 | 0.55 | 0.05 |
| Dec. 19, 2016 | 8.26 | 97% | 30% | 84% | 86 | 4.12% | 0.95% | 1.49 | 0.57 | 0.04 |
| AVG | | 97% | 29% | 83% | 85 | 4.12% | 0.95% | 1.36 | 0.56 | 0.04 |
| SDev | | 0.93% | 1.34% | 1.93% | 0.83 | 0.25% | 0.11% | 0.07 | 0.026 | 0.011 |

The data shows comparable performance with an approximate 1% standard deviation across all KPI's.

Further data demonstrated the ability of either increasing the cleave reagent pH to pH 10 and/or decreasing DMPS concentrations to further improve SBS sequencing methods. It was observed that a cleave reagent (pH 10: does NOT impact bead retention (97%); while there appears no significant impact on performance (data not shown). A 50 mM concentration of DMPS (b132) was compared to a 75 mM concentration of DMPS (b128). See, Table 5.

TABLE 5

Comparision of DMPS b132 (50 mM) To DMPS b128 (75 mM)

| Configuration/Run Date | GR | % Bead Ret | % Mapped | % @ Q25 | AVG RI. | Raw Error | Filtered Error | Output | Lead | Lag |
|---|---|---|---|---|---|---|---|---|---|---|
| b128-Dec. 16, 2016 | 8.17 | 95% | 27% | 85% | 86 | 3.83% | 0.85% | 1.26 | 0.58 | 0.05 |
| b128-Dec. 19, 2016 | 8.17 | 97% | 29% | 84% | 86 | 3.95% | 0.89% | 1.38 | 0.58 | 0.04 |
| b132-Dec. 21, 2016 | 8.17 | 97% | 29% | 84% | 88 | 3.75% | 0.80% | 1.51 | 0.51 | 0.09 |

The data show that decreased DMPS concentration provides a noticeable improvement of lead and suggest improvements in average error rate and read length. See, FIGS. 91A-C, and FIG. 92. It is also suggested that lower DMPS concentration will also support a more advantageous COGS.

In summary, the above data shows that a high pH cleave reagent, such as DMPS, provides an SBS sequencing method comprising: i) an average read length of approximately 85 bp or more; ii) and average raw error rate of approximately 4% or less; iii) bead retention of approximately 97% or more; and iv) a 1× dwell time. Furthermore, identified residual gap-to-product requirements demonstrated an average raw error rate ranging between approximate 4% to 2.5% and an FP @ 0.5% calls ranging between 2 to 0.

A comparison of the DMPS b132 configuration with the TCEP configurations was prepared. See, Table 6.

TABLE 6

Performance comparison for different configurations based on Acrometrix on AIT (107 cycles)

| | | | % Mapped | % @ Q25 | AVG RI. | Raw Error | Filtered Error | Output (Gb) | Lead | Lag |
|---|---|---|---|---|---|---|---|---|---|---|
| GR1.0 Legacy Configuration | n(runs) = 35 | GDP5 | | | | | | | | |
| Average | | | 35.9% | 85.8% | 80 | 2.75% | 0.49% | 1.08 | 0.36 | 0.12 |
| SDev | | | 3.3% | 0.7% | 1.4 | 0.35% | 0.03% | 0.10 | 0.03 | 0.02 |
| GR1.1 Legacy Configuration | n(runs) = 4 | GDP4 | | | | | | | | |
| Average | | | 32% | 86% | 95 | 2.11% | 0.49% | 1.10 | 0.26 | 0.13 |
| SDev | | | 1.3% | 0.5% | 1.1 | 0.27% | 0.05% | 0.10 | 0.05 | 0.03 |
| New SBS AMP 2016 TCEP Configuration | n(runs) = 11 | GDP4 | | | | | | | | |
| Average | | | 31% | 86% | 89 | 3.25% | 0.55% | 1.05 | 0.59 | 0.08 |
| SDev | | | 3% | 1% | 5.3 | 0.27% | 0.03% | 0.06 | 0.06 | 0.06 |

TABLE 6-continued

Performance comparison for different configurations based on Acrometrix on AIT (107 cycles)

| New SBS EA 2016 TCEP Configuration | n(runs) = 9 GDP5 | % Mapped | % @ Q25 | AVG RI. | Raw Error | Filtered Error | Output (Gb) | Lead | Lag |
|---|---|---|---|---|---|---|---|---|---|
| Average | | 37% | 88% | 95 | 2.33% | 0.60% | 1.25 | 0.49 | 0.12 |
| SDev | | 1.50% | 1.14% | 0.6 | 0.15% | 0.04% | 0.03 | 0.05 | 0.01 |
| New SBS DMPS Configuration b132 | n(runs) = 5 GDP4 | % Mapped | % @ Q25 | AVG RI. | Raw Error | Filtered Error | Output (Gb) | Lead | Lag |
| Average | | 29% | 84% | 88 | 3.60% | 0.81% | 1.01 | 0.51 | 0.09 |
| SDev | | 0.40% | 0.80% | 0.55 | 0.12% | 0.05% | 0.03 | 0.05 | 0.01 |

The data show that DMPS b132 configuration (as a TECP replacement) shows KPI's that are very close to TECP results using the second generation ("Early Access") configuration.

In one embodiment, the present invention contemplates a method comprising a nucleic acid sequence wherein the nucleic acid template used for sequencing is derived from a tissue biopsy. In one embodiment, the tissue biopsy comprises a liquid tissue biopsy. Although it is not necessary to understand the mechanism of an invention it is believed that a liquid tissue biopsy is compatible with SBS sequencing methods in order to sequence a nucleic acid sequence within the liquid tissue biopsy. See, Table 7.

TABLE 7

Platform KPIs For DMPS b132 SBS Configuration

Liquid Biopsy Sample Type/Configuration (New SBS Chemistry) - Early Access

| Sample Barcode | Rel. Abundance | Sequencing Cycles | GenePanel/Library |
|---|---|---|---|
| BC1 | 1/6" | 107 | WT Horizon cfDNA |
| BC2 | 1/6" | 107 | WT Horizon cfDNA |
| BC3 | 1/6" | 107 | AIT (HD780 %1 cfDNA) |
| BC4 | 1/6" | 107 | AIT (HD780 %1 cfDNA) |
| BC5 | 1/6" | 107 | AIT (HD780 %5 cfDNA) |
| BC6 | 1/6" | 107 | AIT (HD780 %5 cfDNA) |

New SBS DMPS LB Configuration b132

| | | | | | | | | | |
|---|---|---|---|---|---|---|---|---|---|
| Average | 33% | 85% | 90 | 3.33% | 0.78% | 1.58 | 0.45 | 0.11 |
| SDev | 0.40% | 0.80% | 0.33 | 0.12% | 0.03% | 0.03 | 0.03 | 0.01 |

New SBS EA 2016 TCEP Configuration

| | | | | | | | | | |
|---|---|---|---|---|---|---|---|---|---|
| Average | 38% | 88% | 95 | 2.33% | 0.60% | 1.71 | 0.49 | 0.12 |
| SDev | 1.50% | 1.14% | 0.6 | 0.15% | 0.04% | 0.03 | 0.05 | 0.01 |

It can be seen that the platform KPI's for DMPS b132 are very close to TECP Early Access KPI's. The results of the liquid biopsy sequencing runs are shown. See, Table 8.

TABLE 8

Liquid Biopsy Panel Specifications

| Parameter | Detail |
|---|---|
| Panel Size | 12 Genes/16.7 kb |
| Insight Size | 732 unique variant positions |
| Amplicons | 330 |
| Average Amplicon Size | 134 bp |
| DNA Input | 10 ng × 4 |
| Throughput | 10-40 samples per run |
| Variant Frequency Cutoff | 1% |

TABLE 8-continued

Liquid Biopsy Panel Specifications

| Parameter | Detail |
|---|---|
| Variant Insight Coverage (6-plex) | >500x: 99.973% (KPI 98%) |
| | >200x: 99.984% (KPI 99%) |
| Variant Insight Coverage (10-plex in-silico) | >500x: 99.843% |
| | >200x: 99.978% |

The data shows outstanding coverage at both amplicon and variant insight levels.

The accuracy of sequencing nucleic acids in liquid biopsy samples is shown below in a series of tables demonstrating the sensitivity and selectivity when using a commercially available tumor panel (e.g., Actionable Insights Tumor Panel, Qiagen). See, Tables 9-11.

TABLE 9

Summary: Performance at 0.5% Frequency Cut-Off and AQ >20 Using BioX KPI's

| | 200X coverage | 500X coverage | Sensitivity | Specificity | Precision | LAF |
|---|---|---|---|---|---|---|
| Actionable Insights Tumor Panel (ATP) V2.0 (FFPE) | 99% | 98% | 99% | 99% | 95% | 10% |
| Actionable Insights Tumor Panel (ATP) V2.0 (FFPE) | 99% | 98% | 95% | 95% | 90% | 5% |
| Actionable Insights Tumor Panel (ATP) V2.0 (plasma) | 99% | 98% | 90% | 90% | 90% | 1% |

TABLE 10

Detailed: Performance at 0.5% Frequency Cut-Off and AQ >20

| | Sample name | Total number of reads | Average read length | % mapped reads | >500x read coverage | >1000x read coverage | Average error rate [%] | All Sensitivity | All Specificity | All Precision |
|---|---|---|---|---|---|---|---|---|---|---|
| Legacy GR1.0 (n = 2) | Average | 2,179,003 | 80.51 | 86.50 | 99.55 | 98.06 | 0.40 | 0.94 | 1.00 | 0.84 |
| Early Access WAL Runs (n = 18) | Average | 2,164,234 | 94.24 | 94.62 | 100.00 | 99.54 | 0.43 | 1.0000 | 0.9999 | 0.9872 |
| Early Access MAN Runs (n = 4) | Average | 2,008,043 | 93 | 94.53 | 99.94 | 99.77 | 0.44 | 0.9688 | 0.9991 | 0.9410 |
| b132 (DMPS Configuration) | 44206_000135_3_BC03 | 2,724,486 | 91.24 | 93.79 | 100 | 99.87 | 0.65 | 1 | 1 | 0.83 |
| | 44206_000135_4_BC04 | 2,600,349 | 91.23 | 93.73 | 200 | 99.74 | 0.66 | 1 | 1 | 0.89 |
| | 44241_000131_3_BC03 | 2,576,587 | 91.98 | 93.04 | 100 | 99.87 | 0.66 | 1 | 1 | 1 |
| | 44241_000131_4_BC04 | 2,569,219 | 91.58 | 88.13 | 99.87 | 99.74 | 0.67 | 1 | 1 | 1 |
| | 44302_000134_3_BC03 | 2,706,162 | 89.46 | 94.43 | 100 | 99.87 | 0.71 | 0.88 | 1 | 1 |
| | 44302_000134_4_BC04 | 2,576,711 | 89.46 | 94.49 | 100 | 99.74 | 0.72 | 1 | 1 | 1 |
| | 50138_000136_3_BC03 | 2,670,057 | 88.74 | 94.98 | 100 | 99.87 | 0.43 | 0.88 | 1 | 1 |
| | 50138_000130_4_BC04 | 2,554,371 | 88.78 | 94.99 | 100 | 99.74 | 0.43 | 1 | 1 | 1 |
| | Average | 2,622,245 | 90 | 93.47 | 99.98 | 99.81 | 0.62 | 0.9700 | 1.0000 | 0.9725 |

KPIs refers to secondary analysis specifications for coverage (200x and 500x) and variant call (precision, sensitivity, specificity). All b132 runs (n=8) have better sensitivity, specificity and precision compared to generation 1 ("Legacy") Nucleotides GR 1.0 Baseline and generation 2 ("Early Access") Configurations. All KPI's (sensitivity, specificity, precision) and coverage requirement for 10-plex are met.

We also plexed a number of libraries (eight) together in the liquid biopsy (LB) sample pools.

with $Et_3N$ (0.54 mL, 3.87 mmol) and 5.0 g molecular sieve-3A, and stirred for 30 min under Ar atmosphere. The reaction flask was then placed on an ice-bath to bring the temperature to sub-zero, and slowly added with 1.8 eq 1M $SO_2Cl_2$ in $CH_2Cl_2$ (1.8 mL) and stirred at the same temperature for 1.0 hour. Then the ice-bath was removed to bring the flask to room temperature, and added with a solution of potassium thiotosylate (1.5 g) in 4 mL dry DMF and stirred for 0.5 hour at room temperature.

TABLE 11

Degree of Plexing on 1% LB sample (n = 8)

| Plexing | Total number of reads | Total number of bases | Average read length | >200x read coverage | >500x read coverage | >1000x read coverage | Average error rate [%] | All TPs | All FPs | All FNs | All Sensitivity | All Specificity | All Precision |
|---|---|---|---|---|---|---|---|---|---|---|---|---|---|
| 6-plex | 2,622,245 | 234,184,033 | 90.309 | 100.000 | 99.984 | 99.805 | 0.616 | 7.750 | 0.250 | 0.250 | 0.970 | 1.000 | 0.973 |
| 8-plex | 1,966,684 | 175,634,383 | 90.308 | 100.000 | 99.935 | 99.659 | 0.616 | 7.875 | 0.375 | 0.125 | 0.985 | 1.000 | 0.958 |
| 10-plex | 1,573,347 | 140,504,711 | 90.305 | 100.000 | 99.833 | 98.853 | 0.621 | 7.625 | 0.125 | 0.375 | 0.955 | 1.000 | 0.985 |
| 12-plex | 1,311,123 | 117,093,757 | 90.313 | 100.000 | 99.805 | 98.320 | 0.623 | 7.750 | 0.250 | 0.250 | 0.970 | 1.000 | 0.973 |
| 16-plex | 970,231 | 86,653,104 | 90.315 | 99.935 | 99.675 | 97.719 | 0.625 | 7.750 | 0.375 | 0.250 | 0.970 | 1.000 | 0.919 |
| 20-plex | 786,674 | 70,258,227 | 90.314 | 99.935 | 98.805 | 95.958 | 0.629 | 7.500 | 0.125 | 0.500 | 0.940 | 1.000 | 0.985 |
| 24-plex | 655,561 | 58,542,087 | 90.305 | 99.838 | 98.320 | 92.675 | 0.631 | 7.250 | 0.500 | 0.750 | 0.908 | 1.000 | 0.936 |

* Values are average over 8 HD780 1% cfDNA barcodes

EXAMPLES

The following examples are provided in order to demonstrate and further illustrate certain preferred embodiments and aspects of the present invention and are not to be construed as limiting the scope thereof.

Example 1

Synthesis of 3'-O-(methylthiomethyl)-5'-O-(tert-butyldimethylsilyl)-2'-deoxythymidine (2)

5'-O-(tert-butyldimethylsilyl)-2'-deoxythymidine (1) (2.0 g, 5.6 mmol) was dissolved in a mixture consisting of DMSO (10.5 mL), acetic acid (4.8 mL), and acetic anhydride (15.4 mL) in a 250 mL round bottom flask, and stirred for 48 hours at room temperature. The mixture was then quenched by adding saturated $K_2CO_3$ solution until evolution of gaseous $CO_2$ was stopped. The mixture was then extracted with EtOAc (3×100 mL) using a separating funnel. The combined organic extract was then washed with a saturated solution of $NaHCO_3$ (2×150 mL) in a partitioning funnel, and the organic layer was dried over $Na_2SO_4$. The organic part was concentrated by rotary evaporation. The reaction mixture was finally purified by silica gel column chromatography (Hex:EtOAc/7:3 to 1:1), see FIG. 8. The 3'-O-(methylthiomethyl)-5'-O-(tert-butyldimethylsilyl)-2'-deoxythymidine (2) was obtained as white powder in 75% yield (1.75 g, $R_f$=0.6, hex:EtOAc/1:1). H-NMR ($CDCl_3$): $\delta_H$ 8.16 (s, 1H), 7.48 (s, 1H), 6.28 (m, 1H), 4.62 (m, 2H), 4.46 (m, 1H), 4.10 (m, 1H), 3.78-3.90 (m, 2H), 2.39 (m, 1H), 2.14, 2.14 (s, 3H), 1.97 (m, 1H), 1.92 (s, 3H), 0.93 (s, 9H), and 0.13 (s, 3H) ppm.

Example 2

Synthesis of 3'-O-(ethyldithiomethyl)-2'-deoxythymidine (4)

Compound 2 (1.75 g, 4.08 mmol), dried overnight under high vacuum, dissolved in 20 mL dry $CH_2Cl_2$ was added Then 2 eq EtSH (0.6 mL) was added and stirred additional 40 min. The mixture was then diluted with 50 mL $CH_2Cl_2$ and filtered through celite-S in a funnel. The sample was washed with adequate amount of $CH_2Cl_2$ to make sure that the product was filtered out. The $CH_2Cl_2$ extract was then concentrated and purified by chromatography on a silica gel column (Hex:EtOAC/1:1 to 1:3, $R_f$=0.3 in Hex:EtOAc/1:1). The resulting crude product was then treated with 2.2 g of $NH_4F$ in 20 mL MeOH. After 36 hours, the reaction was quenched with 20 mL saturated $NaHCO_3$ and extracted with $CH_2Cl_2$ by partitioning. The $CH_2Cl_2$ part was dried over $Na_2SO_4$ and purified by chromatography (Hex:EtOAc/1:1 to 1:2), see FIG. 8. The purified product (4) was obtained as white powder in 18% yield, 0.268 g, $R_f$=0.3, Hex:EtOAc/1:2).

$^1$H NMR in $CDCl_3$: $\delta_H$ 11.25 (1H, S), 7.65 (1H, S), 6.1 (1H, m), 5.17 (1H, m), 4.80 (2H, S), 4.48 (1H, m), 3.96 (1H, m), 3.60 (2H, m), 3.26 (3H, s), 2.80 (2H, m), 2.20 (2H, m) and 1.14 (3H, m) ppm.

Example 3

Synthesis of the triphosphate of 3'-O-(ethyldithiomethyl)-2'-deoxythymidine (5)

In a 25 mL flask, compound 4 (0.268 g, 0.769 mmol) was added with proton sponge (210 mg), equipped with rubber septum. The sample was dried under high vacuum for overnight. The material was then dissolved in 2.6 mL $(MeO)_3PO$ under argon atmosphere. The flask, equipped with Ar-gas supply, was then placed on an ice-bath, stirred to bring the temperature to sub-zero. Then 1.5 equivalents of $POCl_3$ was added at once by a syringe and stirred at the same temperature for 2 hour under Argon atmosphere. Then the ice-bath was removed and a mixture consisting of tributylammonium-pyrophosphate (1.6 g) and $Bu_3N$ (1.45 mL) in dry DMF (6 mL) was prepared. The entire mixture was added at once and stirred for 10 min. The reaction mixture was then diluted with TEAB buffer (30 mL, 100 mM) and stirred for additional 3 hours at room temperature. The crude product was concentrated by rotary evaporation, and purified by 018 Prep HPLC (method: 0 to 5 min 100% A followed by gradient up to 50% B over 72 min, A=50 mM TEAB and B=acetonitrile). After freeze drying of the target fractions, the semi-pure product was further purified by ion exchange HPLC using PL-SAX Prep column (Method: 0 to 5 min 100% A, then gradient up to 70% B over 70 min, where A=15% acetonitrile in water, B=0.85M TEAB buffer in 15% acetonitrile). Final purification was carried out by C18 Prep HPLC as described above resulting in ~25% yield of compound 5, see FIG. 8.

Example 4

Synthesis of $N^4$-Benzoyl-5'-O-(tert-butyldimethylsilyl)-3'-O-(methylthiomethyl)-2' deoxycytidine (7)

Figure 9:
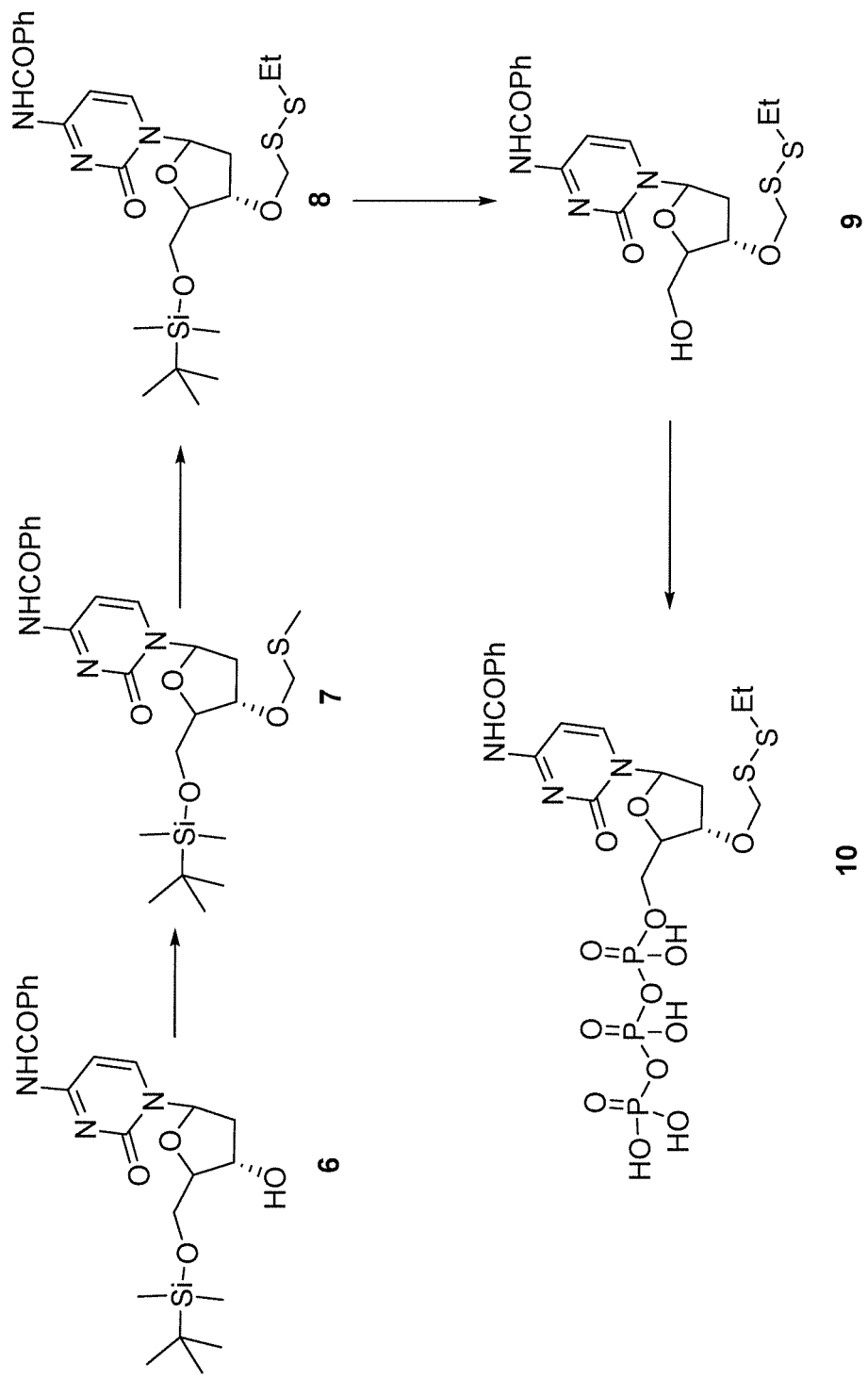
FIG. 9 shows the synthesis of 3'-O-(ethyldithiomethyl)-dCTP (10).

The synthesis of 3'-O-(ethyldithiomethyl)-dCTP (10) was achieved according to FIG. 9. N-benzoyl-5'-O-(tert-butyldimethylsilyl)-2'-deoxycytidine (6) (50.0 g, 112.2 mmol) was dissolved in DMSO (210 mL) in a 2 L round bottom flask. It was added sequentially with acetic acid (210 mL) and acetic anhydride (96 mL), and stirred for 48 h at room temperature. During this period of time, a complete conversion to product was observed by TLC($R_f$=0.6, EtOAc:hex/ 10:1 for the product).

The mixture was separated into two equal fractions, and each was transferred to a 2000 mL beaker and neutralized by slowly adding saturated $K_2CO_3$ solution until $CO_2$ gas evolution was stopped (pH 8). The mixture was then extracted with EtOAc in a separating funnel. The organic part was then washed with saturated solution of $NaHCO_3$ (2×1 L) followed by with distilled water (2×1 L), then the organic part was dried over $Na_2SO_4$.

The organic part was then concentrated by rotary evaporation. The product was then purified by silica gel flash-column chromatography using puriflash column (Hex: EtOAc/1:4 to 1:9, 3 column rums, on 15 um, HC 300 g puriflash column) to obtain $N^4$-benzoyl-5'-O-(ter-butyldimethylsilyl)-3'-O-(methylthiomethyl)-2'-deoxycytidine (7) as grey powder in 60% yield (34.0 g, $R_f$=0.6, EtOAc:hex/9:1), see FIG. 9.

$^1$H-NMR of compound 7 (CDCl$_3$): $\delta_H$ 8.40 (d, J=7.1 Hz, 1H), 7.93 (m, 2H), 7.64 (m, 1H), 7.54 (m, 3H), 6.30 (m, 1H), 4.62 & 4.70 (2×d, J=11.59 Hz, 2H), 4.50 (m, 1H), 4.19 (m, 1H), 3.84 & 3.99 (2×dd, J=11.59 & 2.79 Hz, 2H), 2.72 (m, 1H), 2.21 (m, 1H), 2.18 (s, 3H), 0.99 (s, 9H), and 0.16 (s, 6H) ppm.

Example 5

$N^4$-Benzoyl-3'-O-(ethyldithiomethyl)-5'-O-(tert-butyldimethylsilyl)-2'-deoxycytidine (8)

$N^4$-Benzoyl-5'-O-(tert-butyldimethylsilyl)-3'-O-(methylthiomethyl)-2'-deoxycytidine (7) (2.526 g, 5.0 mmol) dissolved in dry $CH_2Cl_2$ (35 mL) was added with molecular sieve-3A (10 g). The mixture was stirred for 30 minutes. It was then added with Et$_3$N (5.5 mmol), and stirred for 20 minutes on an ice-salt-water bath. It was then added slowly with 1M $SO_2Cl_2$ in $CH_2Cl_2$ (7.5 mL, 7.5 mmol) using a syringe and stirred at the same temperature for 2 hours under $N_2$-atmosphere. Then benzenethiosulfonic acid sodium salt (1.6 g, 8.0 mmol) in 8 mL dry DMF was added and stirred for 30 minutes at room temperature. Finally, EtSH was added (0.74 mL) and stirred additional 50 minutes at room temperature. The reaction mixture was filtered through celite-S, and washed the product out with $CH_2Cl_2$. After concentrating the resulting $CH_2CH_2$ part, it was purified by flash chromatography using a silica gel column (1:1 to 3:7/Hex:EtOAc) to obtain compound 8 in 54.4% yield (1.5 g), see FIG. 9. $^1$H-NMR of compound 8 (CDCl$_3$): $\delta_H$ 8.40 (m, 1H), 7.95 (m, 2H), 7.64 (m, 1H), 7.54 (m, 3H), 6.25 (m, 1H), 4.69 & 4.85 (2×d, J=11.60 Hz, 2H), 4.50 (m, 18), 4.21 (m, 1H), 3.84 & 3.99 (2×dd, J=11.59 & 2.79 Hz, 2H), 2.75 (m, 3H), 2.28 (m, 1H), 1.26 (m, 3H), 0.95 (s, 9H), and 0.16 (s, 6H) ppm.

Example 6

$N^4$-Benzoyl-3'-O-(ethyldithiomethyl)-2'-deoxycytidine (9)

$N^4$-Benzoyl-3'-O-(ethyldithiomethyl)-5'-O-(tert-butyldimethylsilyl)-2'-deoxycytidine (8, 1.50 g, 2.72 mmol) was dissolved in 50 mL THF. Then 1M TBAF in THF (3.3 mL) was added at ice-cold temperature under nitrogen atmosphere. The mixture was stirred for 1 hour at room temperature. Then the reaction was quenched by adding 1 mL MeOH, and solvent was removed after 10 minutes by rotary evaporation. The product was purified by silica gel flash chromatography using gradient 1:1 to 1:9/Hex:EtOAc to result in compound 9 (0.78 g, 65% yield, Rf=0.6 in 1:9/Hex:EtOAc), see FIG. 9. $^1$H-NMR of compound 9 (CDCl$_3$): $\delta_H$ 8.41 (m, 1H), 8.0 (m, 2H), 7.64 (m, 2H), 7.50 (m, 2H), 6.15 (m, 1H), 4.80 & 4.90 (2×d, J=11.60 Hz, 2H), 4.50 (m, 1H), 4.21 (m, 1H), 4.00 & 3.85 (2×dd, J=11.59 & 2.79 Hz, 2H), 2.80 (m, 2H), 2.65 (m, 1H), 2.40 (m, 1H), and 1.3 (s, 3H) ppm.

Finally, the synthesis of compound 10 was achieved from compound 9 following the standard synthetic protocol described in the synthesis of compound 5 (see FIG. 8).

Example 7

Figure 10:
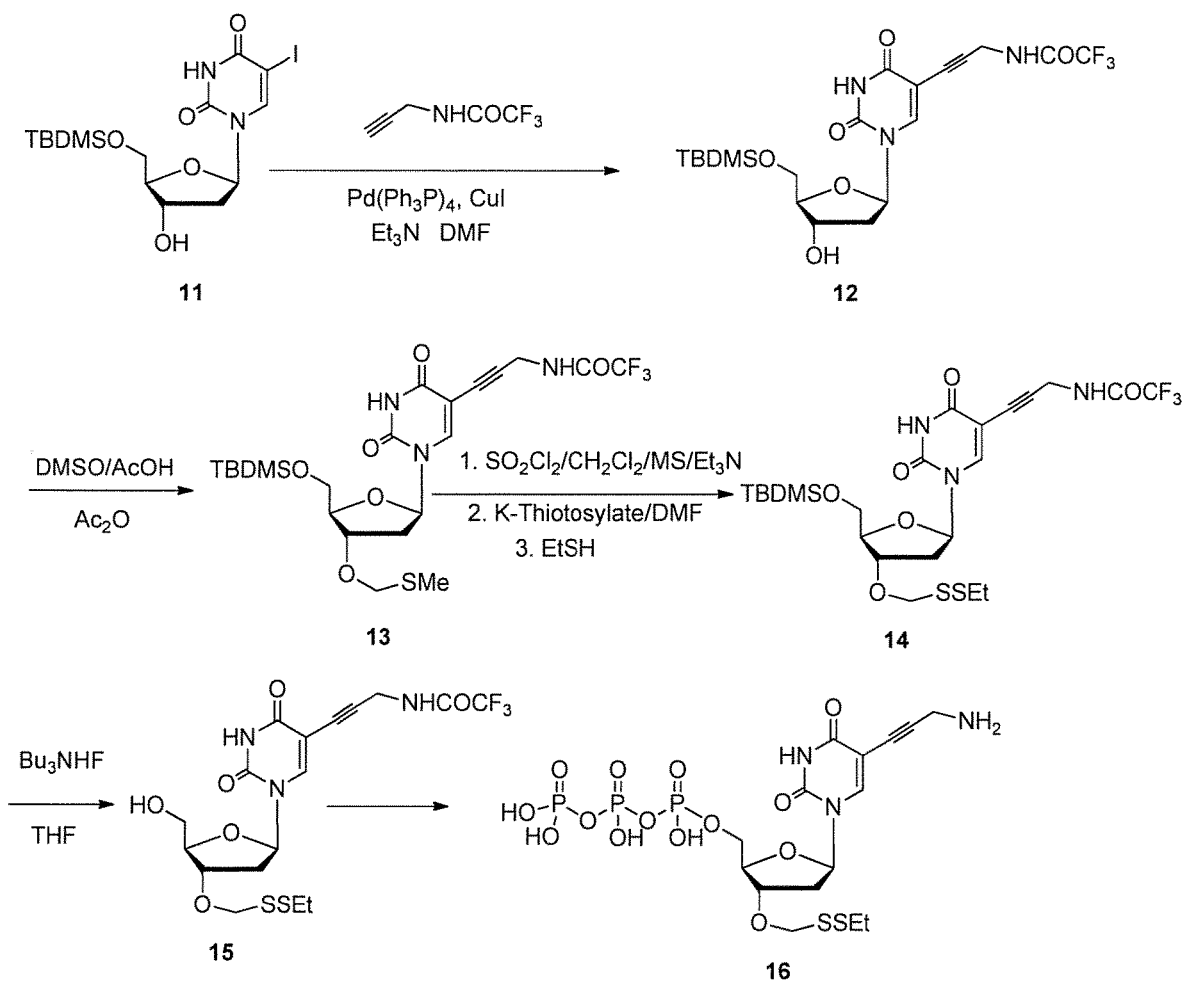
FIG. 10 shows a synthetic route of the labeled nucleotides specific for labeled dT intermediate.
Figure 11:
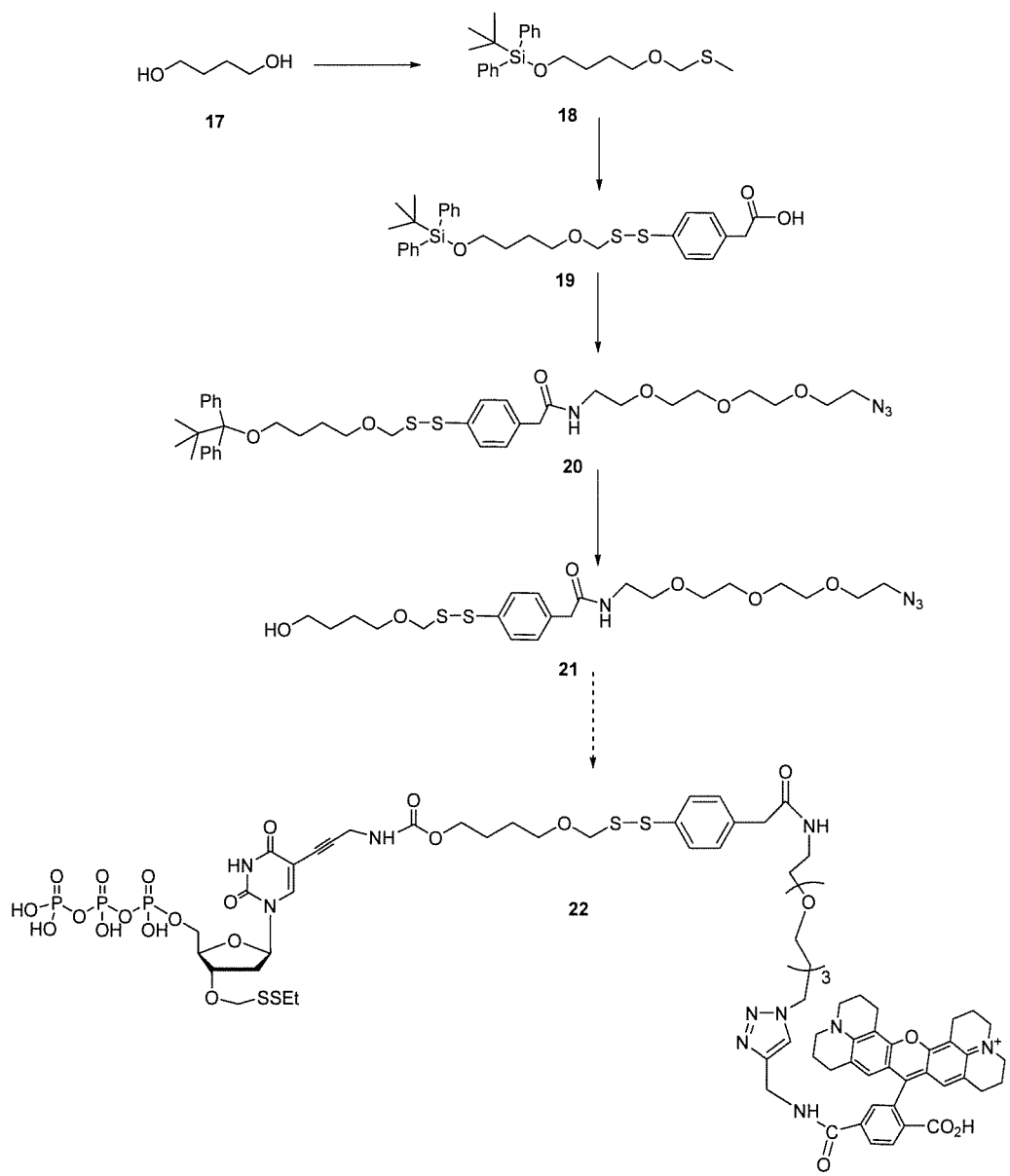
FIG. 11 shows a cleavable linker synthesis starting from an 1,4-dutanediol.

The synthesis of the labeled nucleotides can be achieved following the synthetic routes shown in FIG. 10 and FIG. 11. FIG. 10 is specific for the synthesis of labeled dT intermediate, and other analogs could be synthesized similarly.

Synthesis of 5'-O-(tert-butyldimethylsilyl)-5-(N-trifluoroacetyl-aminopropargyl)-2'-deoxyuridine (12)

5'-O-(tert-butyldimethylsilyl)-5-iodo-2'-deoxyuridine (11, 25.0 g, 53.4 mmol) was dissolved in dry DMF (200 mL) in a 2-neck-round bottom flask. The reaction flask is flushed with Ar-gas filled balloon. It was then added with, freshly opened, vacuum dried tetrakis(triphenylphosphine)palladium (0) (6.16 g, 5.27 mmol) and CuI (2.316 g, 12.16 mmol) and stirred at room temperature for 10 minutes under argon atmosphere. Next, N-trifluoroacetyl-propargylamine (23.99 g, 157.8 mmol, 2.9 eq) and Et$_3$N (14.7 mL, 105.5 mmol) were added sequentially. The mixture was stirred for 3.0 hours at room temperature and reaction completion was confirmed by TLC (Rf=0.5 in EtOAc:Hex/3:2 for the product).

Solvent was then removed by rotary evaporation. The resulting crude product was dissolved in 500 mL EtOAc and transferred into a separating funnel. The organic part was then washed with saturated NaHCO$_3$ (2×400 mL) and saturated NaCl (2×400 mL) solutions, respectively. The EtOAc part was then dried over anhydrous Na$_2$SO$_4$. After filtering off the Na$_2$SO$_4$ salt, the filtrate was concentrated using a rotary evaporator. It was then purified by a silica gel flash chromatography (1:1 Hex:EtOAc to 2:3 Hex:EtOAc, 200 gm, 15 um HP puriflash column, 3 column runs) after binding to 3×40 gm silica gel resulting in 21.994 g of 12 (83.88% yield), see FIG. 10.

$^1$H-NMR in compound 12 (DMF-d$_7$): $\delta_H$ 11.65 (brs, 1H), 10.15 (brs, 1H), 8.15 (brs, 1H, H6), 6.37 (t, J=5.99 Hz, 1H, H1'), 5.42 (m, 1H), 4.41 (m, 1H), 4.37 (brs, 2H, for NH—CH, of propargylamine group), 4.00 (m, 1H), 3.84-3.97 (m, 2H), 2.30 (m, 1H, H2'), 2.20 (m, 1H, H2'), 0.97 (s, 9H, 3×—CH$_3$, TBDMS) and 0.19 (s, 6H, 2× CH$_3$, TBDMS) ppm.

Example 8

Synthesis of 5'-O-(tert-butyldimethylsilyl)-3'-O-(methylthiomethyl)-5-(N-trifluoroacetyl-aminopropargyl)-2'-deoxyuridine (13)

Compound 12 (21.99 g, 44.77 mmol) was dissolved in DMSO (90 mL) in a 1000 mL round bottom flask. It was then added sequentially with AcOH (40 mL) and acetic anhydride (132 mL) and stirred for 48 hours at room temperature. The reaction completion was confirmed by TLC (R$_f$=0.5; Hex:EtOAc/1:1 for the product).

The reaction mixture was then transferred to 2,000 mL beaker, and neutralized by saturated K$_2$CO$_3$ until the evolution of CO$_2$ gas was ceased (~pH 8.0). The mixture was then transferred into a separating funnel and extracted (2×500 mL CH$_2$Cl$_2$). The combined organic part was then washed with saturated NaHCO$_3$ (1×500 mL) and dried over Na$_2$SO$_4$. After filtering off the Na$_2$SO$_4$, the organic part was concentrated by rotary evaporation and purified by silica gel flash chromatography (Hex:EtOAc/7:3 to 1:1) producing 12.38 g of compound 13 (~50% yield), see FIG. 10. TLC: R$_f$=0.5; Hex:EtOAc/1:1, $^1$H-NMR of compound 13 (DMSO-d$_6$): δH 11.69 (s, 1H), 10.01 (s, 1H), 7.93 (s, 1H, H6), 6.07 (m, 1H, H1'), 4.69 (m, 2H), 4.38 (m, 1H), 4.19 (m, 2H), 4.03 (m, H), 3.75 (m, 2H), 2.34 (m, 1H), 2.14 (m, 1H), 2.07 (s, 3H), 0.86 (s, 9H) and 0.08 (s, 6H) ppm.

The synthesis of the compounds 14, 15 and 16 can achieved following the synthetic protocols of the related steps described for compounds 5 and 10. Synthesis of other N-trifluoroacetyl-aminopropargyl nucleobases by described as in U.S. Pat. No. 8,017,338 [38], incorporated herein by reference. Removal of the N-trifluoroacetyl group to produce the aminopropargyl nucleobases may be produced by solvolysis under mild conditions [45].

On the other hand, the cleavable linker synthesis can be achieved as shown in FIG. 11, starting from an 1,4-dutanediol and is described in Example 9.

Example 9

Synthesis of 4-O-(tert-butyldiphenylsilyl)-butane-1-O-(methylthiomethyl), 18

18.3 g 1,4-butanediol, 17 (18.3 g, 203.13 mmol) dissolved in 100 mL dry pyridine in a 1 L flask was brought to sub-zero temperature on an ice-bath under nitrogen atmosphere. It was added with tert-butyldiphenylsilylchloride (TBDPSCl, 19.34 g, 70.4 mmol) slowly with a syringe. The reaction flask was allowed to warm up to room temperature with the removal of the ice-bath and stirring continued for overnight at room temperature. The solvent was then removed by rotary evaporation and purified by flash chromatography using silica gel column (7:3 to 1:1/Hex:EtOAc) resulting in 4-O-(tert-butyldiphenylsilyl)-butane-1-ol (13.7 g, 59.5% yield, R$_f$ 0.7 with 1:1/Hex:EtOAc, $^1$H NMR (CDCl$_3$): $\delta_H$ 7.70 (4H, m), 7.40 (4H, m), 3.75 (2H, m), 3.65 (m, 2H), 3.70 (4H, m) and 1.09 (9H, m) ppm. Of the resulting product, 6.07 g (18.5 mmol) was dissolved in 90 mL dry DMSO, see FIG. 11. It was then added with acetic acid (15 mL) and acetic anhydride (50 mL). The mixture was stirred for 20 hours at room temperature. It was then transferred to a separating funnel and washed with 300 mL distilled water by partitioning with the same volume of EtOAc. The EtOAc part was then transferred to a 1,000 mL beaker and neutralized with saturated K$_2$CO$_3$ solution. The aqueous part was removed by partitioning and the EtOAc part was then further washed with distilled water (3×300 mL) and dried over MgSO$_4$. The EtOAc part was then concentrated and purified by flash chromatography on a silica gel column (Hex: EtOAc/97:3 to 90:10) to obtain 4-O-(tert-butyldiphenylsilyl)-1-O-(methylthiomethyl)-butane, 18 (5.15 g, 71.7% yield, R$_f$=0.8 in 9:1/Hex:EtOAc). $^1$H NMR (CDCl$_3$): δH 7.70 (4H, m), 7.40 (6H, m), 4.62 (2H, s), 3.70 (2H, m), 3.50 (2H, m), 2.15 (2H, s), 1.70 (4H, m) and 1.08 (9H, m) ppm.

Example 10

Synthesis of Compound 19

Compound 18 (2.0 g, 5.15 mmol) was dissolved in 40 mL dry CH$_2$Cl$_2$, and added with 10 g molecular sieve-3A and 0.78 mL Et$_3$N (5.66 mmol). The mixture was stirred under N$_2$ gas at room temperature for 30 min. Then the flask was placed on an ice-bath to bring the temperature to sub-zero. It was then added slowly with 7.7 mL of 1M SO$_2$Cl$_2$/CH$_2$Cl$_2$ solution (7.7 mmol) and stirred under N$_2$ for 1 hour. Then the ice-bath was removed and benzenethiosulfonic acid-Na salt (1.6 g, 8.24 mmol) in 8 mL DMF was added and stirred for 30 minutes at room temperature. Then 4-mercaptophenylacetic acid (1.73 g, 10.3 mmol, 2.0 eq) in 7 mL dry DMF was added and stirred for 2 hours. The entire crude sample was then filtered through celite-S and the product was washed out by EtOAc. EtOAc extract was then concentrated by rotary evaporation and purified on a silica gel column (1:1 to 3:7/Hex:EtOAc) to obtain 1.19 g of compound 19 in 43% yield, see FIG. 11, R$_f$=0.5 Hex:EtOAc/3:7. $^1$H NMR (CDCl$_3$): 7.65 (4H, m), 7.55 (2H, m), 7.45 (6H, m), 7.20 (2H, s), 4.80 (2H, m), 3.65 (4H, m), 3.50 (2H, m), 1.60 (4H, m), and 1.09 (9H, s) ppm.

Example 11

Synthesis of Compound 20

Compound 19 (0.6 g, 1.11 mmol) dissolved in 20 mL dry DMF was treated with DSC (0.426 g, 1.5 eq) and Et$_3$N (0.23 mL) at room temperature and stirred for 1.5 hours under nitrogen atmosphere. Then a mixture consisting of 1 I-azido-3,6,9-trioxadecan-1-amine (2.0 eq) and Et$_3$N (2.0 eq) was prepared in 5 mL DMF. The entire solution was added to the reaction mixture at once and stirred for 1 hour. The solvent was then removed under vacuum and purified by silica gel flash chromatography using gradient 0 to 10% CH$_2$Cl$_2$: MeOH to obtain compound 20 in 36% yield (0.297 g. R$_f$=0.8, 10% MeOH:CH$_2$Cl$_2$), see FIG. 11. $^1$H NMR (MeOH-d$_4$): $\delta_H$7.70 (4H, m), 7.55 (2H, m), 7.40 (6H, m), 7.45 (2H, m), 4.85 (2H, s), 3.65-3.30 (22H, m), 1.65 (4H, m), and 1.09 (9H, m) ppm.

Then, the product 20 (0.297 g) was dissolved in 7 mL dry THF in a flask and placed on an ice-bath to bring to sub-zero temperature under nitrogen atmosphere. Then 0.6 mL 1M TBAF in THF was added drop-wise and stirred for 3 hours at ice-cold temperature. The mixture was quenched with 1 mL MeOH and volatiles were removed by rotary evaporation and purified by flash chromatography to obtain 165 mg of the product 21, see Figure ii, $^1$H NMR (MeOH-d4): δH 7.55 (2H, m), 7.25 (2H, m), 4.85 (2H, s), 3.75-3.30 (22H, m) and 1.50 (4H, m) ppm. This product can be coupled to alkyne substituted dye using click chemistry and to nucleotide using CDI as activating agent to result in compound 22.

Figure 12:
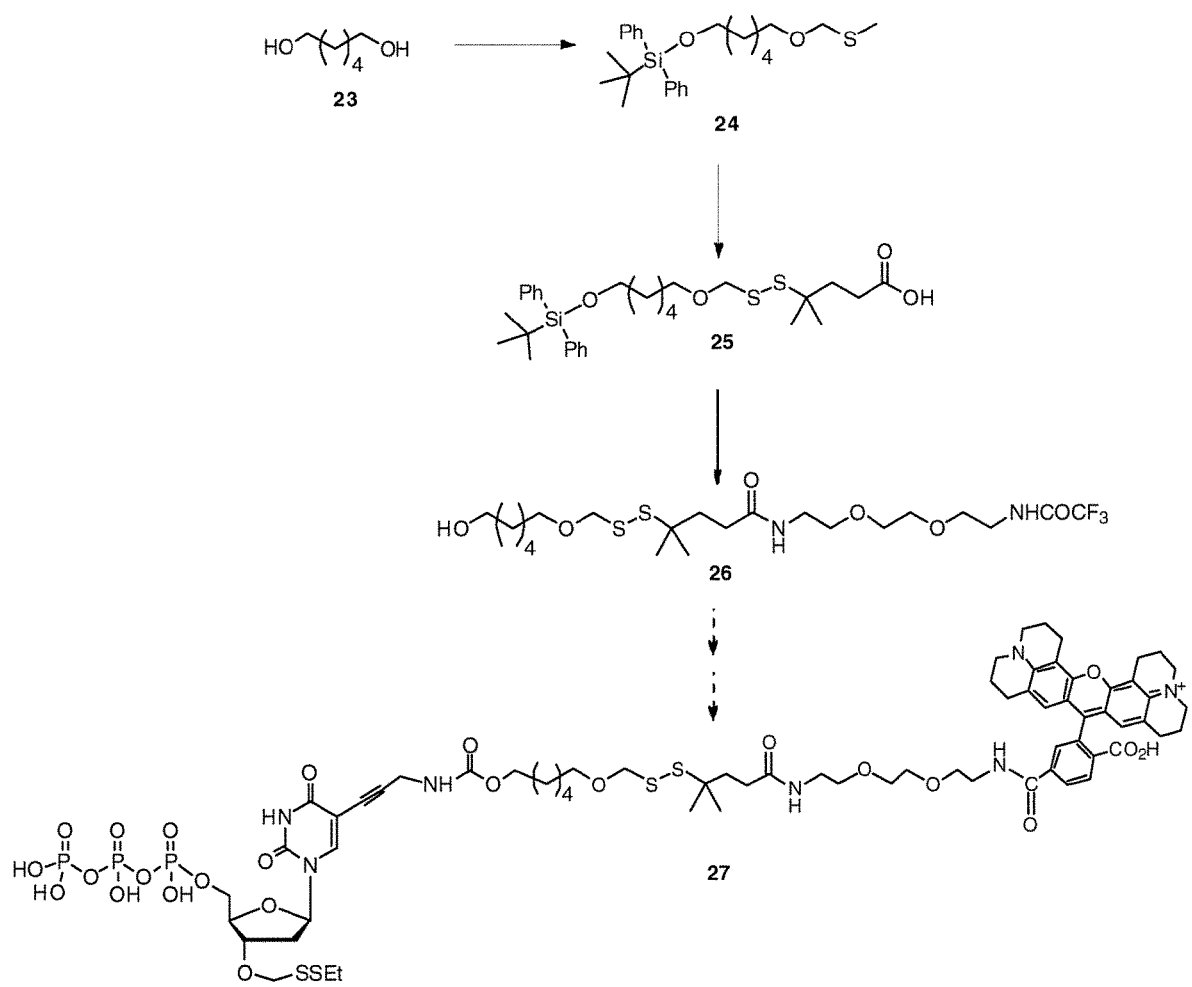
FIG. 12 shows another variant of cleavable linker, where the stabilizing gem-dimethyl group is attached to α-carbon of the cleavable linker.

Another variant of cleavable linker, where the stabilizing gem-dimethyl group attached to α-carbon of the cleavable linker, can be achieved following FIG. 12.

Example 12

In another aspect, the cleavable linker can be compound 30, where the disulfide is flanked by gem-dimethyl groups and attached to a flexible ethylene glycol linker (PEG). The linker is attached to the PA-nucleotide (e.g. compound 33) via carbamate group (—NH—C(=O)O—). The resulting nucleotide analogue in such case can be as in compound 35 (dUTP analogue), which can be synthesized according to the FIG. 13. Other nucleotide analogues (e.g. analogues of dATP, dGTP, dCTP) can be synthesized similarly by replacing PA-nucleotide 33 with appropriate PA-nucleotide analogues at the last step of the reaction sequence.

Example 13

Synthesis of Compound 28

Compound 18 (15.53 g, 40 mmol) (see Example 9) for synthesis of compound 18) was dissolved in 450 mL of dry dichloromethane in a round bottom flask. Molecular sieves (3A, 80 g) and triethylamine (5.6 mL) were added, and the reaction mixture was stirred at 0° C. for 0.5 hour under nitrogen atmosphere. Next, SO$_2$Cl$_2$ (1 M in DCM, 64 mL) was added slowly by a syringe and stirred for 1.0 hour at 0° C. temperature. Then, ice-water bath was removed, and a solution of potassium-thiotosylate (10.9 g, 48.1 mmol) in 20 mL anhydrous DMF was added at once and stirred for 20 minutes at room temperature. The reaction mixture was then poured into 3-mercapto-3-methylbutan-1-ol (4.4 mL, 36 mmol) dissolved in 20 mL DMF in a 2 L round-bottom flask. The resulting mixture was stirred for 0.5 hours at room temperature, and filtered through celite. The product was extracted with ethyl acetate. The combined organic extracts were washed with distilled water in a separatory funnel, followed by concentrating the crude product by rotary evaporation. The product (28) was obtained in 26% yield (5.6 g) after purification by flash chromatography on silica gel using EtOAc:Hexane as mobile phase, see FIG. 13. $^1$H NMR (CDCl$_3$): $δ_H$ 7.67-7.70 (m, 4H), 7.37-7.47 (m, 6H), 4.81 (s, 2H), 3.81 (t, J=6.73 Hz, 2H), 3.70 (t, J=6.21 Hz, 2H), 3.59 (t, J=6.55 Hz, 2H), 1.90 (t, J=6.95 Hz, 2H), 1.58-1.77 (m, 4H), 1.34 (s, 6H), and 1.07 (s, 9H) ppm.

Example 14

Synthesis of Compound 29

Compound 28 (5.1 g, 10.36 mmol) was dissolved in 100 mL anhydrous pyridine in a 500 mL round bottom flask. To this solution, 1,1'-carbonyldiimidazole (CDI) (3.36 g, 20.7 mmol) was added in one portion and the reaction was stirred for 1.0 hour at room temperature under a nitrogen atmosphere. Then, the reaction mixture was poured into a solution consisting of 2,2'-(ethylenedioxy)bis(ethylamine) (7.6 mL, 51.8 mmol) and anhydrous pyridine (50 mL). The mixture was stirred for 1.0 hour at room temperature, and the volatiles were removed by rotary evaporation. The resulting crude product was purified by flash chromatography on silica using MeOH:CH$_2$Cl$_2$/9.5:0.5 to furnish pure compound 29 (4.4 g, 65% yield), see FIG. 13. $^1$H NMR (CDCl$_3$): $δ_H$ 7.63-7.68 (m, 4H), 7.34-7.44 (m, 6H), 4.76 (s, 2H), 4.17 (t, J=7.07 Hz, 2H), 3.65 (t, J=6.16 Hz, 2H), 3.60 (s, 4H), 3.49-3.51 (m, 6H), 3.31-3.39 (m, 2H), 2.88 (m, 2H), 1.9 (t, J=7.06 Hz, 2H), 1.57-1.73 (m, 4H), 1.31 (s, 6H) and 1.03 (s, 9H) ppm.

Example 15

Synthesis of Compound 31

Compound 29 (0.94 g, 1.42 mmol) was dissolved in 40 mL dry THF and treated with 1M TBAF in THF (1.6 mL, 1.6 mmol) at 0° C. under nitrogen atmosphere. The reaction mixture was stirred for 2.0 hours at 0° C., during which time LC-MS confirmed complete removal of the TBDPS protecting group. After removing solvent by rotary evaporation, the product was purified by flash chromatography on C18 Flash Column (gradient: 0-100% B over 50 minutes, where A=50 mM TEAB and B=acetonitrile). The target fractions were combined and lyophilized resulting in pure compound 30 (0.284 g, 47% yield), MS (ES+) calculated for (M+H) 429.21, observed m/z 429.18. Next, compound 30 (0.217 g, 0.51 mmol) was dissolved in 13 mL of dry acetonitrile under a nitrogen atmosphere. To this solution, DIPEA (97.7 uL, 0.56 mmol) and Fmoc-NHS ester (273.6 mg, 0.81 mmol) were added at 0° C. temperature and stirred for 2.0 hours at the same temperature. The product was then purified by flash chromatography on silica gel, 1:1 to 1:9/hex:EtOAc gradient, leading to a semi-pure product, which was further purified using 2-5%/MeOH—CH$_2$Cl$_2$ gradient to obtain compound 31 (0.245 g, 74% yield), see FIG. 13. $^1$H NMR (CDCl$_3$): $δ_H$ 7.70 (2H, d, J=7.3 Hz), 7.59 (2H, d, J=7.6 Hz), 7.32 (2H, m), 7.24 (2H, m), 4.69 (2H, s), 4.35 (2H, m), 4.16 (1H, m), 4.09 (2H, m), 3.60-3.45 (12H, m), 3.36-3.26 (4H, m), 1.82 (2H, m), 1.60 (4H, m) and 1.22 (6H, s) ppm.

Example 16

Synthesis of Compound 32

Compound 31 (93 mg, 0.143 mmol) was dissolved in dry acetonitrile (12.0 mL) in a round bottom flask equipped with magnetic bar and a nitrogen gas source. To this solution, DSC (56 mg, 0.21 mmol) and DIPEA (37.4 μL, 0.21 mmol) were added sequentially, and the resulting mixture was stirred at room temperature for 5.0 hours. Additional DSC (48 mg, 0.18 mmol) and DIPEA (37.4 μL, 0.21 mmol) were added and stirring continued for 15.0 hours at room temperature, during which time TLC showed full conversion to the activated NHS ester. The product 32 was obtained (59 mg, 53% yield) as a thick oil following silica gel flash chromatography purifications using hexane-ethyl acetate (3:7 to 1:9) gradient and was used in the next step, see FIG. 13. $^1$H NMR (CDCl$_3$): $δ_H$ 7.70 (2H, d, J=7.53 Hz), 7.53 (2H, d, J: 7.3 Hz), 7.33 (2H, m), 7.24 (2H, m), 4.69 (2H, s), 4.34 (2H, m), 4.28 (2H, m), 4.16 (1H, m), 4.09 (2H, m), 3.57-3.46

(10H, m), 3.35-3.26 (4H, m), 2.75 (4H, s), 1.74 (4H, m), 1.62 (2H, m) and 1.23 (6H, s) ppm.

Example 17

Synthesis of Compound 34

An aliquot of compound 33 (10 µmols) (synthesized according to Ref. US 2013/0137091 A1) was lyophilized to dryness in a 15 mL centrifuge tube. It was then re-suspended in 1.0 mL of dry DMF with 60 µmols DIPEA. In a separate tube, compound 32 (30 µmols, 3 eq) was dissolved in 3.33 mL dry DMF, and added all at once. The reaction was mixed well by rigorous shaking by hand and placed on the shaker for 12 h at room temperature. Next, piperidine (0.33 mL) was added and shaking continued for 30 minutes at room temperature. The product was then purified by HPLC using C18 column (gradient: 0-70% B over 40 minutes, where A=50 mM TEAB and B=acetonitrile). The product 34 was obtained in 73.3% yield (7.33 umols) after lyophilization of the target fractions, see FIG. 13.

Example 18

Synthesis of Compound 35

An aliquot of compound 34 (4.9 µmols) was dissolved in 1.0 mL distilled water and 0.5M $Na_2HPO_4$ (0.49 mL) in a 15 mL centrifuge tube. In a separate tube, 10 mg of 5-$CR_6$G-NHS ester (17.9 µmol) was dissolved in 0.9 mL of dry DMF. This solution was then added to the reaction mixture all at once and stirred at room temperature for 6.0 hours. The reaction mixture was then diluted with 50 mM TEAB (25 mL). The product was purified by HPLC C18 (gradient: 0-60% B over 70 minutes). Compound 35 was obtained after lyophilization of the target fractions (2.15 µmol, 44% yield in ~98% purity by HPLC, and the structure was confirmed by MS (ES+): calculated for (M−H) $C_{58}H_{76}N_{10}O_{25}P_3S_2$, 1469.36, found m/z 1469.67, see FIG. 13.

Figure 14:
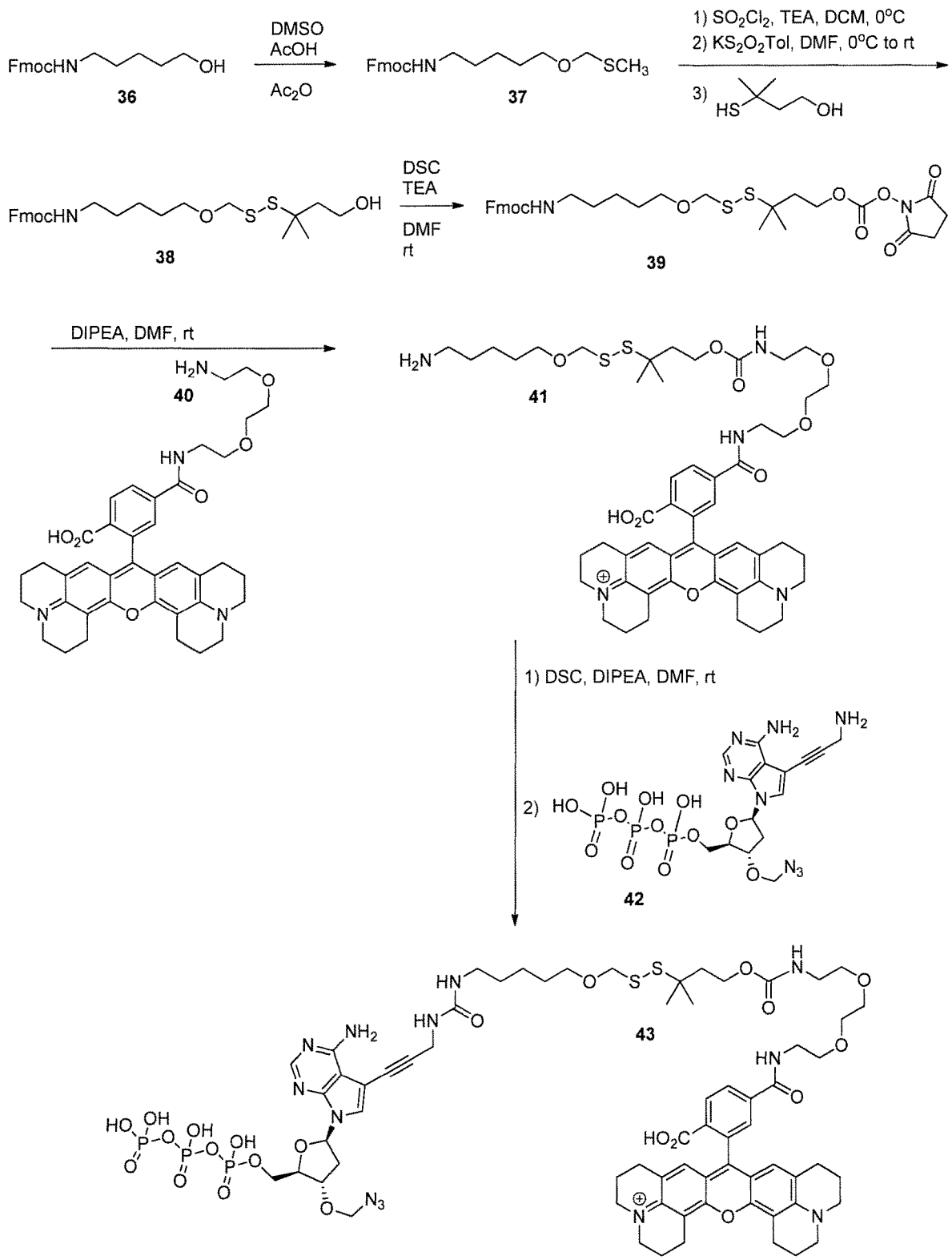
FIG. 14 shows the synthesis of a cleavable linker for dATP analogue where the cleavable disulfide is flanked by gem-dimethyl group and the linker is attached to PA-nucleotide via urea group (—NH(C=O)NH—). For other nucleotide analogues (e.g. for analogues of dCTP, dGTP, dUTP) can be synthesized similarly replacing 42 by appropriate PA-analogues at the last step of the reaction sequence.
Figure 45:
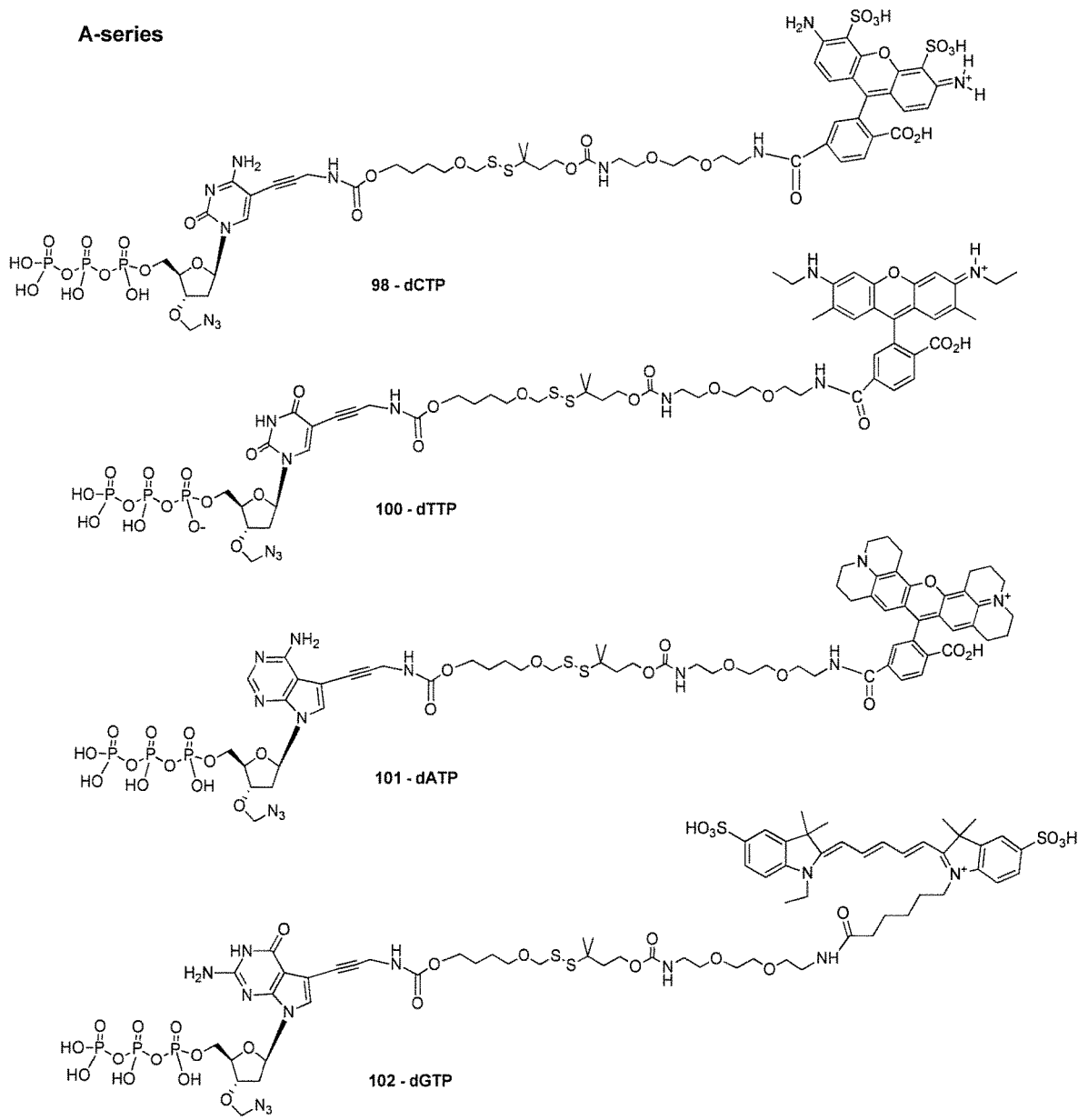
FIG. 45 shows complete chemical structures of four labeled nucleotides corresponding to dCTP, dTTP, dATP and dGTP from top to bottom (A-series, 98, 100, 101, and 102).
Figure 46:
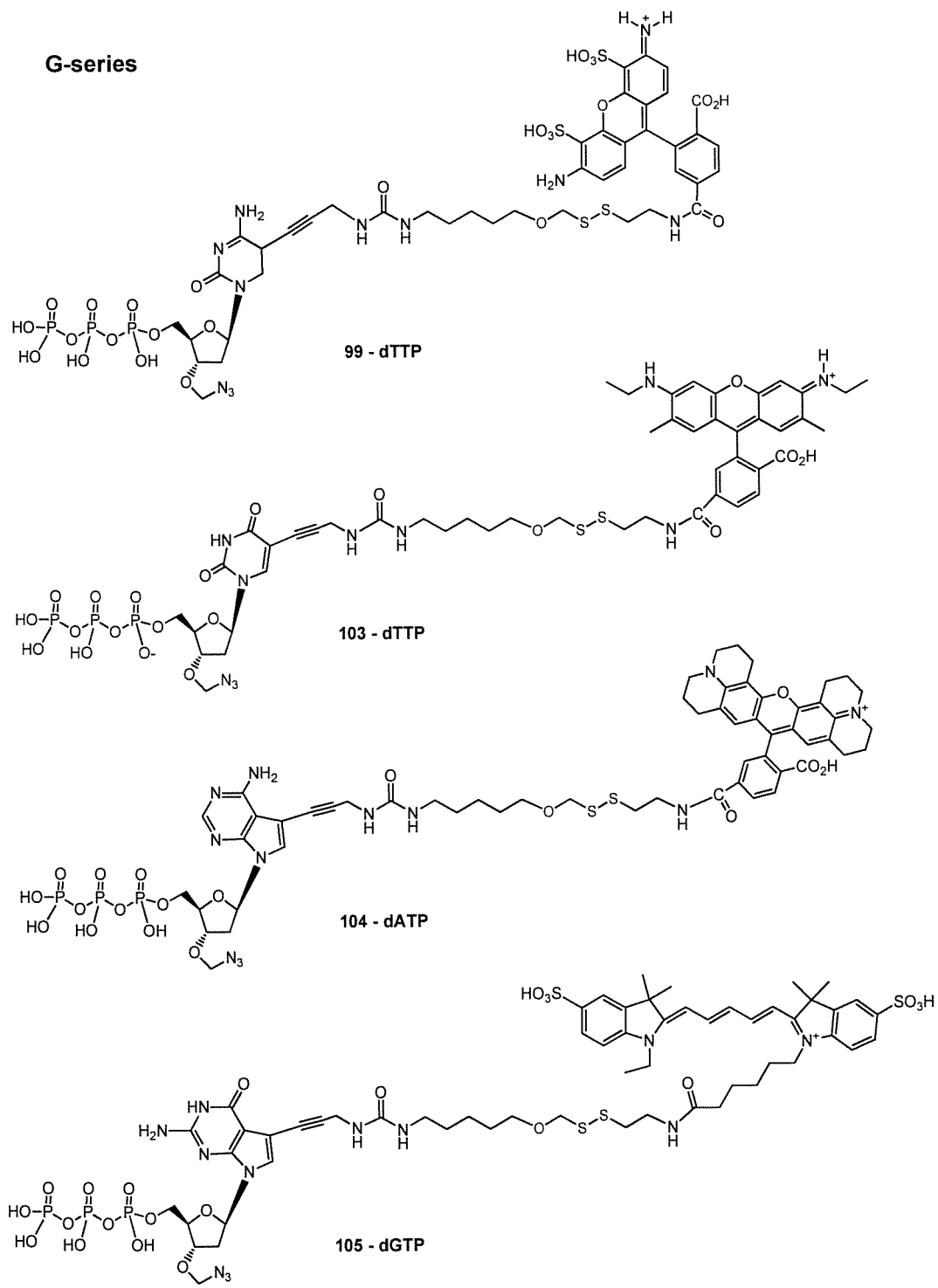
FIG. 46 shows complete chemical structures of four labeled nucleotides corresponding to dCTP, dTTP, dATP and dGTP from top to bottom (G-series, 99, 103, 104, and 105).
Figure 47:
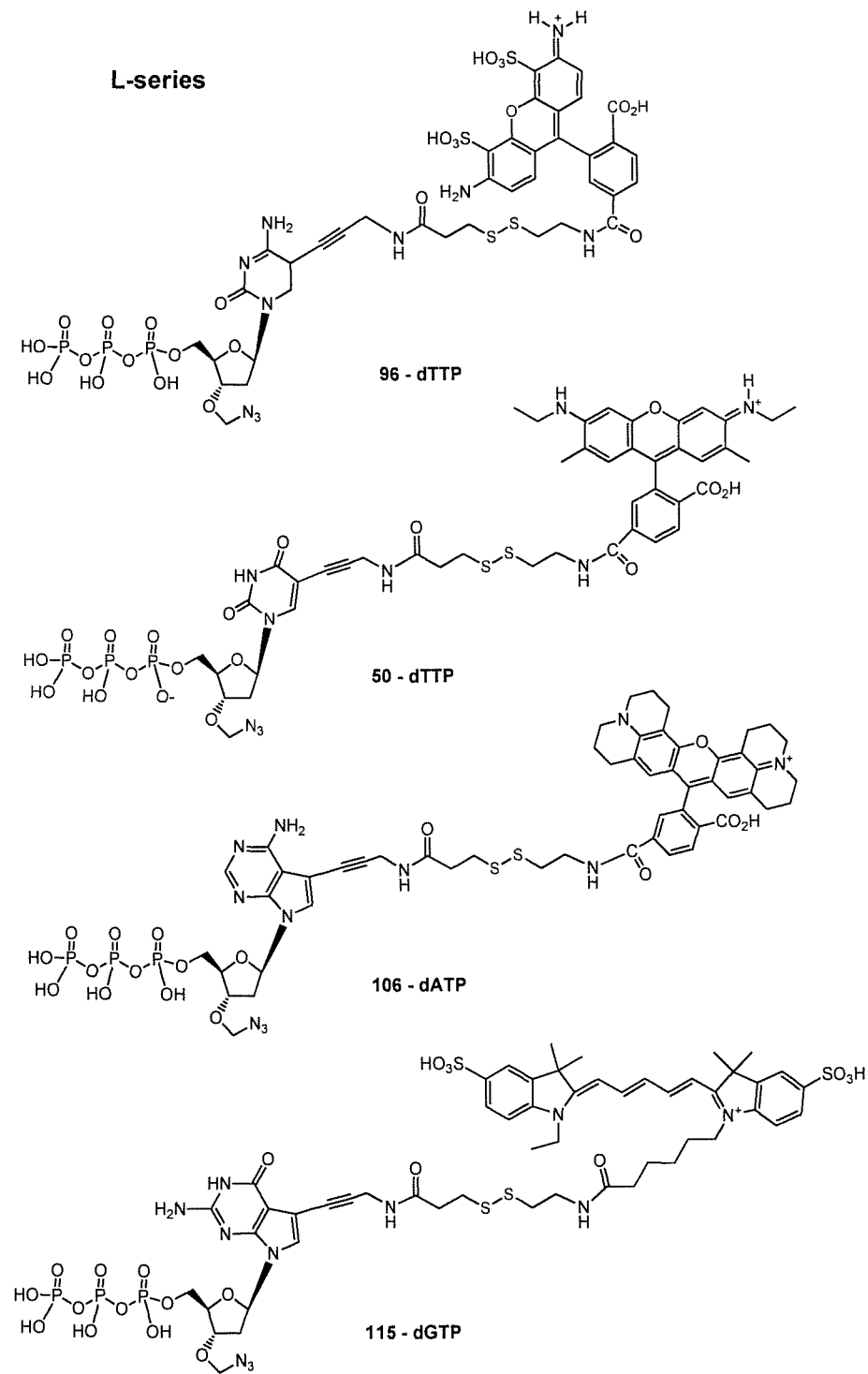
FIG. 47 shows complete chemical structures of four labeled nucleotides corresponding to dCTP, dTTP, dATP and dGTP from top to bottom (L-series, 96, 50, 106, and 115).
Figure 48:
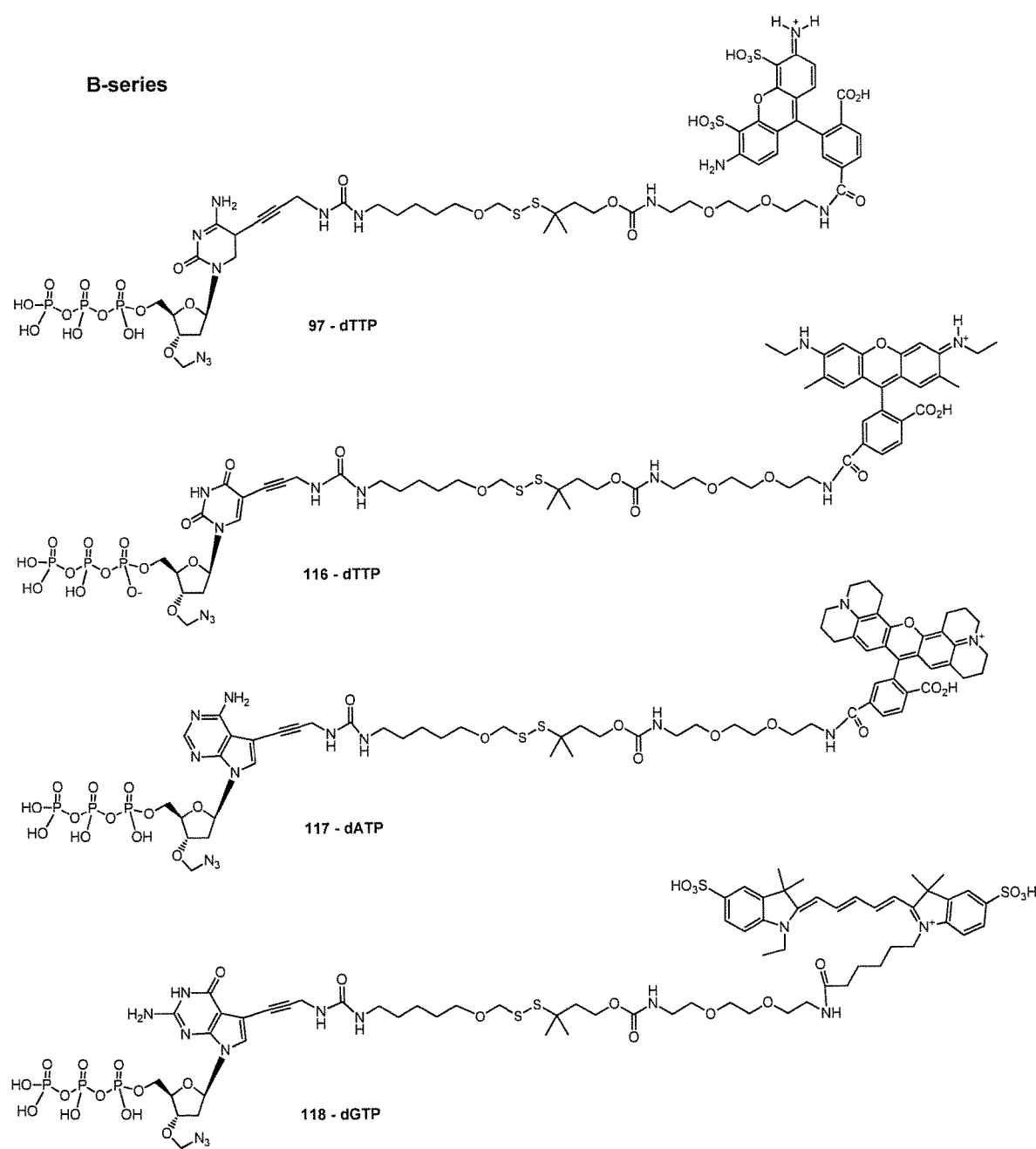
FIG. 48 shows complete chemical structures of four labeled nucleotides corresponding to dCTP, dTTP, dATP and dGTP from top to bottom (B-series: compounds 97, 116, 117, and 118).
Figure 50:
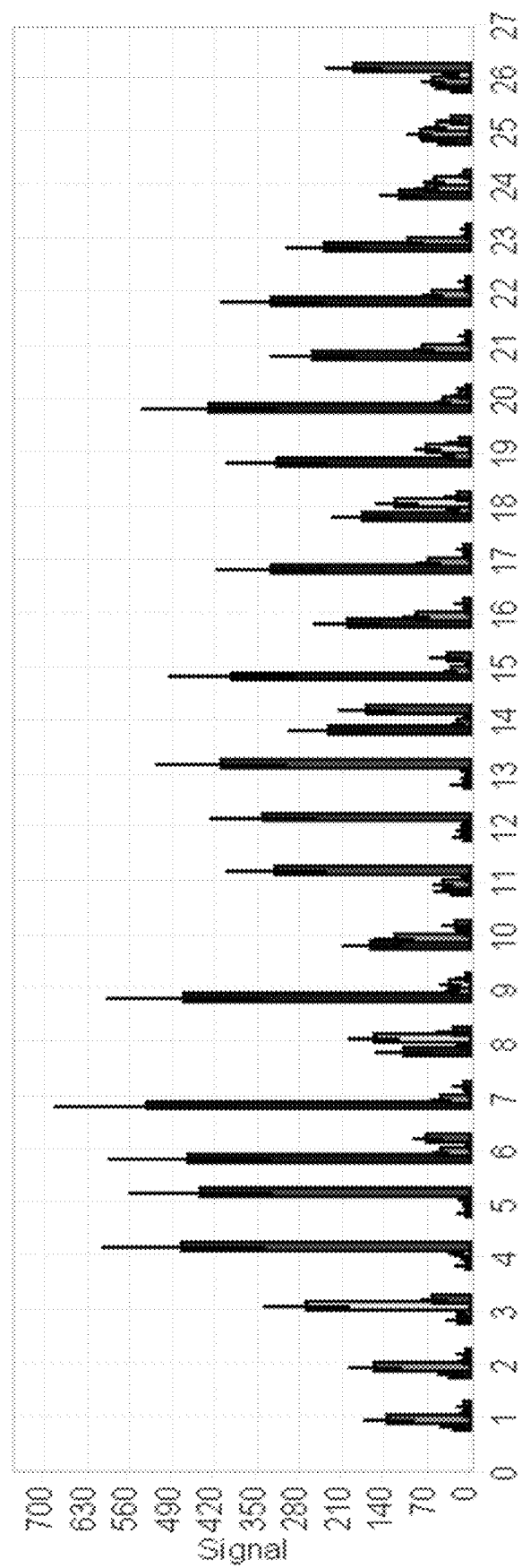
FIG. 50 shows example of intensities generated in sequencing run on GR using novel nucleotides (labeled and non-labeled as in described for FIG. 49), all carrying the —$CH_2$—SS-Me).

Similarly, analogs of dATP, dCTP and dGTP were synthesized following similar procedure described for compound 35, and characterized by HPLC and LC-MS resulting a full set of A-series (98, 100, 101, and 102, FIG. 45). For dATP analog calculated for (M−H) $C_{66}H_{83}N_{12}O_{23}P_3S_2$, 1,568.4348, found m/z 1,568.4400; For dCTP analog calculated for (M−H) $C_{52}H_{65}N_{11}O_{30}P_3S_4$, 1,545.2070, found m/z 1,545.2080 and for dGTP analog calculated for (M−H) $C_{66}H_{93}N_{12}O_{27}P_3S_4$, 1,706.4369, found m/z 1,706.4400. In another aspect, the invention involves nucleotides with cleavable linker as in compound 43 for dATP analogue where the cleavable disulfide is flanked by gem-dimethyl group and the linker is attached to PA-nucleotide via urea group (—NH(C═O)NH—). The compound can be synthesized according to FIG. 14 (for dATP analogue). For other nucleotide analogues (e.g. for analogues of dCTP, dGTP, dUTP) can be synthesized similarly replacing 42 by appropriate PA-analogues at the last step of the reaction sequence.

Example 19

Synthesis of Compound 37

In a 1 L round bottom flask with equipped with stir bar, 5-(fmoc-amino)-1-pentanol (36, 20 g, 62 mmol) was dissolved in DMSO (256 mL) at room temperature. To the solution, AcOH (43 mL) and $Ac_2O$ (145 mL) were added sequentially. The flask was closed with a rubber septum, placed under $N_2$, and stirred at room temperature for 20 h. Reaction completion was confirmed by TLC. The reaction mixture was then transferred to a 3 L beaker and the flask was washed with water. The beaker was cooled in an ice bath and the reaction mixture was neutralized with 50% saturated $K_2CO_3$ (400 mL) for 30 minutes. The mixture was transferred to a separatory funnel and extracted with EtOAc (2×700 mL). The organic phase was then washed with 50% saturated $K_2CO_3$ (2×400 mL), dried over $Na_2SO_4$, filtered and concentrated in vacuo. The crude oil was purified by silica gel chromatography (0 to 20% B over 20 min, A=Hex, B=EtOAc). Collection and concentration of fractions yields compound 37 (17.77 g, 75%) as a white solid, see FIG. 14. $^1$H NMR (CDCl$_3$): $\delta_H$ 7.79 (d, J=7.33, 2H), 7.63 (d, J=7.83, 2H), 7.441 (t, J=7.33, 2H), 7.357 (t, J=7.58, 2H), 4.803 (bs, 1H), 4.643 (s, 2H), 4.43 (d, J=6.82, 2H), 4.24 (t, J=6.82, 1H), 3.54 (t, J=6.32, 2H), 3.251 (m, 1H), 2.167 (s, 3H), 1.657-1.550 (m, 4H), and 1.446-1.441 (m, 2H) ppm.

Example 20

Synthesis of Compound 38

Compound 37 (2.77 g, 7.2 mmol) was dissolved in DCM (60 mL) in a 250 mL round bottom flask equipped with stir bar and septum under $N_2$. To the flask, triethylamine (3.0 mL, 21.6 mL, 3 eq) and 4 Å Molecular Sieves (28 g) were added. The suspension was stirred for 10 min at room temperature, followed by 30 min in an ice bath. To the flask was added $SO_2Cl_2$ (1M solution in DCM, 14.4 mL, 14.4 mmol, 2 eq) and the reaction mixture was stirred in the ice bath for 1 h. Reaction progress was monitored by the disappearance of starting material via TLC (1:1 Hex:EtOAc). Once $SO_2Cl_2$ activation was complete, a solution of potassium thiotosylate (2.45 g, 10.8 mmol, 1.5 eq) in DMF (60 mL) was rapidly added. The reaction mixture was allowed to slowly warm to room temperature for 1 h. The flask was then charged with 3-mercapto-3-methylbutanol (1.8 mL, 14.4 mmol, 2 eq) and stirred at room temperature for 1 h. The reaction mixture was filtered and concentrated in vacuo at 40° C. Purification by FCC (0 to 50% B over 30 min, A=Hex, B=EtOAc) afforded 38 (482 mg, 14%) as a yellow oil, see FIG. 14. $^1$H NMR (CDCl$_3$): $\delta_H$ 7.76 (d, J=7.81, 2H), 7.59 (d, J=7.32, 2H), 7.40 (t, J=7.32, 2H), 7.31 (t, J=7.32, 2H), 4.87 (bs, 1H), 4.79 (s, 2H), 4.40 (d, J=6.84, 2H), 4.21 (t, J=6.84 1H), 3.78 (t, J=6.84, 2H), 3.57 (t, J=6.35, 2H), 3.20 (m, 2H), 1.88 (t, J=6.84, 2H), 1.64-1.50 (m, 4H), 1.42-1.39 (m, 2H) and 1.32 (s, 6H) ppm.

Example 21

Synthesis of Compound 39

Compound 38 (135 mg, 0.275 mmol) was desiccated under vacuum for 2 h in a 50 mL round bottom flask. The vacuum was removed and the flask placed under $N_2$. Compound 38 was dissolved in DMF (3.1 mL) and the flask was charged with DIPEA (96 µL, 0.55 mmol, 2 eq). The solution was stirred for 10 min and then DSC (120 mg, 0.468 mmol, 1.7 eq) was added in one dose as a solid. The reaction mixture was allowed to stir for 2 h and completion was verified via TLC (1:1 Hex:EtOAc). The reaction was then concentrated in vacuo at 35° C. and further dried under high vacuum for 1 h. The crude oil was loaded on to silica gel and purified by FCC (0 to 50% B over 14 min, A=hex, B=EtOAc). The fractions were checked by TLC and concentrated to afford compound 39 (133 mg, 76%) as an oil that crystallized over time, see FIG. 14. $^1$H NMR (CDCl$_3$): $\delta_H$ 7.78 (d, J=7.58, 2H), 7.61 (d, J=7.58, 2H), 7.42 (t, J=7.58, 2H), 7.33 (t, J=7.58, 2H), 4.87 (bs, 1H), 4.80 (s, 2H), 4.48 (t, J=7.07, 2H), 4.44 (d, J=6.82, 2H), 4.24 (t, J=7.07, 1H), 3.58 (t, J=6.32, 2H), 3.22 (m, 2H), 2.83 (s, 4H), 2.08 (m, 2H), 1.649-1.562 (m, 4H), 1.443-1.390 (m, 2H) and 1.366 (s, 6H) ppm.

Example 22

Synthesis of Compound 40

2,2'-(Ethylenedioxy)bis(ethylamine) (92 µL, 635 µmol, 10 eq) and triethylamine (176 µL, 1270 µmol, 20 eq) were dissolved in DMF (10 mL). A separate solution of 6-ROX, NHS ester (40 mg, 64 umol, 1 eq) in DMF (2.7 mL) was also prepared. The 6-ROX, NHS ester solution was added dropwise to a rapidly stirring solution containing the diamine. The reaction stirred for 2 h and progress was monitored by C18 HPLC-MS (0 to 100% B over 10 min, A=50 mM TEAB, B=MeCN). Once complete, the reaction was purified via preparative C18-HPLC (10 to 100% B over 50 min, A=50 mM TEAB, B=MeCN). The fractions were combined and lyophilized to yield compound 40 (20 mg, 48%) as a purple-red solid, see FIG. 14. MS (ES−) calculated for (M−H) C$_{39}$H$_{45}$N$_4$O$_6$ 664.33, found m/z 664.56.

Example 23

Synthesis of Compound 41

Compound 40 (10 mg, 15 µmol) was dissolved in DMF (i mL) and charged with DIPEA (8 µL, 45 µmol, 3 eq). Separately, compound 39 (28 mg, 45 µmol, 3 eq) was dissolved in DMF (0.21 mL). The solution of compound 39 was rapidly added to the solution with compound 40. The reaction was placed on a shaker plate for 1.5 h at which time analytical C18-HPLC (0-100% B over 10 min, A=50 mM Acetate Buffer pH 5.2, B=MeCN) revealed remaining compound 40. Additional compound 39 (13 mg, 21 µmol, 1.4 eq) was added and the reaction was placed on a shaker plate for an additional hour. Without additional analytics, piperidine (300 µL) was added and allowed to react for 10 min. The reaction mixture was then directly injected on to a preparative C18-HPLC (10-100% B over 50 min, A=50 mM TEAB, B=MeCN). The fractions were collected and lyophilized to yield compound 41 (4.7 mg, 34%) as a purple-red solid, see FIG. 14. MS (ES+) calculated for (M+H) C$_{51}$H$_{68}$N$_5$O$_9$S$_2$$^+$ 959.45, found m/z 959.76.

Example 24

Synthesis of Compound 43

A 5 mL sample vial was charged with amine 41 (2 mg, 2 µmol), DSC (0.8 mg, 3 µmol, 1.5 eq), DIPEA (0.7 µL, 4 µmol, 2 eq), and N,N-dimethylformamide (1.7 mL). The reaction mixture was placed on a shaker for 1 h. Reaction progress was monitored by C18-HPLC (0 to 100% B over 10 min, A=50 mM Acetate Buffer pH 5.2, B=MeCN). Next, nucleotide 42 (6 umol, 3 eq, Ref. US 2013/0137091 A1) in 0.1 Na$_2$HPO$_4$ (3.3 mL) was added and the reaction mixture was placed on a shaker overnight. The reaction was next diluted with water and purified by preparative C18HPLC (0 to 60% B over 70 min, A=50 mM TEAB, B=MeCN) to give the title compound 43 (0.5 µmol, 25%), see FIG. 14. MS (ES−) calculated for (M−H) C$_{67}$H$_{37}$N$_{13}$O$_{22}$P$_3$S$_2$ 1581.47, found m/z 1581.65.

Example 25

Figure 15:
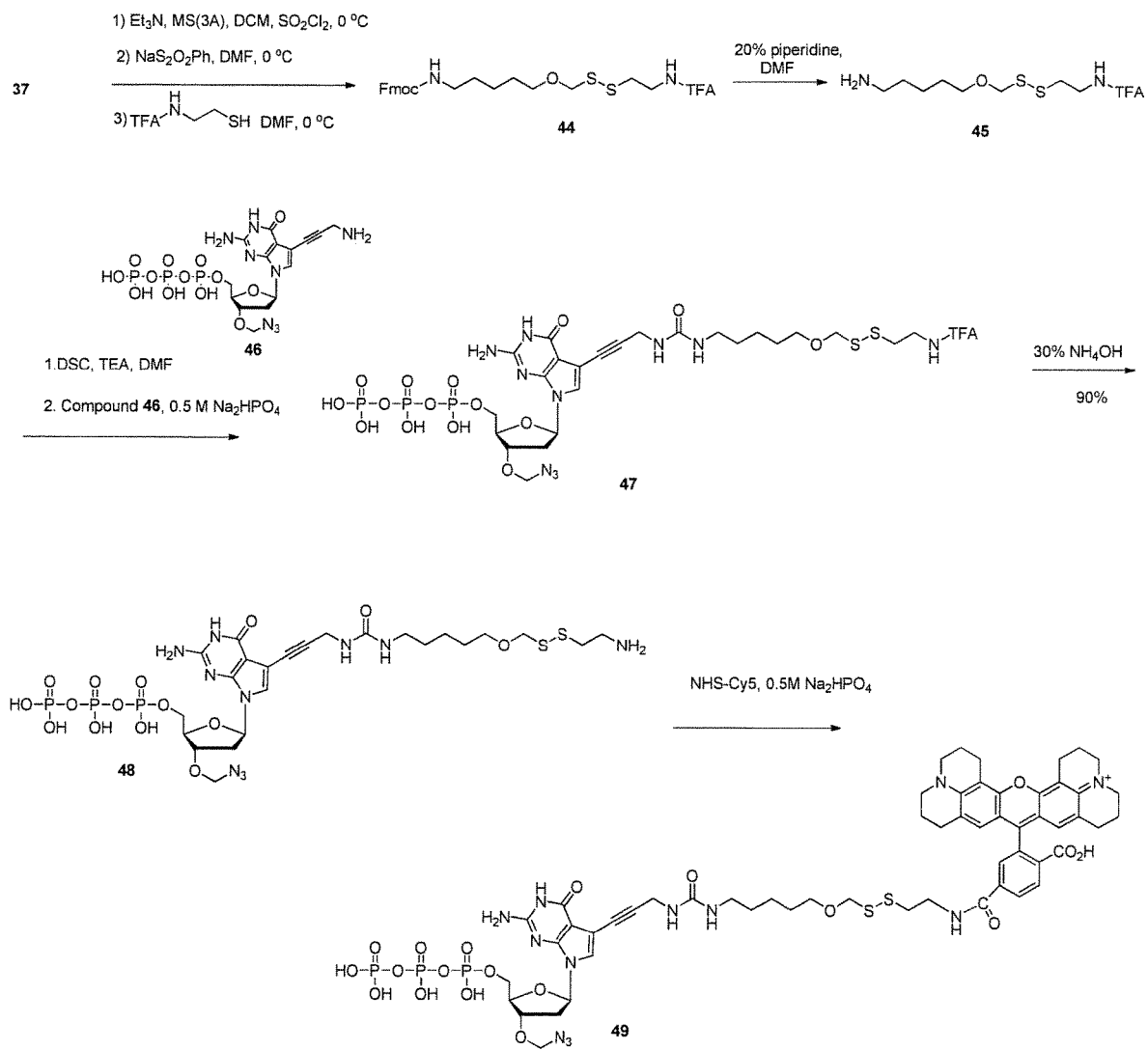
FIG. 15 shows the synthesis of a cleavable linker compound 45, where the linker is tethered to PA-nucleotides via urea functionality and the disulfide is connected to the dye by a two carbon linker. The resulting nucleotide analogue in such case can be as in compound 49 (dGTP analogue). Other nucleotide analogues (e.g. analogues of dATP, dUTP, dCTP) can be synthesized similarly by replacing nucleotide 46 with appropriate PA-nucleotide analogues in the third step of the reaction sequence.

In another aspect, the cleavable linker can be compound 45, where the linker is tethered to PA-nucleotides via urea functionality and the disulfide is connected to the dye by a two carbon linker. The resulting nucleotide analogue in such case can be as in compound 49 (dGTP analogue), which can be synthesized according to the FIG. 15. Other nucleotide analogues (e.g. analogues of dATP, dUTP, dCTP) can be synthesized similarly by replacing nucleotide 46 with appropriate PA-nucleotide analogues in the third step of the reaction sequence.

Example 26

Synthesis of Compound 44

A 100 mL round bottomed flask equipped with a magnetic stir bar was charged with 37 (1.00 g, 2.59 mmol) in CH$_2$Cl$_2$, molecular sieves and triethylamine (0.72 mL, 5.18 mmol). The reaction mixture was stirred for 10 minutes at room temperature and cooled to 0° C. Sulfuryl chloride (4.40 mL, 4.40 mmol) was added slowly and the resultant mixture was stirred for 1 hour at 0° C. TLC analysis using 20% ethyl acetate in hexanes indicated the disappearance of starting material, and a solution of benzenethionosulfonic acid sodium salt (648 mg, 3.89 mmol) in N',N'-dimethylformamide (5 mL) was added in one portion at 0 CC and the reaction mixture was stirred for 20 min at room temperature. Next, N-(trifluoroacetamido)ethanethiol (896 mg, 5.18 mmol) was added in one portion and the resulting mixture was stirred for 30 minutes at room temperature. The molecular sieves were filtered off and the solvents were removed under reduced pressure and the residue was purified via column chromatography on silica gel using 0-20% ethyl acetate-hexanes gradient, to give the title compound 44 (529 mg, 39%) as a yellowish oil. $^1$H NMR (CDCl$_3$), see FIG. 15: $\delta_H$ 7.76 (d, J=7.52 Hz, 2H), 7.57 (d, J=7.50 Hz, 2H), 7.40-7.38 (m, 2H), 7.30-7.25 (m, 21), 4.82 (s, 2H), 4.42 (d, 2H), 4.21-4.20 (m, 1H), 3.70-3.67 (m, 2H), 3.59-3.55 (m, 2H), 3.17-3.16 (m, 2H) and 1.64-1.40 (m, 6H) ppm.

Example 27

Synthesis of Compound 45

A 25 mL round bottomed flask equipped with a magnetic stir bar was charged with carbamate 44 (100 mg, 0.184 mmol), and 1 mL of 20% piperidine solution in N,N-dimethylformamide at room temperature. The reaction mixture was stirred at room temperature for 10 minutes, then diluted with acetonitrile (5 mL) and purified via reverse phase preparative HPLC using a 0-30% acetonitrile-TEAB buffer gradient to give the title compound 45 (11 mg, 20%) as a clear oil, see FIG. 15. $^1$H NMR (400 MHz, CD$_3$OD) $\delta_H$ 4.90 (s, 2H), 3.64-3.60 (m, 2H), 3.32 (s, 2H), 2.98-2.93 (m, 2H), 2.86-2.82 (m, 2H), 1.66-1.60 (m, 2H), 1.50-1.48 (m, 2H) and 1.33-1.30 (m, 2H) ppm.

Example 28

Synthesis of Compound 47

A 5 mL sample vial was charged with amine 45 (0.960 mg, 3.0 µmol), DSC (1.15 mg, 4.5 µmol) and triethylamine (60 µL, 6.0 µmol) and shaken for 2 hours at room temperature. Then a solution consisting of 3 eq of nucleotide 46 in 200 µL (ref. US 2013/0137091 A1) in N,N-dimethylformamide was added. The reaction mixture was placed on a shaker for 12 hours. The reaction was next diluted with TEAB buffer and purified by preparative reverse phase HPLC using a 0-30% acetonitrile: 50 mM TEAB buffer gradient to give the title compound 47 (in 14% yield), see FIG. 15. MS (ES-): calculated for (M-H) $C_{26}H_{37}F_3N_{10}O_{16}P_3S_2$, 959.10, found m/z 959.24.

Example 29

Synthesis of Compound 48

Nucleotide 47 (1 µmol) was dissolved in TEAB buffer (200 µL of 50 mM aqueous soln.) and treated with 200 µL of ammonium hydroxide (30% aqueous soln.) for 50 minutes at room temperature. The reaction was then diluted with TEAB buffer (1 mL of 1M solution) and distilled water (5 mL). The resulting mixture was purified via C18-HPLC, 0-30% Acetonitrile: 50 mM TEAB buffer gradient to afford the title compound 48 (0.40 µmol, 90%), see FIG. 15. MS (ES-): calculated for (M-H) $C_{24}H_{38}N_{10}O_{15}P_3S_2$, 863.12, found m/z 863.45.

Example 30

Synthesis of Compound 49

An aliquot of compound 48 (0.04 µmols) was dissolved in 0.1 mL distilled water and 0.5M $Na_2HPO_4$ (20 µL) in a 3 mL eppendorf tube. In a separate tube, 1 mg of ROX-NHS ester (0.168 µmol) was dissolved in 48 µL of dry DMF. This solution was then added to the reaction mixture all at once and stirred at room temperature for 6.0 hours. The reaction mixture was then diluted with 50 mM TEAB (5 mL). The product was purified by C18-HPLC using (0-60% B gradient, A=50 mM TEAB, B=acetonitrile). Compound 49 was obtained after lyophilization of the target fractions (0.03 µmol, 30% yield), see FIG. 15. MS (ES-) calculated for (M-H), $C_{57}H_{67}N_{12}O_{19}P_3S_2^+$ 1380.33, found 1380.25.

Cleavage Comparison with Regular Disulfide Linked Nucleotides

Figure 4:
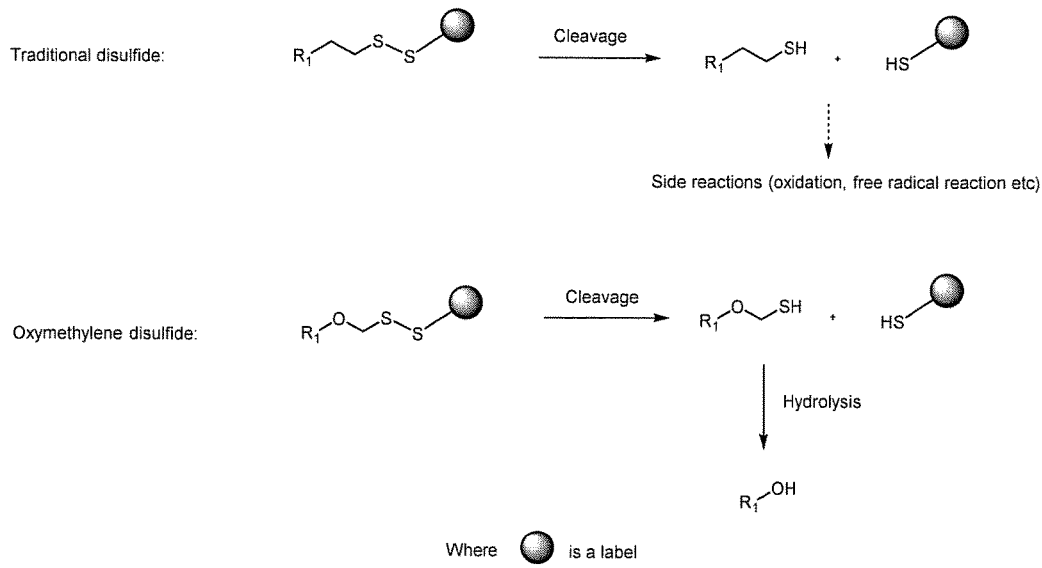
FIG. 4 shows the cleavage reactions products a traditional sulfide and oxymethylene sulfide linked labeled nucleotides.
Figure 16:
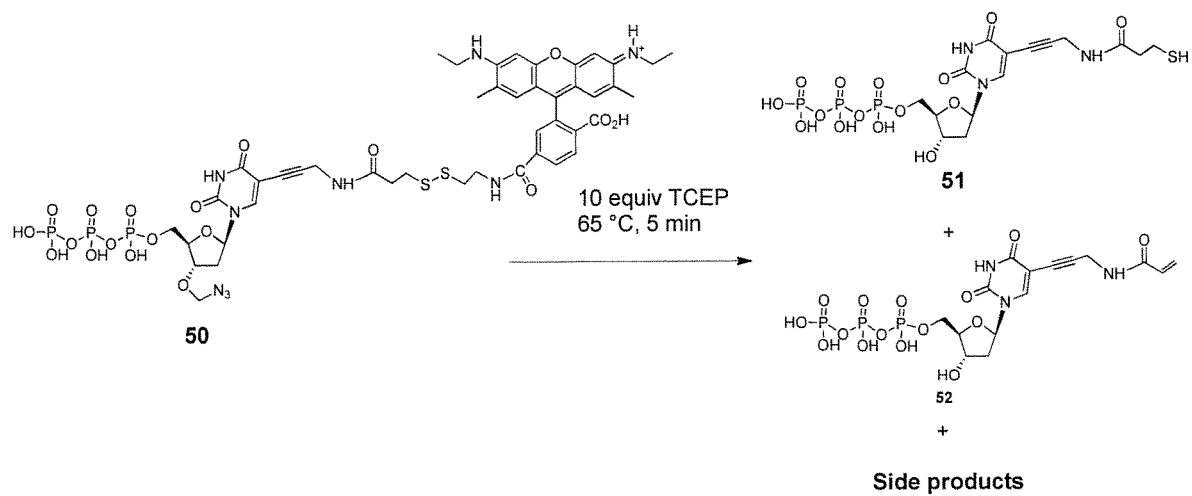
FIG. 16 shows that when labeled nucleotide 50 was exposed to 10 eq of TCEP at 65° C., it generated a number of side products including compound 52 along with the expected product 51.
Figure 17:
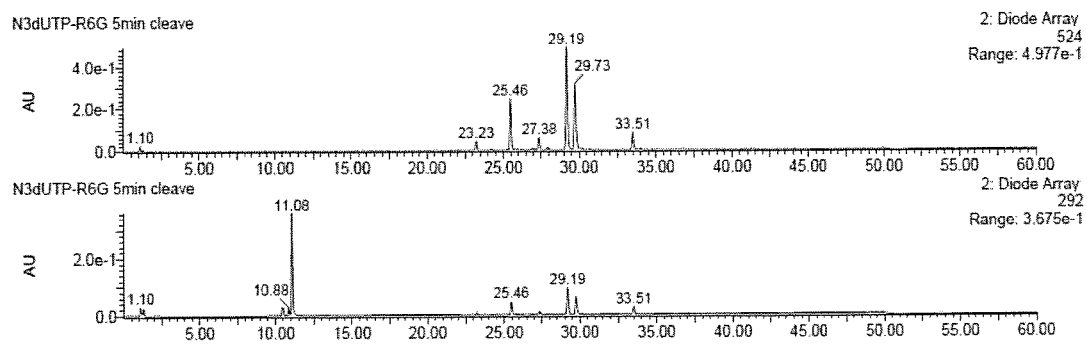
FIG. 17 shows an LC-MS trace of the TCEP exposed product of compound 50, extracted at 292 nm (bottom) and 524 nm (top), analyzed after 5 minutes exposure, where peak at 11.08 min corresponds to compound 51, peak at 10.88 min to compound 52 and other peaks to side products.
Figure 18:
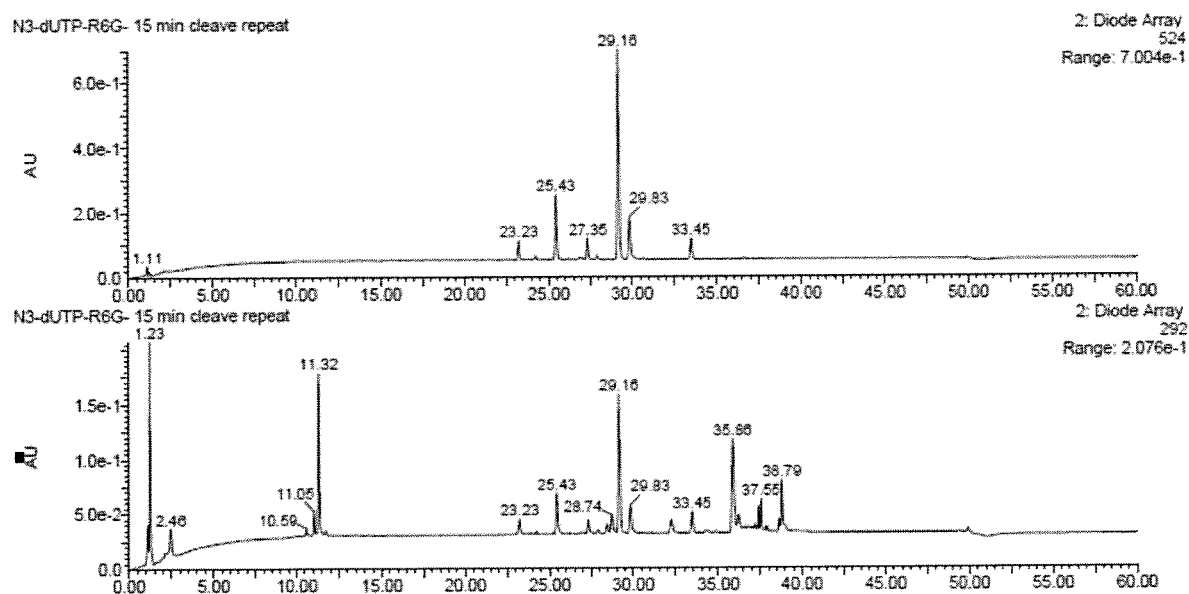
FIG. 18 shows an LC-MS trace of the TCEP exposed product of compound 50, extracted at 292 nm (bottom) and 524 nm (top), analyzed after 15 minutes exposure; where peak at 1.32 min corresponds to compound 51 and other peaks to side products.
Figure 19:
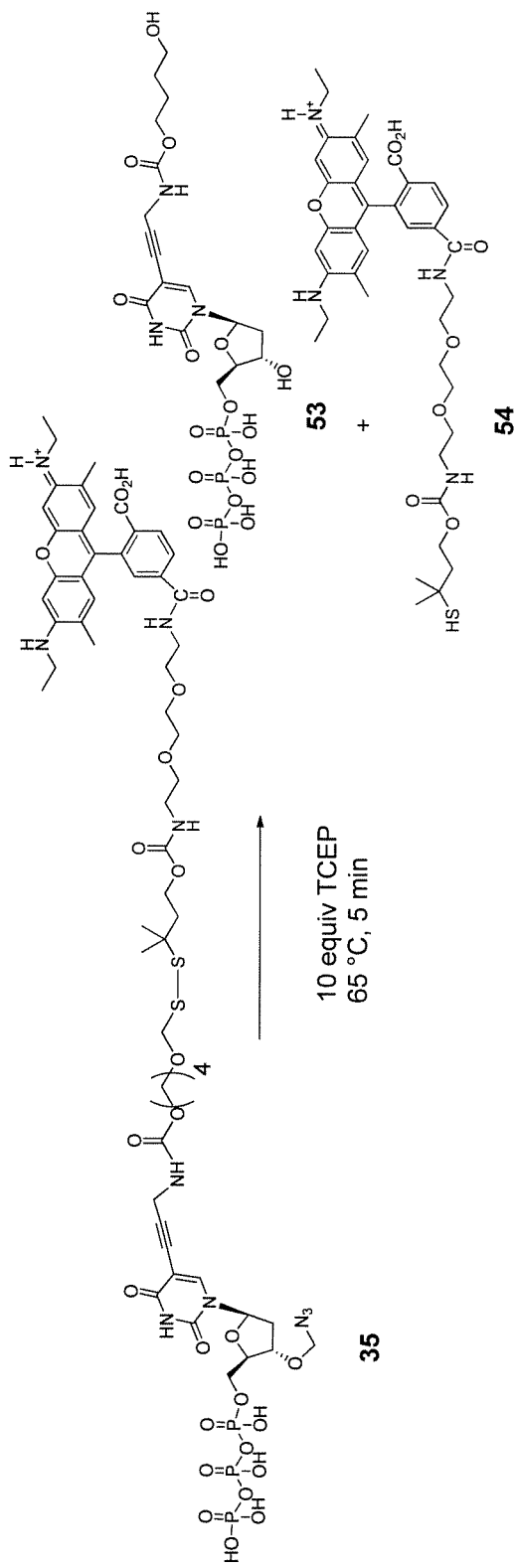
FIG. 19 shows that under identical cleavage conditions, the oxymethylenedisulfide linked nucleotide 35 cleanly produced the desired cleavage products, compounds 53 and 54. The methylene thiol segment (—CH_2SH) of the linker was fully eliminated from the nucleotide upon cleavage of the disulfide group
Figure 20:
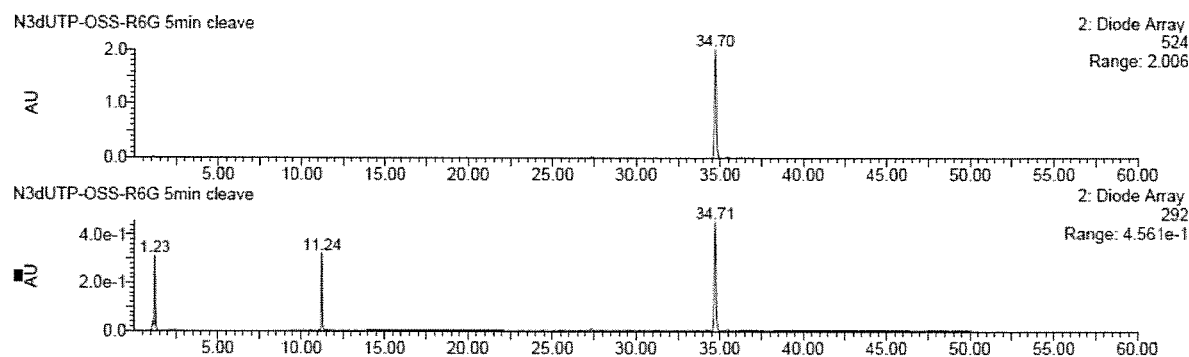
FIG. 20 shows an LC-MS trace of the TCEP exposed product of compound 35, extracted at 292 nm (bottom) and 524 nm (top), analyzed after 5 minutes exposure, where peak at 11.24 min corresponds to compound 53 and peak at 34.70 min to compound 54.
Figure 21:
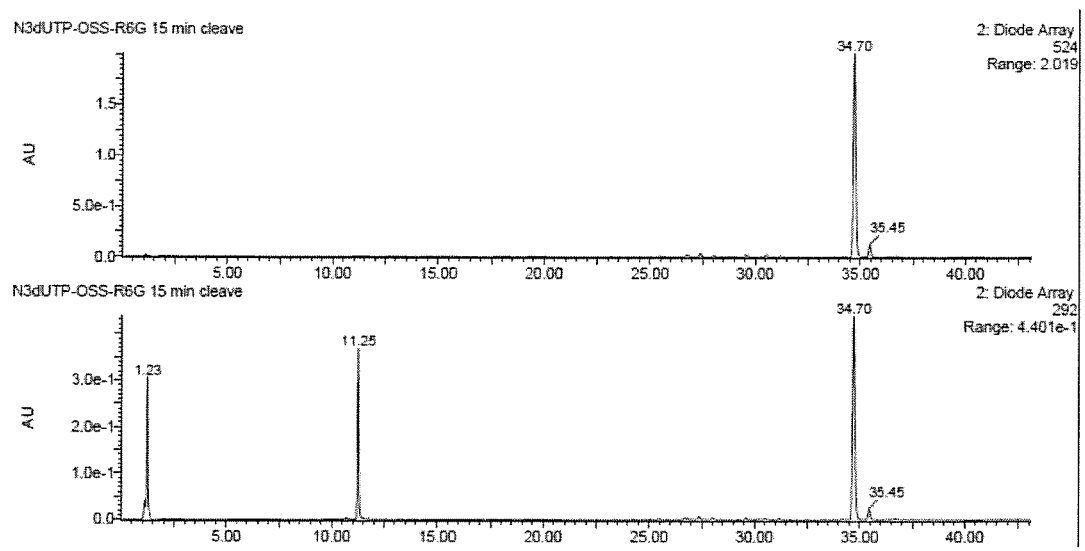
FIG. 21 shows LC-MS trace of the TCEP exposed product of compound 35, extracted at 292 nm (bottom) and 524 nm (top), analyzed after 15 minutes exposure, where peak at 11.25 min corresponds to compound 53 and peak at 34.70 min to compound 54.
Figure 22:
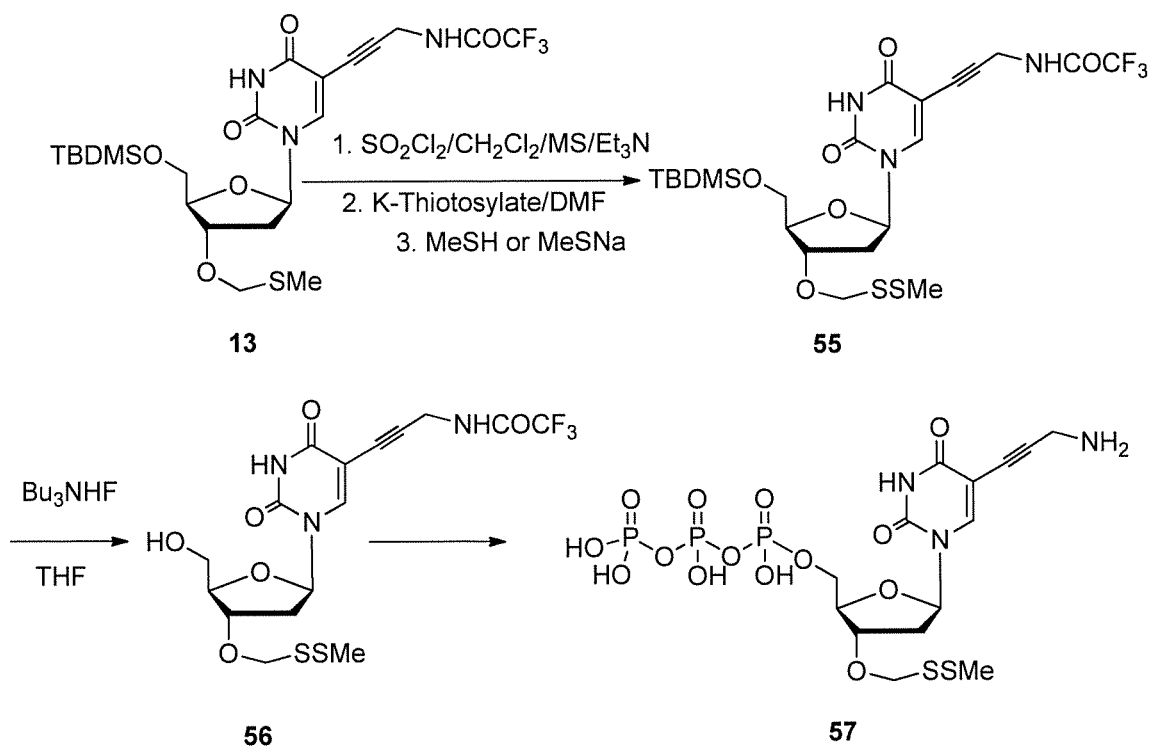
FIG. 22 shows the synthesis of 3'-OCH_2—SS-Me analogues with the replacement of mercaptoethanol (EtSH) by methanethiol or sodium thiomethoxide at the appropriate step, different from that of 3'-OCH_2—SS-Et (FIG. 10).

This new class of nucleotides containing cleavable oxymethylenedisulfide (—OCH$_2$—SS—) linker, disclosed herein, was compared with regular disulfide (—SS—) linked nucleotide (e.g. nucleotide 50, described in US Pat. Appln. 2013/0137091 [46]) under reducing phosphine based cleavage conditions. A stark difference in these two classes of nucleotides was observed. When labeled nucleotide 50 was exposed to 10 eq of TCEP at 65° C., it generated a number of side products including compound 52 along with the expected product 51 identified by LC-MS (FIG. 16, and FIG. 17, 5 minutes exposure). The proportion of the unwanted side products increased over time (FIG. 18, 15 minutes exposure). Under identical cleavage conditions, the oxymethylenedisulfide linked nucleotide 35 cleanly produced the desired cleavage products, compounds 53 and 54. The methylene thiol segment (—CH$_2$SH) of the linker was fully eliminated from the nucleotide upon cleavage of the disulfide group (FIG. 20 and FIG. 21, 5 minutes exposure). In addition, a prolonged exposure to TCEP did not generate further side products as revealed by LC-MS (FIG. 22, 15 minutes exposure). Therefore, this new class of nucleotides could offer significant advantages in the use of DNA sequencing by synthesis (SBS) by eliminating side reactions inherent to the presence of a thiol group as shown in FIG. 4.

Example 31

Synthesis of Compound 57

In another embodiment, the 3'-OH group of the nucleotides can be capped with —CH$_2$—SS-Et or —CH$_2$SS-Me, and the fluorophore dyes are attached to the nucleobases via one of the cleavable —OCH$_2$SS— linkers described earlier (e.g. as in compound 35, 43, and 49).

The synthesis of PA nucleotides with 3'-OCH$_2$SS-Et and —OCH$_2$—SS-Me, can be achieved according to FIG. 10 and FIG. 22, respectively. The difference in the synthesis of 3'-OCH$_2$SS-Me analogues from that of 3'-OCH$_2$—SS-Et (FIG. 10) is the replacement of mercaptoethanol (EtSH) by methanethiol or sodium thiomethoxide at the appropriate step as shown in FIG. 22. The —OCH$_2$—SS-Me group is the smallest structure among all possible 3'-O—CH$_2$—SS—R analogues. Therefore, nucleotide analogues with 3'-OCH$_2$—SS-Me capping group should perform better than those of other analogues in terms of enzymatic incorporation rates and cleavability by reducing agents such as TCEP.

Figure 23:
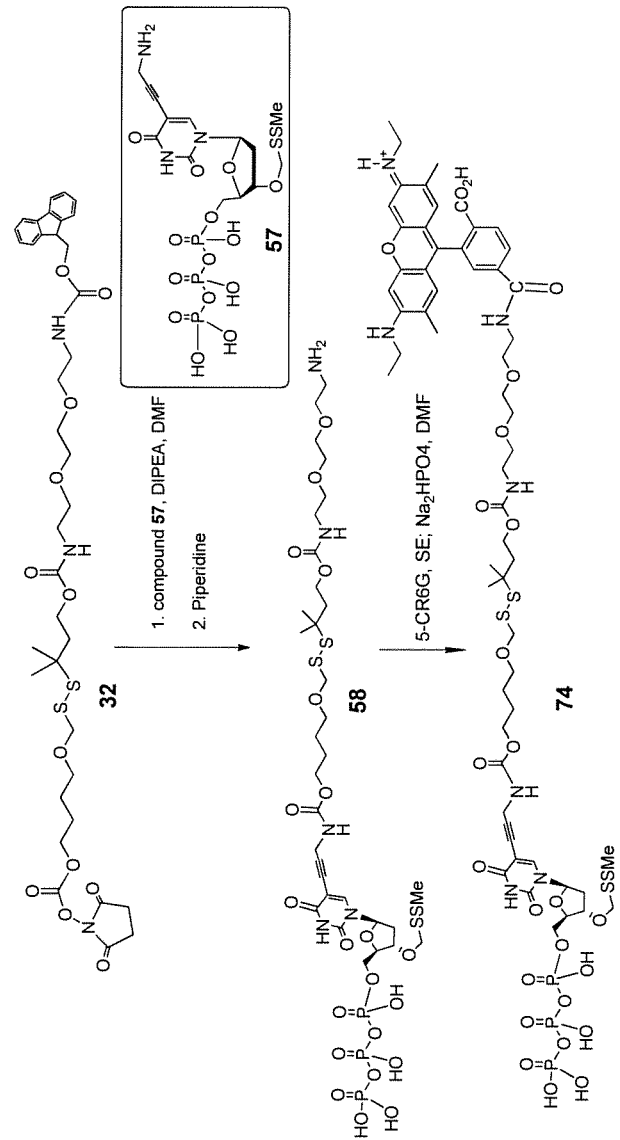
FIG. 23 shows the coupling of PA-nucleotide (e.g. 57) to the appropriate cleavable —OCH_2—SS— linkers, and finally to fluorophore dye using the activated linker 32.

Next, the resultant PA-nucleotide (e.g. 57) can be coupled to the appropriate cleavable —OCH$_2$—SS— linkers, and finally to fluorophore dye as shown in the FIG. 23 using the activated linker 32. And other nucleotides with differing dyes can be synthesized similarly using the appropriate PA-nucleotides (e.g. PA analogues of dATP, dGTP, dCTP) and NHS activated dyes (Alexa488-NHS, ROX-NHS, Cy5-NHS ester etc.) achieving nucleotide analogues labeled with different fluorophore reporting groups.

Example 32

Figure 24:
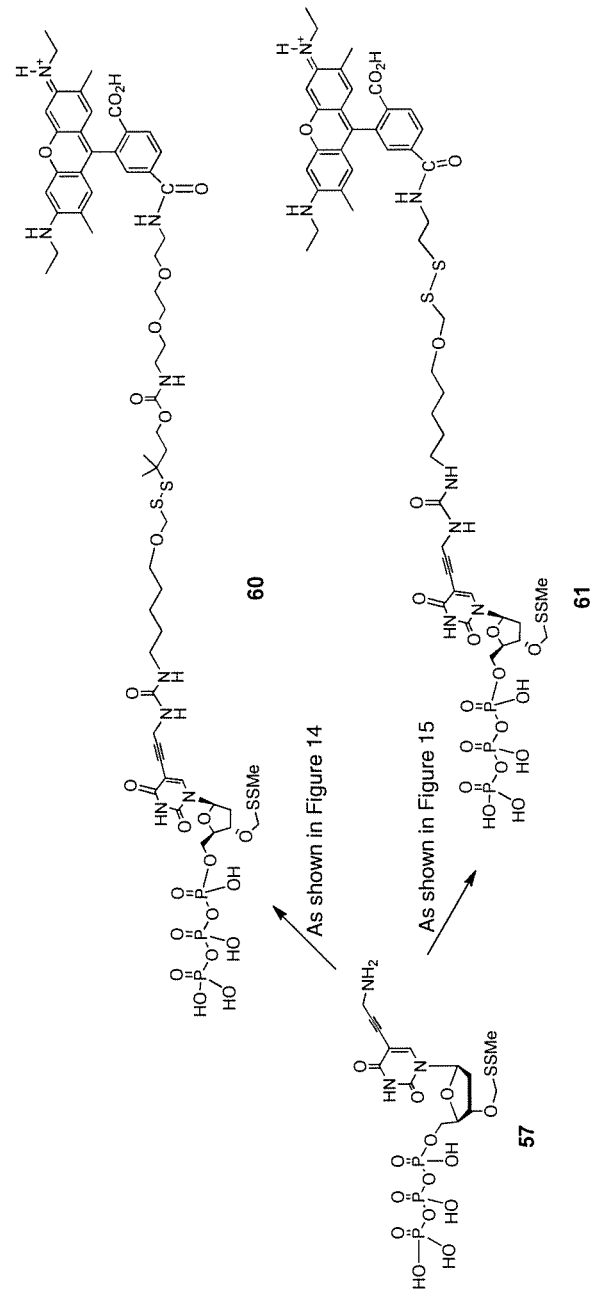
FIG. 24 shows nucleotide analogues with different linker achieved, compounds 60 and 61.

Nucleotide analogues with different linker can be achieved following the protocols described, as shown in in the synthesis of compounds 60 and 61 (FIG. 24).

Figure 26:
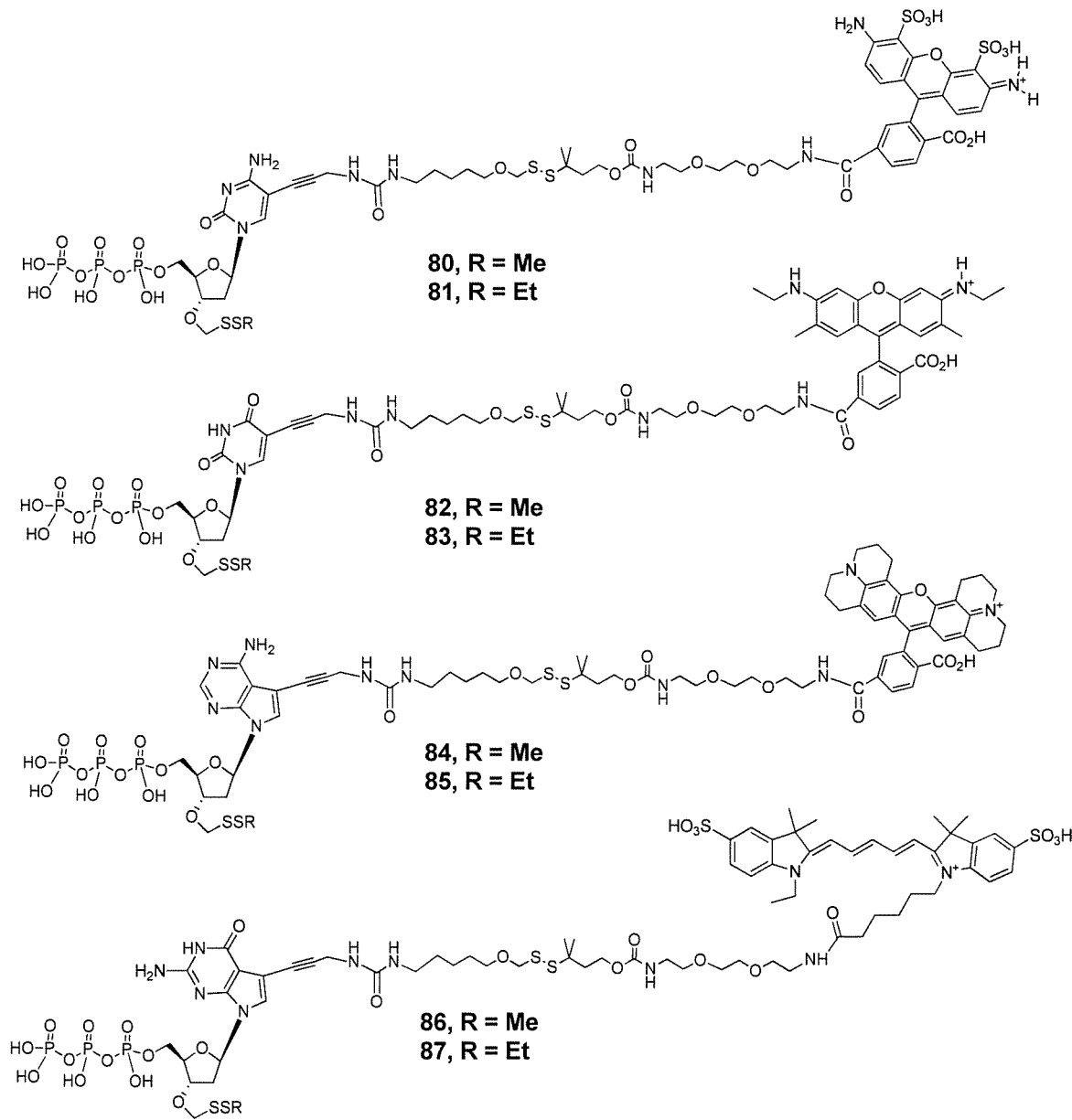
FIG. 26 shows the structure of 4-nucleotide analogues labeled by different fluorophore reporting groups, where R=Me- or Et-group.
Figure 27:
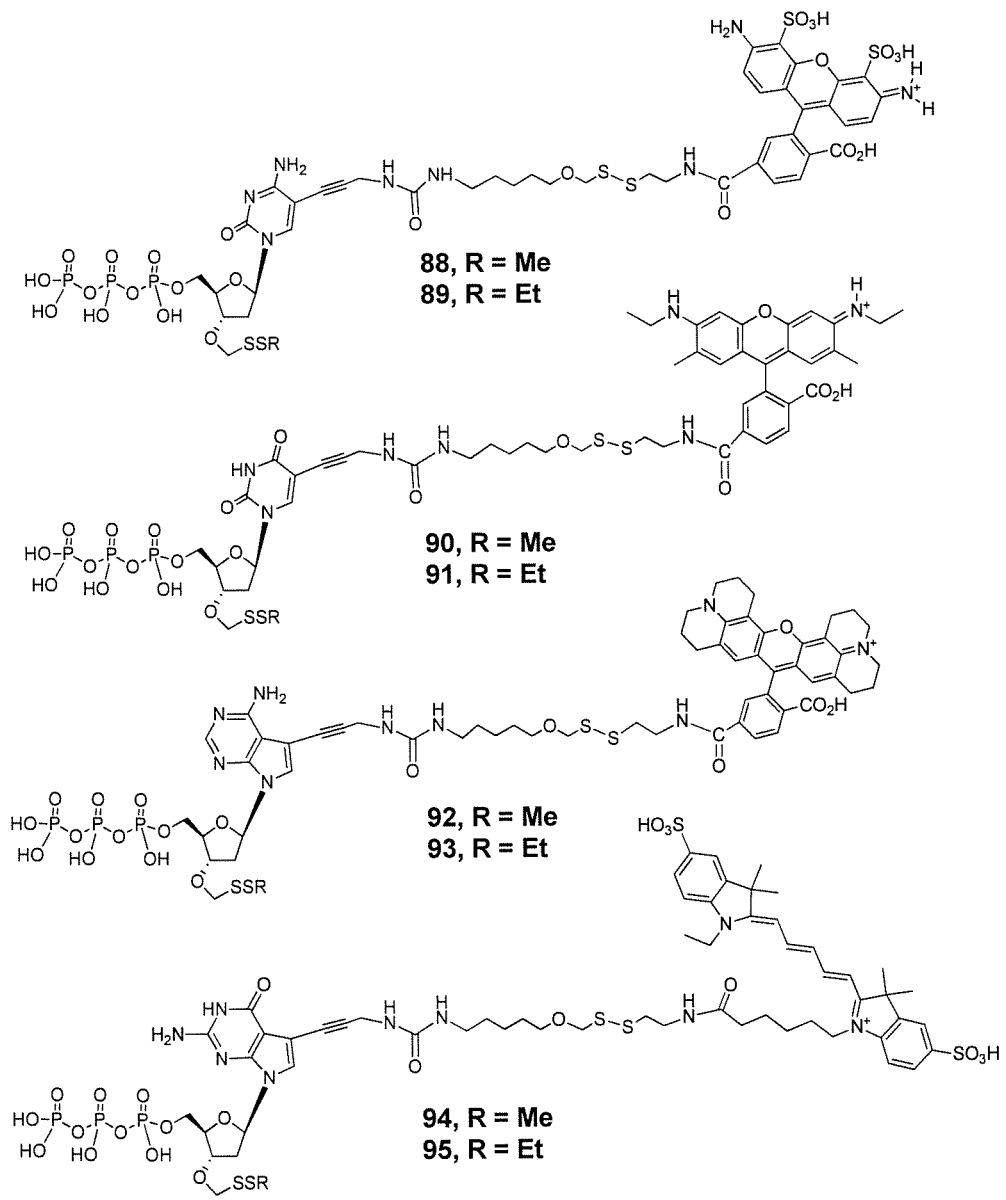
FIG. 27 shows the structure of 4-nucleotide analogues labeled by different fluorophore reporting groups, where R=Me- or Et-group.

Diverse sets of 3'-OCH$_2$SS-Et and 3'-OCH$_2$—SS-Me nucleotides with cleavable linkers —OCH$_2$—SS—, but differing in the chain lengths and substitution at the α-carbons can be synthesized similarly. The resulting classes of nucleotides are shown in the FIG. 25, FIG. 26, and FIG. 27. Among nucleotides shown in the FIG. 25, the cleavable linker is flanked by stabilizing gem-dimethyl group attached to flexible ethylene-glycol linker and attached to PA-nucleobase via carbamate functional group (—NH—C(C=O)—O—), while in FIG. 26, the carbamate group is replaced by urea group (—NH—C(C=O)—NH—). On the other hand, among nucleotides shown in FIG. 27, the disulfide group is attached to primary carbon chain, and tethered to the PA-nucleobase by urea functional group.

Example 33

Synthesis of Compound 64

A 250 mL round bottom flask was charged with compound 62 (3.0 g, 4.58 mmol), 25 mL dry CH$_2$Cl$_2$, 3-A molecular sieves (5.0 g) and cyclohexene (0.55 mL, 5.4 mmol). The resulting mixture was stirred for 10 minutes at room temperature under a nitrogen atmosphere. The reaction flask was then placed on an ice-bath and SO$_2$Cl$_2$ (6.8 mL, 1M in CH$_2$Cl$_2$, 1.5 eq) was added slowly via a syringe, and stirred for 1 hour at 0° C. Next, an extra 0.5 eq of SO$_2$Cl$_2$ were added to ensure complete conversion to compound 63.

The volatiles were removed under vacuum while keeping the temperature close to 10° C. The resulting solid was re-suspended in 20 mL of dry DMF and kept under a nitrogen atmosphere.

Figure 43:
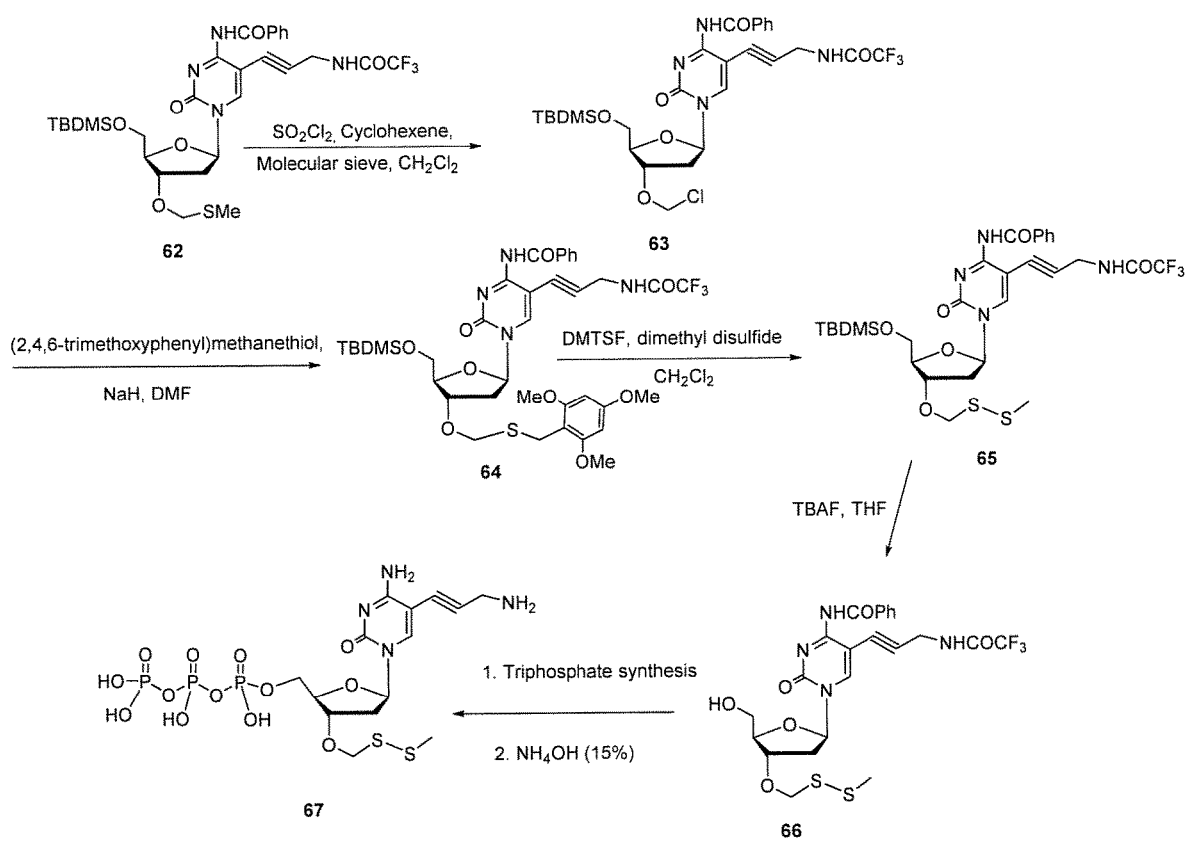
FIG. 43 shows a synthetic scheme illustrating the synthesis of compounds 63-67 from compound 62. The synthesis is described in Example 33, Example 34 and Example 35.

In a separate flask, (2,4,6-trimethoxyphenyl)methanethiol (2.45 g, 11.44 mmol) was dissolved in dry DMF (30 mL) under nitrogen atmosphere, and treated with NaH (274.5 mg, 60% in oil) producing a grey slurry. To this, compound 63 was added at once and stirred at room temperature for 3 hrs under nitrogen atmosphere. The reaction mixture was then filtered through Celite®-S (20 g) in a funnel eluting the product with EtOAc (100 mL). The EtOAc solution was then washed with distilled water (2×100 mL). The EtOAc extract was dried over $Na_2SO_4$, concentrated by rotary evaporation, and purified by flash chromatography (column: 120 g RediSepRfGold, gradient: 80% Hex to 50 Hex:EtOAc). See FIG. 43. The target compound (64) was obtained as white solid (1.2 g, 32% yield, $R_f$: 0.4, Hex:EtOAc/3:2). $^1$H NMR (CDCl$_3$): δH 8.13 (m, 3H), 7.43 (m, 1H), 7.32 (m, 2H), 6.12 (m, 1H), 6.00 (s, 2H), 4.62 (m, 2H), 4.31 (m, 3H), 4.00 (m, 1H), 3.82-3.60 (m, 13H), 2.39 (m, 1H), 1.84 (m, 1H), 0.78 (m, 9H), and 0.01 (m, 6H) ppm.

Example 34

Synthesis of Compound 65

Compound 64 (1.2 g 1.46 mmol) was dried under high vacuum with $P_2O_5$ in a desiccator overnight and dissolved in 30 mL of anhydrous $CH_2Cl_2$ in a 100 mL flask equipped with a magnetic stirrer. To this was added dimethyldisulfide (0.657 mL, 7.3 mmol), and the reaction flask was placed on an ice-bath. Dimethyl(methylthio)sulfonium tetrafluoroborate (DMTSF, 316 mg, 1.1 eq) was then added and stirred for 1.5 hr at 0° C. The reaction mixture was transferred to a 250 mL separatory funnel and neutralized with 50 mL of 0.1M aq. solution of NaHCO$_3$, and extracted with $CH_2Cl_2$ (2×50 mL). See FIG. 43. The organic portion was dried over $Na_2SO_4$ and concentrated by rotary evaporation. The crude product was purified on a silica gel column (80 g RediSepRf gold) using gradient 80-50% Hex-EtOAc to result in 0.82 g of compound 65 (82% yield, $R_F$=0.5, Hex:EtOAc/3:2). $^1$H NMR (CDCl$_3$): δH 8.15 (m, 3H), 7.42 (m, 1H), 7.35 (m, 2H), 6.11 (m, 1H), 4.80-4.65 (m, 2H), 4.34 (m, 1H), 4.28 (m, 2H), 4.10 (m, 1H), 3.83-3.67 (m, 2H), 2.49 (m, 1H), 2.34 (s, 3H), 1.90 (m, 1H), 0.78 (m, 9H), and 0.10 (m, 6H) ppm.

Example 35

Synthesis of Compound 66

A round bottomed flask equipped with a magnetic stirrer was charged with compound 65 (0.309 g, 0.45 mmol) and 10.0 mL dry $CH_2Cl_2$ (10.0 mL) and placed on an ice-bath under a nitrogen atmosphere. TBAF (0.72 mL, 0.72 mmol, in 1M solution) was added slowly via syringe. The reaction mixture was stirred for 3 hours at 0° C. The reaction mixture was then transferred to a separatory funnel and quenched with 0.5 M NaHCO$_3$ solution (50 mL). The resulting mixture was extracted with EtOAc (2×100 mL) and dried over $Na_2SO_4$. The product 66 was obtained as a white powder after silica gel column chromatography in 76% yield (196 mg, $R_f$=0.3, Hex:EtOAc/1:1) on a 40 g RediSepRf column using gradient 7:3 to 2:3 Hex:EtOAc. See FIG. 43. $^1$H NMR (CDCl$_3$): δH 8.40 (s, 1H), 8.25 (m, 2H), 7.60 (m, 1H), 7.52 (m, 2H), 6.21 (m, 1H), 4.90-80 (m, 2H), 4.65 (m, 1H), 4.40 (m, 2H), 4.25 (m, 1H), 4.05-3.85 (m, 2H), 2.62 (m, 1H), 2.50 (s, 3H) and 2.31 (m, 1H) ppm.

The product 67 was obtained after phosphorylation of compound 66 (confirmed by LC-MS m/z (M–H) 611.19 for $C_{14}H_{23}N_4O_{32}P_3S_2$ for 67) via standard triphosphate synthesis method (see the synthesis of compound 5 for detail and see FIG. 8). It was further converted to dye labeled products according to procedure described for compounds presented in FIG. 13, FIG. 14, and FIG. 15.

Example 36

Synthesis of Compound 70

Figure 44:
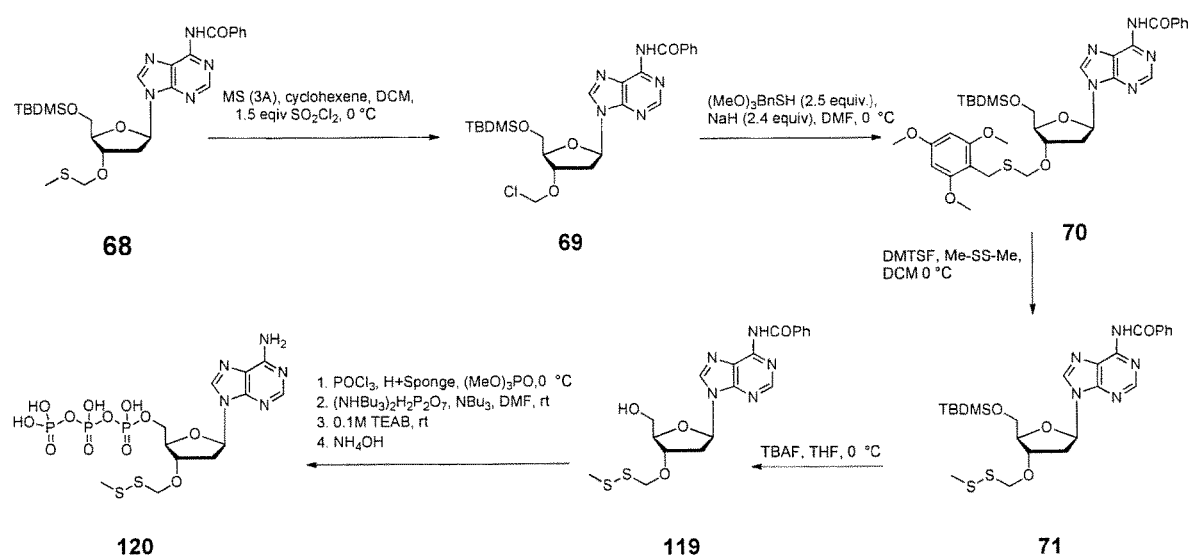
FIG. 44 shows a synthetic scheme illustrating the synthesis of compounds 69-71 and 119-120 from compound 68. The synthesis is described in Examples 36-38.

Compound 68 (7.3 g, 13.8 mmol) was dried in a desiccator overnight and dissolved in anhydrous DCM (70 mL) in a dry 500 mL round bottom flask equipped with a stirbar and rubber septum under an atmosphere of $N_2$. Cyclohexene (1.54 mL, 15.2 mmol, 1.1 equiv) and dry 3-Å molecular sieves (16.6 g) were added to the reaction mixture and the resulting suspension was stirred for 20 min at 0° C. in an ice-water bath. Next, $SO_2Cl_2$ (1 M solution in DCM, 32.7 mL, 2.36 eqiv) was added and the resulting mixture was stirred at 0° C. for 1 h. Reaction progress was monitored by the disappearance of the starting material via TLC (100% EtOAc). Once the $SO_2Cl_2$ activation was complete, a mixture of (MeO)$_3$BnSH (7.4 g, 34.5 mmol, 2.5 eqiv) and NaH (1.32 g, 33.12 mmol, 60% in mineral oil) in DMF (120 mL) was prepared and rapidly added in one portion. The reaction was allowed to slowly warm to room temperature and stirred for 1 h. The reaction mixture was filtered and concentrated in vacuo at 40° C. Purification by column chromatography on silica gel (eluted with 0 to 60% ethyl acetate:hexanes gradient 15 mins, followed by 60% ethyl acetate:hexanes for 45 mins) afforded the desired compound 70 (4.2 g, 43.7% yield) as a clear oil. See FIG. 44. $^1$H NMR (CDCl$_3$): $δ_H$ 8.72 (s, 1H), 8.31 (s, 1H), 7.94 (m, 2H), 7.52 (m, 1H), 7.44 (m, 2H), 6.41 (m, 1), 6.03 (s, 2H), 4.67 (s, 2H), 4.50 (m, 1H), 4.10 (m, 1H), 3.73 (m, 13H), 2.52 (m, 2H), 0.81 (s, 9H) and 0.002 (d, 6H) ppm.

Example 37

Synthesis of Compound 71

Compound 70 (2 g, 2.87 mmol) was dissolved in anhydrous DCM (38 mL) in a 200 mL round bottom flask equipped with stirbar and a rubber septum under an atmosphere of $N_2$ and cooled on an ice-water bath. To this mixture was added dimethyldisulfide (1.3 mL, 14.36 mmol, 5 equiv), followed by addition of DMTSF (620 mg, 3.15 mmol, 1.1 equiv) as a solution in DCM (20 mL), in one portion. The resulting mixture was allowed to slowly warm to room temperature and then stirred for an additional 4 h. The reaction was quenched by addition of a saturated aqueous solution of NaHCO$_3$(100 mL), extracted with DCM (150 mL×2) and EtOAc (200 mL) dried over $Na_2SO_4$ and concentrated in vacuo. Purification by column chromatography on silica gel (eluted with 0 to 60% ethyl acetate:hexanes gradient 15 mins, followed by 60% ethyl acetate:hexanes for 45 mins) afforded the desired compound 71 (1 g, 62% yield) as a white powder. See FIG. 44. $^1$H NMR (CDCl$_3$): $δ_H$ 8.69 (s, 1H), 8.24 (s, 1H), 7.94 (m, 1H), 7.51 (m, 1H), 7.42 (m, 2H), 6.41 (m, 1H), 4.82 (m, 2H), 4.57 (m, 1H), 4.15 (m, 1H), 3.77 (m, 2H), 2.61 (m, 2H), 2.40 (s, 3H), 0.81 (s, 9H) and 0.00 (d, 6H) ppm.

Example 38

Synthesis of Compound 72

Compound 71 (562 mg, 1.25 mmol) was dissolved in anhydrous THF (30 mL) in a 100 mL round bottom flask equipped with a stirbar and rubber septum under an atmosphere of $N_2$ and cooled on an ice-water bath. TBAF (1.5 mL of 1 M soln. in THF, 1.5 equiv) was then added dropwise and stirred at 0° C. for 2 h. The reaction progress was monitored by TLC (100% ethyl acetate $R_f$ for compound 72=0.205, $R_f$ for compound 71=0.627). Upon reaction completion methanol (5 mL) was added, the reaction was concentrated on the rotary and the residue was purified via column chromatography on silica gel (eluted with 0 to 60% ethyl acetate: hexanes gradient 15 mins, followed by 60% ethyl acetate: hexanes for 45 mins) to afford the desired compound 72 (280 mg, 62% yield) as white powder. See FIG. 44. $^1$H NMR (CDCl$_3$): $\delta_H$ 8.69 (s, 1H), 8.02 (s, 1H), 7.95 (m, 2H), 7.53 (m, 1H), 7.44 (m, 2H), 6.25 (m, 1H), 4.83 (m, 2H), 4.70 (m, 1H), 4.29 (m, 1H), 3.93 (m, 1H), 3.74 (m, 1H), 2.99 (m, 1H), 2.43 (s, 3H) and 2.41 (m, 1H) ppm.

Compound 72 was then converted to triphosphate 73 following standard triphosphate synthesis described earlier (see the synthesis of compound 5 in FIG. 8).

Example 39

Synthesis of Compound 108

Figure 53:
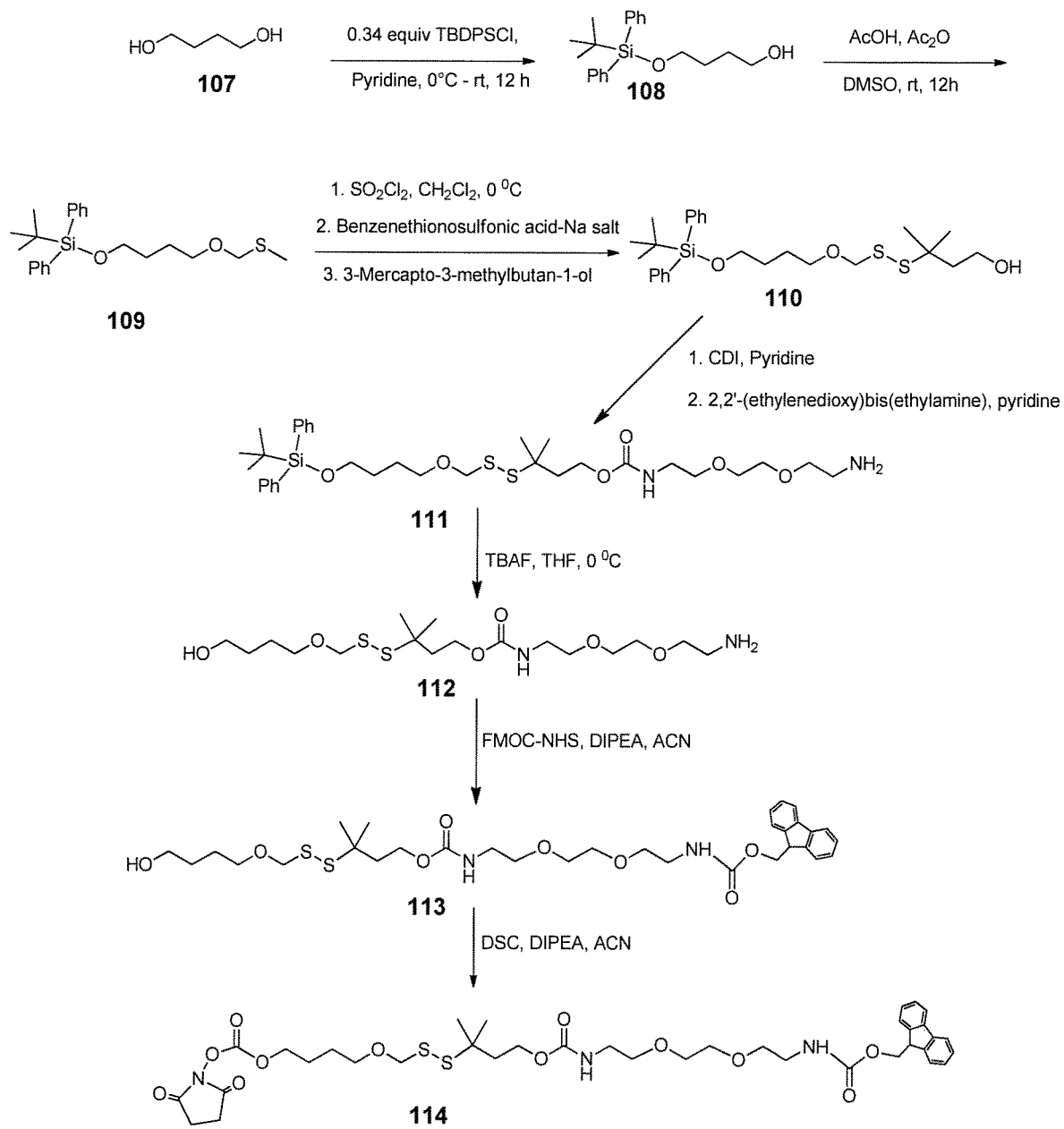
FIG. 53 is a schematic that shows one embodiment of a synthesis of NHS activated form of common linker.

A 1 L round bottom flask equipped with a stirbar was charged with 1,4-butanediol (18.3 g, 203.13 mmol) in 100 mL of anhydrous pyridine and cooled to 0° C. under a nitrogen atmosphere. tert-Butyldiphenylsilylchloride (13.8 mL, 70 mmol) was then added dropwise via syringe, the reaction was allowed to gradually warm to room temperature and stirring continued at rt for 12 h. The volatiles were removed by rotary evaporation and the residue absorbed onto 80 grams of silica gel. Purification via flash column chromatography on silica gel using 30 to 50% ethyl acetate in hexanes gradient resulted in 4-O-(tert-butyldiphenylsilyl)-butane-1-ol, 108 (13.7 g, 59.5% yield, $R_f$=0.7 with 1:1/hexanes:ethyl acetate, $^1$H NMR (CDCl$_3$): $\delta_H$ 7.70 (m, 4H), 7.40 (m, 6H), 3.75 (m, 2H), 3.65 (2H, m), 1.70 (m, 4H), 1.09 (m, 9H,) ppm. The synthesis is illustrated in FIG. 53.

Example 40

Synthesis of Compound 109

A 250 mL round bottom flask equipped with a magnetic stir bar and was charged with compound 108 (6.07 g, 18.5 mmol) and 90 mL anhydrous DMSO. Acetic acid (15 mL) and acetic anhydride (50 mL) were sequentially added and the reaction was stirred for 20 h at room temperature, transferred to a separatory funnel and partitioned between 300 mL distilled water and 300 mL of ethyl acetate. The organic layer was then transferred to a 1 L beaker and neutralized using a saturated aqueous $K_2CO_3$ solution (500 mL). The organic layer was washed with distilled water (3×300 mL) and dried over MgSO$_4$. The volatiles were removed under reduced pressure and the residue was purified via flash column chromatography on a silica gel (hexanes:ethyl acetate/97:3 to 90:10) to obtain 4-O-(tert-butyldiphenylsilyl)-1-O-(methylthiomethyl)-butane, 109 (5.15 g, 71.7% yield, $R_f$=0.8 in 9:1/hexanes:ethyl acetate). $^1$H NMR (CDCl$_3$): $\delta_H$ 7.70 (m, 4H,), 7.40 (m, 6H), 4.62 (s, 2H), 3.70 (m, 2H), 3.50 (m, 2H,), 2.15 (s, 2H), 1.70 (m, 4H), 1.08 (m, 9H) ppm. The synthesis is illustrated in FIG. 53.

Example 41

Synthesis of Compound 110

A 1 L round bottom flask equipped with a magnetic stirbar was charged with compound 109 (15.5 g, 40 mmol), anhydrous dichloromethane (450 mL), 3 Å molecular sieves (80 g) and triethylamine (5.6 mL) and the reaction was stirred at 0° C. for 30 min under a nitrogen atmosphere. Next, $SO_2Cl_2$ (64 mL of 1 M soln. in dichloromethane) was added slowly via syringe and stirred for 1 h at 0° C. Ice bath was then removed and a solution of potassium-thiotosylate (10.9 g, 48.1 mmol) in 20 mL anhydrous DMF was added at once. The resulting mixture was stirred for 20 min at room temperature, added at once to a 2 L round bottom flask containing a solution of 3-mercapto-3-methylbutan-1-ol (4.4 mL, 36 mmol) in DMF (20 mL). The reaction was stirred for 30 min at room temperature, and then filtered through celite-S. The product was partitioned between equal amounts of ethyl acetate and water. The organic extracts were washed with distilled water in a separatory funnel, followed by concentrating the crude product by rotary evaporation. Purification by flash column chromatography on silica gel using ethyl acetate:hexanes gradient gave the title compound 110 (5.6 g, 26%). $^1$H NMR (CDCl$_3$): $\delta_H$ 7.67-7.70 (m, 4H), 7.37-7.47 (m, 6H), 4.81 (s, 2H), 3.81 (t, J=6.73 Hz, 2H), 3.70 (t, J=6.21 Hz, 2H), 3.59 (t, J=6.55, 2H), 1.90 (t, J=6.95 Hz, 2H), 1.58-1.77 (m, 4H), 1.34 (s, 6H), and 1.07 (s, 9H) ppm. The synthesis is illustrated in FIG. 53.

Example 42

Synthesis of Compound 111

A 500 mL round bottom flask equipped with a magnetic stir bar was charged with compound 110 (5.1 g, 10.36 mmol), anhydrous pyridine (100 mL) and 1,1'-carbonyldiimidazole (CDI) (3.36 g, 20.7 mmol) under a nitrogen atmosphere. The reaction mixture was stirred for 1 h at room temperature and poured into a solution of 2,2'-(ethylenedioxy)bis(ethylamine) (7.6 mL, 51.8 mmol) in anhydrous pyridine (50 mL). Stirring continued for 1 h and the volatiles were removed by rotary evaporation. The resulting crude was purified via flash column chromatography on silica gel using (0-15% methanol in $CH_2Cl_2$) to furnish compound 111 (4.4 g, 65% yield). $^1$H NMR (CDCl$_3$): $\delta_H$ 7.63-7.68 (m, 4H), 7.34-7.44 (m, 6H), 4.76 (s, 2H), 4.17 (t, J=7.07 Hz, 2H), 3.65 (t, J=6.16 Hz, 2H), 3.60 (s, 4H), 3.49-3.51 (m, 6H), 3.31-3.39 (m, 2H), 2.88 (m, 2H), 1.9 (t, J=7.06 Hz, 2H), 1.57-1.73 (m, 4H), 1.31 (s, 6H) and 1.03 (s, 9H) ppm. The synthesis is illustrated in FIG. 53.

Example 43

Synthesis of Compound 113

A 50 mL round bottom flask equipped with a magnetic stir bar was charged with compound 111 (0.94 g, 1.42 mmol), anhydrous THF (40 mL) and of TBAF (1.6 mL of 1 M soln. in THF, 1.6 mmol) at 0° C. under nitrogen atmosphere. The reaction mixture was stirred for 2.0 h at 0° C., during which time LC-MS showed complete removal of the TBDPS protecting group. After removing the volatiles on the rotary, the product was purified via flash chromatography on silica gel (0-5% methanol in dichloromethane gradient, to give pure compound 112 (0.284 g, 47% yield), MS (ES+) calculated for (M+H) 429.21, observed m/z 429.18.

Next, compound 112 (0.217 g, 0.51 mmol) was dissolved in anhydrous acetonitrile (13 mL) under a nitrogen atmosphere and cooled to 0° C. DIPEA (97.7 µL, 0.56 mmol) and Fmoc-NHS ester (273.6 mg, 0.81 mmol) were added and the reaction stirred at 0° C. for 2 h. Purification by flash column chromatography on silica gel, using 50 to 90% ethyl acetate in hexanes gradient, produced a semi-pure product, which was further purified via column chromatography on silica gel using 2-5% methanol in $CH_2Cl_2$ gradient to furnish compound 113 (0.245 g, 74% yield). $^1$H NMR (CDCl$_3$): $\delta_H$ 7.70 (2H, d, J=7.3 Hz), 7.59 (2H, d, J=7.6 Hz), 7.32 (2H, m), 7.24 (2H, m), 4.69 (2H, s), 4.35 (2H, m), 4.16 (1H, m), 4.09 (2H, m), 3.60-3.45 (12H, m), 3.36-3.26 (4H, m), 1.82 (2H, m), 1.60 (4H, m) and 1.22 (6H, s) ppm. The synthesis is illustrated in FIG. 53.

Example 44

Synthesis of Compound 114

A 50 mL round bottom flask equipped with a magnetic stir bar was charged with compound 7 (170 mg, 0.26 mmol), anhydrous acetonitrile (15 mL), DSC (100 mg, 0.39 mmol) and DPIEA (68 µL, 0.39 mmol). The reaction mixture was stirred at room temperature for 3 h and additional DSC (100 mg, 0.39 mmol) and DIPEA (68 µL, 0.39 mmol) were added. The resulting mixture was stirred at room temperature for 12 h. Reaction progress was followed by TLC ($R_f$=0.4 for starting material, product $R_f$=0.8 in 9:1/ethyl acetate: hexanes). The volatiles were removed by rotary evaporation, and the residue remaining was purified via 3-successive silica gel columns using hexanes-ethyl acetate gradient to give compound 114 (121 mg, 59% yield). $^1$H NMR (CDCl$_3$): $\delta_H$ 7.81 (m, 2H), 7.63 (m, 2H), 7.42 (m, 2H), 7.33 (m, 2H), 4.78 (s, 2H), 4.43 (m, 2H), 4.37 (t, J=7.65 Hz, 2H), 4.25 (m, 2H), 4.18 (m, 2H), 3.67-3.55 (m, 10H), 3.39 (m, 4H), 2.84 (s, 4H), 1.88 (m, 4H), 1.73 (m, 4H), and 1.32 (s, 6H) ppm. The synthesis is illustrated in FIG. 53.

Example 45

Synthesis of Compound 117

Figure 54:
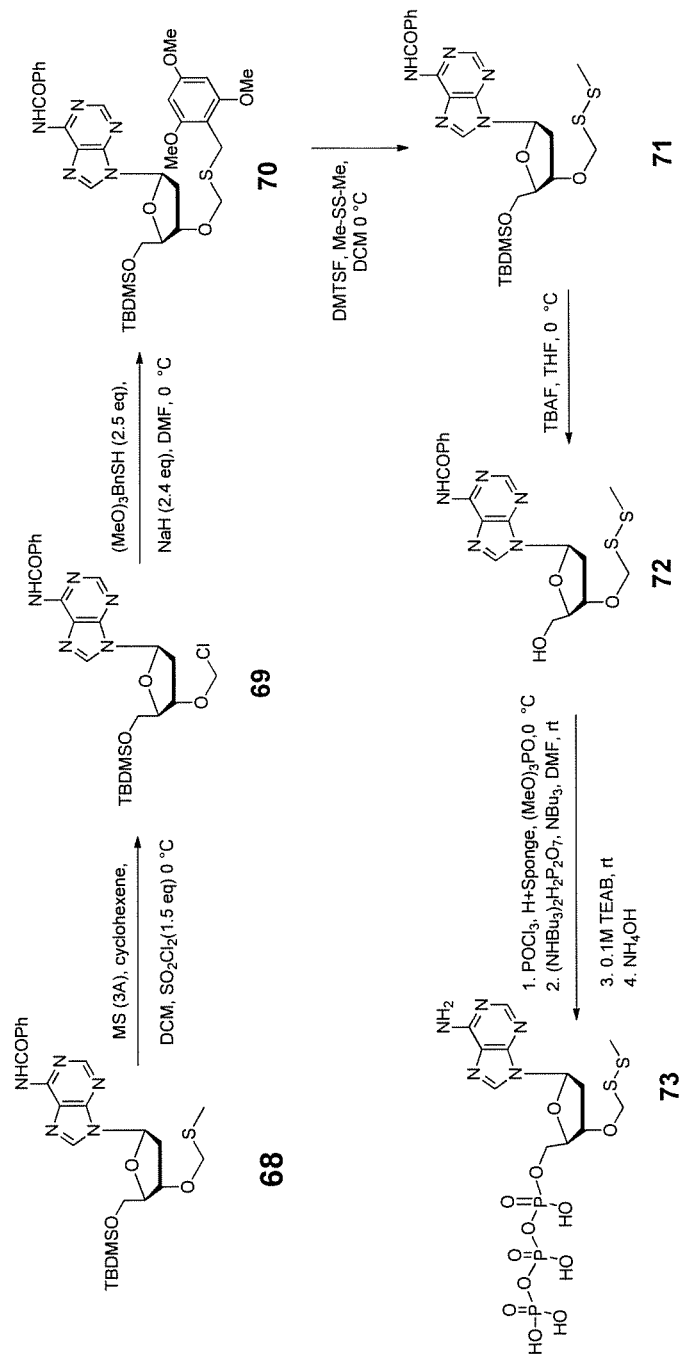
FIG. 54 is a schematic that shows one embodiment of the synthesis of MeSSdATP.

A 500 mL round bottom flask equipped with a magnetic stir bar was charged with compound 68 (7.3 g, 13.8 mmol, pre-dried in a desiccator overnight), anhydrous dichloromethane (70 mL), cyclohexene (1.54 mL, 15.2 mmol) and 3-Å molecular sieves (16.6 g) and the resulting suspension was stirred for 20 min at 0° C. under a nitrogen atmosphere. Next, $SO_2Cl_2$ (1 M solution in dichloromethane, 32.7 mL, 2.36 equiv) was added and the resulting mixture was stirred at 0° C. for 1 h. Reaction progress was monitored via TLC for disappearance of the starting material (100% ethyl acetate). Once the $SO_2Cl_2$ activation was complete, a mixture of (MeO)$_3$BnSH (7.4 g, 34.5 mmol, 2.5 eqiv) and NaH (1.32 g, 33.12 mmol, 60% in mineral oil) in DMF (120 mL) was prepared and rapidly added in one portion. The reaction was allowed to slowly warm to room temperature and stirred for 1 h. The reaction mixture was filtered and concentrated in vacuo at 40° C. Purification by column chromatography on silica gel using 0 to 60% ethyl acetate in hexanes gradient afforded the desired compound 70 (4.2 g, 43.7% yield) as a clear oil. $^1$H NMR (CDCl$_3$): $\delta_H$ 8.72 (s, 1H), 8.31 (s, 1H), 7.94 (m, 2H), 7.52 (m, 1H), 7.44 (m, 2H), 6.41 (m, 1H), 6.03 (s, 2H), 4.67 (s, 2H), 4.50 (m, 1H), 4.10 (m, 1H), 3.73 (m, 13H), 2.52 (m, 2H), 0.81 (s, 9H) and 0.002 (d, 6H) ppm. The synthesis is illustrated in FIG. 54.

Example 46

Synthesis of Compound 71

A 200 mL round bottom flask equipped with a magnetic stir bar was charged with compound 117 (2.0 g, 2.87 mmol) and dichloromethane (38 mL) under an atmosphere of $N_2$ and cooled on an ice-water bath. To this mixture was added dimethyldisulfide (1.3 mL, 14.36 mmol, 5 equiv), followed by addition of DMTSF (620 mg, 3.15 mmol, 1.1 equiv) as a solution in dichloromethane (20 mL). The resulting mixture was allowed to slowly warm to room temperature and stirred for an additional 4 h. The reaction was then quenched by addition of a saturated aqueous solution of NaHCO$_3$(100 mL), extracted with dichloromethane (150 mL×2) and ethyl acetate (200 mL) dried over Na$_2$SO$_4$ and concentrated in vacuo. Purification by column chromatography on silica gel (eluted with 0 to 60% ethyl acetate in hexanes gradient) gave the desired compound 71 (1.0 g, 62%) as a white powder. $^1$H NMR (CDCl$_3$): $\delta_H$ 8.69 (s, 1H), 8.24 (s, 1H), 7.94 (m, 1H), 7.51 (m, 1H), 7.42 (m, 2H), 6.41 (m, 1H), 4.82 (m, 2H), 4.57 (m, 1H), 4.15 (m, 1H), 3.77 (m, 2H), 2.61 (m, 2H), 2.40 (s, 3H), 0.81 (s, 9H) and 0.00 (d, 6H) ppm. The synthesis is illustrated in FIG. 54.

Example 47

Synthesis of Compound 119

Compound 71 (562 mg, 1.25 mmol) was dissolved in anhydrous THF (30 mL) in a round bottom flask equipped with a stir bar and rubber septum under an atmosphere of $N_2$ and cooled on an ice-water bath. TBAF (1.5 mL of 1 M soln. in THF, 1.5 equiv) was then added dropwise and stirred at 0° C. for 2 h. The reaction progress was monitored by TLC (100% ethyl acetate $R_f$ for compound 119=0.2, $R_f$ for compound 71=0.6). Upon reaction completion methanol (5 mL) was added, the reaction was concentrated on the rotary and the residue was purified via column chromatography on silica gel (eluted with 0 to 60% ethyl acetate:hexanes gradient 15 mins, followed by 60% ethyl acetate in hexanes for 45 mins) to afford the desired compound 119 (280 mg, 62% yield) as white powder. $^1$H NMR (CDCl$_3$): $\delta_H$ 8.69 (s, 1H), 8.02 (s, 1H), 7.95 (m, 2H), 7.53 (m, 1H), 7.44 (m, 2H), 6.25 (m, 1H), 4.83 (m, 2H), 4.70 (m, 1H), 4.29 (m, 1H), 3.93 (m, 1H), 3.74 (m, 1H), 2.99 (m, 1H), 2.43 (s, 3H) and 2.41 (m, 1H) ppm.

Compound 119 was then converted to triphosphate 120 using the standard triphosphate synthesis method vide infra, except the de-protection was carried out by treating with 10% NH$_4$OH for 5 h at room temperature to minimize —SSMe cleavage. Yield 25%; HRMS-ES$^+$: calculated for C$_{12}$H$_{20}$N$_5$O$_{12}$P$_3$S$_2$. 582.976, observed m/z 582.975 The synthesis is illustrated in FIG. 54.

Example 48

Synthesis of Compound 123

Figure 55:
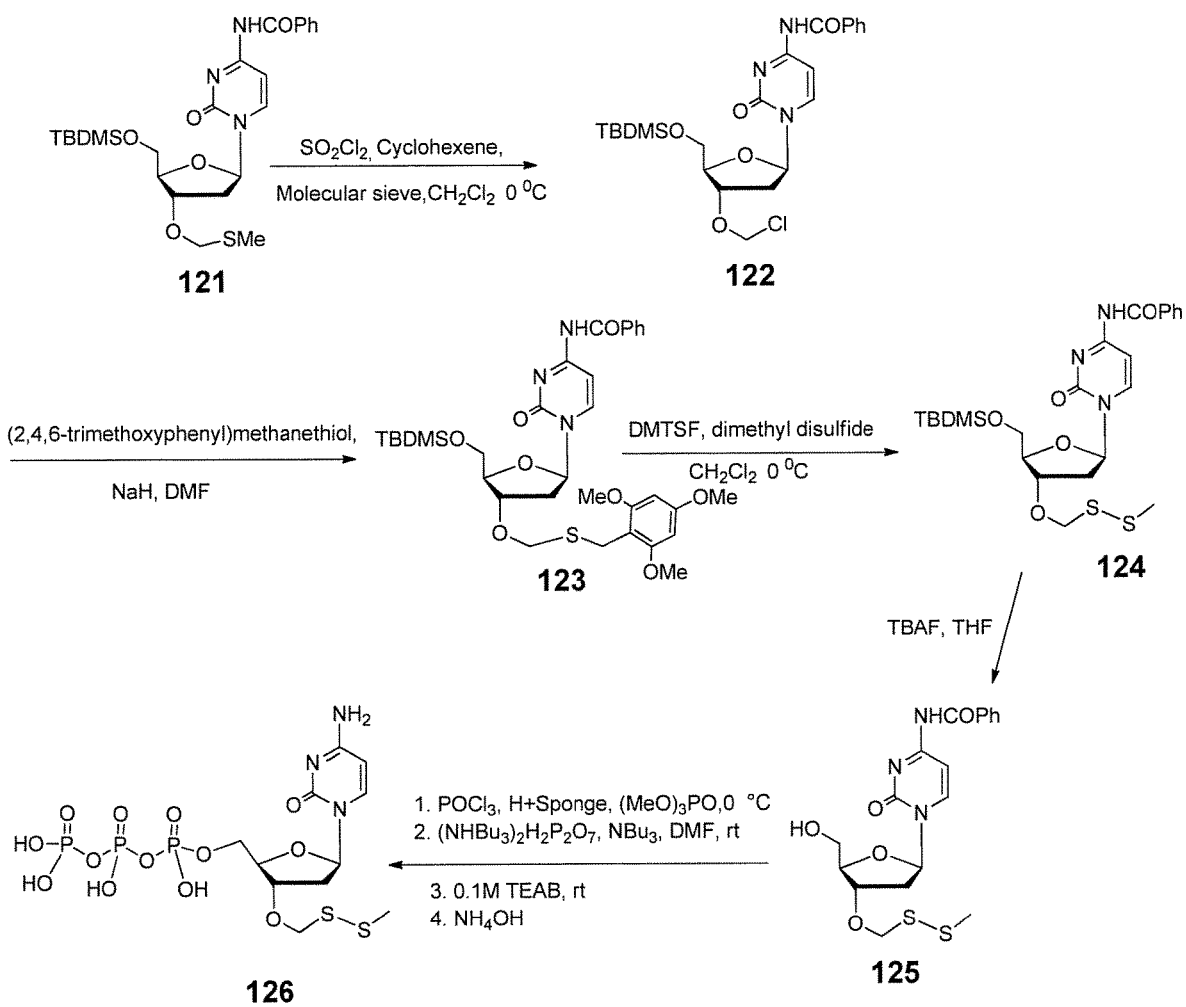
FIG. 55 is a schematic that shows one embodiment of the synthesis of MeSSdCTP.

Compound 121 (2.5 g, 4.94 mmol) was dried in a desiccator overnight and dissolved in anhydrous dichloromethane (25 mL) in a dry round bottom flask equipped with a stirbar and rubber septum under an atmosphere of $N_2$. Cyclohexene (0.55 mL, 1.1 equiv) and dry 3-Å molecular sieves (6.0 g) were added to the reaction mixture and the resulting suspension was stirred for 20 min at room temperature. The reaction flask was then placed on an ice-salt-water bath to bring the temperature to sub-zero and $SO_2Cl_2$ (7.4 mL, 1 M solution in dichloromethane) was added slowly with a syringe. The resulting mixture was stirred at 0° C. for 1 h followed by addition of 0.5 equivalents of $SO_2Cl_2$ to bring the reaction to completion. Reaction progress was monitored via TLC by the disappearance of the starting material. Next, a suspension of $(MeO)_3BnSH$ (2.65 g, 12.35 mmol, 2.5 eqiv) and NaH (0.472 g, 11.85 mmol, 60% in mineral oil) in DMF (40 mL) was prepared in a separate flask. The reaction mixture was combined and slowly warmed to room temperature and stirred for 1 h. The reaction mixture was then filtered through a glass sintered funnel to remove MS, the filtrate was quenched by addition of 50 mM aqueous $NaH_2PO_4$ solution (50 mL) and extracted with dichloromethane. The combined organics were dried over $Na_2SO_4$ and concentrated in vacuo. Purification by column chromatography on silica gel using hexanes:ethyl acetate gradient gave the desired compound 123 (1.4 g, 42.2% yield). $^1$H NMR ($CDCl_3$): $\delta_H$ 8.29 (m, 1H), 7.77 (m, 2H), 7.48 (m, 1H), 7.38 (m, 2H), 6.15 (m, 1H), 5.99 (m, 2H), 4.55 (m, 2H), 4.32 (m, 1H), 4.00 (m, 1H), 3.80 (m, 1H), 3.75 (m, 1H), 3.69 (m, 9H), 2.52 (m, 1H), 1.97 (m, 1H), 0.80 (m, 9H) and 0.011 (m, 6H) ppm. The synthesis is illustrated in FIG. 55.

Example 49

Synthesis of Compound 124

Compound 123 (1.4 g, 2.08 mmol) was dissolved in anhydrous dichloromethane (42 mL) in a 200 mL round bottom flask equipped with stirbar and a rubber septum under an atmosphere of $N_2$ and cooled to at 0° C. To this mixture was added dimethyldisulfide (0.93 mL, 10.4 mmol, 5 equiv), followed by addition of DMTSF (450 mg, 2.28 mmol, 1.1 equiv). The resulting mixture was stirred at 0° C. for 2 h. The reaction was quenched by addition 50 mM $NaHCO_3$ (100 mL), extracted with dichloromethane (100 mL×2) and dried over $Na_2SO_4$ and concentrated in vacuo. The product was purified by column chromatography on silica gel (eluted with 0 to 30% ethyl acetate in dichloromethane gradient to afford the desired compound 124 (0.93 g, 83.1%) as a white powder. $^1$H NMR ($CDCl_3$): $\delta_H$ 8.48 (m, 1H), 7.93 (m, 2H), 7.56 (m, 1H), 7.47 (m, 1H),7.37 (m, 2H) 6.00 (m, 1H), 4.73 (m, 2H), 4.34 (m, 1H), 4.07 (m, 1H), 3.84 (m, 1H), 3.73 (m, 1H), 2.44 (m, 1H), 2.33 (m, 3H), 2.25 (m, 1H), 0.76 (m, 9H) and 0.01 (m, 6H) ppm. The synthesis is illustrated in FIG. 55.

Example 50

Synthesis of Compound 125

Compound 124 (930 mg, 1.73 mmol) was dissolved in anhydrous THF (52 mL) in a 100 mL round bottom flask equipped with a stirbar and rubber septum under an atmosphere of $N_2$ and cooled to 0° C. on an ice-water bath. TBAF (3.5 mL of 1 M soln. in THF, 1.5 equiv) was then added drop-wise and stirred at 0° C. for 4 h. Upon reaction completion methanol (5 mL) was added to quench the reaction, the volatiles were removed under reduced pressure, and the residue was purified via column chromatography on silica gel (0 to 75% ethyl acetate in hexanes gradient) to afford the desired compound 125 (425 mg, 58% yield) as white powder. $^1$H-NMR ($CDCl_3$): $\delta_H$ 8.24 (m, 1H), 7.81 (m, 1H), 7.51-7.42 (m, 2H), 7.41 (m, 2H), 6.09 (m, 1H), 4.80 (m, 2H), 4.50 (m, 1H), 4.17 (m, 1H), 3.94 (m, 1H), 3.80 (m, 1H), 2.58 (m, 1H), 2.40 (m, 3H) and 2.41 (m, 1H) ppm. The synthesis is illustrated in FIG. 55.

Example 51

Synthesis of Compound 126

Compound 125 was then converted to triphosphate 126 using the standard triphosphate synthesis procedure vide infra; the final de-protection step was carried out by treating with 10% $NH_4OH$ for 2 h at room temperature to minimize —SSMe cleavage. 30% yield. HR MS-ES$^+$: calculated for $C_{11}H_{20}N_3O_{13}P_3S_2$, 558.965; observed m/z 558.964. The synthesis is illustrated in FIG. 55.

Example 52

Synthesis of Compound 130

A 100 mL round bottom flask equipped with a magnetic stir bar was charged with 127 (2.0 g, 2.8 mmol) and dried in a desiccator over $P_2O_5$ under high vacuum for 12 h. Dichloromethane (40 mL) was added under $N_2$ and the resulting solution cooled on a salt-ice bath for 15 minutes. Cyclohexene (0.34 mL, 3.4 mmol) was added, followed by dropwise addition of $SO_2Cl_2$ (3.4 mL, 1 M soln. in dichloromethane, 3.4 mmol). The resulting mixture was stirred for 30 minutes, and the reaction progress was monitored by TLC (ethyl acetate:hexanes/1:1, 127 $R_f$=0.5, 128 $R_f$=0.15 for —$CH_2Cl$ decomposed product). Additional $SO_2Cl_2$ (3.1 mL, 1 M soln. in dichloromethane, 3.1 mmol) was added drop-wise and the reaction mixture was stirred for another 40 minutes to ensure complete conversion to compound 128. This mixture was then concentrated under high vacuum at 0° C.

Figure 56:
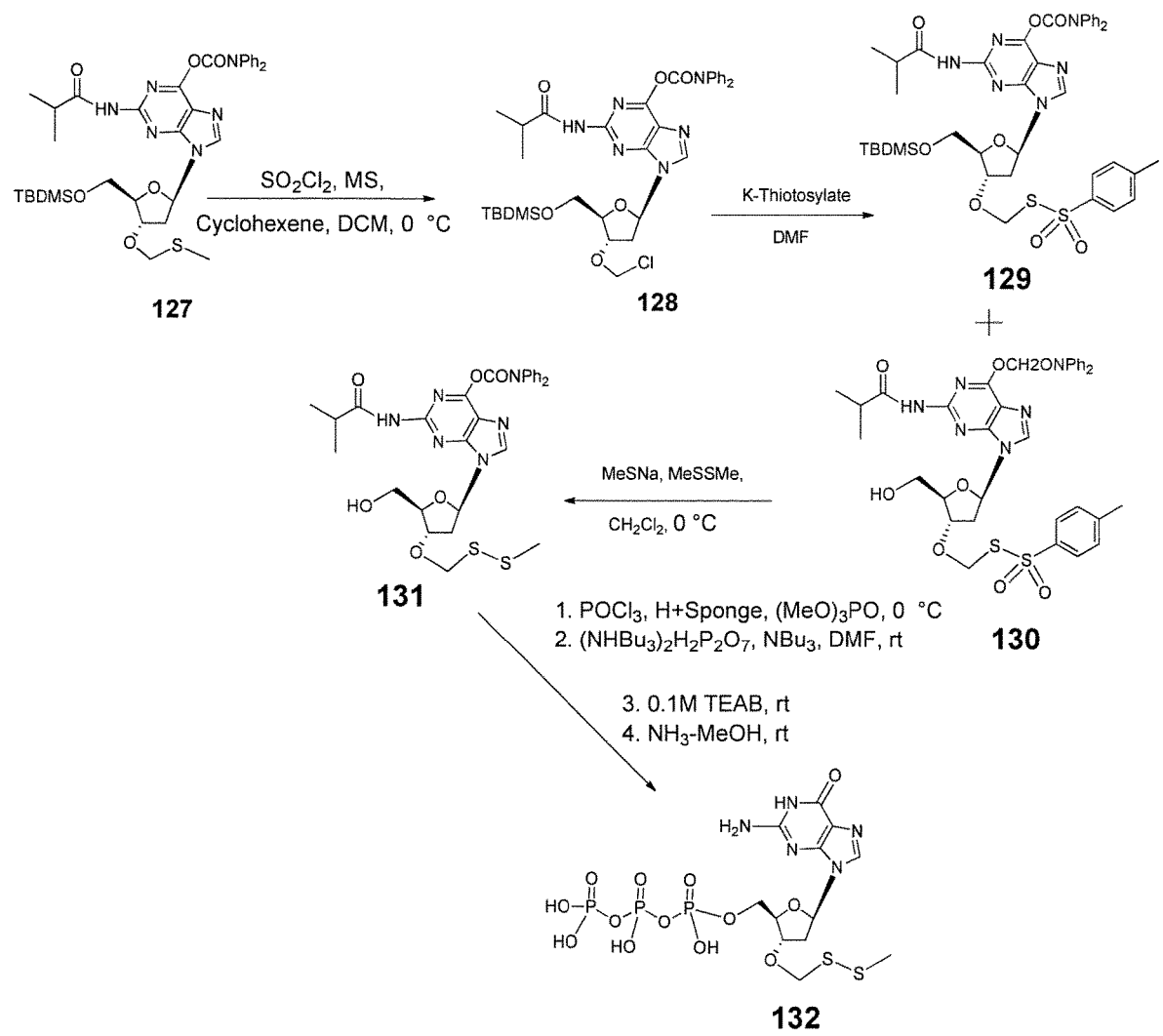
FIG. 56 is a schematic that shows one embodiment of the synthesis of MeSSdGTP.

Anhydrous dichloromethane (40 mL) was then added to the residue under $N_2$ and the mixture was stirred at 0° C. until all solids dissolved. A solution of potassium p-toluenethiosulfonate (0.96 g, 425 mmol) in DMF (8 mL) was added slowly and the resulting reaction mixture was stirred at 0° C. for 1 h. The mixture was first concentrated under reduced pressure at 0° C., and then at room temperature. The residue was purified by flash column chromatography on silica gel column using 0 to 100% ethyl acetate in hexanes gradient to give compound 130 as a cream solid (1.1 g, 51%; TLC $R_f$: 0.35, ethyl acetate:hexanes 2:1). MS (ES) m/z: 733 [M+1]. $^1$H NMR ($CDCl_3$, 400 MHz): $\delta_H$ 8.02 (br.s, 1H), 7.94 (s, 1H), 7.88 (d, J=8.3 Hz, 2H), 7.45 (m, 4H), 7.38 (m, 6H), 7.27 (m, 2H), 6.01 (t, J=6.6 Hz 1H), 5.46 & 5.38 (AB, $J_{AB}$=12.1 Hz, 2H), 4.97 (m, 1H), 3.86 (m, 1H), 3.74 (dd, J=12.5, 2.8 Hz, 1H), 3.55 (dd, J=12.5, 2.9 Hz, 1H), 2.87 (m, 1H), 2.65 (m, 1H), 2.43 (s, 3H), 2.17 (m, 1H), 1.26 (d, J=6.8 Hz, 3H), 1.25 (d, J=6.9 Hz, 3H) ppm. The synthesis is illustrated in FIG. 56.

Example 53

Synthesis of Compound 131

To a solution of 130 (1.1 g 1.5 mmol) in dichloromethane (anhydrous, 40 mL) cooled in on an ice-water bath was added dimethyldisulfide (0.66 mL, 7.5 mmol) under $N_2$. The resulting mixture was stirred for 15 min and NaSMe (0.23 g, 3.3 mmol) was added in one portion. The resulting reaction mixture was stirred at 0° C. for 4 h (the reaction progress was monitored by TLC (ethyl acetate:hexanes/2:1, 130 $R_f$=0.35, 131 $R_f$=0.45). The mixture was filtered through Celite-S and concentrated under reduced pressure. The residue was purified on silica gel column, eluted with ethyl acetate in hexanes (0-100%)) to afford compound 131 as a white solid (0.68 g, 75%; TLC $R_f$: 0.45, Ethyl acetate/hexanes/2:1). MS (ES) m/z: 625 [M+L+]. $^1$H NMR (CDCl$_3$): $\delta_H$ 8.02 (s, 1H), 8.00 (br. s, 1H), 7.45 (m, 4H), 7.39 (m, 4H), 7.28 (m, 2H), 6.24 (t, J=6.2 Hz, 1H), 5.05 (m, 1H), 4.99 & 4.94 (AB, J$_{AB}$=11.4 Hz, 2H), 4.27 (m, 1H), 3.99 (dd, J=12.5, 2.3 Hz, 1H), 3.86 (dd, J=12.5, 2.3 Hz, 1H), 3.12 (m, 1H), 2.74 (m, 1H), 2.52 (s, 3H), 2.50 (m, 1H), 1.30 (d, J=6.6 Hz, 3H) and 1.29 (m, 3H) ppm. The synthesis is illustrated in FIG. 56.

Example 54

Synthesis of Compound 132

Compound 131 was then converted to triphosphate 132 via standard triphosphate synthesis method described in standard method section. 25% yield; HRMS-ES$^+$: calculated for $C_{12}H_{20}N_5O_{13}P_3S_2$, 598.971, observed m/z 598.970. The synthesis is illustrated in FIG. 56.

Example 55

Synthesis of Compound 134

Compound 133 (4.47 g, 10.7 mmol) and (2,4,6-trimethoxyphenyl)methanethiol (TMPM-SH) were dried under high vacuum for 2 h and then placed in a desiccator with P$_2$O$_5$ for 12 h. Compound 133 was dissolved in anhydrous CH$_2$Cl$_2$ (50.0 mL) and cyclohexene (10 mL, 96.6 mmol) was added. The resulting mixture was stirred for 15 minutes at −10° C. under a nitrogen atmosphere. Next a freshly prepared solution of 1 M SO$_2$Cl$_2$ in CH$_2$Cl$_2$ (25 mL, 26.75 mmol) was added drop-wise via addition funnel, and the resulting mixture stirred for 1 hour at −10° C. The volatiles were removed in vacuo while keeping the bath temperature at 10° C. The residue was then dissolved in anhydrous DMF (52 mL) and kept under a nitrogen atmosphere.

Figure 57:
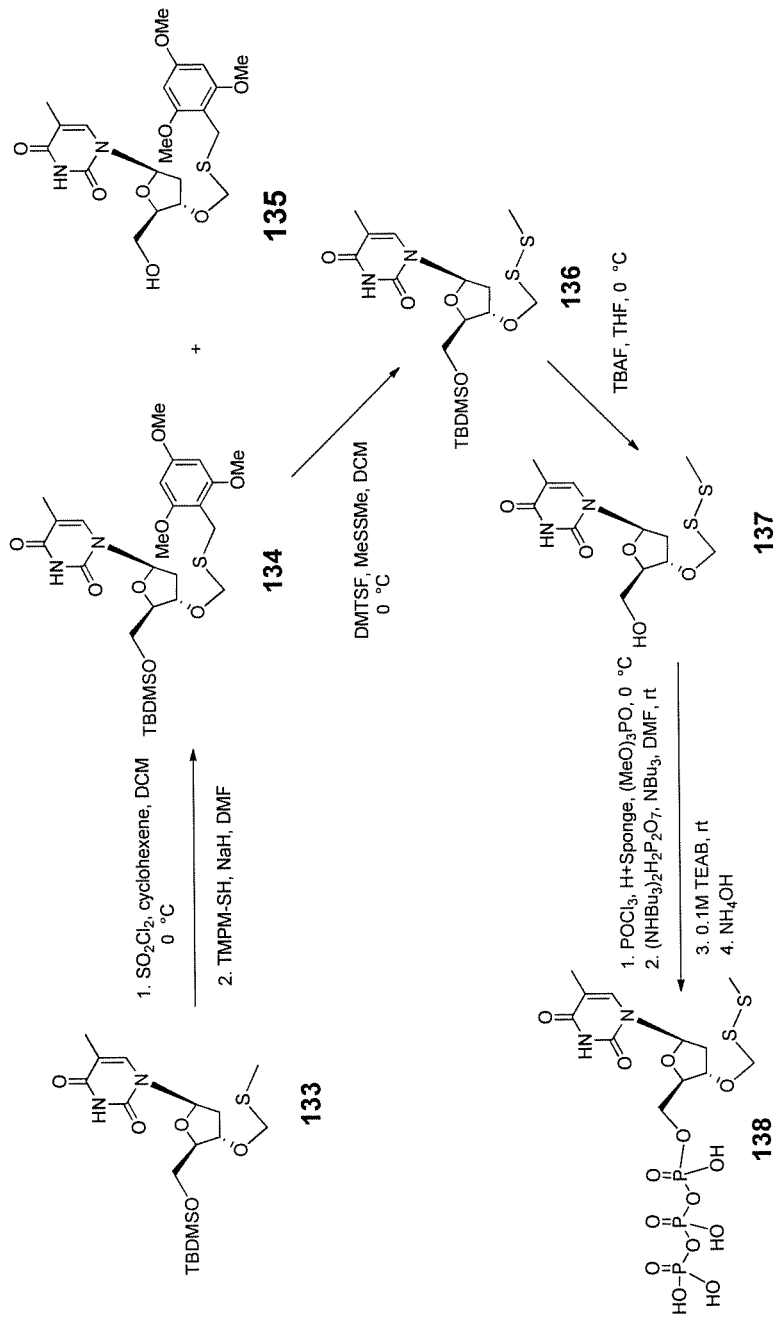
FIG. 57 is a schematic that shows one embodiment of the synthesis of MeSSdTTP.

In a separate flask, (2,4,6-trimethoxyphenyl)methanethiol (4 g, 18.7 mmol) was dissolved in anhydrous DMF (48 mL) under a nitrogen atmosphere and cooled to 0° C. NaH (1.1 g, 26.8 mmol, 60% in mineral oil) was then added and the resulting grey slurry was stirred for 15 minutes at 0° C. It was added to the former solution in one portion and the reaction was stirred at room temperature for 1 h. The reaction mixture was then partitioned in a reparatory funnel (150:300 mL/brine:ethyl acetate). The organic layer was then washed with brine (2×150 mL). The aqueous layer was back-extracted (4×50 mL ethyl acetate). The combined organic layer was dried over anhydrous sodium sulfate. The solvent was removed and product was purified by flash chromatography on silica gel column (column: 120 g RediSepRfGold—ISCO, gradient 0-100% ethyl acetate in hexanes). The target compound 134 was obtained as white solid in 22% yield (1.35 g). $^1$H NMR (CDCl$_3$): $\delta_H$ 8.17 (s, 1H), 7.39 (d, 1H), 6.30 (m, 1H), 6.12 (s, 2H), 4.71 (dd, 2H), 4.43 (m, 1H), 4.04 (m, 1H), 3.87 (m, 1H), 3.83 (m, 9H), 3.74 (dd, 1H), 2.74 (m, 1H), 2.34 (ddd, 1H), 1.93 (m, 2H) 1.53 (s, 3H), 0.93 (m, 9H), 0.11 (m, 6H) ppm. LCMS (ESI) [M–H$^+$] observed 581, R$_f$=0.59 (4:6/hexanes-ethyl acetate). And compound 135 was also isolated as a side product in 22.5% yield (1.13 g). $^1$H NMR (CDCl$_3$): $\delta_H$ 8.55 (s, 1H), 7.41 (m, 1H), 6.12 (M, 3H), 4.76 (dd, 2H), 4.47 (m, 1H), 4.01 (m, 1H), 3.90 (m, 1H), 3.82 (m, 9H), 3.75 (m, 1H), 2.29 (m, 2H), 2.04 (s, 3H) and 1.91 (m, 2H) ppm. LCMS (ESI) [M–H$^+$] observed 467. The synthesis is illustrated in FIG. 57.

Example 56

Synthesis of Compound 136

Compound 134 (3.6 g, 6.2 mmol) in a 100 mL round bottom flask was dried under high vacuum for 2 h and then placed in a vacuum desiccator with P$_2$O$_5$ for 12 h. Anhydrous CH$_2$Cl$_2$ (96 mL) and dimethyldisulfide (2.8 mL, 30.9 mmol) were added, and the reaction cooled to 0° C. Dimethyl(methylthio)sulfonium tetrafluoroborate (DMTSF, 1.34 g, 6.82 mmol) was then added and the reaction stirred for 1 h at 0° C. The reaction mixture was next transferred to a 250 mL separatory funnel and neutralized with 90 mL of 0.1 M aqueous solution of NaHCO$_3$, and extracted with ethyl acetate (2×200 mL). Combined organic layer was dried over anhydrous sodium sulfate and concentrated on the rotary. The residue was purified by flash chromatography on a silica gel column using 30-50% ethyl acetate in hexanes gradient. The target compound 136 was obtained as white solid (2.1 g, 77% yield). $^1$H NMR (CDCl$_3$): $\delta_H$ 7.99 (s, 1H), 7.47 (d, 1H), 6.29 (dd, 1H), 4.87 (dd, 2H), 4.49 (m, 1H), 4.13 (m, 1H), 3.88 (m, 2H), 3.5 (m, 1H), 2.47 (s, 3H), 2.45 (dd, 1H), 2.04 (dd, 1H) and 1.54 (s, 2H), 0.93 (m, 9H) and 0.13 (m, 6H) ppm. LCMS (ESI) [M–H$^+$] observed 447.0. The synthesis is illustrated in FIG. 57.

Example 57

Synthesis of Compound 137

Compound 136 (2.16 g, 4.8 mmol) in a 100 mL round bottom flask dried under high vacuum for 2 h, was dissolved in anhydrous THF (40 mL) followed by addition of acetic acid (1.2 mL) and TBAF in THF (6.7 mL of 1 M solution, 6.72 mmol). The reaction mixture was stirred for 1 hour at 0° C. and then for 2 additional hours at room temperature. The volatiles were removed in vacuo and the residue purified via flash chromatography on 40 g RediSepRf gold column using 0-8% Methanol in dichloromethane gradient. The target compound 137 was obtained as white solid (1.45 g, 90% yield). $^1$H NMR (CDCl$_3$): $\delta_H$ 8.12 (s, 1H), 7.36 (d, 1H), 6.11 (t, 1H), 4.87 (dd, 2H), 4.57 (m, 1H), 4.14 (q, 1H), 3.94 (dd, 1H), 3.83 (m, 1H), 2.50 (s, 3H), 2.4 (m, 2H), 1.93 (s, 3H) ppm; LCMS (ESI) [M–H$^+$] observed 333. The synthesis is illustrated in FIG. 57.

Example 58

Synthesis of Compound 138

The product 138 was obtained after phosphorylation of compound 137 using the standard triphosphate synthesis method vide infra. 40% yield, HR LC-MS: calculated for $C_{12}H_{21}N_2O_{14}P_3S_2$, 573.965; observed m/z 573.964. The synthesis is illustrated in FIG. 57.

Example 59

Synthesis of Compound 141

A 100 mL round bottom flask equipped with a magnetic stir bar was charged with compound 139 (2.23 g, 3.55 mmol), CH$_2$Cl$_2$ (20 mL), 3-Å molecular sieves (3.5 g) and cyclohexene (0.60 mL). The resulting mixture was stirred for 20 minutes at room temperature under a nitrogen atmosphere. The reaction was cooled to 0° C. and SO$_2$Cl$_2$ (5.4 mL, 1 M in CH$_2$Cl$_2$, 1.5 equiv) were added slowly via a syringe. The reaction was stirred for 1.5 h at 0° C. and an additional 1.8 mL of SO$_2$Cl$_2$ (1 M soln. in dichloromethane) was added and stirring continued for 40 minutes at 0° C. to ensure complete conversion to compound 140. The volatiles were removed under reduced pressure while keeping the bath temperature close to 10° C. The resulting solid was re-suspended in 20 mL of anhydrous DMF and kept under a nitrogen atmosphere.

Figure 58:
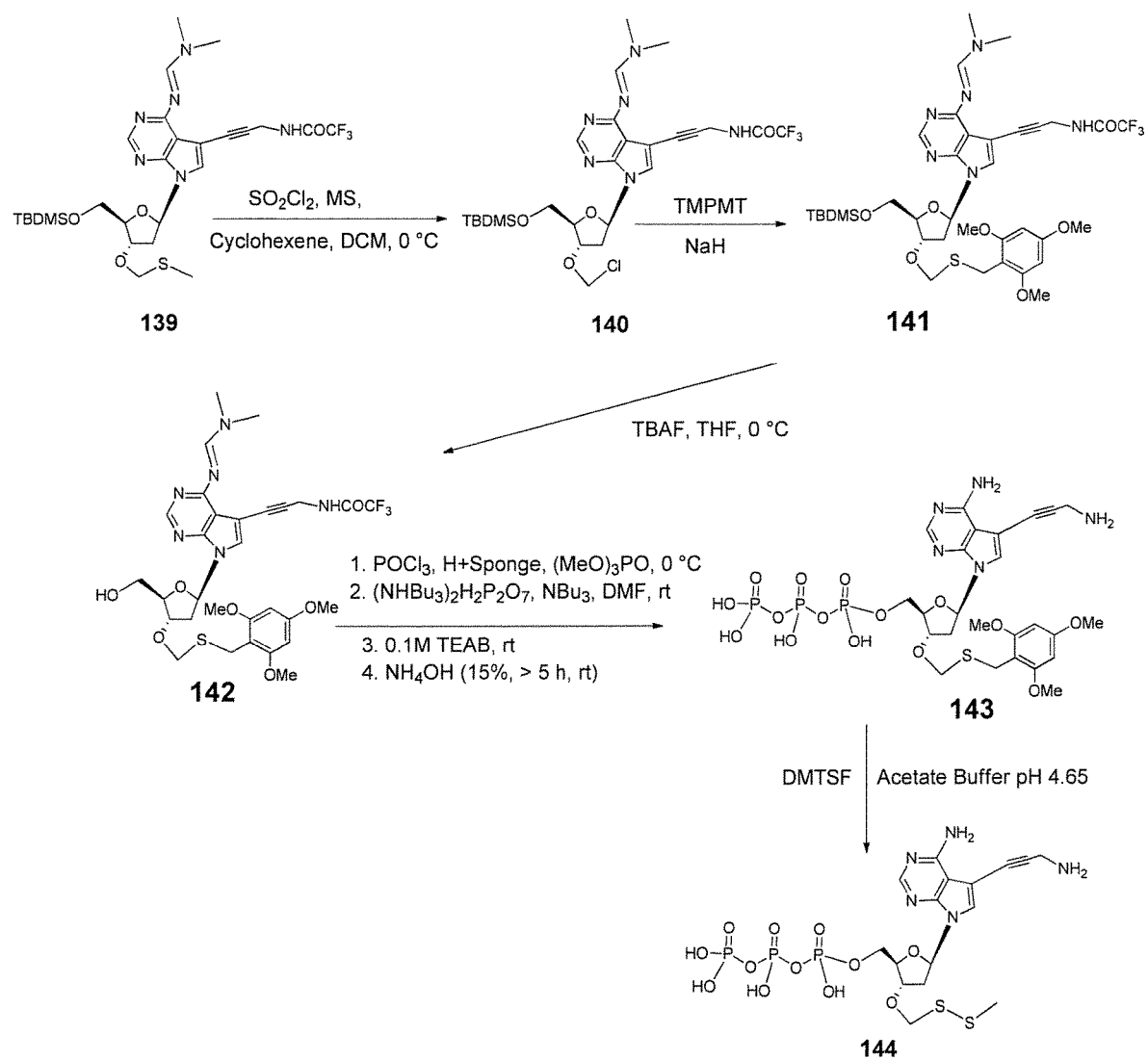
FIG. 58 is a schematic that shows one embodiment of the synthesis of MeSSdATP-PA.

In a separate flask, (2,4,6-trimethoxyphenyl)methanethiol (1.98 g, 9.25 mmol) was dissolved in anhydrous DMF (15 mL) and treated with NaH (247 mg, 60% in mineral oil, 6.17 mM) producing a dark grey slurry. Next, compound 140 solution was added in one portion and the reaction was stirred at room temperature for 1 h. The reaction mixture was then partitioned between distilled water (150 mL) and ethyl acetate (150 mL). The organic layer was further washed with distilled water (2×150 mL) and dried over Na$_2$SO$_4$. The volatiles were removed under reduced pressure and the residue was purified by flash column chromatography on silica gel column using 80 to 100% ethyl acetate in hexanes gradient. The target compound 141 was obtained as white solid (798 mg, 28%). $^1$H NMR (CDCl$_3$): $\delta_H$ 8.33 (s, 1H), 7.57 (m, 1H), 6.53 (m, 2H), 6.00 (s, 2H), 4.62 (m, 2H), 4.44 (m, 1H), 4.32 (m, 2H), 3.97 (m, 1H), 3.80-3.60 (m, 11H), 3.10 (m, 6H), 2.36 (m, 1H), 2.24 (m, 1H), 0.80 (m, 9H) and 0.01 (m, 6H) ppm. Further confirmed by LC-MS: observed m/z 795.25 for (M–H). The synthesis is illustrated in FIG. 58.

Example 60

Synthesis of Compound 142

A 100 mL round bottomed flask equipped with a magnetic stir bar was charged with compound 141 (0.779 gm, 0.98 mmol, vacuum dried over P$_2$O$_5$ for 12 h) and dry THF (20.0 mL), and cooled to 0° C. under a nitrogen atmosphere. TBAF (1.17 mL, 1M solution in THF, 1.17 mmol) was added slowly via a syringe and the reaction mixture was stirred for 1.5 h at 0° C. Next, an additional TBAF (1 mL, 1 M solution in THF, 1 mmol) was added and reacted for 3 h at 0° C. The reaction mixture was then transferred to a separatory funnel and quenched by addition of methanol (5 mL), distilled water (100 mL) was added and the reaction extracted with ethyl acetate (2×100 mL). The organics were dried over Na$_2$SO$_4$ and concentrated in vacuo. Column chromatography of the residue on silica gel using 80-100% ethyl acetate in hexanes gradient afforded compound 142 as a white powder (525 mg, 79%). $^1$H NMR (Methanol-d4): $\delta_H$ 8.33 (s, 1H), 7.19 (m, 1H), 6.06 (m, 2H), 6.03 (m, 1H), 4.72 (m, 2H), 4.64 (m, 1H), 4.57 (m, 1H), 4.35 (m, 2H), 4.17 (m, 1H), 3.75 (m, 9H), 3.16 (m, 6H), 2.80 (m, 1H) and 2.28 (m, 1H) ppm; LC-MS: M–H observed m/z 680.0. The synthesis is illustrated in FIG. 58.

Example 61

Synthesis of Compound 143

Compound 143 was synthesized from compound 142 via standard triphosphate synthesis procedure described in the standard methods section. Yield 65%, LRMS-ES$^+$: calculated for C$_{25}$H$_{33}$N$_5$O$_{15}$P$_3$S–, 768.09; observed m/z 768.54 (M–H). The synthesis is illustrated in FIG. 58.

Example 62

Synthesis of Compound 144

A 50 mL conical tube was charged with compound 143 (3.80 mL of 5.25 mM soln. in HPLC grade water, 20 µmols) and pH 4.65 acetate buffer (4.75 mL), and quickly combined with 9.0 mL of freshly prepared DMTSF (80 mM) solution in pH 4.65 acetate buffer. The resulting mixture was shaken at room temperature for 2 h and quenched by addition of saturated aqueous solution of NaHCO$_3$ (2 mL). The product was immediately purified on preparative HPLC (column: 30×250 mm Cis Sunfire, method: 0 to 2.0 min 100% A, followed by 50% B over 70 min, flow: 25 mL/min, A=50 mM TEAB, B m acetonitrile). The appropriate fractions were lyophilized and combined after dissolving in HPLC grade water to furnish 23.4 umols of compound 144 (73% yield). LRMS-ES$^+$: calculated for C$_{16}$H$_{23}$N$_5$O$_{12}$P$_3$S$_2$–, 634.00, m/z observed 634.42 for (M–H). The synthesis is illustrated in FIG. 58.

Figure 59:
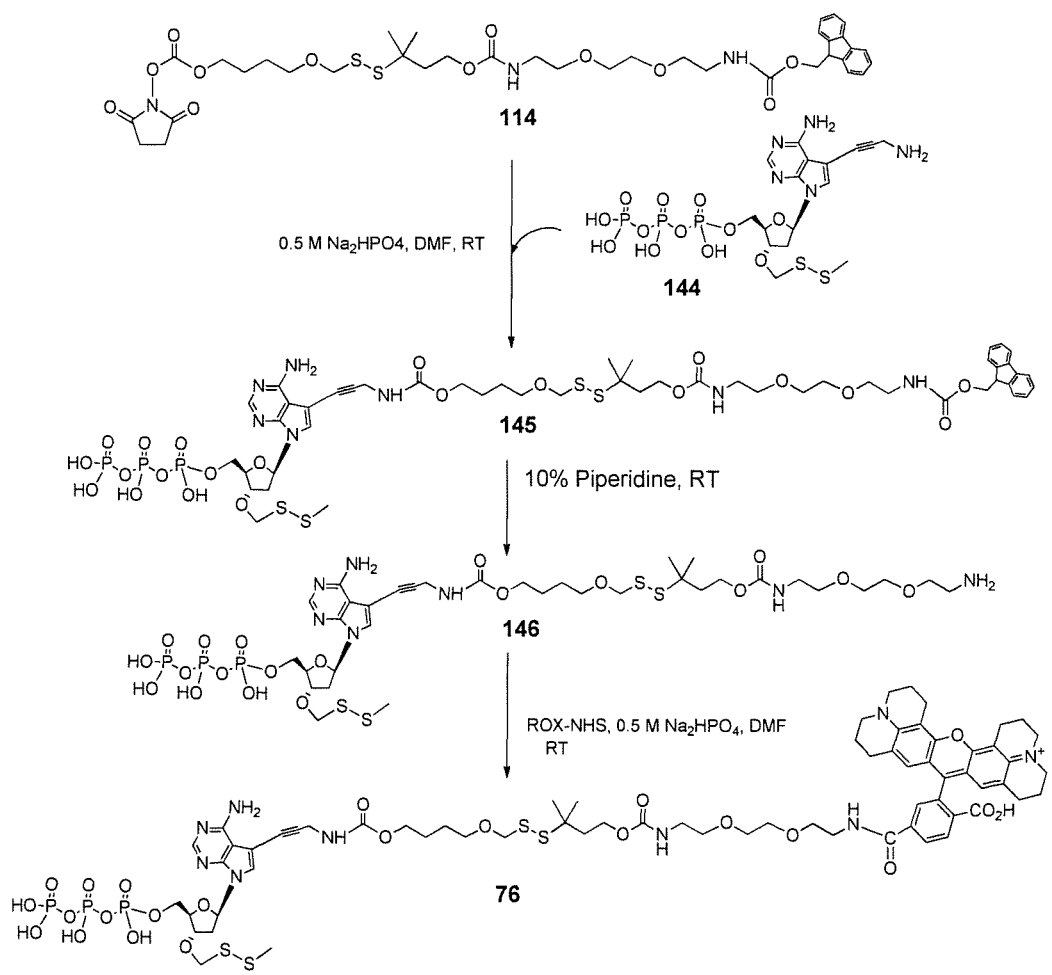
FIG. 59 is a schematic that shows one embodiment of the synthesis of 76.

Compound 144 was converted to dye labeled product (76) according to procedure described in standard methods section (FIG. 59). Compound 146 was obtained in 75% yield in two steps, LRMS-ES+: calculated for C$_{34}$H$_{59}$N$_7$O$_{19}$P$_3$S$_4$, 1090.20, m/z observed 1090.24 for (M+H). Compound 76 was obtained in 50-70% yield from 146, HRMS-ES$^+$: calculated for C$_{67}$H$_{86}$N$_9$O$_{23}$P$_3$S$_4$, 1605.393; observed m/z 1605.380 for (M–H).

Example 63

Synthesis of Compound 150

A 250 mL round bottom flask was charged with compound 148 (3.0 g, 4.58 mmol), 25 mL dry CH$_2$Cl$_2$, 3-A molecular sieves (5.0 g) and cyclohexene (0.55 mL, 5.4 mmol). The resulting mixture was stirred for 10 minutes at room temperature under a nitrogen atmosphere. The reaction flask was then placed on an ice-bath, SO$_2$Cl$_2$ (6.8 mL, 1 M in CH$_2$Cl$_2$, 1.5 eq) was added slowly via a syringe, and the reaction stirred for 1 h at 0° C. Next, an extra 0.5 eq of SO$_2$Cl$_2$ was added to ensure complete conversion to compound 149. The volatiles were removed under vacuum while keeping the temperature close to 10° C. The resulting solid was re-suspended in 20 mL of dry DMF and kept under a nitrogen atmosphere.

Figure 60:
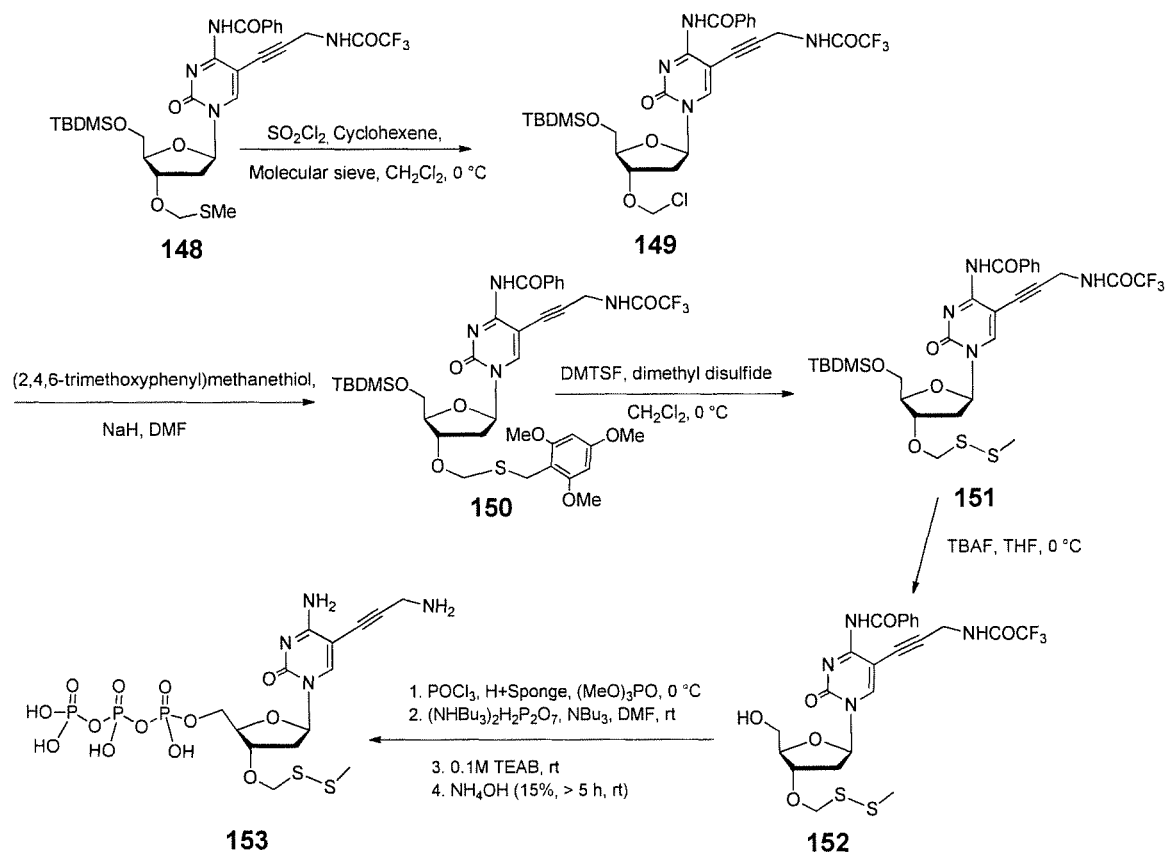
FIG. 60 is a schematic that shows one embodiment of the synthesis of MeSSdCTP-PA.

In a separate flask, (2,4,6-trimethoxyphenyl)methanethiol (2.45 g, 11.44 mmol) was dissolved in dry DMF (30 mL) under nitrogen atmosphere, and treated with NaH (274.5 mg, 60% in silicon oil) producing a grey slurry. To this, compound 149 was added at once and the reaction stirred at room temperature for 3 h under nitrogen atmosphere. The reaction mixture was then filtered through Celite®-S washed with ethyl acetate (100 mL). The ethyl acetate solution was washed with distilled water (2×100 mL), the organic extract was dried over Na$_2$SO$_4$, concentrated in vacuo and purified via flash column chromatography on silica gel column using 20 to 50% ethyl acetate in hexanes gradient. The target compound 150 was obtained as white solid (1.2 g, 32% yield, R$_f$ 0.4, hexanes:ethyl acetate/3:2). $^1$H NMR (CDCl$_3$): $\delta_H$ 8.13 (m, 3H), 7.43 (m, 1H), 7.32 (m, 2H), 6.12 (m, 1H), 6.00 (s, 2H), 4.62 (m, 2H), 4.31 (m, 3H), 4.00 (m, 1H), 3.82-3.60 (m, 13H), 2.39 (m, 1H), 1.84 (m, 1H), 0.78 (m, 9H), and 0.01 (m, 6H) ppm. The synthesis is illustrated in FIG. 60.

Example 64

Synthesis of Compound 151

Compound 150 (1.2 g 1.46 mmol) was dried under high vacuum with $P_2O_5$ in a desiccator overnight and dissolved in 30 mL of anhydrous $CH_2Cl_2$ in a 100 mL flask equipped with a magnetic stir bar. To this was added dimethyldisulfide (0.657 mL, 7.3 mmol), and the reaction flask was placed on an ice-bath. Dimethyl(methylthio)sulfonium tetrafluoroborate (DMTSF, 316 mg, 1.1 eq) was added and stirred for 1.5 hr at 0° C. The reaction mixture was transferred to a 250 mL separatory funnel and neutralized with 50 mL of 0.1 M aq. solution of $NaHCO_3$, and extracted with $CH_2Cl_2$ (2×50 mL). The organic layer was dried over $Na_2SO_4$ and concentrated by rotary evaporation. The crude product was purified on a silica gel column using gradient 80-50% ethyl acetate in hexanes gradient to result in 0.82 g of compound 151 (82% yield, $R_F$=0.5, hexanes:ethyl acetate 3:2). $^1$H NMR ($CDCl_3$): $\delta_H$ 8.15 (m, 3H), 7.42 (m, 1H), 7.35 (m, 2H), 6.11 (m, 1H), 4.80-4.65 (m, 2H), 4.34 (m, 1H), 4.28 (m, 2H), 4.10 (m, 1H), 3.83-3.67 (m, 2H), 2.49 (m, 1H), 2.34 (s, 3H), 1.90 (m, 1H), 0.78 (m, 9H), and 0.10 (m, 6H) ppm. The synthesis is illustrated in FIG. 60.

Example 65

Synthesis of Compound 152

A 100 mL round bottomed flask equipped with a magnetic stir bar was charged with compound 151 (0.309 g, 0.45 mmol), and 10.0 mL dry THF (10.0 mL) and placed on an ice-bath under a nitrogen atmosphere. TBAF (0.72 mL, 1 M soln. in THF, 0.72 mmol) was added slowly via syringe. The reaction mixture was stirred for 3 h at 0° C. The reaction mixture was then transferred to a separatory funnel and quenched with 0.5 M aqueous soln. of $NaHCO_3$ (50 mL). The resulting mixture was then extracted with ethyl acetate (2×100 mL) and dried over $Na_2SO_4$. The product 152 was obtained as a white powder after silica gel column chromatography in 76% yield (196 mg, $R_f$=0.3, hexanes:ethyl acetate/1:1) on silica gel column using gradient 7:3 to 2:3 hexanes:ethyl acetate. $^1$H NMR ($CDCl_3$): Su 8.40 (s, 1H), 8.25 (m, 2H), 7.60 (m, 1H), 7.52 (m, 2H), 6.21 (m, 1H), 4.90-80 (m, 2H), 4.65 (m, 1H), 4.40 (m, 2H), 4.25 (m, 1H), 4.05-3.85 (m, 2H), 2.62 (m, 1H), 2.50 (s, 3H) and 2.31 (m, 1H) ppm. The synthesis is illustrated in FIG. 60.

Example 66

Synthesis of Compound 153

Figure 61:
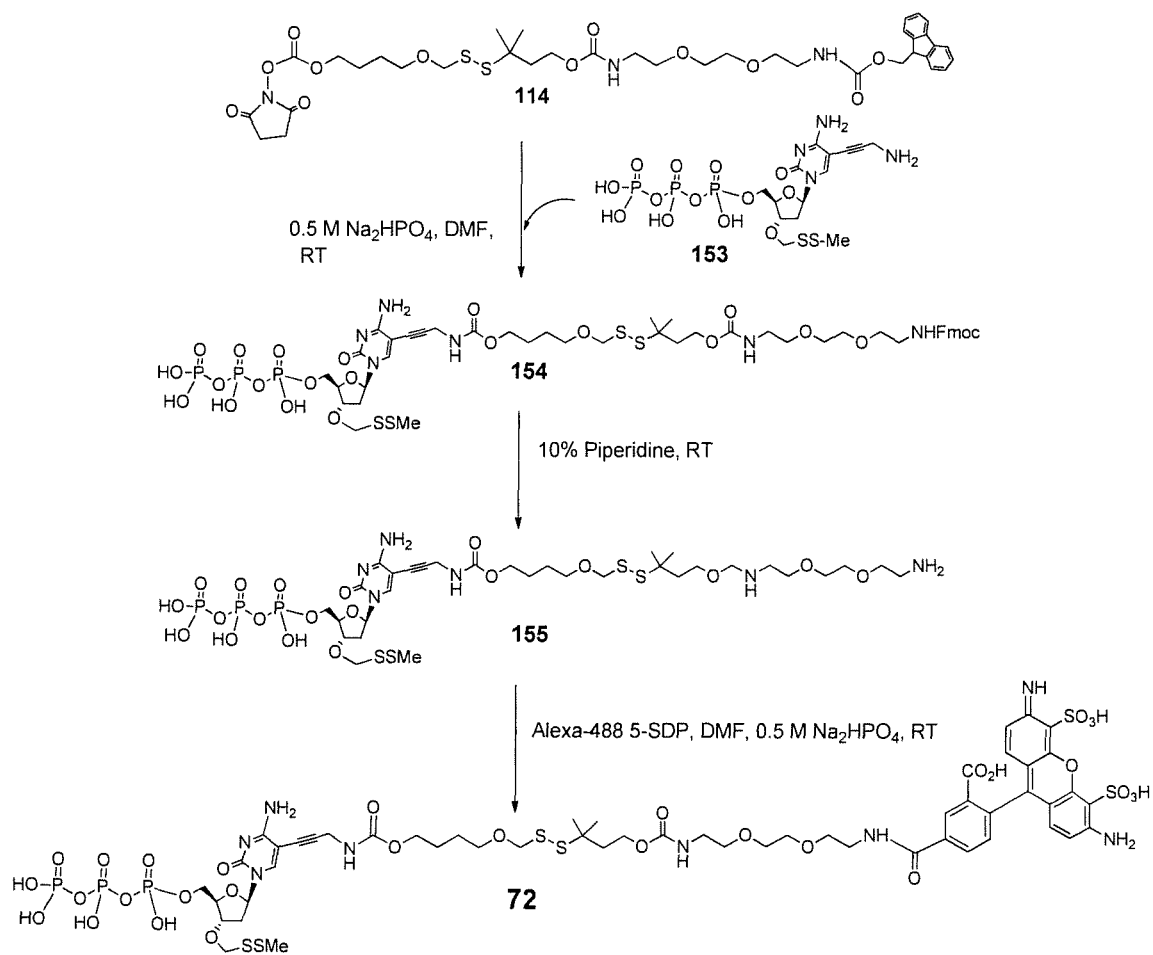
FIG. 61 is a schematic that shows one embodiment of the synthesis of 72.

Compound 153 was obtained after phosphorylation of compound 152 in 30% yield using the standard triphosphate synthesis method vide infra (LC-MS: calculated for $C_{14}H_{23}N_4O_{13}P_3S_2$, 610.98; observed m/z 611.11 (M−H). It was further converted to dye labeled product (72) according to procedure described in standard method section (FIG. 61). Compound 155 was obtained in 49% yield in two steps, and compound 72 in 60-85% yield, HRMS-ES$^+$: calculated $C_{33}H_{68}N_8O_{30}P_3S_6$, 1581.156 (M−H); found m/z 1582.160.

Example 67

Synthesis of Compounds 159 & 160

A 100 mL round bottom flask equipped with a magnetic stir bar was charged with compound 157 (2.04 g, 2.39 mmol) and was dried on high vacuum over 12 h. After flushing the reaction vessel with argon, 13 mL anhydrous $CH_2Cl_2$ and cyclohexanesene (0.30 mL, 2.86 mmol) were added sequentially. The reaction flask was then placed on an ice-water-salt bath and stirred for 10 min to bring the mixture below 0° C. $SO_2Cl_2$ (4.0 mL, 1 M in $CH_2Cl_2$, 4.0 mmol) was added drop-wise via a syringe over 2 min, and the reaction mixture stirred for 1 h at 0° C. An additional 0.8 equiv. of $SO_2Cl_2$ (2.0 mL, 2.0 mmol) was added drop-wise over 1 min and the reaction was stirred for an additional Y h at 0° C. Next, the volatiles were removed in vacuo while keeping the bath temperature at ~10° C. The resulting solid was re-suspended in 15 mL of dry DMF and kept under an argon atmosphere.

Figure 62:
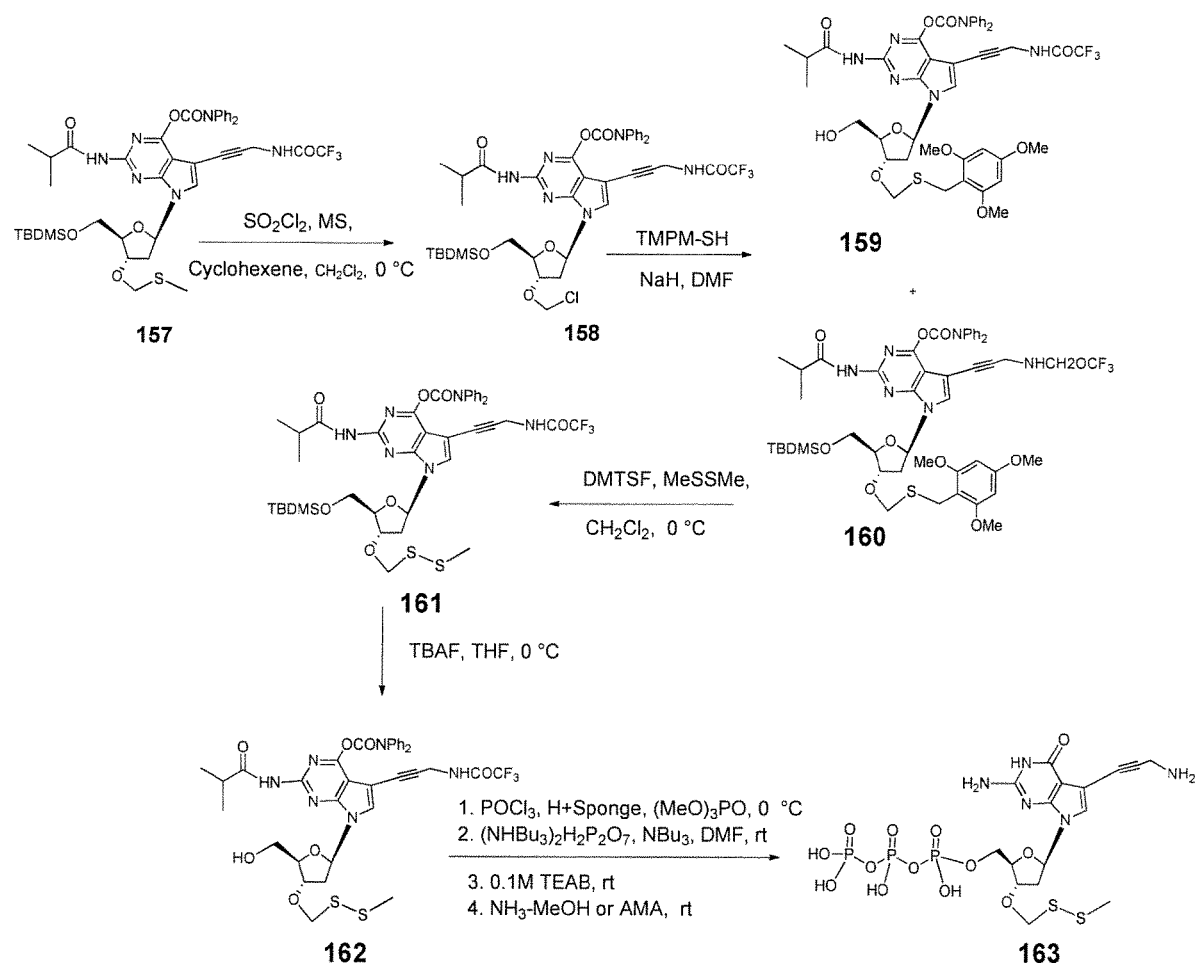
FIG. 62 is a schematic that shows one embodiment of the synthesis of MeSSdGTP-PA.
Figure 63:
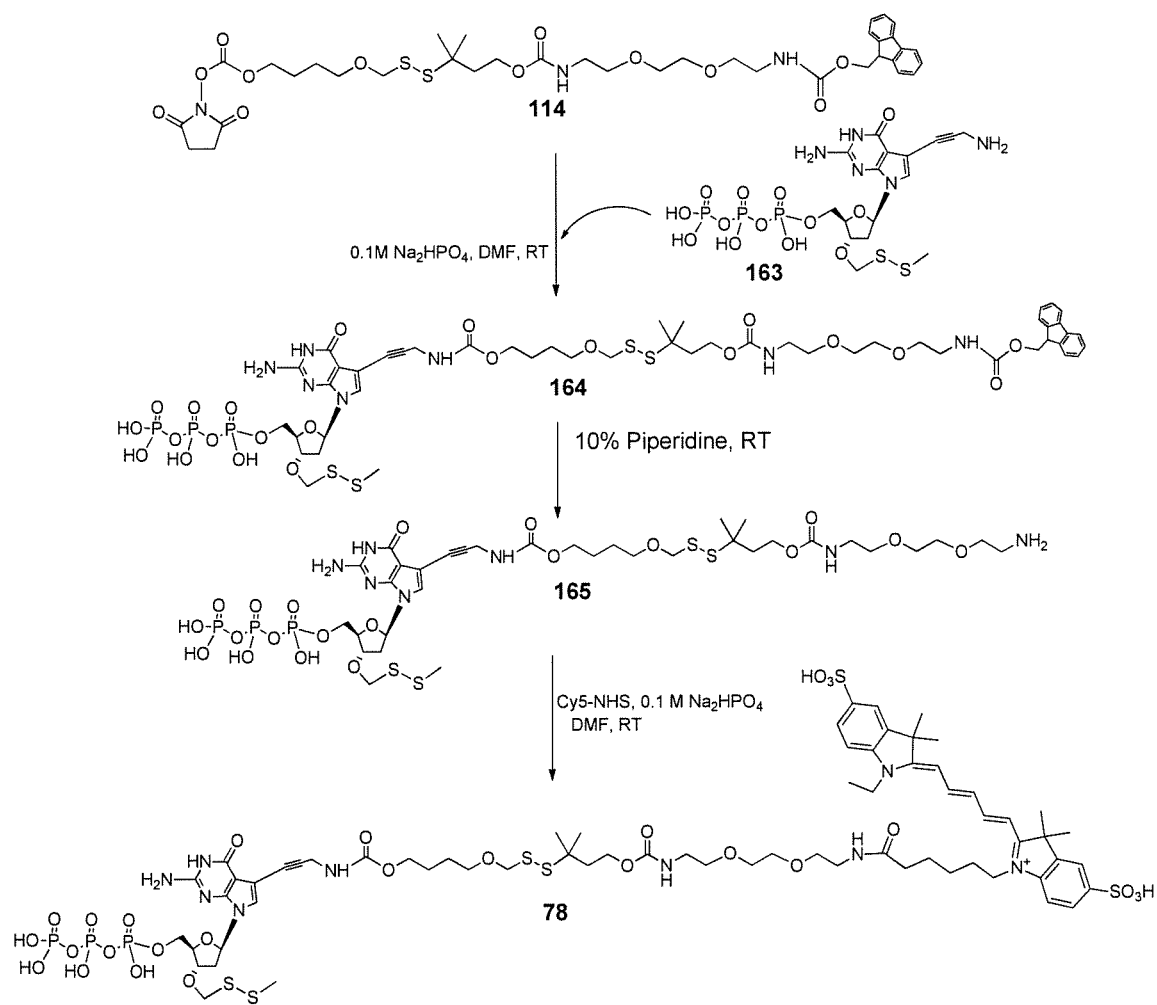
FIG. 63 is a schematic that shows one embodiment of the synthesis of MeSSdGTP-ARA-Cy5.

In a separate 100 mL flask, (2,4,6-trimethoxyphenyl)methanethiol (TMPM-SH, 1.27 g, 6.0 mmol, vacuum dried overnight) was dissolved in dry DMF (16 mL) under argon atmosphere and treated with NaH (195 mg, 60% in oil, 4.88 mmol) producing a grey slurry TMPMT-SNa salt. The mixture was stirred until gas formation subsided (Ca. 10 min). To this, TMPMT-SNa salt was added at once and the mixture was stirred at room temperature under argon atmosphere until TLC (micro-workup: dichloromethane/water; solvent: hexanes:ethyl acetate/1:1) confirmed complete conversion (1 h). The reaction mixture was then filtered through Celite®-S (10 g) in a filtration funnel eluting the product with dichloromethane (100 mL). The dichloromethane solution was then washed with water (3×100 mL). The aqueous layer was extracted with 3×100 mL dichloromethane. Combined dichloromethane extract was dried over $Na_2SO_4$ and concentrated by rotary evaporation. It was then purified by flash chromatography (column: 100 g, gradient: 25%-50% hexanes:ethyl acetate 5 CV, then 50% EE 10 CV). The target compound 160 was obtained as a white foam (1.22 g, 51% yield). $^1$H NMR (DMSO-d$_6$): $\delta_H$ 10.63 (s, 1H), 10.15 (s, 1H), 7.95 (s, 1H), 7.3-7.5 (m, 8H), 7.20-7.3 (m, 2H), 6.40 (m, 1H), 6.15 (m, 1H), 4.69 (m, 2H), 4.50 (dd, 1H), 4.30 (m, 2H), 3.95 (m, 1H), 3.81 (m, 11H), 3.3 (m, 4H), 2.7 (m, 1H), 1.05 (m, 8H), 0.8 (m, 9H) and 0.11 (m, 6H) ppm. LCMS: 1019.371 Da. The synthesis is illustrated in FIG. 62.

Additionally, the TBDMS-deprotected product 159 was obtained as a side product in 25% yield (0.48 g). $R_f$=0.2/hexanes:ethyl acetate/1:1. $^1$H NMR (DMSO-d$_6$): $\delta_H$ 10.63 (s, 1H), 10.15 (s, 1H), 7.95 (s, 1H), 7.3-7.5 (m, 8H), 7.20-7.3 (m, 2H), 6.40 (m, 1H), 6.15 (m, 1H), 4.69 (m, 2H), 4.50 (dd, 1H), 4.30 (m, 2H), 3.95 (m, 1H), 3.81 (m, 11H), 3.5 (m, 1H), 3.3 (m, 4H), 2.7 (m, 1H), and 1.04 (m, 8H) ppm. LCMS: 905.286 Da.

Example 68

Synthesis of Compound 161

A 100 mL round bottom flask equipped with a magnetic stir bar and rubber septum was charged with compound 160 (0.36 g, 0.35 mmol) and dried for 12 h on high vacuum. After flushing with argon, 7 mL dry dichloromethane and dimethyldisulfide (0.16 mL, 1.76 mmol) were added. The reaction flask was placed on an ice-bath and stirred for 10 min to bring the mixture to 0° C. Dimethyl(methylthio)sulfonium tetrafluoroborate (DMTSF, 80 mg, 0.4 mmol) was then added and the reaction was stirred for at 0° C. until TLC (micro-workup: dichloromethane/water; solvent: Hexanes: Ethyl acetate/1:1). The reaction mixture was transferred to a 250 mL separatory funnel, neutralized with 50 mL of 0.1 M aq. solution of $NaHCO_3$ and extracted with $CH_2Cl_2$ (3×50 mL). The organic layer was dried over $Na_2SO_4$ and concentrated by rotary evaporation. The crude product was purified on a silica gel column (column: 25 g. gradient: 10%-50% hexanes:ethyl acetate 3 CV, then 50% ethyl acetate 5 CV). The target compound 161 was obtained as yellow foam (0.23 g, 74% yield). The synthesis is illustrated in FIG. 62.

Example 69

Synthesis of Compound 162

A 100 mL round bottomed flask equipped with a magnetic stir bar was charged with compound 161 (0.18 g, 0.20 mmol), dissolved in 7.0 mL dry THF and placed on an ice-bath under an argon atmosphere. The mixture was stirred for 10 min to bring it to 0° C. and 0.28 mL Acetic acid were added. TBAF (1 M in THF, 0.47 mL, 0.47 mmol) was added dropwise via syringe over 1 min. The reaction mixture was stirred for 0.5 h at 0° C. and then 1 h at rt. TLC (hexanes: ethyl acetate/1:1) still showed starting material. Additional TBAF (1 M in THF, 0.47 mL, 0.47 mmol) was added dropwise via syringe over 1 min and the reaction mixture was stirred for 1 h at room temperature. Next, the mixture was quenched with 2 mL methanol and stirred for 10 min at rt. The solvent was removed by rotary evaporation, and the crude product was purified by silica gel column chromatography (column: 10 g, hexanes:ethyl acetate/1:1 to 100% over 2 CV, then 100% Ethyl acetate over 20 CV to yield compound 162 as a white foam (96 mg, 62%). The synthesis is illustrated in FIG. 62.

Example 70

Synthesis of Compound 163

Compound 163 was obtained after phosphorylation of compound 162 using the standard triphosphate synthesis method vide infra; except in the de-protection step AMA or methanolic ammonia were used instead of ammonium hydroxide. It was further converted to the dye labeled product 78 according to the standard procedure below. Compound 78 was obtained in 97% yield from compound 165. HRMS-ES' calculated $C_{67}H_{96}N_9O_{27}P_3S_6$ (M−H) 1743.395, found 1743.390. The synthesis is illustrated in FIG. 62.

Example 71

Synthesis of Compound 169

A 100 mL round bottom flask was charged with compound 167 (3.120 g, 5.66 mmol), 30.0 mL dry $CH_2Cl_2$, 3-A molecular sieves (5.0 g) and cyclohexanesene (0.70 mL, 6.9 mmol). The resulting mixture was stirred for 10 minutes at room temperature under a nitrogen atmosphere. The reaction flask was then placed on an ice-bath. To this, $SO_2Cl_2$ (8.5 mL, 1M in $CH_2Cl_2$, 1.5 equiv) was added slowly via a syringe, and stirred for 1 hour at 0° C. Next, an additional 4.0 mL of 1 M $SO_2Cl_2$ was added and stirred for 40 minutes to ensure complete conversion to compound 168. The volatiles were removed under vacuum while keeping the temperature close to 10° C. The resulting solid was re-suspended in 20 mL of dry DMF and kept under a nitrogen atmosphere.

Figure 64:
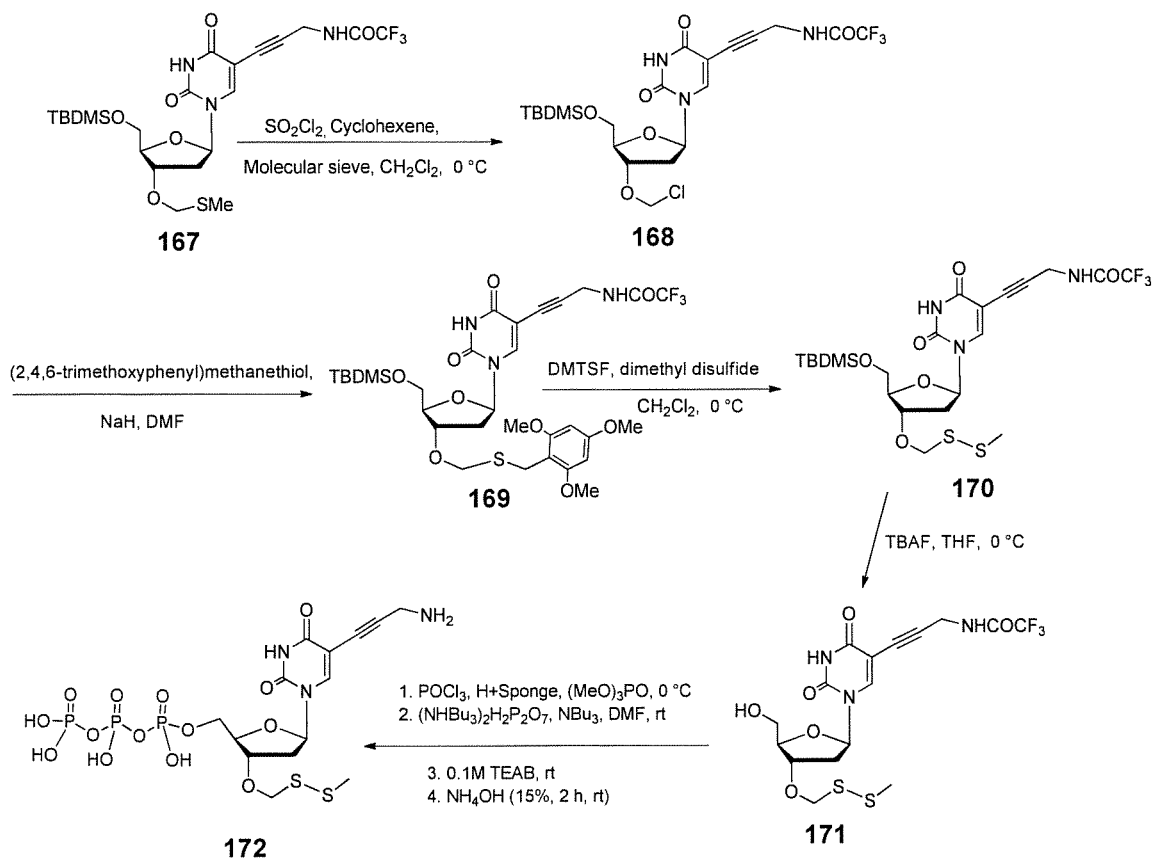
FIG. 64 is a schematic that shows one embodiment of the synthesis of MeSSdUTP-PA.

In a separate flask, (2,4,6-trimethoxyphenyl)methanethiol (3.028 g, 14.15 mmol) was dissolved in dry DMF (40 mL) under nitrogen atmosphere, and treated with NaH (566 mg, 60% in oil, 14.15 mM) producing a grey slurry. To this, compound 168 solution was added at once and stirred at room temperature for 2.5 h under nitrogen atmosphere. The reaction mixture was then filtered through Celite®-S (20 g) with ethyl acetate (200 mL). The ethyl acetate solution was then washed with distilled water (3×200 mL) and dried over $Na_2SO_4$ concentrated by rotary evaporation, and purified by flash chromatography on 120 g RediSepRfGold, gradient: hexanes:ethyl acetate (7:3 to 3:7). The target compound (169) was obtained as white solid (1.43 g, 35.5% yield, R: 0.5, hexanes:ethyl acetate 1:1). $^1$H NMR (CDCl$_3$): $\delta_H$ 7.98 (m, 1H), 6.09 (m, 1H), 6.00 (m, 2H), 4.67-4.51 (m, 2H), 4.30 (m, 1H), 4.22 (m, 2H), 4.00 (m, 1H), 3.80-3-60 (m, 11H), 2.31 (m, 1H), 1.83 (m, 1H), 0.80 (m, 9H) and 0.01 (m, 6H) ppm. The synthesis is illustrated in FIG. 64.

Example 72

Synthesis of Compound 170

Compound 169 (1.43 g 1.99 mmol) was dried under high vacuum over $P_2O$, for 12 h and dissolved in of anhydrous $CH_2Cl_2$ (25 mL) in a flask equipped with a magnetic stir bar and a nitrogen gas source. To this was added dimethyldisulfide (0.89 mL, 9.88 mmol), and the reaction flask was stirred on an ice-bath. Dimethyl(methylthio)sulfonium tetrafluoroborate (DMTSF, 430 mg, 2.19 mmol) was then added and stirred for 1.0 h at 0° C. The reaction mixture was transferred to a 500 mL separatory funnel and quenched with 100 mL of 50 mM aq. solution of $NaHCO_3$, and extracted with $CH_2Cl_2$ (2×150 mL). The organic portion was dried over $Na_2SO_4$ and concentrated by rotary evaporation. The crude product was purified on a silica gel column (80 g RediSepRf gold) using hexanes-ethyl acetate (8:2 to 3:7) gradient to result in 0.622 gm of compound 170 (54% yield, RF=0.6, hexanes:ethyl acetate/1:1). $^1$H NMR (CDCl$_3$): $\delta_H$ 7.99 (brs, 1H, NH), 7.98 (s, 1H), 6.12 (m, 1H), 4.69 (m, 2H), 4.35 (m, 1H), 4.19 (m, 2H), 4.06 (m, 1H), 3.80 (m, 1H), 3.60 (m, 2H), 2.40 (m, 1H), 2.33 (s, 3H), 1.88 (m, 1H), 0.78 (m, 9H), and 0.10 (m, 6H) ppm. The synthesis is illustrated in FIG. 64.

Example 73

Synthesis of Compound 171

A 100 mL round bottomed flask equipped with a magnetic stir bar was charged with compound 170 (0.623 g, 1.06 mmol, vacuum dried over $P_2O_5$ for 12 h) and anhydrous THF (20.0 mL) and placed on an ice-bath under a nitrogen atmosphere. TBAF (1.27 mL, 1 M solution in THF, 1.27 mmols) was added slowly via syringe. The reaction mixture was stirred for 1.5 h at 0° C., and an additional 0.9 mL of 1 M TBAF soln. in THF was added and stirred a total of 4 h at 0° C. The reaction mixture was then transferred to a separatory funnel and quenched with 0.5 M $NaHCO_3$ solution (50 mL). The resulting mixture was extracted with ethyl acetate (2×100 mL) and dried over $Na_2SO_4$. The product 171 was obtained as a white powder after silica gel column chromatography in 63% yield (311 mg) on a 80 g RediSepRf column using gradient 7:3 to 3:7 ethyl acetate in hexanes. $^1$H NMR (methanol-d): $\delta_H$ 8.16 (s, 1H), 6.06 (m, 1H), 4.79 (m, 2H), 4.69 (m, 1H), 4.40 (m, 1H), 4.14 (m, 2H), 3.99 (m, 1H), 3.63 (m, 2H), 2.36 (m, 3H), 2.32 (m, 1H), and 2.08 (m, 1H) ppm, LRMS-ES–: M–H observed m/z 468.0 Da. The synthesis is illustrated in FIG. 64.

Example 74

Synthesis of Compound 172

Figure 65:
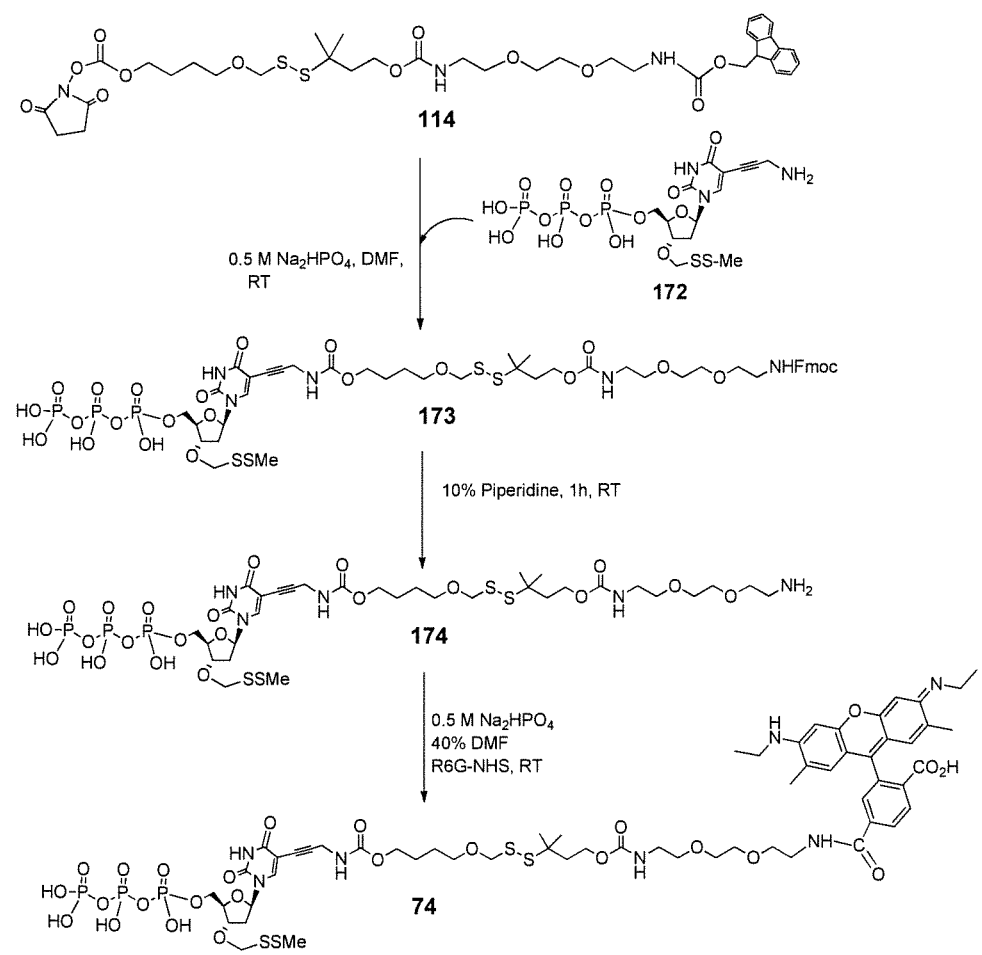
FIG. 65 is a schematic that shows one embodiment of the synthesis of 74.

The product 172 was obtained in 58% yield after phosphorylation of compound 171 using via standard triphosphate synthesis method. LRMS calculated $C_{14}H_{21}N_3O_{14}P_3S_2$, (M–H), 611.97, found 612.15. Compound 171 was further elaborated to the dye labeled product (74) according to standard procedure described in standard method section vide infra (FIG. 65). Compound 174 was obtained in 74% yield in two steps (HRMS-ES' calculated $C_{32}H_{55}N_5O_{12}P_3S_4$(M–H) 1066.15, found 1066.42. Compound 74 was obtained in 62% yield (HRMS-ES' calculated $C_{59}H_{80}N_7O_{25}P_3S_4^-$ (M–H), 1507.330, found 1507.325.

Example 75

Standard Method for Triphosphate Synthesis

Nucleoside (160 µmol) and proton sponge (1.5 equiv) pre-dried under high vacuum over $P_2O_3$, were dissolved in trimethylphosphate (0.8 mL) in a 25 mL pear-shaped flask under $N_2$-atmosphere and stirred for 20 minutes until all solids were completely dissolved. The flask was then placed on an ice-water bath to bring the reaction to (−5 to 0° C.). Then, $POCl_3$ (1.5 eq.) was added in one portion via syringe and the reaction stirred for 1 h.

A mixture of n-butylammonium-pyrophosphate (0.36 g), n-$Bu_3N$ (0.36 mL) and anhydrous DMF (1.3 mL) was prepared in a 15 mL conical tube producing a thick slurry. Once completely dissolved, it was rapidly added at once to the vigorously stirring mixture and stirred for 15 mins at room temperature.

The reaction mixture was then poured into 100 mL of 0.1 M TEAB buffer in a 250 mL round bottom flask and stirred for 3 h at room temperature. It was then concentrated down to 25 mL in vacuo and treated with 25 mL of ammonium hydroxide (28-30% $NH_3$ content) for 8 h at room temperature. After removing most of the volatiles under reduced pressure, the reaction crude was resuspended in 0.1M TEAB buffer (30 mL) and purified by C18 preparative—HPLC (30×250 mm, C18 Sunfire column, method: 0 to 2 min 100% A, followed by 50% B over 70 mins, flow 25 mL/min; A=50 mM TEAB, B=ACN). The target fractions were lyophilized, and combined after dissolving in HPLC grade water (20 mL). This semi-pure product was further purified by ion exchange HPLC on PL-SAX Prep column (method: 0 to 5 min 100% A, then linear gradient up to 70% B over 70 min, where A=15% acetonitrile in water, B=0.85 M TEAB buffer in 15% acetonitrile). Final purification was carried out by C18 Prep HPLC as described above. The nucleoside triphosphates were obtained in 20-65% yield following lyophilization.

Example 76

Figure 66:
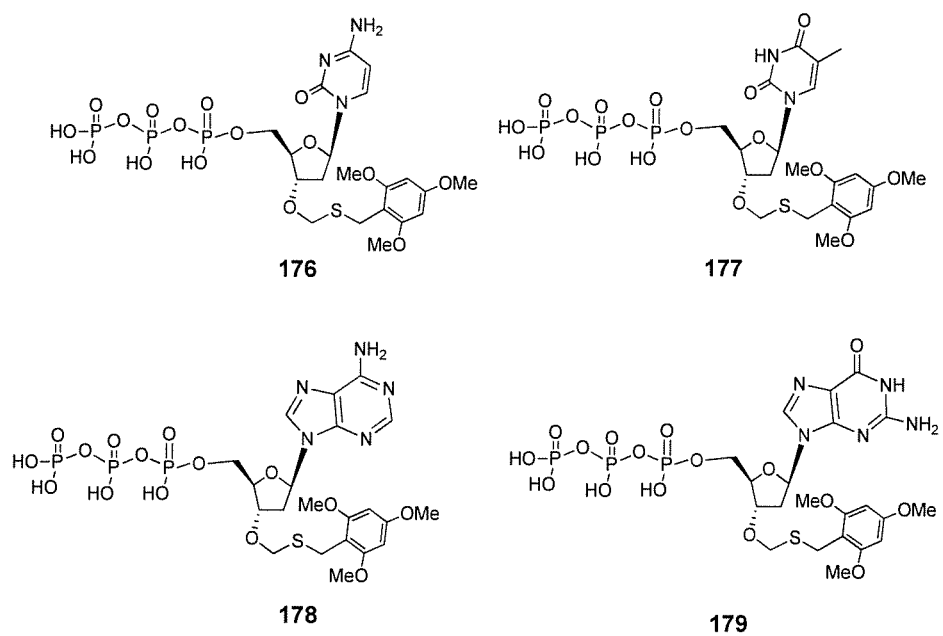
FIG. 66 is a schematic that shows the structures of 3'-$OCH_2$S-(2,4,6-trimethoxyphenyl)methane-dNTPs.
Figure 67:
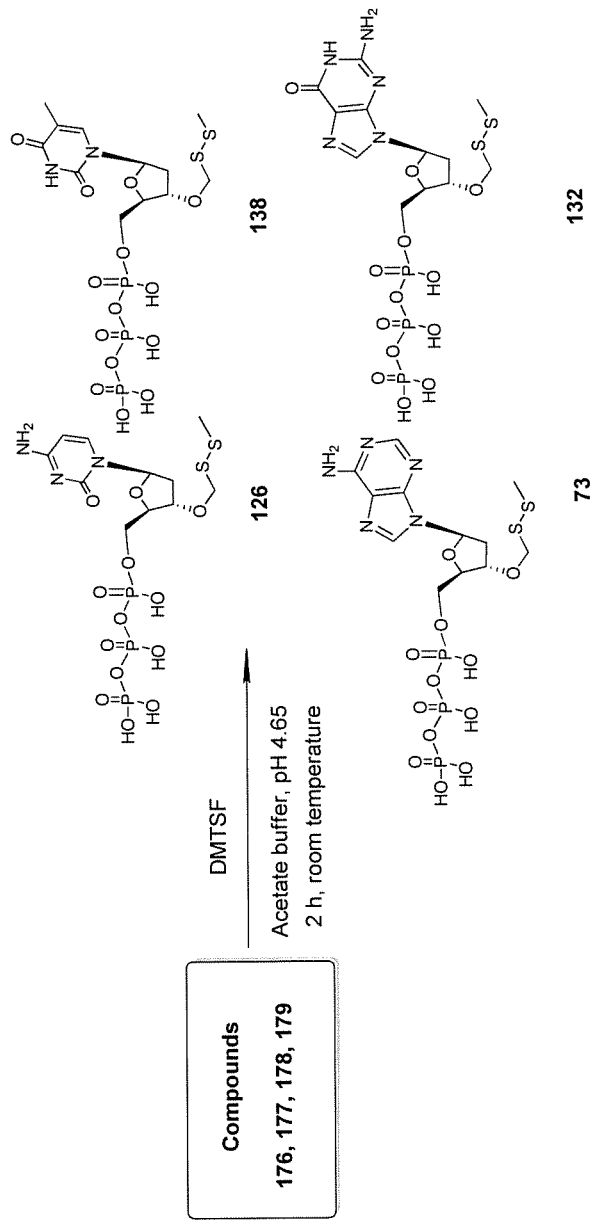
FIG. 67 is a schematic that shows one embodiment of the synthesis of 3'-($OCH_2$SSMe)-dNTPs from 3'-$OCH_2$S-(2,4,6-trimethoxyphenyl)methane-dNTPs.
Figure 69:
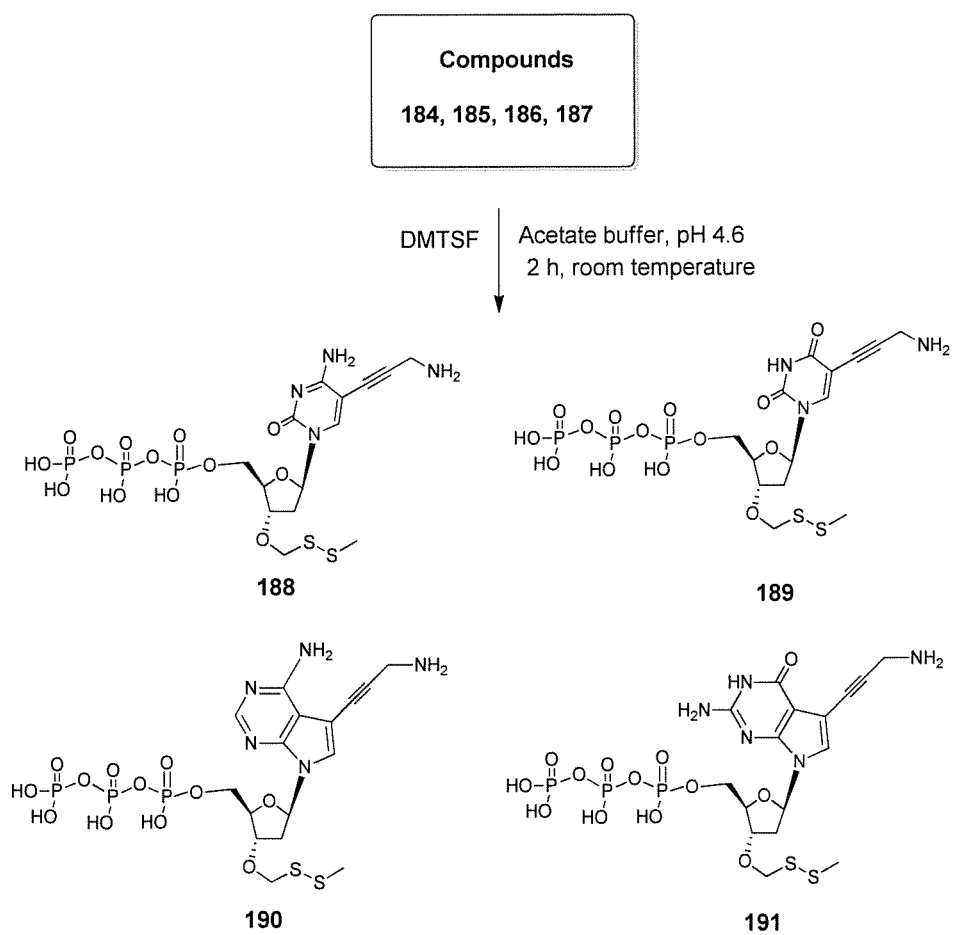
FIG. 69 is a schematic that shows one embodiment of the synthesis of 3'-($OCH_2$SSMe)-dNTP-PA from 3'-$OCH_2$S-(2,4,6-trimethoxyphenyl)methane-dNTP-PAs.
Figure 70:
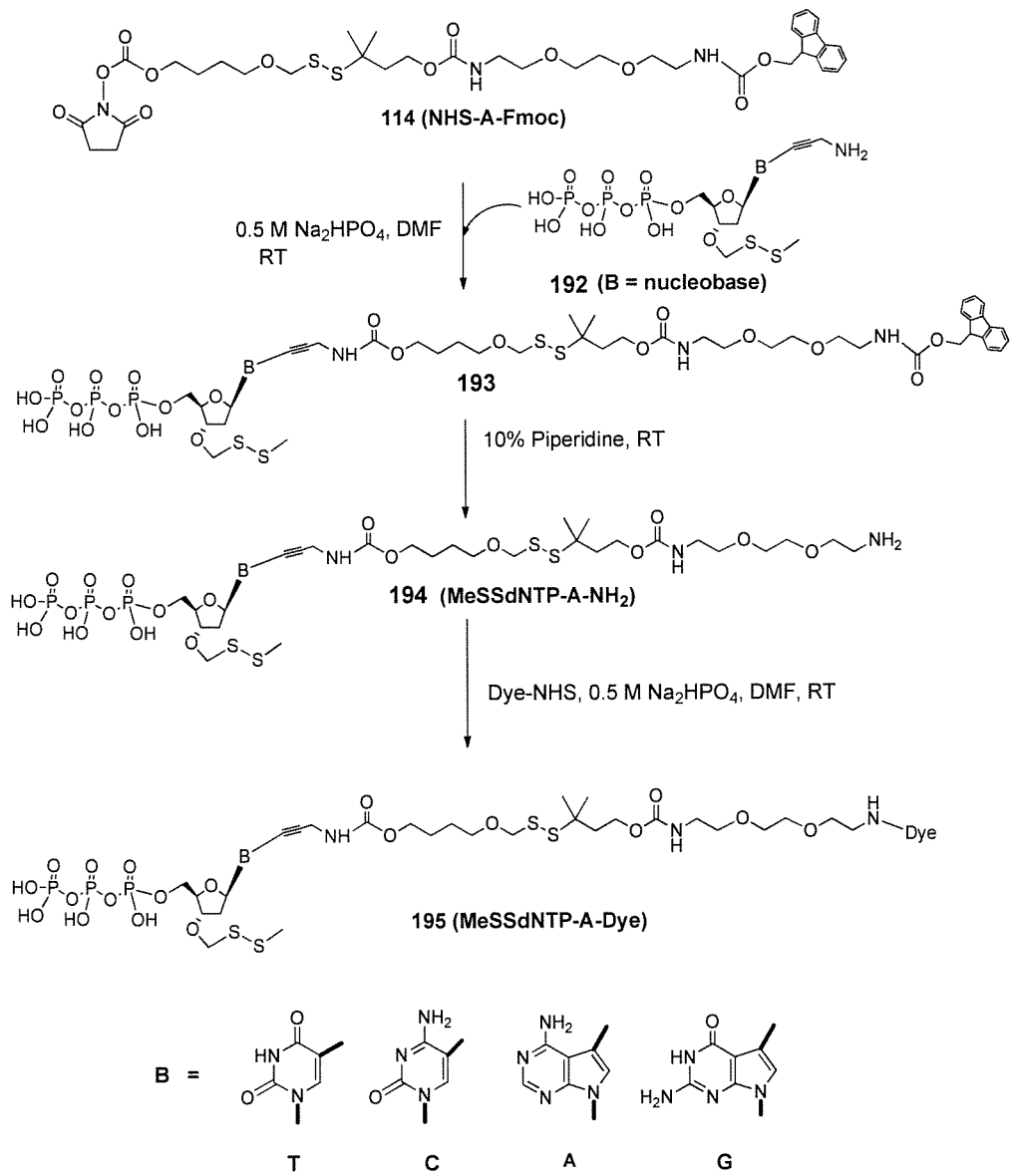
FIG. 70 is a schematic that shows linker installation and conjugation of fluorescent dye.

Standard Method for Converting of 3'-$OCH_2$S-(2,4,6-Trimethoxyphenyl)methane-dNTP to 3'-($OCH_2$SSMe)-dNTP Using DMTSF A 50 mL conical tube was charged with 3'-$OCH_2$S-(2,4,6-trimethoxyphenyl)methane-dNTP (3.80 mL of 5.25 mMolar soln. in HPLC grade water, 20 µmols) and pH=4.65 acetate buffer (5.20 mL), and quickly combined with 9.0 mL of DMTSF (80 mMolar soln. in pH-4.65 acetate buffer). The resulting mixture was shaken at room temperature for 2 h and the reaction was quenched by 2.0 mL of saturated $NaHCO_3$ solution, and immediately purified by prep-HPLC on 30×250 mm C18 Sunfire column, method: 0 to 2.0 min 100% A, followed by linear gradient up to 50% B over 70 min, flow: 25 mL/min, A=50 mM TEAB, B=acetonitrile. The target fractions were lyophilized and combined after dissolving in HPLC grade water to result in 50-75% yield of 3'-($OCH_2$SSMe)-dNTP depending on nucleotide. Structural examples of 3'-$OCH_2$S-(2,4,6-trimethoxyphenyl)methane-dNTPs are illustrated in FIG. 66.

Example 77

Standard Method for Conjugation of NHS Activated Linker

MeSSdNTP-PA (10 ummol) dissolved in HPLC grade water (2 mL) was diluted with freshly prepared 0.5 M aqueous soln. of $Na_2HPO_4$ (I mL). In a conical tube, the NHS-activated linker (NHS-A-Fmoc, 114, 35 mg, 2.5 eq.) was dissolved in anhydrous DMF (2.0 mL). It was then added to the MeSSdNTP-PA/$Na_2HPO_4$ solution at once and stirred for 8 h at room temperature.

The reaction was then diluted with 0.1 M TEAB buffer (2.0 mL) and treated with piperidine (0.6 mL). The mixture was stirred at room temperature for 1 h, diluted further with 0.1 M TEAB (10 mL) and quickly purified by prep HPLC on 30×250 mm C18 Sunfire column, method: 0 to 2.0 min 100% A, followed by linear gradient up to 50% B over 70 min, flow rate: 25 mL/min, A=50 mM TEAB, B=acetonitrile. The target fractions were lyophilized and combined after dissolving in HPLC grade water resulting in 45-75% yield of MeSSdNTP-A-$NH_2$.

Example 78

Standard Method for Labeling with NHS Dye

MeSSdNTP-A-$NH_2$ (4.55 µmol) in 2.0 mL of HPLC grade water was diluted with $Na_2HPO_4$ (0.8 mL of 0.5 Molar aqueous soln.) in a 15 mL conical tube, and combined with NHS-activated dye (2.5 eq.) in 1.4 mL of anhydrous DMF. The reaction mixture was stirred for 8 h at room temperature, diluted with 0.1 M TEAB buffer (40 mL) and purified by prep-HPLC on 30×250 mm C18 Sunfire column, method: 0 to 5 min 100% A, followed by linear gradient up to 50% B over 70 mins, flow rate 25 mL/min). The target fractions were lyophilized and combined after dissolving in HPLC grade water to result in 50-80% yield of labeled product.

Example 79

Attachment of Cleavable Linkers and Markers to Nucleobases

Figure 71:
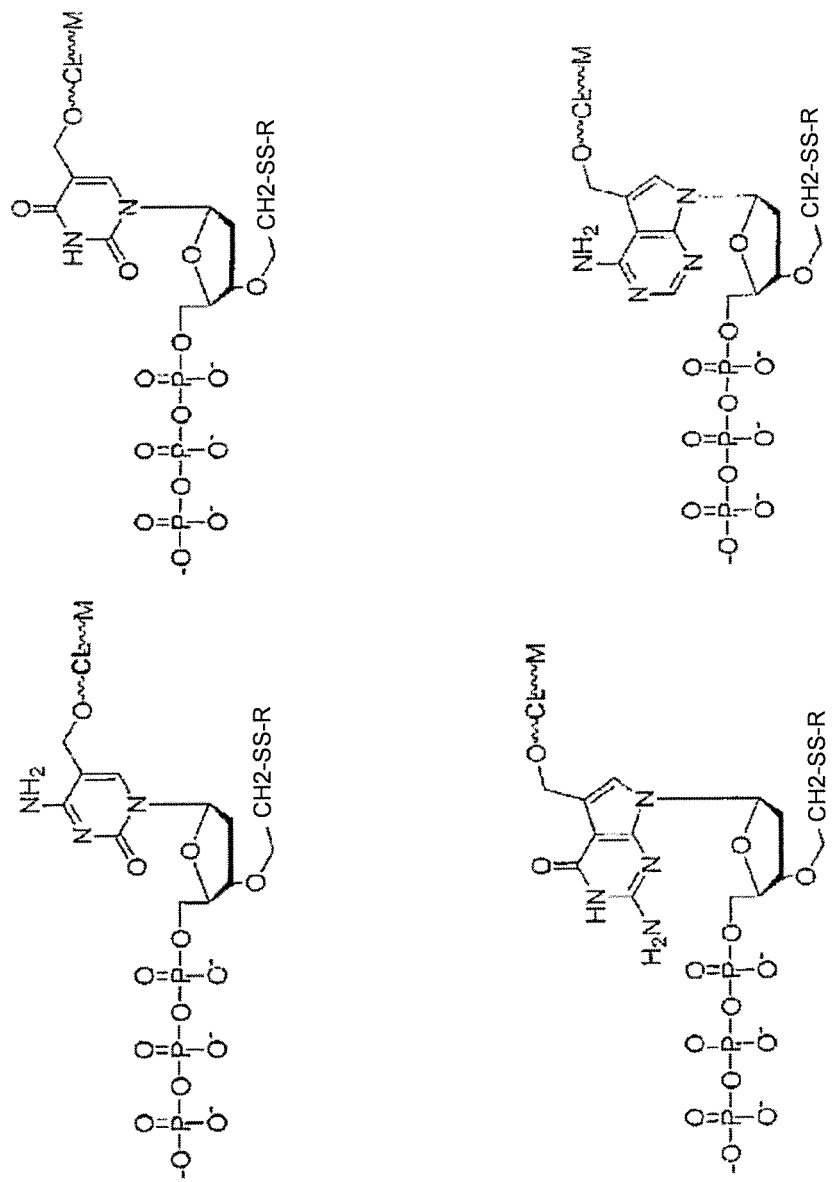
FIG. 71 shows structures of hydroxymethyl derivatives nucleobases derivatives that could be used to attach linkers and terminating groups of the present invention. R=reversibly terminating group, CL=cleavable linker of the present invention.

One of the preferred moieties used to attach cleavable linkers is propargyl based or allyl based. Other means of attaching cleavable linkers and dyes are also contemplated. In particular, attachments to the base moiety that result with little or no residual linker after dye cleavage are particularly preferred. Attachments to the base that result with residual linkers after cleavage that do not carry charge are also preferred. These features are important to ensure that the nucleotides are incorporated in the efficient manner by the enzyme into growing strand of nucleic acid after the cleavage of the label/dye. One particular embodiment contemplated by the present invention comprises the use of hydroxymethyl modified base moieties to attach cleavable dyes. Examples of such compounds are shown in FIG. 71. FIG. 72 shows the structures of hydroxymethyl derivatives after cleavage of the dye and the 3'-O protective group.

Example 80

Cleavage of Cleavable Linkers and 3'-O Protective Groups

Figure 73:
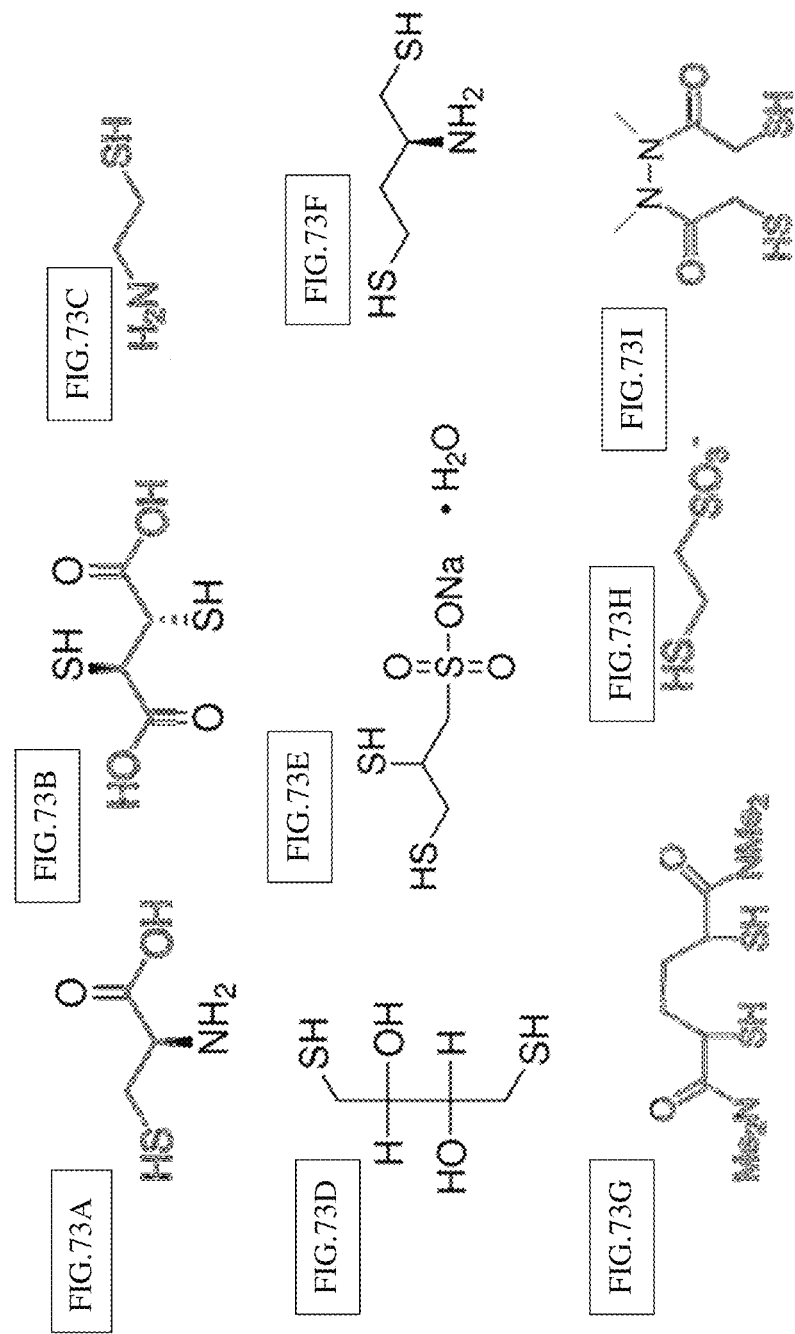
FIG. 73A-I shows examples of compounds carrying thiol, function that could be used to perform cleavage of dithio-based linkers and terminating groups of the present invention: 73A) cysteamine, 73B)—dithio-succinic acid, 73C)—cysteamine, 73D)—dithiothreitol, 73E)—2,3-Dimercapto-1-propanesulfonic acid sodium salt, 73F)—dithiobutylamine, 73G)—meso-2,5-dimercapto-N,N,N',N'-tetramethyladipamide, 73H) 2-mercaptoethane sulfonate, 73I)—N,N'-dimethyl, N,N'-bis(mercaptoacetyl)-hydrazine.

A variety of cleaving agents can be used to cleave the linkers and protective groups of the present invention. For example, a variety of thiol carrying compounds can be used as described in ("Thiol-Disulfide Interchange", Singh, R., and Whitesides, G. M., Sulfur-Containing Functional Groups; Supplement S, Patai, S., Eds., J. Wiley and Sons, Ltd., 1993. p 633-658,) [15]. In particular compounds with reduced thiol groups pKas can be used to achieve fats and efficient cleavage yields, for example dithiobutylamine, DTBA (Lukesh et. al., J. Am. Chem. Soc., 2012, 134 (9), pp 4057-4059 [16]). Examples of thiol bearing compounds that can be used to perform cleavage of the current invention are shown in FIG. 73A-1.

Figure 74:
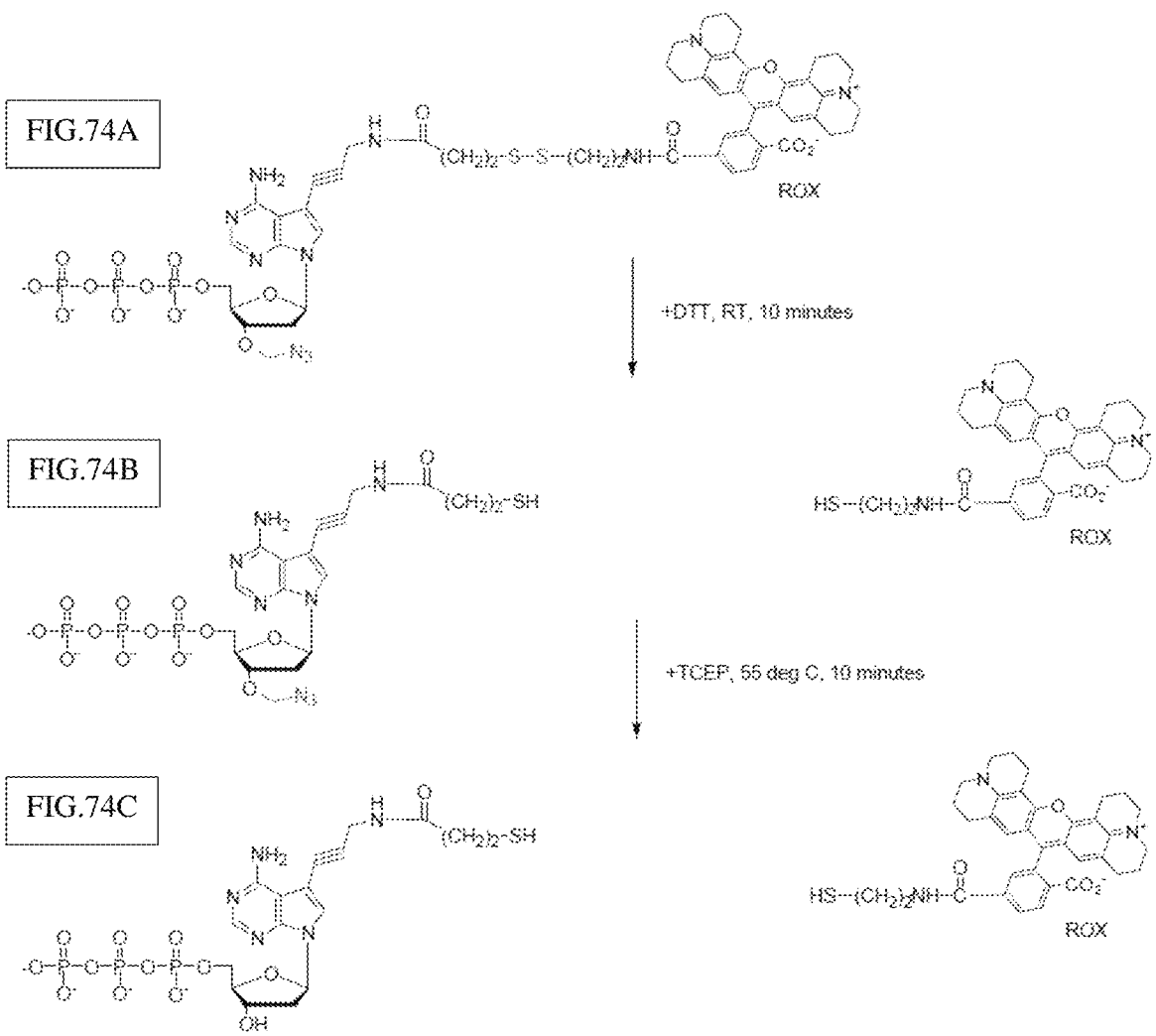
FIG. 74A-C shows an example of selective and stepwise cleavage of linker and 3'-protective group—chemical structures and reaction scheme.
Figure 75:
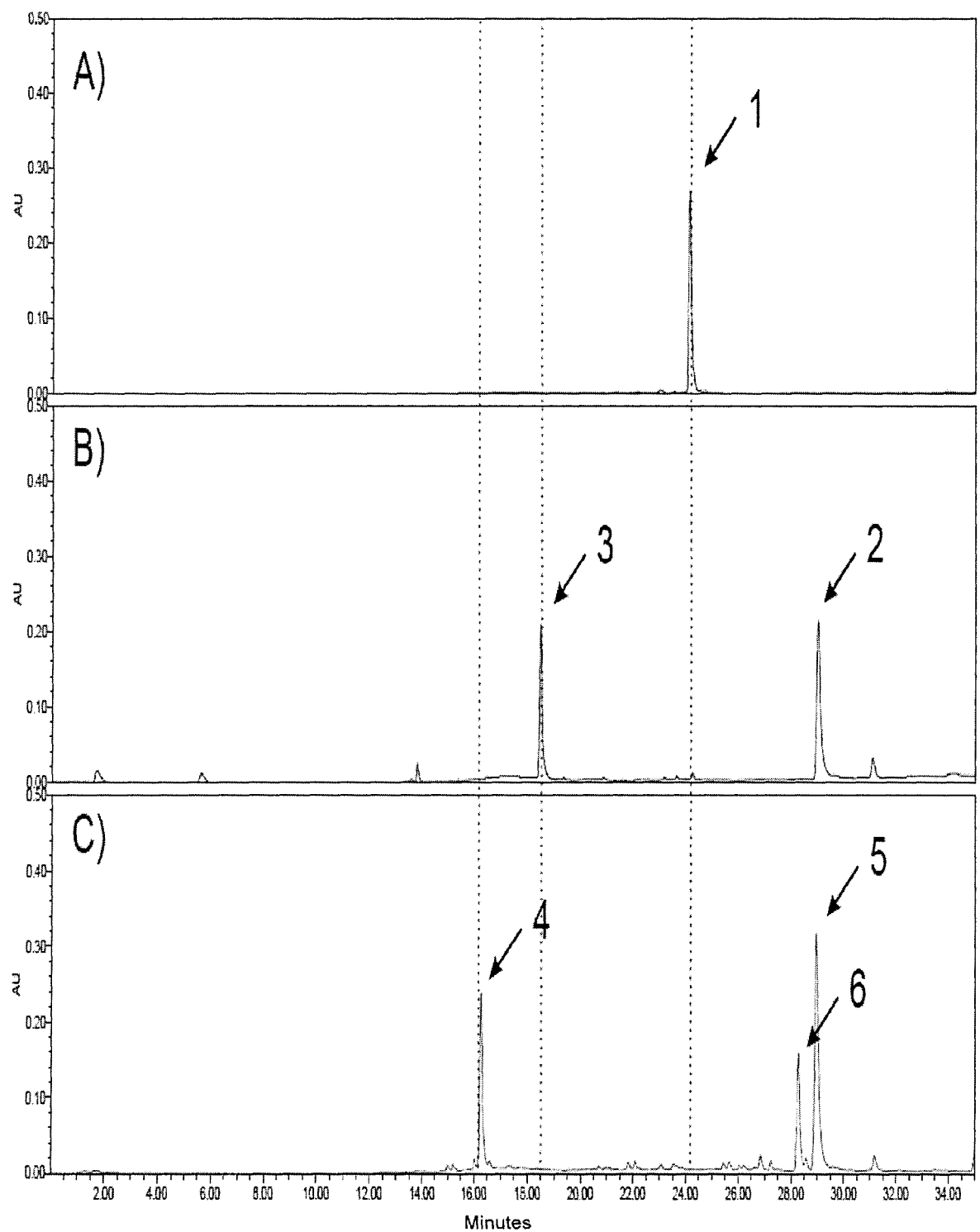
FIG. 75A-C shows an example of selective and stepwise cleavage of linker—chromatograms associated with each step of the cleavage.
Figure 76:
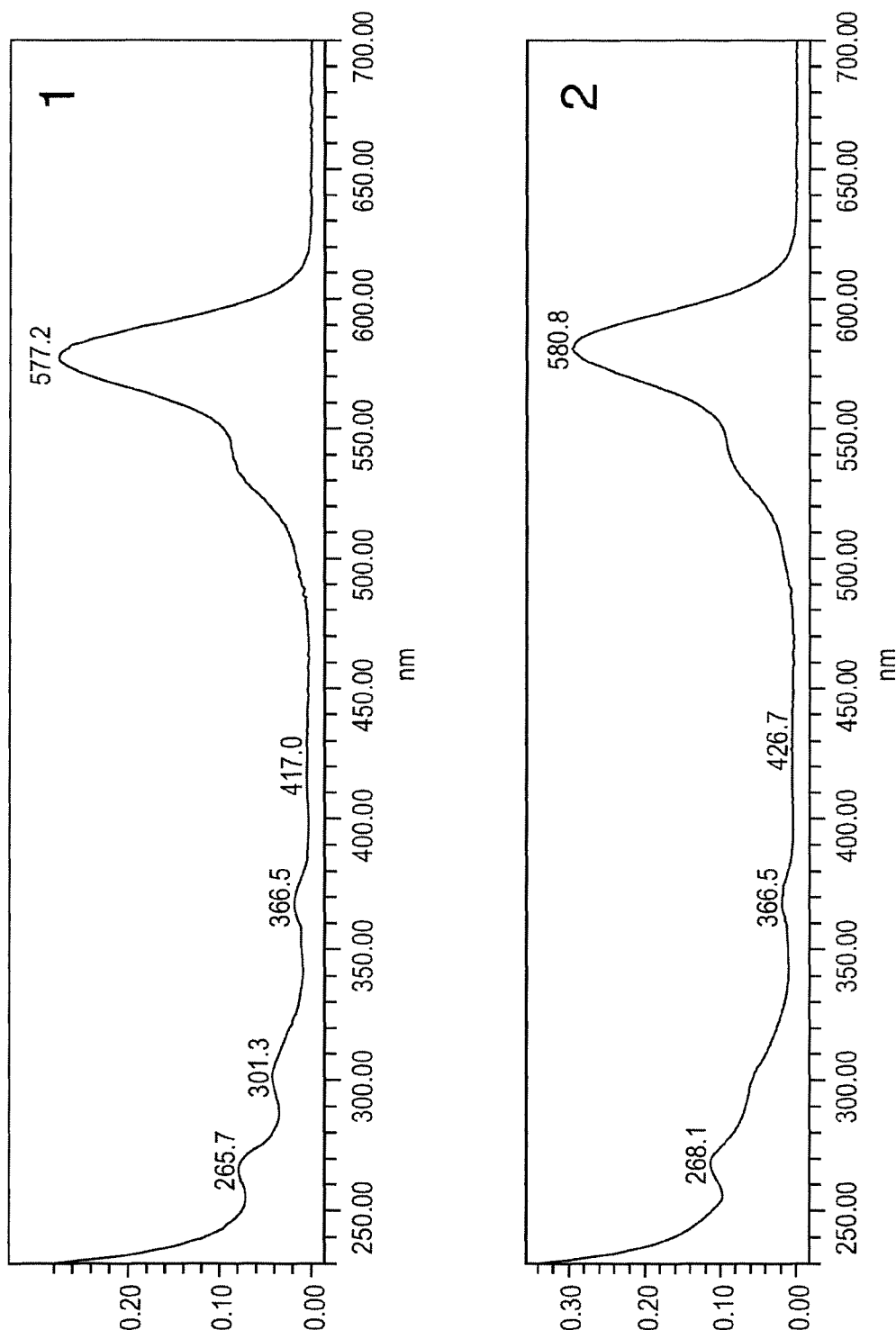
FIG. 76 shows an example of selective and stepwise cleavage of linker—absorption spectar extracted from peaks corresponding to all steps of selective cleavage reactions.
Figure 76:
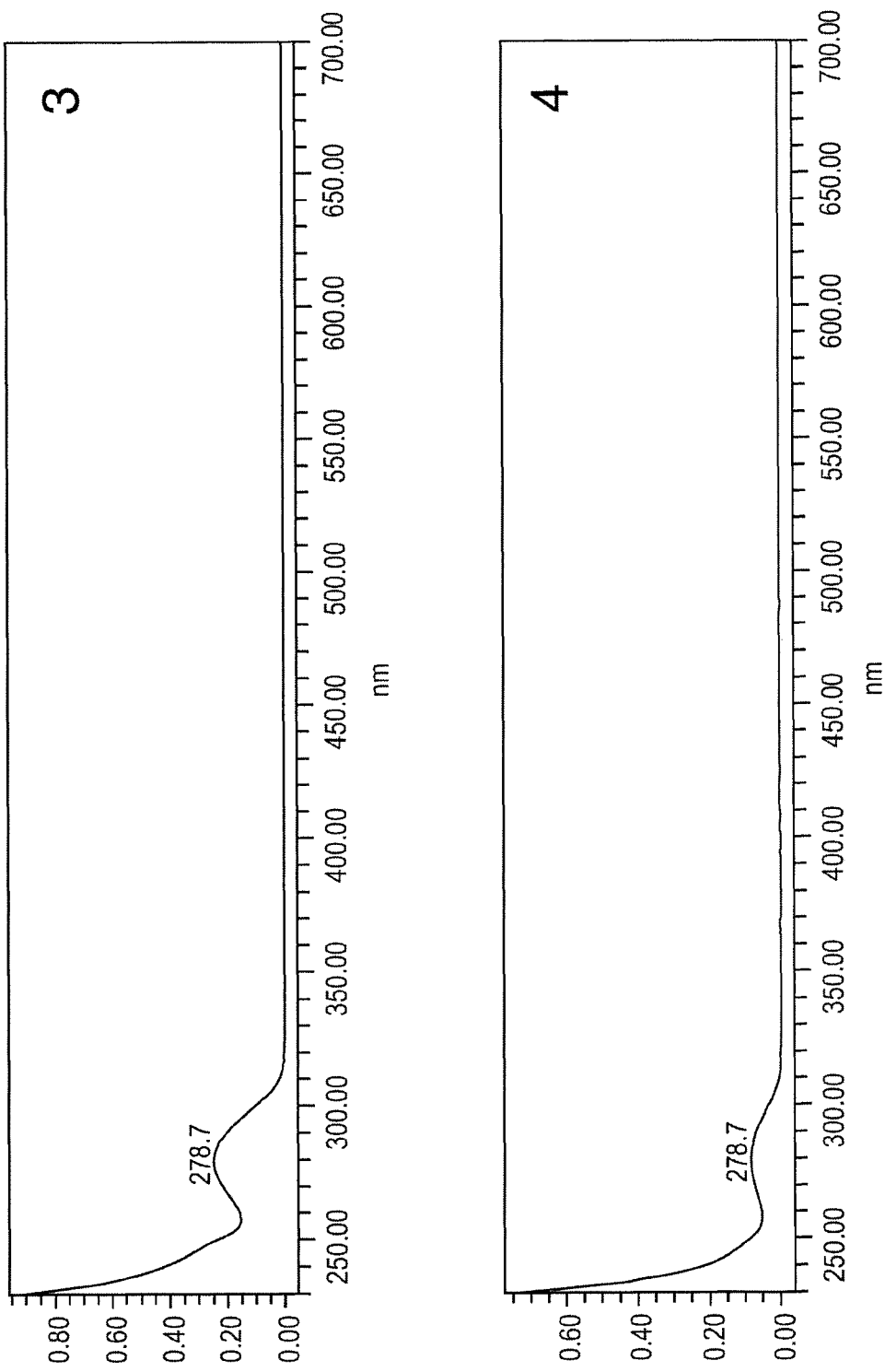
Figure 76:
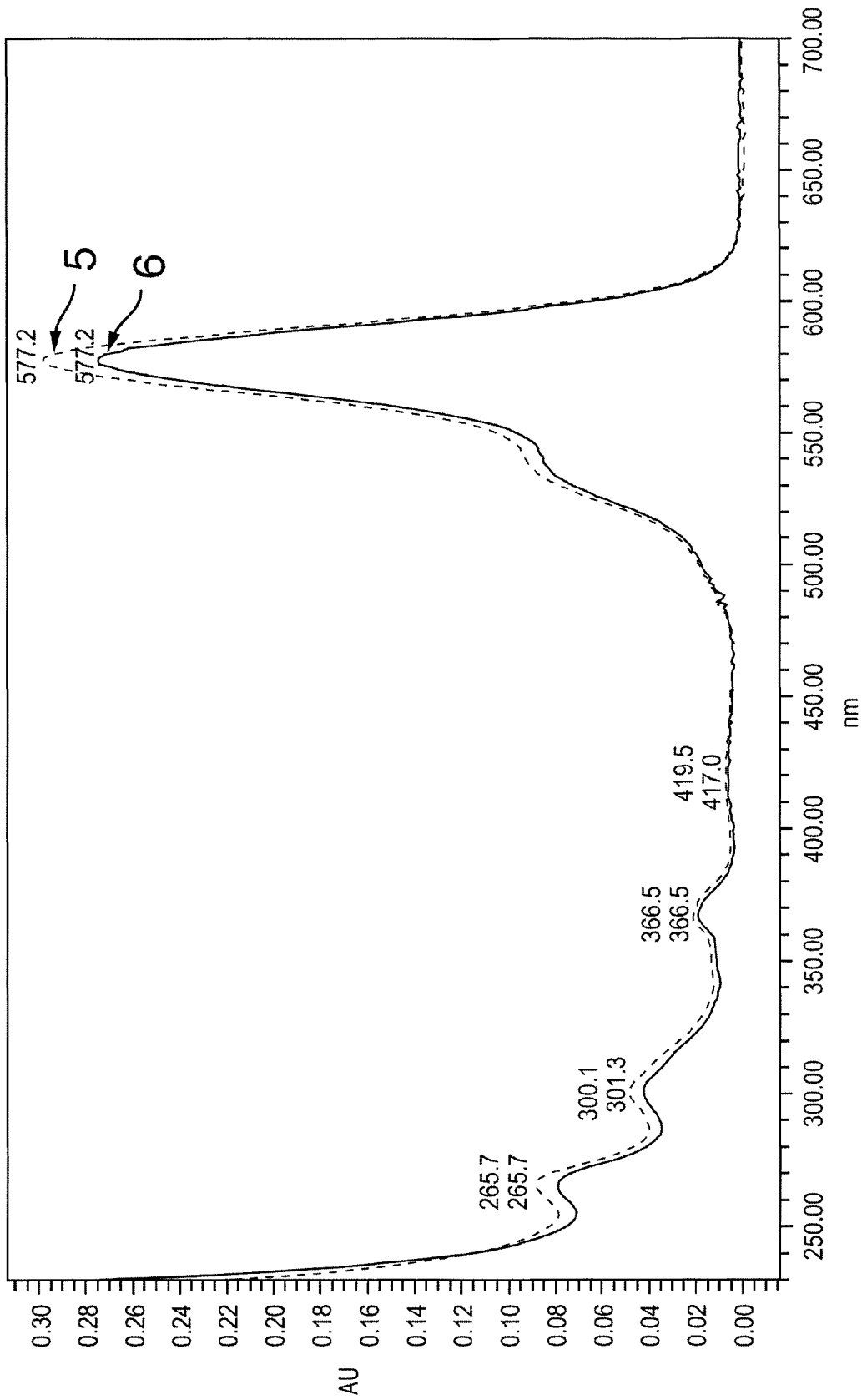

Another class of compounds that are suitable for cleaving the dithio terminating groups and linkers of the present invention are phosphines (Harpp et al., J. Am. Chem. Soc. 1968 90 (15) 4181-4182 [12], Burns et al., J. Org. Chem. 1991, 56, 2648-2650 [13], Getz et al., Analytical Biochemistry 273, 73-80 (1999) [14]). Examples of phosphines useful to cleave dithio based protective groups and linkers of the present invention include: triphenylphosphine, tributylphosphine, tris-hydroxymethyl-phosphine (THMP), tris-hydroxypropyl-phosphine (THPP), tris-carboethoxy-phosphine (TCEP). In certain cases it may be desired to be able to selectively cleave either the linker or the 3'-protective group selectively. This can be achieved by designing protective group and linker as well as selection of cleavage reagents. For example, a combination of 3'-azidomethyl ether protecting group and disulfide linker bearing nucleotide can be used for this purpose. In this case, selective cleavage of the disulfide bridge can be accomplished by using thiol based cleaving reagent and removal of 3'-azidomethyl ether protecting groups can be achieved by using phosphine such as TCEP. Example of such procedure is illustrated in FIG. 74A-C, FIGS. 75A-C, and FIG. 76. FIG. 74A-C shows schemes of chemical reactions taking place and structures of the compounds formed; FIG. 75 A-C shows HPLC chromatograms collected at each stage and FIG. 76 absorption spectra extracted from each peak. Step A) Labeled, 3'-O-protected nucleotide shows one peak (1) and absorption at both nucleotide (280 nm; note the max for the propargyl cpds is shifted towards 280-290 nm) and the dye (575 nm). Step B) Treatment with DTT produces peak 2 with absorption peak of the dye (575 nm) and migrating slower (more hydrophobic) and peak 3 with (278 nm) absorption and faster migration due to more hydrophilic character. Step C) Additional treatment with TCEP produces peak 4 with absorption max at 278 and without the dye at even lower retention time consistent with the loss of the 3'-OH protective group. The cleaved dye splits into additional peak (5, 6) but both peaks have identical absorption.

Figure 77:
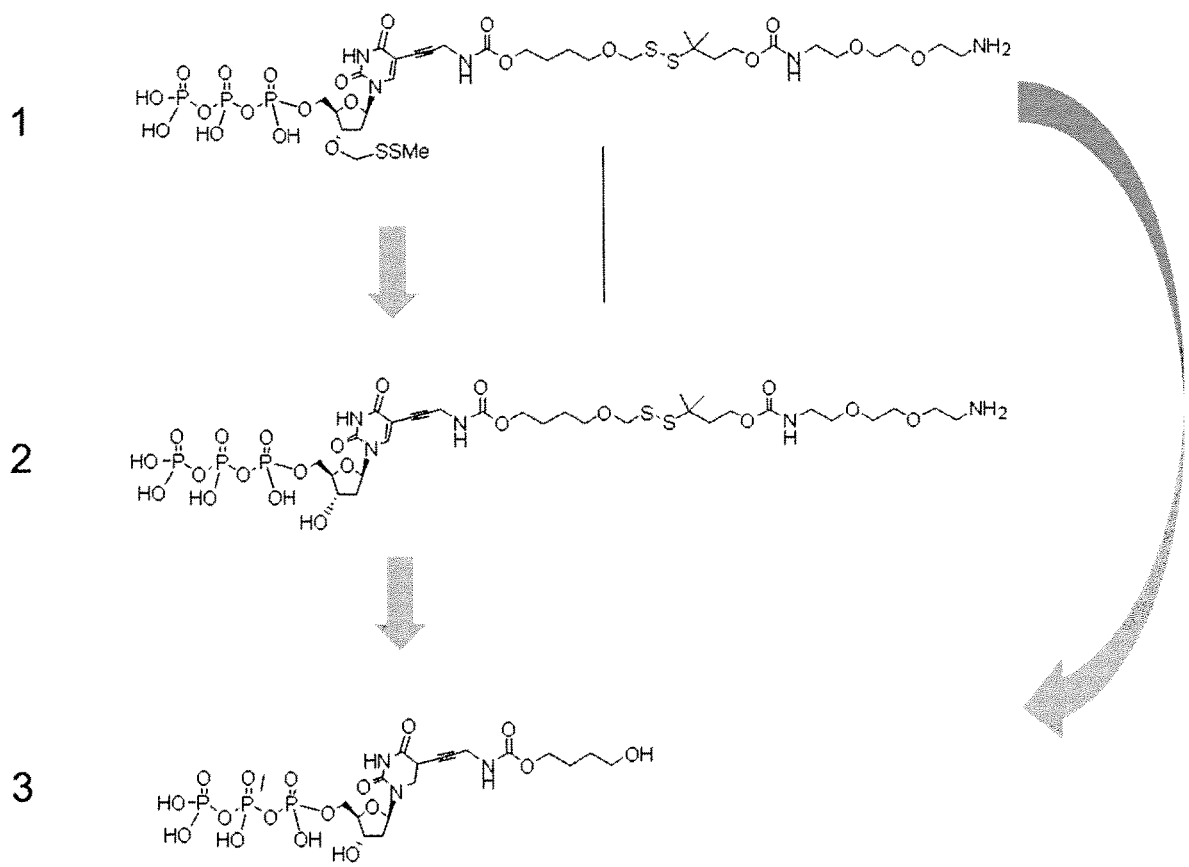
FIG. 77 shows cleavage reaction scheme for nucleotide bearing dithio protecting group on the 3' and ditho based linker.
Figure 78:
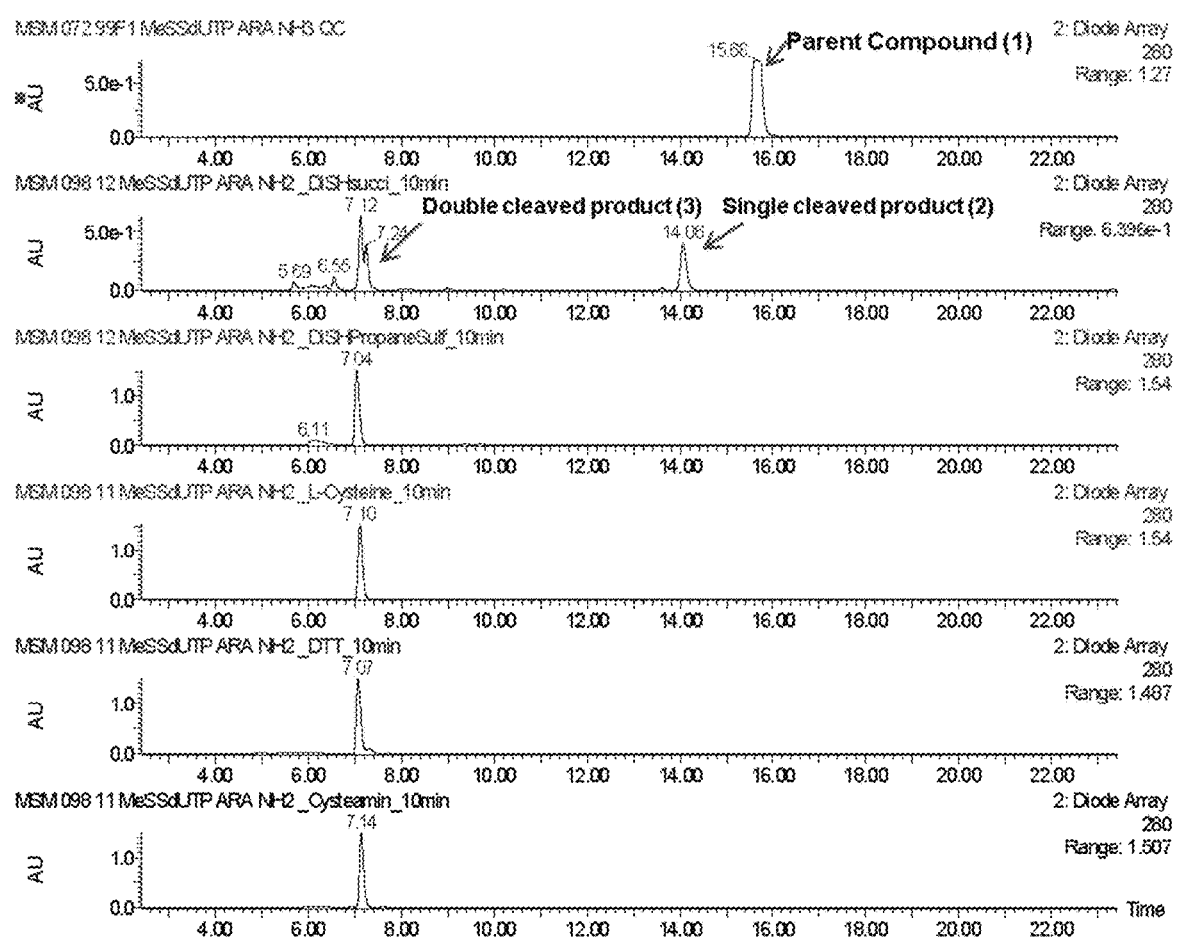
FIG. 78A shows chromatograms of starting material and cleavage reaction mixtures analyzed by RP-HPLC after 10 minutes of incubation with cleave reagents: dithiosuccinic acid, L-cysteine, dithiothreitol (DTT) and cysteamine.
FIG. 78B shows compositions of reaction mixtures as analyzed by RP-HPLC.

Another example of cleavage is shown in FIG. 77 and FIG. 78A-B. FIG. 77 shows scheme for cleavage reaction using nucleotide carrying dithio based protective group on the 3' end and dithio based linker. As this figure shows the cleavage reaction could be performed as one step or 2 step process. FIG. 78A-B shows results of cleavage experiments performed using variety of cleavage agents: dithiosuccinic acid, L-cysteine, DTT and cysteamine. FIG. 78 (A) shows RP-HPLC chromatograms generated for starting material and reaction mixtures after incubation with cleavage agents dithiosuccinic acid, L-cysteine, DTT and cysteamine. FIG. 78 (B) shows identified compositions of reaction mixtures indicating full cleavage of both linker and the 3'-protective groups in case of L-cysteine, DTT and cysteamine, and selective cleavage of 3'-O-protective group in case of dithiosuccinic acid. This indicates that selectivity can be achieved by choosing structures of linker, protecting group and the nature of cleaving agent (i.e., with varying pKa of the SH groups and degree of steric hindrance). In addition to these a variety of suitable cleaving agents can be used such as Bis(2-mercaptoethyl)sulfone (BMS) and N,N'-dimethyl-N,N'-bis(mercaptoacetyl)hydrazine (DMH) (Singh et al., Bioorg. Chem., 22, 109-115 (1994) [17]. Reactions can be further catalyzed by inclusion of selenols (Singh et al. Anal Biochem. 1995 Nov. 20; 232(1):86-91 [18]). Borohydrides, such as sodium borohydrides can also be used for this purpose (Stahl et al., Anal. Chem., 1957, 29 (1), pp 154-155 [19]) as well as ascorbic acid (Nardai et al., J. Biol. Chem. 276, 8825-8828 (2001) [20]). In addition, enzymatic methods for cleavage of disulfide bonds are also well known such as disulfide and thioreductase and can be used with compounds of the present invention (Holmgren et. al., Methods in Enzymology, Volume 252, 1995, Pages 199-208 [21]).

Example 81

Scavengers

Accordingly to the cleave agent used one skilled in the art needs to choose a scavenger agent which will remove excess of cleave agent after cleavage reaction is completed. For example, for thiol bearing cleave agents, a scavenger capable of reacting with free SH group can be used. For example, alkylating agents such as iodoacetamide or maleimide derivatives can be used (U.S. Pat. No. 8,623,598 [47], herein incorporated by reference). For borohydrides, one skilled in the art could use ketone bearing compounds, for example levulinic acid or similar compound. Finally, one could also use oxidizing reagent to oxidize excess cleave agent to non-reactive species, for example periodate (Molecules 2007, 12(3), 694-702 [48]).

Example 82

Modular Synthesis

Figure 13:
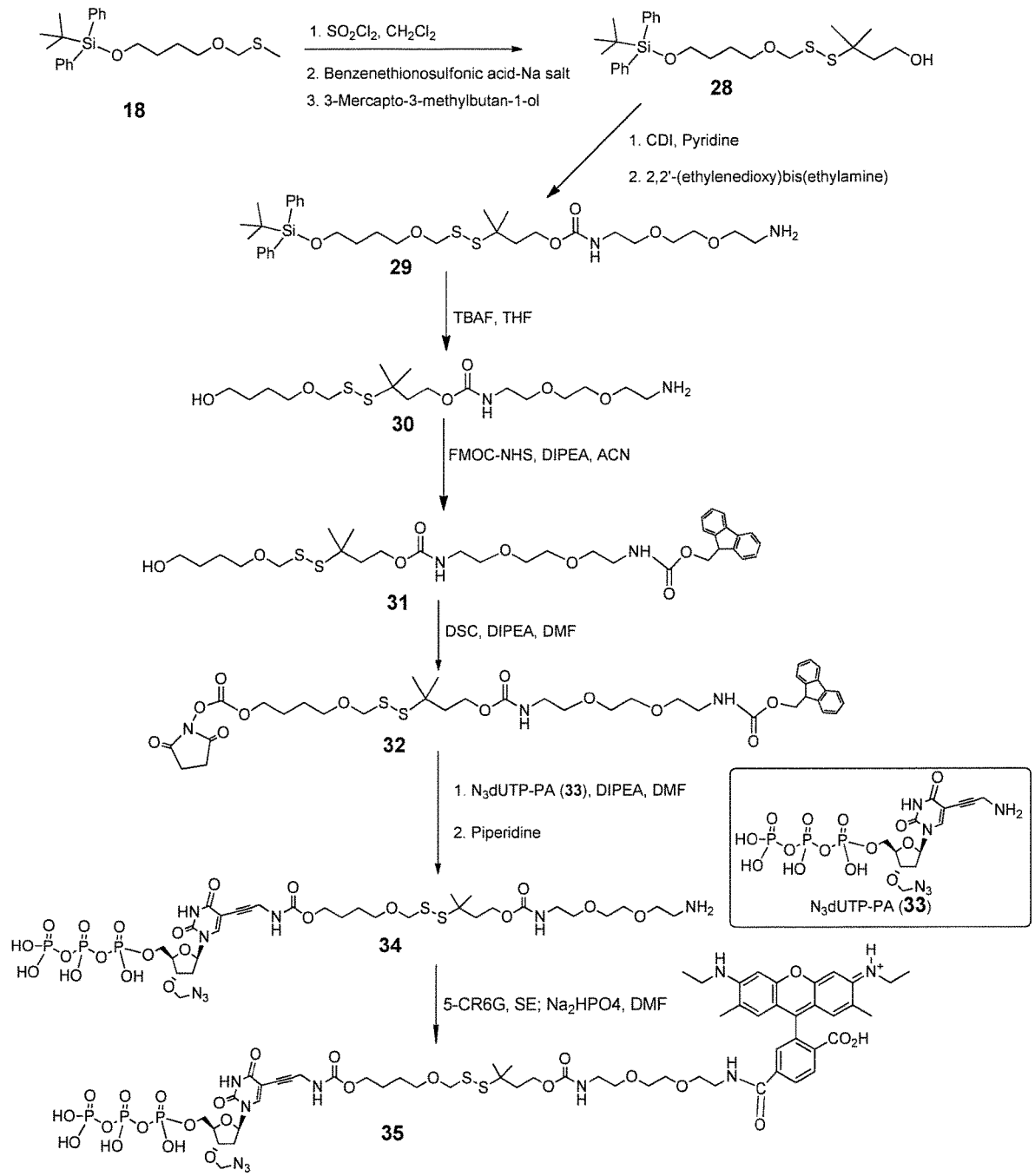
FIG. 13 shows the synthesis of a cleavable linker, where the disulfide is flanked by gem-dimethyl groups and attached to a flexible ethylene glycol linker (PEG). The linker is attached to the PA-nucleotide via carbamate group (—NH—C(=O)O—). The resulting nucleotide analogue in such case can be as in compound 35 (dUTP analogue).

Labeled nucleotides of the present invention require several steps of synthesis and involve linking variety of dyes to different bases. It is desirable to be able to perform linker and dye attachment in a modular fashion rather than step by step process. The modular approach involves pre-building of the linker moiety with protecting group on one end and activated group on the other. Such pre-built linker can then be used to couple to propargylamine nucleotide, deprotect the masked amine group and then couple the activated dye. This has the advantage of fewer steps and higher yield as compare to step-by-step synthesis. For example, Compound 32 in FIG. 13 is an example of preactivated linker comprising cleavable functionality, with activated active group (disuccinimidyl carbonate) and masked/protected amine (Fmoc). After coupling to free amine on propargylamine nucleotide the protective group can be conveniently removed for example by treatment with base (aq. Ammonia, piperidine) and can be coupled to activated (NHS) dye molecule.

Example 83

Linkers of the present invention were tested to measure their hydrophobicity. The log P value of a compound, which is the logarithm of its partition coefficient between n-octanol and water $\log(c_{external}/c_{water})$ is a well-established measure of the compound's hydrophilicity (or lack thereof) [49]. Low hydrophilicities and therefore high log P values cause poor absorption or permeation. In this case, the log P value was calculated using predicitive software, the table below shows the results, indicating that the linkers (such as those in FIG. 25) are hydrophobic linkers, while some commercially used linkers are hydrophilic.

| Linker | Molecular Formula | LogP | | | |
|---|---|---|---|---|---|
| | | Osiris* | ChemDraw | Molinsp. ** | MarvinSketch |
| Legacy | C8H16N2O2S2 | 0.60 | 0.49 | −0.14 | −0.76 |
| New | C22H43N3O8S2 | 2.57 | 2.09 | 1.30 | 0.71 |
| ILMN PEG11 | C43H74N6O18 | −1.80 | −1.80 | −2.37 | −1.30 |
| ILMN PEG23 | C63H114N6O28 | −2.74 | −3.60 | −4.34 | −1.77 |

Example 84

Figure 85:
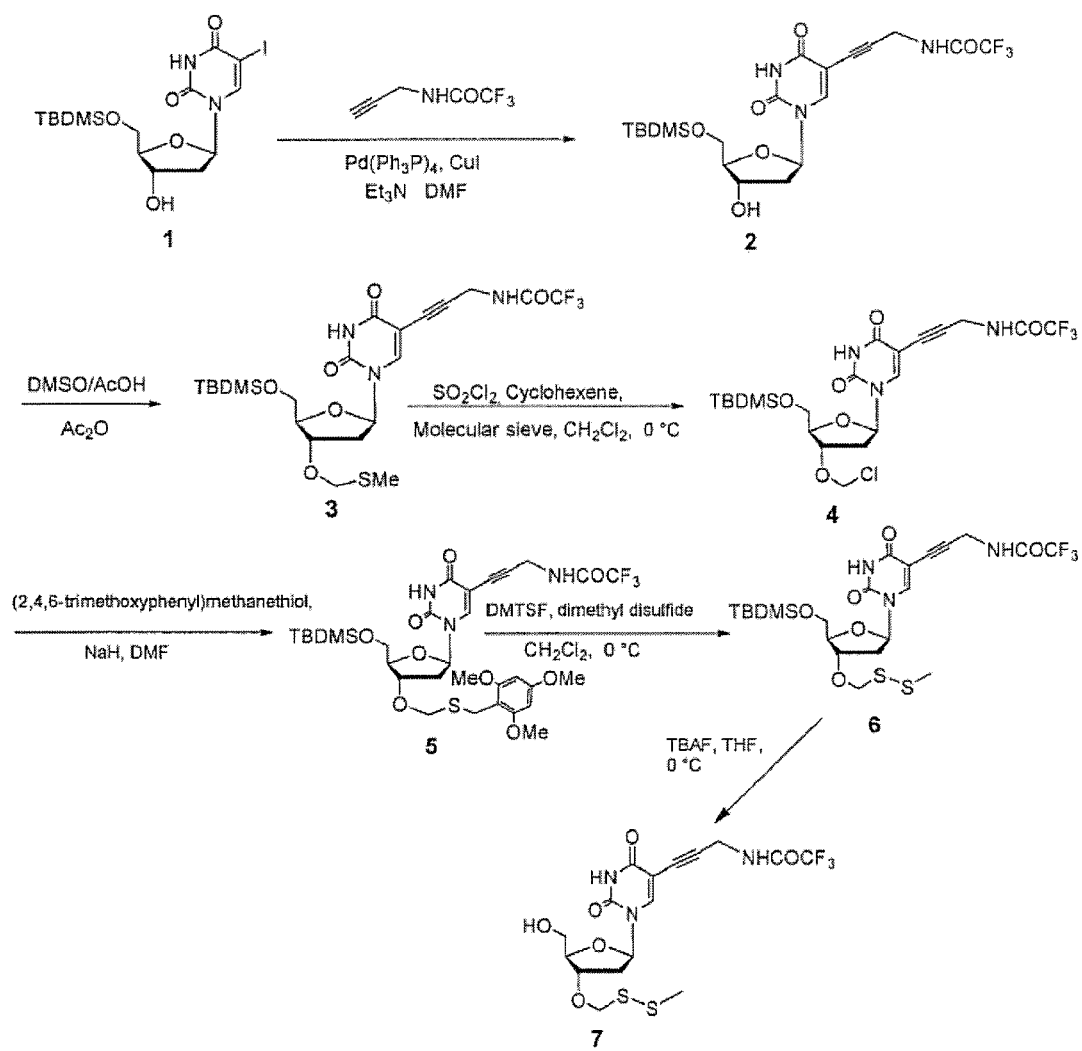
FIG. 85 presents one embodiment to synthesize 3'-O-(methylinethylenedisulfide) 5-(N-triflouroacetyl-aminopropargyl)-dU ((MeSSdU-PA(COCF3), 7) in accordance with Example 84.

This example shows the synthesis of 3'-0-(methylmethylenedisulfide) 5-(N-triflouroacetyl-aminopropargyl)-dU ((MeSSdU-PA(COCF3), 7). See, FIG. 85.

A. Synthesis of 5'-0-(tert-hu0,1dimethylsilyl)-5-(N-trifluoroacetyl-aminopropargyl)-2'-deoxyuridine (2)

5'-O-(tert-butyldimethylsilyl)-5-iodo-2'-deoxyuridine (1, 25.00 g, 53.37 mmol) was dissolved in dry DMF (200 mL) and treated with tetrakis(triphenylphosphine)palladium (0) (6.16 g, 5.27 mmol) and CuI (2.316 g, 12.16 mmol) at room temperature for 10 minutes under argon atmosphere. Then N-trifluoroacetyl-propargylamine (23.99 g, 157.8 mmol) and Et3N (14.7 mL, 105.5 mmol) were added sequentially and stirred for 3.0 h at room temperature. Solvent was then removed by rotary evaporation. The resulting crude product was dissolved in 500 mL EtOAc and transferred into a separating funnel. The organic part was then washed with saturated NaHCO$_3$(2×400 mL) and saturated NaCl (2×400 mL) solutions, respectively.

The EtOAc part was then dried over anhydrous Na2SO4. After filtrating off the Na2SO4 salt, the filtrate ethyl acetate part was concentrated using a rotary evaporator. It was then purified by a silica gel Flash chromatography (1:1 Hex: EtOAc to 2:3 Hex:EtOAc, 200 g, 15u HP puriflash column, 3× injection) bonding to 3×40 g silica gel resulting in 21.994 g of 2 (83.88% yield). HR-MS: Obs 492.1773, calcd for C20H29F3N3O6Si [M+11]+492.1699. 1H-NMR in DMF-d7: 6H 11.65 (brs, 1H, NH), 10.15 (brs, 1H, NH), 8.15 (brs, 1H), 6.37 (t, J=5.99 Hz), 5.42 (m, 1H), 4.41 (m, 1H), 4.37 (brs, 2H, for NH—CH2 of propargylamine group), 4.00 (m, 1H), 3.84-3.97 (m, 2H), 2.30 (m, 1H), 2.20 (m, 1H), 0.97 (s, 9H) and 0.19 (s, 6H) ppm. B.

Synthesis of 5'-0-(tert-butyldimerthylsilyl)-3'-0-(inethylthioinethyl)-5-(N-trifluoroacetylaminopropargyl)-2'-deoxyuridine (3)

Compound 2 (21.99 g, 44.77 mmol) obtained in the earlier step was dissolved in DMSO (90 mL) in a 1000 mL round bottom flask. It was then added sequentially with AcOH (40 mL) and acetic anhydride (132 mL) and stirred for 48 hours at room temperature. The reaction mixture was neutralized by slowly saturated K2CO3 until the evolution of CO2 gas was ceased. The mixture was then transferred into a separating funnel and further extracted (2×500 mL CH2Cl2). The combined organic part was then washed with saturated NaHCO$_3$(1×500 mL) and dried over Na2SO4. The organic part was purified by silica gel flash chromatography (Hex: EtOAc/7:3 to 1:1) yielding 12.38 g UtaisilfunitS4b§ 0.03/ n884alculated for C22H33F3N3O6SSi (M+H)+552.17. 1 H-NMR of compound 3 (DMSO-d6): 6H 11.69 (s, 1H), 10.01 (s, 1H), 7.93 (s, 1H), 6.07 (m, 1H), 4.69 (m, 2H), 4.38 (m, 1H), 4.19 (m, 2H), 4.03 (m, 1H), 3.75 (m, 2H), 2.34 (m, 1H), 2.14 (m, 1H), 2.07 (s, 3H), 0.86 (s, 9H) and 0.08 (s, 6H) ppm.

C. Synthesis of 3'-0-(TMPMT)-5'-0-(tert-butyldimethylsilyl)-S—(N-trifluoroacetyl-aminopropargyl)-2'-deoxyuridine (5)

A round bottom flask was charged with compound 3 (3.120 g, 5.66 mmol), 30.0 mL dry CH2Cl2, 3-A molecular sieves (5.0 g) and cyclohexene (0.70 mL, 6.9 mmol). The reaction flask was then placed on an ice-bath. To this, SO2Cl2 (8.5 mL, 1M in CH2Cl2, 1.5 eq) was added slowly via a syringe, and stirred for 1 hour at 0° C. Next, an extra of 4.0 mL of 1M SO2Cl2 was added and stirred an additional 40 minutes to ensure complete conversion to compound 4. The volatiles were removed under vacuum while keeping the temperature close to 10° C. The resulting solid was re-suspended in 20 mL of dry DMF and kept under a nitrogen atmosphere.

In a separate flask, (2,4,6-trimethoxyphenyl)methanethiol (3.0 g, 14.15 mmol) was dissolved in dry DMF (40 mL) under nitrogen atmosphere, and treated with NaH (566 mg, 60% in oil, 14.15 mM) producing a grey slurry. To this, compound 4 solution was added at once and stirred at room temperature for 2.5 hours under nitrogen atmosphere. The reaction mixture was then filtered through Celite®-S (20 g) in a funnel eluting the product with EtOAc (200 mL). The EtOAc solution was then washed with distilled water (3×200 mL). The EtOAc extract was dried over Na2SO4, concentrated by rotary evaporation, and purified by flash chromatography (column: 120 g RediSepRfGold, gradient: 7:3 Hex:EtOAc to 3:7 Hex:EtOAc). The target compound (5) was obtained as white solid (1.43 g, 35.5% yield, Rf: 0.5, Hex:EtOAc/1:1). 1H NMR (CDCl3): 8H 7.98 (m, 1H), 6.09 (m, 1H), 6.00 (m, 2H), 4.67-4.51 (m, 2H), 4.30 (m, 111), 4.22 (m, 2H), 4.00 (m, 1H), 3.80-3-60 (m, 11H), 2.31 (m, 1H), 1.83 (m, 1H), 0.80 (m, 9H) and 0.01 (m, 6H) ppm.

D. Synthesis of 3'-0-(methylmethylenedisulfide)-5'49-(tert-butyidimethylsilyl-5-(N-trifluoroacetylaminopropargyl)-2'-deoxyuridine (6)

Compound 5 (1.43 g 1.99 mmol) was dried under high vacuum with P2O5 in a desiccator overnight and dissolved in 25 mL of anhydrous CH2Cl2 in a flask equipped with a magnetic stirrer and nitrogen gas source. To this was added dimethyldisulfide (0.89 mL, 9.88 mmol), and the reaction flask was stirred on an ice-bath. Dimethyl(methylthio)sulfonium tetrafluoroborate (DMTSF, 430 mg, 2.19 mmol) was then added and stirred for 1.0 hours at 0° C. The reaction mixture was transferred to a 500 mL separatory funnel and quenched with 100 mL of 50 mM aq. solution of NaHCO$_3$, and extracted with CH2Cl2 (2×150 mL). The organic portion was dried over Na2SO4 and concentrated by rotary evaporation. The crude product was purified on a silica gel column (80 g RediSepRf gold) using gradient 8:2/Hex:EtOAc to to 3:7/Hex-EtOAc to result in 0.622 g of compound 6 (54% yield, RF=0.6, Hex:EtOAc/1:1). 1H NMR (CDCl3): 811 7.99 (brs, 1H, NH), 7.98 (s, 1H), 6.12 (m, 1H), 4.69 (m, 2H), 4.35 (m, 1H), 4.19 (m, 2H), 4.06 (m, 1H), 3.80 (m, 1H), 3.60 (m, 2H), 2.40 (m, 1H), 2.33 (s, 3H), 1.88 (m, 1H), 0.78 (m, 9H), and 0.10 (m, 6H) ppm.

E. Synthesis of 3'-O-(methylmethylenedisulfide)-5-(N-trifluoroacetyl-amino-propargyl)-2' deoxyuridine (7)

A round bottomed flask equipped with a magnetic stirrer was charged with compound 6 (0.623 g, 1.06 mmol, vacuum dried with P205 overnight) and anhydrous THE (20.0 mL) and placed on an ice-bath under a nitrogen atmosphere. TBAF (1.27 mL, 1.27 mmol, in 1 M solution) was added slowly via syringe. The reaction mixture was stirred for 1.5 hours at 0° C. Then, an extra of 0.9 mL 1M TBAF was added and stirred a total of 4 hours at ice-cold temperature. The reaction mixture was then transferred to a separatory funnel and quenched with 0.5 M NaHCO$_3$ solution (50 mL). The resulting mixture was extracted with EtOAc (2×100 mL) and dried over Na2SO4. The product 7 was obtained as a white powder after silica gel column chromatography in 63% yield (311 mg) on a 80 g RediSepRf column using gradient 7:3 to 3:7 Hex:EtOAc. 1H NMR (MeOH-d4): 611 8.16 (s, 1H), 6.06 (m, 1H), 4.79 (m, 2H), 4.69 (ni, 1H), 4.40 (m, 1H), 4.14 (m, 2H), 3.99 (m, 1H), 3.63 (m, 2H), 2.36 (m, 3H), 2.32 (m, 1H), and 2.08 (m, 1H) ppm. Further confirmed by LC-MS: M–H observed m/z 468.0.

Example 85

Figure 86:
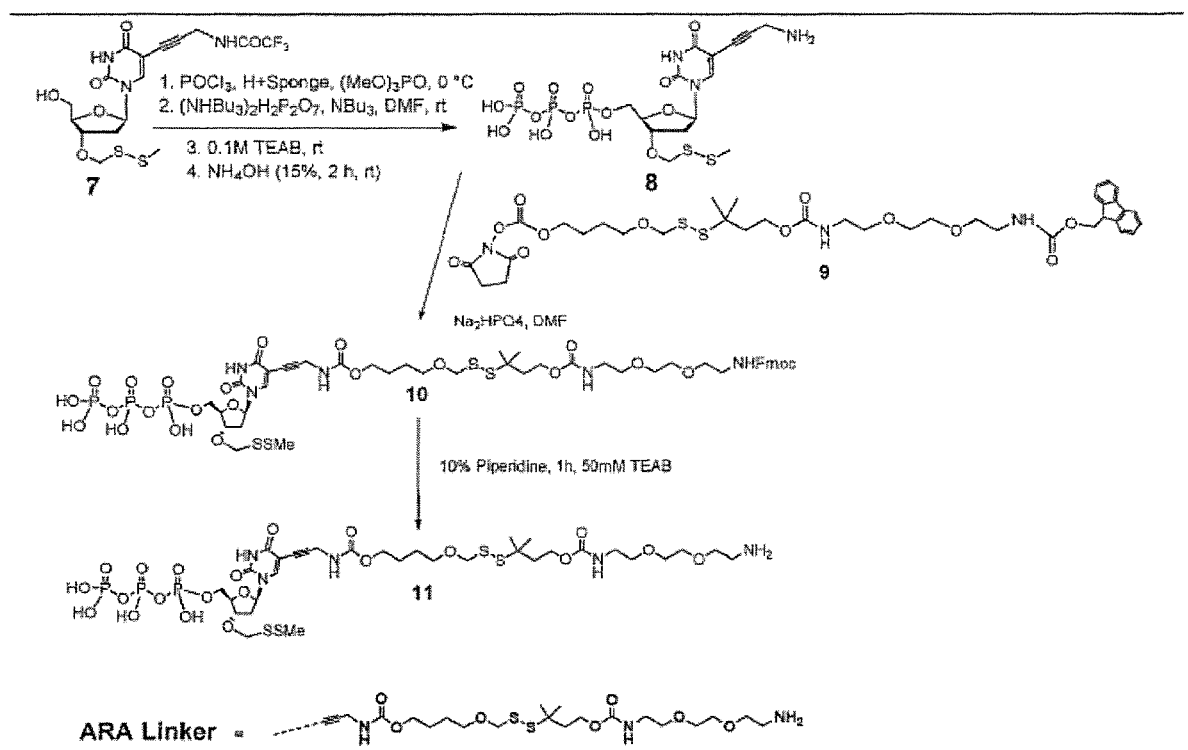
FIG. 86 presents one embodiment to synthesize 3'-O-(methylinethylenedisulfide)-5-(aminopropargyl)-2'-deoxyuridine (MeSSdUTPPA,8) in accordance with Example 85.
Figure 87A:
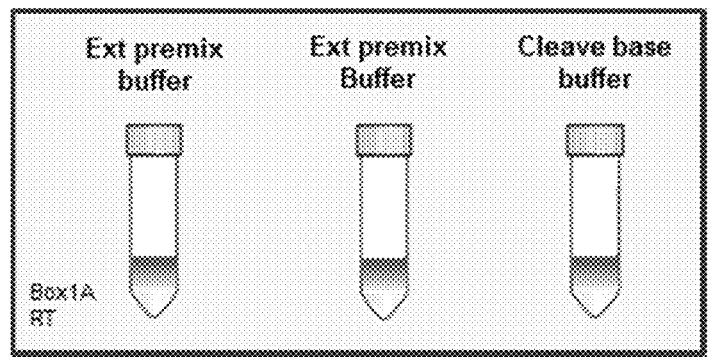
FIG. 87A-C presents a schematic of one embodiment of a kit comprising reagents as disclosed herein to perform SBS sequencing.
Figure 87B:
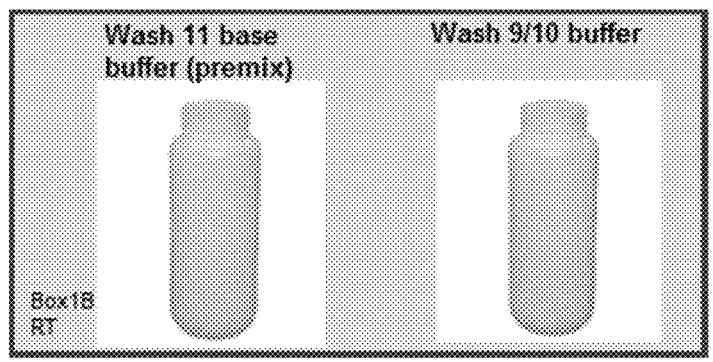
Figure 87C:
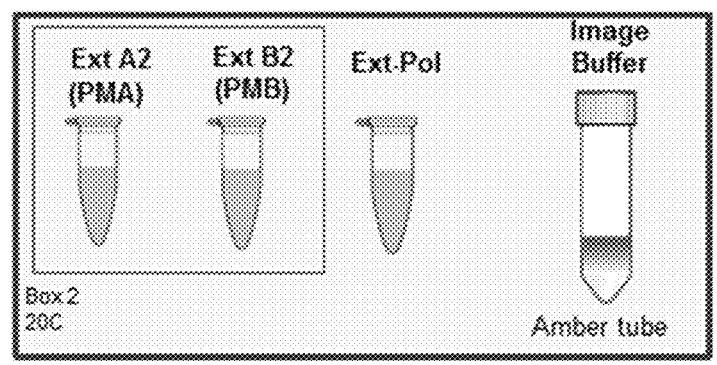
Figure 87D:
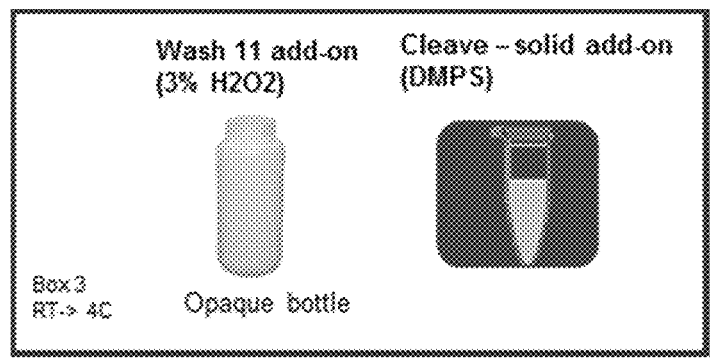
FIG. 87D: An exemplary Box 3 comprising containers of wash add-on reagents and a cleave-solid add-on reagent.

This example shows the synthesis of 3'-0-(methylethylenedisulfide)-5-(aminopropargyl)-2'-deoxyuridine (MeSSdUTPPA,8). See, FIG. 86. Vacuum-dried sample of compound 7 (155 mg, 330 nmol) and proton sponge (100 mg) were placed in a 25 mL pear-shaped flask containing a magnetic stirring bar under Ar-atmosphere. The solids were suspended in trimethylphosphate (1.4 mL) and stirred for –30 minutes at room temperature until all solids were completely dissolved. The flask was then placed in a ice-salt water bath and stirred for 10 minutes to bring the flask to sub-zero temperature (–5 to 0° C.). Then POCl3 (50 µL, 570 nmol) was added at once using a microsyringe. The mixture was then stirred at the same temperature for 1 hour. Next, a premix of pyrophosphate-Bu3N-DMF was prepared as quickly as possible in a 15 mL centrifuge tube producing a thick solution (pyrophosphate-Bu3NH+0.73 g, Bu3N 0.73 mL, dry DMF 2.6 mL). Once completely dissolved, the mixture was rapidly added to the rigorously stirring reaction mixture at once. The reaction mixture was stirred at room temperature for 15 mins. The reaction mixture was then poured into 200 mL of 0.1M TEAB buffer in a 500 mL round bottom evaporation flask. The mixture was stirred for 3 hours at room temperature. The reaction mixture was then treated with 60 mL of ammonium hydroxide (28-30% NH$_3$ content) for 1 h at room temperature. The mixture was then concentrated by rotary evaporation and purified by prep—HPLC (19×250 mm, C18 Sunfire, Waters, method: 0 to 2 min 100% A, followed by 20% B over 70 mins, flow 14 mL/min; A 50 mM TEAB, B=ACN). The target fractions (Rf=32-37 mins) were lyophilized and combined after dissolving in HPLC grade water to result in 103 nmol of MeSSdUTP-PA, 8 (58% yield). The product was confirmed by LC-MS m/z (M–H) 612.00.

Example 86

This example shows the synthesis of Synthesis of MeSSdUTP-ARA-NH2, 11:

Compound MeSSdUTP-PA (8) was aliquoted in a 15 mL centrifuge tube (2.16 mL (6.92 mM=15 µmol). It was diluted with 0.8 mL HPLC grade water and 1.5 mL of freshly prepared 0.5 M Na2HPO4 in HPLC grade water. In a separate tube, 35 mg of activated linker NHS-ARA-Fmoc (10, 44 µmol) was suspended in 3.0 mL dry DMF. This solution was was added to the MeSSdUTP-PA/Na2HPO4 solution in once and gently shaken by hand. It was then placed on shaker and allowed to react for overnight at room temperature. Next day, HPLC analysis showed quantitative conversion to conjugated product (10). It was diluted with 1.0 mL of 0.1 M TEAB buffer. To this, 0.7 mL of piperidine was added and stirred on a shaker for 1 hour at room temperature. The product was then immediately purified by prep HPLC on 30×250 mm C18 Sunfire—Waters column, method: 0 to 2.0 min 100% A, followed by 50% B over 70 min, flow rate: 25 mL/min, A=50 mM TEAB, B=acetonitrile, 1 injection only. The target fractions (Rf=46 min) were combined and lyophilized, and final product was dissolved in HPLC grade water and the concentration was determined by UV-spectrophotometry to result in 6.8 nmol of MeSSdUTPARA-N1-12, 11 (45% yield in two steps). The product was further confirmed by LR-LC-MS, observed m/z 1067.

Example 87

This example presents a general method for cleavage studies as presented herein.

A stock solution of 100 mM cleave reagent (see Table-1) was prepared in 1.0 M TE buffer (pH 8.5, Sigma # T9285) in a 15.0 mL centrifuge tube. Then an aliquot of 20 µL (2,000 nmol) of it was diluted with 76.9 uL distilled water in a 1.0 mL centrifuge tube and added with 3.07 µL of 6.5 mM MeSSdUTP-ARA-NH2 (11, 20 nmol) to obtain—100 µL of total volume (Final concentration: 20 mM cleaving agent, 0.2 mM nucleotide, 200 mM TE buffer). The mixture tube was heated at 65 degree C. on a pre-heated thermocycler by shaking gently. The mixture was immediately analyzed by LC-MS after 10 minutes. The % conversion was determined by relative peak areas of the respective peaks extracted at 280 mu wavelength.

Example 88

Figure 96:
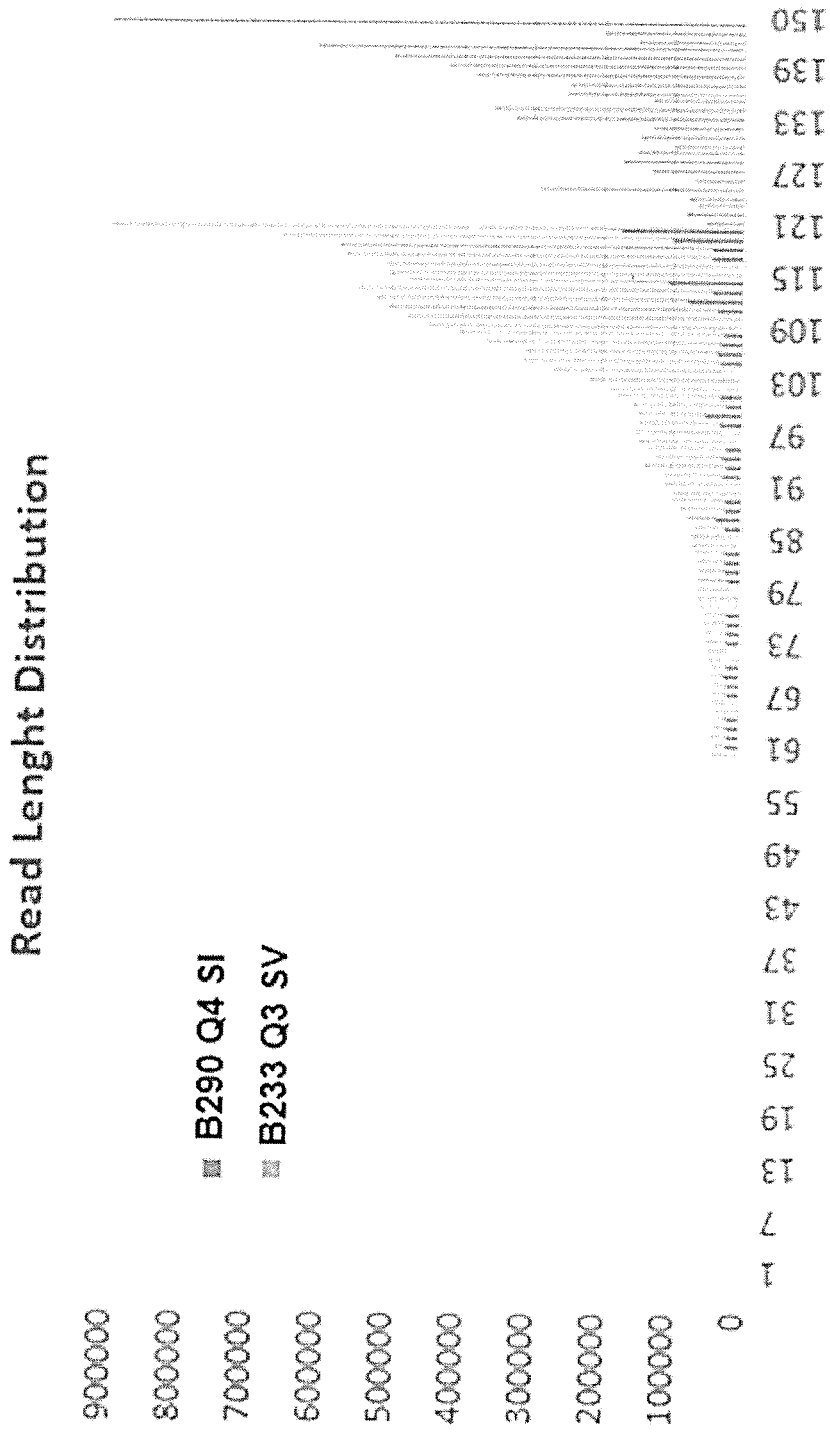
FIG. 96 is a graph showing a comparison of read length in DNA sequencing under two different conditions/configurations. In one configuration (B290), a compound is used as a sequencing additive, i.e. 5-Chloro-2-methyl-4-isothiazolin-3-one is utilized in the extend reagent for the extension reaction. In the other configuration (B233), this compound is not utilized in the extend reagent for the extension reaction. As can be seen from the chart, a significant improvement in read length is observed for the B290 configuration (157 cycles) as compared to the B233 configuration (137 cycles).
Figure 97:
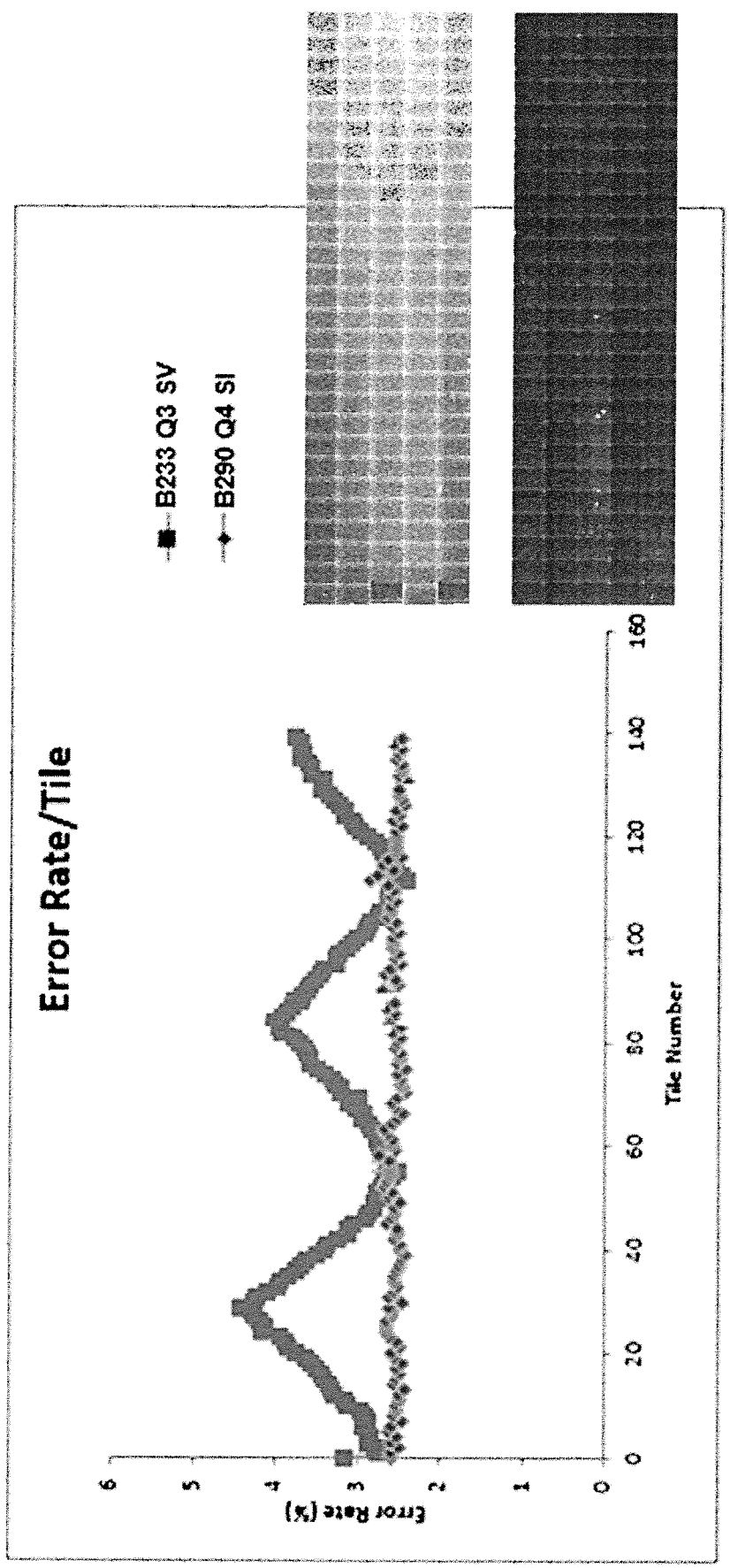
FIG. 97 is a graph showing a comparison of error rate (per tile) in DNA sequencing under two different conditions/configurations. In one configuration (B290), a compound is used as a sequencing additive, i.e. 5-Chloro-2-methyl-4-isothiazolin-3-one is utilized in the extend reagent for the extension reaction. In the other configuration (B233), this compound is not utilized in the extend reagent for the extension reaction. As can be seen from the chart, a significant improvement in read quality (reduced degradation from the inlet to the outlet region of the flow cell) is observed for the B290 configuration (157 cycles) as compared to the B233 configuration (137 cycles).
Figure 98:
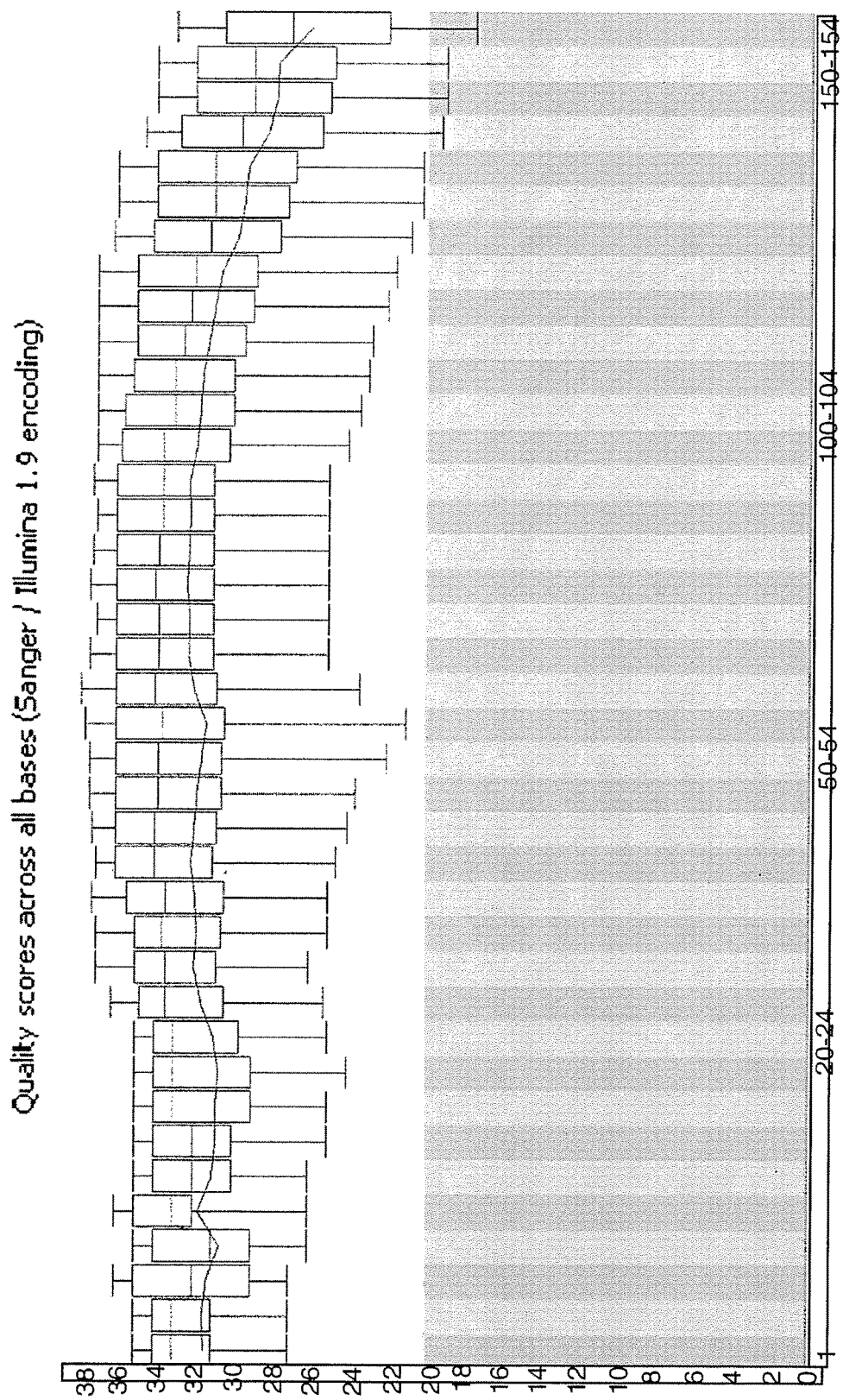
FIG. 98 is a graph showing the quality score distribution across all bases where 5-Chloro-2-methyl-4-isothiazolin-3-one is utilized in the extend reagent for the extension reaction (with Q30 reaching 70-75%).
Figure 99:
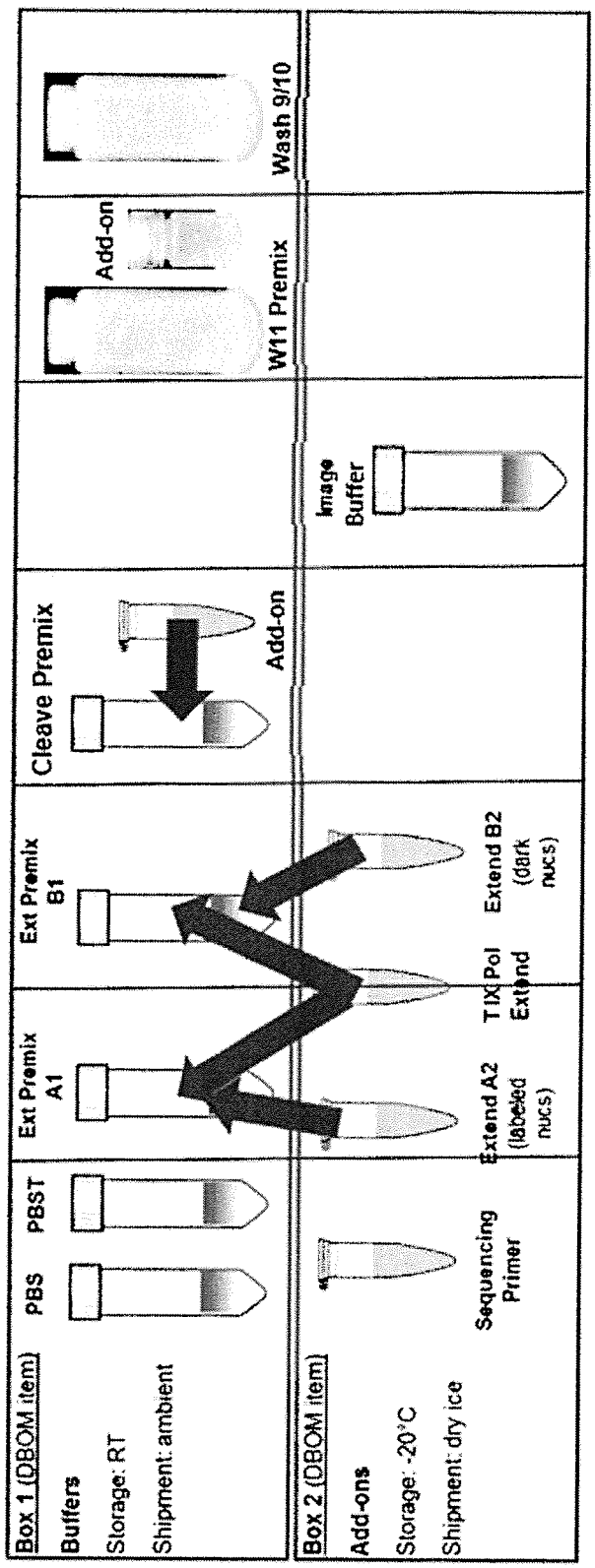
FIG. 99 presents a schematic of one embodiment of a kit (with arrows to show the work flow) comprising reagents as disclosed herein to perform SBS sequencing, and in particular, extension reactions for SBS sequencing. Box 1 comprises containers of extension premix, wash and a cleave base buffer. Box 2 comprises containers of nucleotide analogues (both labeled and unlabeled), DNA polymerase and an imaging buffer. This kit does not contain CMIT.
Figure 100:
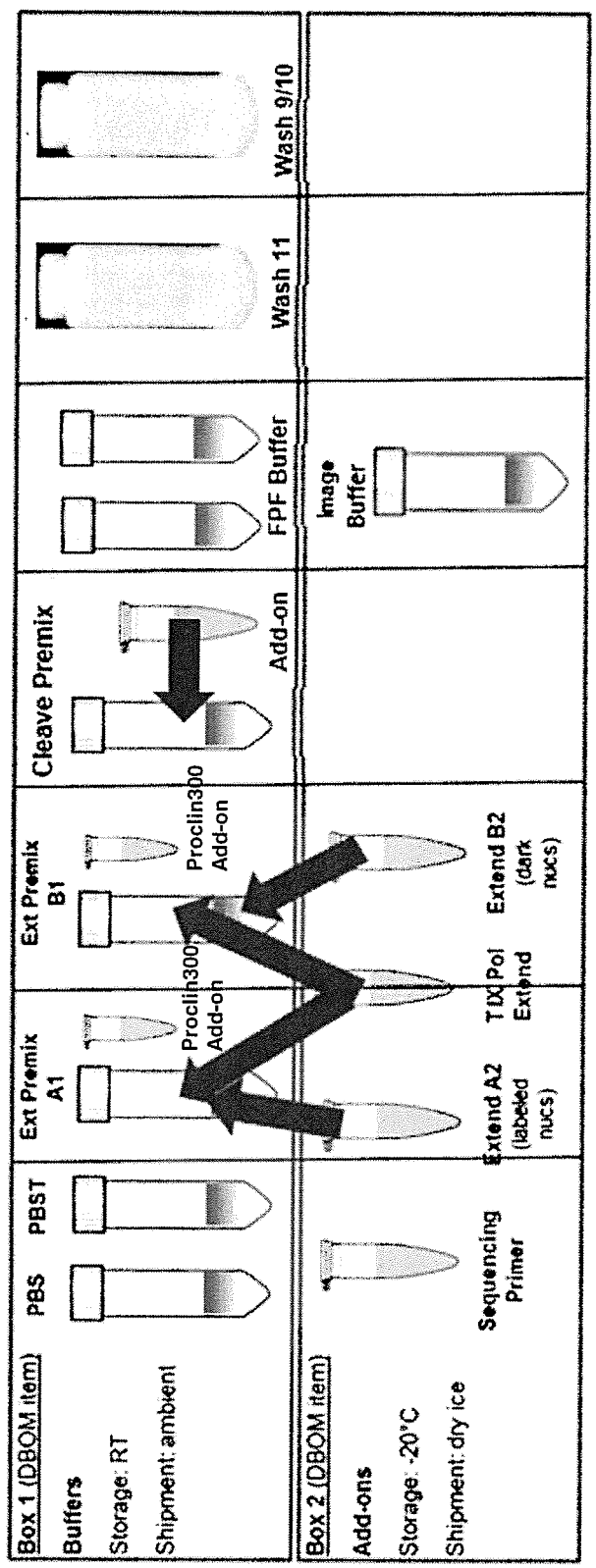
FIG. 100 presents a schematic of one embodiment of a kit (with arrows to show the work flow) comprising reagents as disclosed herein to perform SBS sequencing, and in particular, extension reactions for SBS sequencing. Box 1 comprises containers of extension premix, wash and a cleave base buffer. Box 2 comprises containers of nucleotide analogues (both labeled and unlabeled), DNA polymerase, an imaging buffer and CMIT (in the form of "Proclin") as a sequencing additive or "add-on." The arrows show the mixing of these components to make the extend reagent.

In this example, a comparison is made in DNA sequencing under two different conditions/configurations. In one configuration (B290), a compound is used as a sequencing additive, i.e. 5-Chloro-2-methyl-4-isothiazolin-3-one is utilized in the extend reagent for the extension reaction. In the other configuration (B233), this compound is not utilized in the extend reagent for the extension reaction. As can be seen from FIG. 96, a significant improvement in read length is observed for the B290 configuration (157 cycles) as compared to the B233 configuration (137 cycles). As can be seen from the FIG. 97, a significant improvement in read quality (reduced degradation from the inlet to the outlet region of the flow cell) is observed for the B290 configuration (157 cycles) as compared to the B233 configuration (137 cycles).

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Metzker, M. L. (2010) "Sequencing Technologies—the Next Generation," *Nat. Rev. Genet.* 11(1), 31-46.
2. Fuller, C. W. et al. (2009) "The Challenges of Sequencing by Synthesis," *Nat. Biotechnol.* 27(11), 1013-1023.
3. Hiatt, A. C. and Rose, F. "Enzyme Catalyzed Template-Independent Creation of Phosphodiester Bonds Using Protected Nucleotides," U.S. Pat. No. 5,990,300, application Ser. No. 08/300,484, filed Sep. 2, 1994. (issued Nov. 23, 1999).
4. Buzby, P. R. "Nucleotide Analogs," United States Patent Application Publication Number US 2007-0117104 A1, application Ser. No. 11/295,406, filed Dec. 5, 2005. (published May 24, 2007).
5. Chen, F. et al. (2013) "The History and Advances of Reversible Terminators Used in New Generations of Sequencing Technology," *Genomics Proteomics Bioinformatics* 11(1), 34-40.
6. Tabor, S. and Richardson, C. C. (1995) "A Single Residue in DNA Polymerases of the *Escherichia coli* DNA Polymerase I Family Is Critical for Distinguishing between Deoxy- and Dideoxyribonucleotides," *Proc. Natl. Acad. Sci. U.S.A.* 92(14), 6339-6343.
7. Perler, F. B. and Southworth, M. W. "Thermostable Dna Polymerase from 9on-7 and and Method for Producing the Same," U.S. Pat. No. 5,756,334, application Ser. No. 08/271,364, filed Jul. 6, 1994. (issued May 26, 1998).
8. Southworth, M. W. et al. (1996) "Cloning of Thermostable DNA Polymerases from Hyperthermophilic Marine Archaea with Emphasis on *Thermococcus* Sp. 9 Degrees N-7 and Mutations Affecting 3'-5' Exonuclease Activity," *Proc. Natl. Acad. Sci. U.S.A.* 93(11), 5281-5285.
9. Evans. S. J. et al. (2000) "Improving Dideoxynucleotide-Triphosphate Utilisation by the Hyper-Thermophilic DNA Polymerase from the Archaeon *Pyrococcus Furiosus,*" *Nucleic Acids Res.* 28(5), 1059-1066.
10. Arezi, B. et al. (2002) "Efficient and High Fidelity Incorporation of Dye-Terminators by a Novel Archaeal DNA Polymerase Mutant," *J. Mol. Biol.* 322(4), 719-729.
11. Smith, G. P. et al. "Modified Polymerases for Improved Incorporation of Nucleotide Analogues," WIPO PCT Patent Publication Number WO/2005/024010, Application PCT/GB20041003891, filed Sep. 10, 2004. (published Mar. 17, 2005).
12. Harpp, D. N. et a. (1968) "Organic Sulfur Chemistry. I. The Disulfide-Phosphine Reaction. Desulfurization with Tris(Diethylamino)Phosphine," *J. Am. Chem. Soc.* 90(15), 4181-4182.
13. Burns, J. A. et al. (1991) "Selective Reduction of Disulfides by Tris(2-Carboxyethyl)Phosphine," *J. Org. Chem.* 56(8), 2648-2650.
14. Getz, E. B. et al. (1999) "A Comparison between the Sulfhydryl Reductants Tris(2-Carboxyethyl)Phosphine and Dithiothreitol for Use in Protein Biochemistry," *Anal. Biochem.* 273(1), 73-80.
15. Singh, R. and Whitesides, G. M. (1993) "Thiol-Disulfide Interchange," in Sulfur-Containing Functional Groups (Supplement, S. and Patai, S., Eds.), pp 633-658, J. Wiley and Sons, Ltd.
16. Lukesh, J. C. et al. (2012) "A Potent, Versatile Disulfide-Reducing Agent from Aspartic Acid," *J. Am. Chem. Soc.* 134(9), 4057-4059.
17. Singh, R. and Whitesides, G. M. (1994) "Reagents for Rapid Reduction of Native Disulfide Bonds in Proteins," *Bioorg. Chem.* 22, 109-115.
18. Singh, R. and Kats, L. (1995) "Catalysis of Reduction of Disulfide by Selenol," *Anal. Biochem.* 232(1), 86-91.
19. Stahl, C. R. and Siggia, S. (1957) "Determination of Organic Disulfides by Reduction with Sodium Borohydride," *Anal. Chem.* 29(1), 154-155.
20. Nardai, G. et al. (2001) "Protein-Disulfide Isomerase- and Protein Thiol-Dependent Dehydroascorbate Reduction and Ascorbate Accumulation in the Lumen of the Endoplasmic Reticulum," *J. Biol. Chem.* 276(12), 8825-8828.
21. Holmgren, A. and Bjornstedt, M. (1995) "[21] Thioredoxin and Thioredoxin Reductase," in *Methods in Enzymology, pp* 199-208, Academic Press.
22. Chen, C.-Y. (2014) "DNA Polymerases Drive DNA Sequencing-by-Synthesis Technologies: Both Past and Present," *Frontiers in Microbiology* 5.
23. Ju, J. et al. "Four-Color Dna Sequencing by Synthesis Using Cleavable Fluorescent Nucleotide Reversible Terminators," U.S. Pat. No. 7,883,869, application Ser. No. 12/312,903, filed Jul. 9, 2009. (issued Feb. 8, 2011).
24. Ju, J. et al. "Massive Parallel Method for Decoding DNA and RNA," U.S. Pat. No. 8,088,575, application Ser. No. 12/804,284, filed Jul. 19, 2010. (issued Jan. 3, 2012).
25. Ju, J. et al. "Chemically Cleavable 3'-O-Allyl-Dntp-Allyl-Fluorophore Fluorescent Nucleotide Analogues and Related Methods." U.S. Pat. No. 8,796,432, application Ser. No. 12/084,457, filed Apr. 30, 2008. (issued Aug. 5, 2014).
26. Balasubramanian, S. "Polynucleotide Sequencing," U.S. Pat. No. 6,833,246, application Ser. No. 10/113,221, filed Mar. 29, 2002. (issued Dec. 21, 2004).
27. Balasubramanian, S. et al. "Labelled Nucleotides," U.S. Pat. No. 7,785,796, application Ser. No. 12/460,741, filed Jul. 23, 2009. (issued Aug. 31, 2010).
28. Milton, J. et al. "Labelled Nucleotides," U.S. Pat. No. 7,414,116, application Ser. No. 10/525,399, filed Feb. 23, 2005. (issued Aug. 19, 2008).
29. Metzker, M. L. et al. (1994) "Termination of DNA Synthesis by Novel 3'-Modified-Deoxyribonucleoside 5'-Triphosphates," Nucleic Acids Res. 22(20), 4259-4267.

30. Ju, J. et al. (2006) "Four-Color DNA Sequencing by Synthesis Using Cleavable Fluorescent Nucleotide Reversible Terminators," *Proc. Natl. Acad. Sc. U.S.A.* 103(52), 19635-19640.
31. Ruparel, H. et al. (2005) "Design and Synthesis of a 3'-O-Allyl Photocleavable Fluorescent Nucleotide as a Reversible Terminator for DNA Sequencing by Synthesis," *Proc. Natl. Acad. Sci. U.S.A.* 102(17), 5932-5937.
32. Bergmann, F. et al. "Compound for Sequencing by Synthesis," United States Patent Application Publication Number US 2015-0140561 A1, application Ser. No. 14/542,980, filed Nov. 17, 2014. (published May 21, 2015).
33. Kwiatkowski, M. "Compounds for Protecting Hydroxyls and Methods for Their Use," United States Patent Application Publication Number US 2002-0015961 A1, application Ser. No. 09/952,719, filed Sep. 12, 2001. (published Feb. 7, 2002).
34. Gardner, A. F. et al. (2012) "Rapid Incorporation Kinetics and improved Fidelity of a Novel Class of 3'-Oh Unblocked Reversible Terminators," *Nucleic Acids Res.* 40(15), 7404-7415.
35. Litosh, V. A. et al. (2011) "Improved Nucleotide Selectivity and Termination of 3'-Oh Unblocked Reversible Terminators by Molecular Tuning of 2-Nitrobenzyl Alkylated Homedu Triphosphates," *Nucleic Acids Res.* 39(6), e39-e39.
36. Bowers, J. et al. (2009) "Virtual Terminator Nucleotides for Next Generation DNA Sequencing," *Nat. Meth.* 6(8), 593-595.
37. Zhao, C. et al. "Compositions and Methods for Nucleotide Sequencing," U.S. Pat. No. 8,399,188, application Ser. No. 12/442,925, filed Dec. 23, 2009. (issued Mar. 19, 2013).
38. Zon, G. "Reversible Di-Nucleotide Terminator Sequencing," U.S. Pat. No. 8,017,338, application Ser. No. 12/275,161, filed Nov. 20, 2008. (issued Sep. 13, 2011).
39. Wang, Z. et al. (2010) "Desulfurization of Cysteine-Containing Peptides Resulting from Sample Preparation for Protein Characterization by MS," *Rapid Commum. Mass Spectrom.* 24(3), 267-275.
40. Jung, A. et al. (2002) "7-Deaza-2'-Deoxyguanosine Allows PCR and Sequencing Reactions from CpG Islands," *Mol. Pathol.* 55(1), 55-57.
41. Kutyavin, I. V. (2008) "Use of Base-Modified Duplex-Stabilizing Deoxynucleoside 5'-Triphosphates to Enhance the Hybridization Properties of Primers and Probes in Detection Polymerase Chain Reaction," *Biochemistry* 47(51), 13666-13673.
42. Semenyuk, A. et al. (2006) "Synthesis of RNA Using 2'-O-Dtm Protection," *J. Am. Chem. Soc.* 128(38), 12356-12357.
43. Semenyuk, A. and Kwiatkowski, M. (2007) "A Base-Stable Dithiomethyl Linker for Solid-Phase Synthesis of Oligonucleotides," *Tetrahedron Lett.* 48(3), 469-472.
44. Semenyuk, A. (2006) "Novel Methods for Synthesis of High Quality Oligonucleotides," Uppsala University.
45. Bellamy, A. J. et al. (2007) "The Use of Trifluoroacetyl as an N- and O-Protecting Group During the Synthesis of Energetic Compounds Containing Nitramine and/or Nitrate Ester Groups," *Propellants Explos. Pyrotech.* 32(1), 20-31.
46. Gordon, S. and Olejnik, J. "Methods and Compositions for Incorporating Nucleotides," United States Patent Application Publication Number US 2013-0137091 A1, application Ser. No. 13/305,415, filed Nov. 28, 2011. (published May 30, 2013).
47. Olejnik, J. et al. "Methods and Compositions for Inhibiting Undesired Cleaving of Labels," U.S. Pat. No. 8,623,598, application Ser. No. 12/405,866, filed Mar. 17, 2009. (issued Jan. 7, 2014).
48. Montazerozohori, M. et al. (2007) "Fast and Highly Efficient Solid State Oxidation of Thiols," *Molecules* 12(3), 694.
49. Clark, D. E. (1999) "Rapid Calculation of Polar Molecular Surface Area and Its Application to the Prediction of Transport Phenomena. 2. Prediction of Blood-Brain Barrier Penetration," *J. Pharm. Sci.* 88(8), 815-821.
50. Oxidation of organic sulfur compounds with hydrogen peroxide in the presence of crown ethers; Moscow University Chemistry Bulletin; 2008, 63, 48.
51. Molecular basis of the mechanism of thiol oxidation by hydrogen peroxide in aqueous solution: challenging the SN2 paradigm; Chem Res Toxicol., 2012, 25, 741.

The invention claimed is:

1. A method of incorporating nucleotides, comprising:
   a) providing i) a plurality of nucleic acid primers and template molecules, and ii) an extend reagent comprising polymerase, a plurality of nucleotide analogues, wherein said nucleotide analogues comprise a 3'-O position capped by a disulfide-based 3'-terminator group and a label attached through a cleavable disulfide linker to the base, and 5-Chloro-2-methyl-4-isothiazolin-3-one;
   b) hybridizing at least a portion of said primers to at least a portion of said template molecules so as to create hybridized primers; and
   c) exposing said hybridized primers to said extend reagent in an extension reaction under conditions such that a first nucleotide analogue is incorporated into at least a portion of said hybridized primers so as to create extended primers comprising an incorporated nucleotide analogue, wherein 5-Chloro-2-methyl-4-isothiazolin-3-one inhibits cleavage of said disulfide-based 3'-terminator group during said extension reaction.

2. The method of claim 1, wherein said disulfide-based 3'-terminator group comprises methylenedisulfide as a cleavable protecting group.

3. The method of claim 1, wherein said extend reagent further comprises 2-Methyl-4-isothiazolin-3-one.

4. The method of claim 1, further comprising:
   d) detecting said label of a first labeled nucleotide analogue.

5. The method of claim 4, further comprising:
   e) cleaving said linker with a cleaving reagent so as to remove said label.

6. The method of claim 5, wherein cleaving reagent also removes said disulfide-based 3'-terminator group.

7. The method of claim 6, wherein said cleaving reagent is a thiol-containing compound.

8. The method of claim 7, wherein the thiol-containing compound is a vicinal dithiol-based compound.

9. The method of claim 4, wherein the vicinal dithiol-based compound is di-mercaptopropanesulfonate.

10. A method for detecting labeled nucleotides in a nucleic acid sequence comprising the steps of
    a) providing i) nucleic acid template and primer capable of hybridizing to said template so as to form a primer/template hybridization complex, ii) an extend reagent comprising polymerase, a plurality of nucleotide analogues, and 5-Chloro-2-methyl-4-isothiazolin-3-one, wherein said nucleotide analogues comprise a nucleobase and a sugar, said sugar comprising a cleavable protecting group on the 3'-O, wherein said cleavable protecting group comprises a disulfide-based 3'-terminator group, and wherein at least a portion of said nucleotide analogues further comprises a first detectable label attached via a cleavable disulfide-containing linker to the nucleobase; and iii) a cleave reagent comprising a thiol-containing compound;

b) hybridizing at least a portion of said primers to at least a portion of said template molecules so as to create hybridized primers; and c) exposing said hybridized primers to said extend reagent in an extension reaction under conditions such that a first nucleotide analogue comprising a first detectable label is incorporated into at least a portion of said hybridized primers in a polymerase catalyzed primer extension reaction so as to create extended primers comprising an incorporated nucleotide analogue in a modified primer/template hybridization complex, wherein 5-Chloro-2-methyl-4-isothiazolin-3-one inhibits cleavage of said disulfide-based 3'-terminator group during the extension reaction;

d) detecting said first detectable label of said deoxynucleoside triphosphate in said modified primer/template hybridization complex; and e) introducing said cleave reagent under conditions so as to remove said cleavable protecting group and said detectable label from said modified primer/template hybridization complex.

11. The method of claim 10, wherein the method further comprises incorporating a second nucleotide analogue comprising a second detectable label during a repeat of step c).

12. The method of claim 10, wherein the thiol-containing compound is a vicinal dithiol-based compound.

13. The method of claim 12, wherein the vicinal dithiol-based compound is di-mercaptopropanesulfonate.

14. The method of claim 11, wherein the nucleobase of said second nucleotide analogue is different from the nucleobase of said first nucleotide analogue.

15. The method of claim 10, wherein said extend reagent comprises a mixture of at least 4 differently labeled nucleotide analogues representing analogs of A, G, C and T or U.

16. The method of claim 10, wherein said detecting allows for the determination of the nucleobase of said incorporated first nucleotide analogue.

17. The method of claim 10, wherein said disulfide-based 3'-terminator group comprises methylenedisulfide as a cleavable protecting group.

18. The method of claim 10, wherein said extend reagent further comprises 2-Methyl-4-isothiazolin-3-one.

19. The method of claim 10, further comprising:
f) introducing a scavenger that interacts with the cleave reagent.

20. The method of claim 19, wherein said scavenger is cystamine.

* * * * *